US009204624B2

(12) United States Patent  
McWhirter et al.

(10) Patent No.: US 9,204,624 B2  
(45) Date of Patent: Dec. 8, 2015

(54) NON-HUMAN ANIMALS WITH MODIFED IMMUNOGLOBULIN HEAVY CHAIN SEQUENCES

(71) Applicant: Regeneron Pharmaceuticals, Inc., Tarrytown, NY (US)

(72) Inventors: John McWhirter, Tarrytown, NY (US); Cagan Gurer, Valhalla, NY (US); Karolina A. Meagher, Tarrytown, NY (US); Lynn Macdonald, White Plains, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 14/498,523

(22) Filed: Sep. 26, 2014

(65) Prior Publication Data

US 2015/0020224 A1    Jan. 15, 2015

Related U.S. Application Data

(63) Continuation of application No. 14/185,679, filed on Feb. 20, 2014.

(60) Provisional application No. 61/766,765, filed on Feb. 20, 2013, provisional application No. 61/879,338, filed on Sep. 18, 2013.

(51) Int. Cl.
| | |
|---|---|
| *A01K 67/027* | (2006.01) |
| *C12P 21/08* | (2006.01) |
| *C07K 16/46* | (2006.01) |
| *C07K 16/00* | (2006.01) |

(52) U.S. Cl.
CPC .............. *A01K 67/0278* (2013.01); *C07K 16/00* (2013.01); *A01K 2217/072* (2013.01); *A01K 2227/105* (2013.01); *A01K 2267/01* (2013.01); *C07K 2317/10* (2013.01); *C07K 2317/24* (2013.01); *C07K 2317/51* (2013.01)

(58) Field of Classification Search
CPC ............. A01K 67/028; A01K 2267/01; A01K 2227/105; A01K 2217/072; C07K 16/00; C07K 2317/10; C07K 2317/24
USPC ................................ 800/13, 18, 6; 530/387.3
See application file for complete search history.

(56) References Cited

U.S. PATENT DOCUMENTS

| | | | |
|---|---|---|---|
| 5,545,807 A | 8/1996 | Surani et al. | |
| 6,162,963 A | 12/2000 | Kucherlapati et al. | |
| 6,596,541 B2 | 7/2003 | Murphy et al. | |
| 6,657,103 B1 | 12/2003 | Kucherlapati et al. | |
| 6,673,986 B1 | 1/2004 | Kucherlapati et al. | |
| 7,501,552 B2 | 3/2009 | Lonberg et al. | |
| 7,910,798 B2 | 3/2011 | Tanamachi et al. | |
| 8,158,419 B2 | 4/2012 | Lonberg et al. | |
| 8,502,018 B2 | 8/2013 | Murphy et al. | |
| 2004/0018626 A1 | 1/2004 | Murphy et al. | |
| 2006/0015957 A1 | 1/2006 | Lonberg et al. | |
| 2011/0111406 A1 | 5/2011 | Igawa et al. | |
| 2011/0145937 A1 | 6/2011 | Macdonald et al. | |
| 2011/0195454 A1 | 8/2011 | McWhirter et al. | |
| 2012/0021409 A1 | 1/2012 | McWhirter et al. | |
| 2012/0096572 A1 | 4/2012 | Macdonald et al. | |
| 2012/0167237 A1 | 6/2012 | Bradley et al. | |
| 2012/0322108 A1 | 12/2012 | Macdonald et al. | |
| 2013/0096287 A1 | 4/2013 | Macdonald et al. | |
| 2013/0243759 A1 | 9/2013 | Friedrich et al. | |
| 2013/0323235 A1 | 12/2013 | Craig et al. | |
| 2013/0323791 A1 | 12/2013 | MacDonald et al. | |

FOREIGN PATENT DOCUMENTS

| | | | |
|---|---|---|---|
| KR | 1020050042792 A | 5/2005 | |
| WO | 90/04036 A1 | 4/1990 | |
| WO | 98/24893 A2 | 6/1998 | |
| WO | 02/066630 A1 | 8/2002 | |
| WO | WO 2004/106375 A1 | 12/2004 | |
| WO | WO 2006/117699 A | 11/2006 | |
| WO | 2009/097006 A2 | 8/2009 | |
| WO | 2010/039900 A2 | 4/2010 | |

(Continued)

OTHER PUBLICATIONS

Wheeler (2001) Theriogenology. vol. 56, 1345-1369.*
Prelle et al. (2002) Anat. Histol. Embryol., vol. 31, 169-186.*
Munoz et al. (2009) Stem Cell Rev. and Rep., vol. 5, 6-9.*
Clark et al. (2003) Nature Reviews: Genetics. vol. 4, 825-833.*
Niemann et al (2005) Rev. Sci, Tech. Off. Int. Spiz. vol. (24), 285-298.*
PCT/US2014/17427 International Search Report mailed Aug. 1, 2014.
PCT/US2013/029624 Invitation to Pay Additional Fees and Where Applicable, Protest Fee mailed May 17, 2013, 9 pages.

(Continued)

*Primary Examiner* — Anne Marie S Wehbe
(74) *Attorney, Agent, or Firm* — Brownstein Hyatt Farber Schreck, LLP; Rita S. Wu; Yong-Jin Choi

(57) ABSTRACT

Non-human animals, e.g., mammals, e.g., mice or rats, are provided comprising an immunoglobulin heavy chain locus that comprises a rearranged human immunoglobulin heavy chain variable region nucleotide sequence. The rearranged human immunoglobulin heavy chain variable region nucleotide sequence may be operably linked to a heavy or light chain constant region nucleic acid sequence. Also described are genetically modified non-human animals comprising an immunoglobulin light chain locus comprising one or more but less than the wild type number of human immunoglobulin light chain variable region gene segments, which may be operably linked to a light chain constant region nucleic acid sequence. Also provided are methods for obtaining nucleic acid sequences that encode immunoglobulin light chain variable domains capable of binding an antigen in the absence of a heavy chain.

27 Claims, 107 Drawing Sheets

(56) References Cited

FOREIGN PATENT DOCUMENTS

| | | |
|---|---|---|
| WO | 2011/004192 A1 | 1/2011 |
| WO | 2011/072204 A1 | 6/2011 |
| WO | 2011/158009 A1 | 12/2011 |
| WO | 2012/063048 A1 | 5/2012 |
| WO | 2012/141798 A1 | 10/2012 |
| WO | 2013/022782 A1 | 2/2013 |
| WO | 2013/041845 A2 | 3/2013 |
| WO | 2013/041846 A2 | 3/2013 |
| WO | 2013/045916 A1 | 4/2013 |
| WO | 2013/059230 A1 | 4/2013 |
| WO | 2013/061078 A1 | 5/2013 |
| WO | 2013/061098 A2 | 5/2013 |
| WO | 2013/079953 A1 | 6/2013 |
| WO | 2013/144566 A2 | 10/2013 |
| WO | 2013/144567 A1 | 10/2013 |
| WO | 2013/171505 A2 | 11/2013 |
| WO | WO 2014/130690 A1 | 8/2014 |

OTHER PUBLICATIONS

Adderson et al., (1991) "Restricted Ig H Chain V Gene Usage in the Human Antibody Response to *Haemophilus influenzae* Type b Capsular Polysaccharide," The Journal of Immunology, 147: 1667-1674.

Adderson et al., (1993) "Restricted Immunoglobulin VH Usage and VDJ Combinations in the Human Response to *Haemophilus influenzae* Type b Capsular Polysaccharide," J. Clin. Invest., 91: 2734-2743.

Bando et al., (2004) "Characterization of VH gene expressed in PBL from children with atopic diseases: detection of homologous VH1-69 derived transcripts from three unrelated patients," Immunology Letters, 94: 99-106.

Baseggio et al., (2010) "CD5 expression identifies a subset of splenic marginal zone lymphomas with higher lymphocytosis: a clinicopathological, cytogenetic and molecular study of 24 cases," Haematologica, 95(4): 604-612.

Bendig, (1995) "Humanization of Rodent Monoclonal Antibodies by CDR Grafting," Methods, 8:83-93.

Berberian et al., (1991) "A VH Clonal Deficit in Human Immunodeficiency VirUS Positive Individuals Reflects a B-Cell Maturational Arrest," Blood, 78(1): 175-179.

Brezinschek et al., (1995) "Analysis of the Heavy Chain Repertoire of Human Peripheral B Cells Using Single-Cell Polymerase Chain Reaction," Journal of Immunology, 155:190-202.

Briney, et al., (2012) "Human Peripheral Blood Antibodies with Long HCDR3s Are Established Primarily at Original Recombination Using a Limited Subset of Germline Genes," PLoS ONE, 7(5):1-13.

Bruggemann et al., (1989) "A repertoire of monoclonal antibodies with human heavy chains from transgenic mice," Proc. Natl. Acad. Sci. USA, 86: 6709-6713.

Bruggemann (2001) "Human Antibody Expression in Transgenic Mice," Archivum Immunologiae et Therapiae Experimentalis, 49: 203-208.

Carbonari et al., (2005) "Hepatitis C Virus Drives the Unconstrained Monoclonal Expansion of VH1-69-Expressing Memory B Cells in Type II Cryoglobulinemia: A Model of Infection-Driven Lymphomagenesis," The Journal of Immunology, 174: 6532-6539.

Chan et al., (2001) "VH1-69 gene is preferentially used by hepatitis C virUS associated B cell lymphomas and by normal B cells responding to the E2 viral antigen," Blood, 97(4): 1023-1026.

Charles et al., (2011) "A flow cytometry-based strategy to identify and express IgM from VH1-69+ clonal peripheral B cells," Journal of Immunological Methods, 363: 210-220.

Choi, et al., (2004) "Characterization and comparative genomic analysis of intronless Adams with testicular gene expression," Genomics, 83(4):636-46. (Abstract Only).

Chothia, et al., (1992) "Structural Repertoire of the Human VH Segments," J. Mol. Biol., 227:799-817.

Davidkova et al., (1997) "Selective Usage of VH Genes in Adult Human B Lymphocyte Repertoires," Scand. J. Immunol., 45: 62-73.

De Wildt, et al., (1999) "Analysis of heavy and light chain pairings indicates that receptor editing shapes the human antibody repertoire", J. Mol. Biol., 285(3):895-901.

Edwards, et al., (2008) "The ADAM metalloproteinases," Molecular Aspects of Medicine, 29(5):258-89.

Featherstone, et al., (2010) "The Mouse Immunoglobulin Heavy Chain V-D Intergenic Sequence Contains Insulators That May Regulate Ordered V(D))J Recombination," Journal of Biological Chemistry, 58(13):9327-38.

Forconi, et al., (2010) "The normal IGHV1-69—derived B-cell repertoire contains stereotypic patterns characteristic of unmutated CLL," Blood, 115(1):71-77.

Giallourakis, et al., (2010) "Elements between the IgH variable (V) and diversity (D) clusters influence antisense transcription and lineage-specific V(D)J recombination, " Proceedings of the National Academy of Sciences of the USA, 107(51):22207-22212.

Han, et al., (2009) "Comprehensive Analysis of Reproductive ADAMs: Relationship of ADAM4 and ADAM6 with an ADAM Complex Required for Fertilization in Mice," Biology of Reproduction, 80:1001-1008.

Hendricks, et al., (2010) "Organization of the variable region of the immunoglobulin heavy-chain gene locus of the rat," Immunogenetics, 62(7):479-86.

Huang et al., (1993) "A Majority of Ig H Chain cDNA of Normal Human Adult Blood Lymphocytes Resembles cDNA for Fegal Ig and Natural Autoantibodies," The Journal of Immunology, 151(10): 5290-5300.

Johnson et al., (1997) "Ig VH1 Genes Expressed in B Cell Chronic Lymphocytic Leukemia Exhibit Distinctive Molecular Features," The Journal of Immunology, 158: 235-246.

Kantor et al., (1997) "An Unbiased Analysis of VH-D-JH Sequences from B-1a, B-1b, and Conventional B Cells," The Journal of Immunology, 158: 1175-1186.

Kim, et al., (2006) "Expression and relationship of male reproductive ADAMs in mouse," Biology of Reproduction, 74 (4):744-750.

Kunert et al., (2004) "Characterization of Molecular Features, Antigen-Binding, and in Vitro Properties of IgG and IgM Variants of 4E10, an Anti-HIV Type 1 Neutralizing Monoclonal Antibody," Aids ReSearch and Human Retroviruses, 20(7): 755-762.

Lefranc et al., (2000) "Nomenclature of the Human Immunoglobulin Genes," Current Protocols in Immunology, A.1P.1-A.1P.37.

Lonberg, (2005) "Human antibodies from transgenic animals," Nature Biotechnology, 23:(9) 1117-1125.

Mageed, et al., (2001) "Rearrangement of the human heavy chain variable region gene V3-23 in transgenic mice generates antibodies reactive with a range of antigens on the basis of VhCDR3 and residues intrinsic to the heavy chain variable region," Clin Exp Immunol, 123:1-8.

Mahmoud et al., (2011) "Limiting CDR-H3 Diversity Abrogates the Antibody Response to the Bacterial Polysaccharide a 1 →3 Dextran," The Journal of Immunology, 187: 879-886.

Mahmoudi et al., "V region gene analysis of human IgM hybridoma monoclonal anti-Sm antibodies," Lupus, 6: 578-589, 1997.

Marasca et al., (2001) "Immunoglobulin Gene Mutations and Frequent Use of VH1-69 and VH4-34 Segments in Hepatitis C VirUS Positive and Hepatitis C VirUS Negative Nodal Marginal Zone B-Cell Lymphoma," American Journal of Pathology, 159(1): 253-261.

Matsuda, et al., (1998) "The Complete Nucleotide Sequence of the Human Immunoglobulin Heavy Chain Variable Region Locus," J. Exp. Med., 188(11):2151-2162.

Miklos et al., (2000) "Salivary gland mucosa-associated lymphoid tissue lymphoma immunoglobulin VH genes show frequent use of V1-69 with distinctive CDR3 features," Blood, 95: 3878-3884.

Moran, et al., (2013) "Mouse platforms jostle for slice of humanized antibody market," Nature Biotechnology, 31 (4):267-268.

Mortari et al., (1993) "Human Cord Blood Antibody Repertoire," The Journal of Immunology, 150(4): 1348-1357.

Muller et al., (1993) "B-Cell Abnormalities in AIDS: Stable and Clonally-Restricted Antibody Response in HIV-1 Infection," Scand. J. Immunol., 38: 327-334.

Paul, (1993) "Fv Structure and Diversity in Three Dimensions," Fundamental Immunology, Third Edition, pp. 292-295.

(56) References Cited

OTHER PUBLICATIONS

Perez, et al., (2010) "Primary cutaneous B-cell lymphoma is associated with somatically hypermutated immunoglobulin variable genes and frequent use of VH1-69 and VH4-59 segments," British Journal of Dermatology, 162:611-618.

Pos, et al., (2008) "VH1-69 germline encoded antibodies directed towards ADAMTSI3 in patients with acquired thrombotic thrombocytopenic purpura," Journal of Thrombosis & Haemostasis, 7:421-428.

Ray, (1991) "Ectopic expression of a c-kitW42 minigene in transgenic mice: recapitulation of W phenotypes and evidence for c-kit function in melanoblast progenitors," Genes Dev., 5(12A):2265-73.

Rodriguez, et al., (2000) "High-efficiency deleter mice show that FLPe is an alternative to Cre-loxP," Nature Genetics, 25:139-140.

Romo-Gonzalez and Vargas-Madrazo, (2005) "Structural analysis of substitution patterns in alleles of human immunoglobulin VH genes," Molecular Immunology, 42:1085-1097.

Sasso, et al., (1993) "A Fetally Expressed Immunoglobulin V H1 Gene Belongs to a Complex Set of Alleles," Journal of Clinical Investigation, 91:2358-2367.

Sasso, et al., (1996) "Expression of the Immunoglobulin VH Gene 51p1 Is Proportional to Its Germline Gene Copy Number" Journal of Clinical Investigation, 97(9):2074-2080.

Sasso, et al., (1990) "Prevalence and Polymorphism of Human Vh3 Genes," Journal of Immunology, 145 (8):2751-2757.

Schelonka, et al., (2005) "A Single DH Gene Segment Creates Its Own Unique CDR-H3 Repertoire and Is Sufficient for B cell Development and Immune Functions," Journal of Immunology, 175:6624-6632.

Seals, et al., (2003) "The ADAMs family of metalloproteases: multidomain: proteins with multiple functions," Genes and Development, 17(1):7-30.

Sibilia, et al., (1997) "Structural Analysis of Human Antibodies to Proteinase 3 from Patients with Wegener Granulomatosis," Journal of Immunology, 159:712-719.

Souroujon, et al., (1989) "Polymorphisms in Human H Chain V Region Genes From The VHIII Gene Family," Journal of Immunology, 143(2):706-711.

Suarez, et al., (2006) "Rearrangement of only one human IGHV gene is sufficient to generate a wide repertoire of antigen specific antibody responses in transgenic mice," Molecular Immunology, 43:1827-1835.

Sui, et al., (2009) "Structural and functional bases for broad-spectrum neutralization of avian and human influenza a viruses," Nature Structural & Molecular Biology, 16(3):265-273.

Suzuki, et al., (1995) "Representation of Rearranged VH Gene Segments in the Human Adult Antibody Repertoire," Journal of Immunology, 154 3902-3911.

Taylor, et al., (1992) "A transgenic mouse that expresses a diversity of human sequence heavy and light chain immunoglobulins," Nucleic Acids ReSearch, 20(23):6287-6295.

Tobin, et al., (2004) "Subsets with restricted immunoglobulin gene rearrangement features indicate a role for antigen selection in the development of chronic lymphocytic leukemia," Blood, 104:2879-2885.

Tuaillon, (2000) "Repertoire analysis in human immunoglobulin heavy chain minilocus transgenic, [mu]MT/[mu]MT mice," Molecular Immunology, 37(5):221-231.

Tuaillon, et al., (1993) "Human immunoglobulin heavy-chain minilocus recombination in transgenic mice: Gene-segment use in µ, and y transcripts," PNAS, 90:2734-2743.

Wagner, et al., (1994) "Antibodies generated from human immunoglobulin miniloci in transgenic mice," Nucleic Acids ReSearch, 22(8):1389-1393.

Wagner, et al., (1996) "Antibody Expression from the Core Region of the Human IgH Locus Reconstructed in Transgenic Mice Using Bacteriophage P1 Clones," GENOMICS, 35:405-414.

Wagner, et al., (1994) "The diversity of antigen-specific monoclonal antibodies from transgenic mice bearing human immunoglobulin gene miniloci," European Journal of Immunology, 24:2672-2681.

Wang, et al., (2009) "Universal epitopes of influenza virus hemagglutinins?," Nature Structural & Molecular Biology, 16(3):233-234.

Widhopf, et al., (2004) "Chronic lymphocytic leukemia B cells of more than 1% of patients express virtually identical immunoglobulins," Blood, 104:2499-2504.

Xu, et al., (2000) "Diversity in the CDR3 Region of VH Is Sufficient for Most Antibody Specificities," Immunity, 13 (1):37-45.

Yamada, et al., (1991) "Preferential Utilization of Specific Immunoglobulin Heavy Chain Diversity and Joining Segments in Adult Human Peripheral Blood B Lymphocytes," Journal of Experimental Medicine, 173;395-407.

International Search Report & Written Opinion with respect to PCT/US2012/026416, mailed Jun. 25, 2012.

International Search Report & Written Opinion with respect to PCT/US2013/029624, mailed Aug. 2, 2013.

International Search Report & Written Opinion with respect to PCT/US2012/060487 mailed Feb. 1, 2013.

Third Party Observations for European Patent Application No. 12783456.2 filed on Mar. 12, 2014.

* cited by examiner

Search of ASAP database for REGN antibodies with UHC CDR3 sequence (AKDYSNYYFDY)

| Antibody | Antigen | Germline VH | Germline JH | CDR3 |
|---|---|---|---|---|
| Search with DYSN or YSNY: | | | | |
| H1H-136B | EGFR | 3-23*04 | J6*02 | AYDYSNYWDHYGMDV |
| H4H1789B | CD48 | 3-23*04 | J5*02 | AKYSNYDYFDP |
| H1H962B | GDF8 | 3-33*04 | J6*02 | AKYSNYGYYNGLDV |
| H2M744H | ANG2 | 1-18*01 | J5*02 | ARDQDYSNFHWLDP |
| H1M1981 | CA9 | 4-31*03 | J6*02 | ARESHYSNYEDYYYGMDV |
| Search with AKDY: | | | | |
| H4H381B | NAV1.7 | 3-23*04 | J4*02 | AKDYYGPFDY |
| H1H1058B | NAV1.7 | 3-23*04 | J4*02 | AKDYCNSTYYYGED |
| Search with YYFDY: | | | | |
| H1H2002B | CA9 | 3-23*01 | J4*02 | AKGYYFDY |
| H1H2221B | CA9 | 3-23*04 | J4*02 | AIGYYFDY |
| H1H2225B | CA9 | 3-23*04 | J4*02 | AKGYYFDY |

FIG. 5

MAID 6031 (ULC into 1661)

| Assay | Probe name | 1º | confirmation | reconfirmation | Parental (1661het) | F1H4 | Copy# modif allele | Copy# WT allele |
|---|---|---|---|---|---|---|---|---|
| LOA | hyg | 0 | 0 | 0 | 1 | 0 | 0 | 0 |
| GOA | UHC-h1a or h1b | 1 | 1 | 1 | 0 | 0 | 1 | 0 |
|  | UHC-h2a or h2b | 1 | 1 | 1 | 0 | 0 | 1 | 0 |
|  | mIgHA1 | 2 | 2 | 2 | 1 | 2 | 1 | 1 |
|  | neo | | | 1 | 0 | 0 | 1 | 0 |
| parental | mIgHd10 | | | 1 | 1 | 2 | 0 | 1 |
|  | 88710T | | | 1 | 1 | 2 | 0 | 1 |
|  | mIgHA7 | | | 1 | 1 | 2 | 0 | 1 |
|  | mIgHp2 | | | 1 | 1 | 2 | 0 | 1 |

Genotype 6031het

FIG. 7

Probes for MAID 6031 (UHC into 1661)

| Name | Forward Primer | Probe | Reverse Primer | Type of Probe | Assay | Location (bp position in UHC) |
|---|---|---|---|---|---|---|
| hyg | TGCGGCCGATCTTAGCC (SEQ ID NO: 151) | ACGAGCGGGTTCGGCCCATTC (SEQ ID NO: 152) | TTGACCGATTCCTTGCGG (SEQ ID NO: 153) | BHQ-1 | LOA | |
| UHC-h1a | TCAGGTGTGATGCTGATCCA AC (SEQ ID NO: 154) | TGCATCTTCCTCCCATTCCTGGGT A (SEQ ID NO: 155) | TGGCTGCTGGGAGAAGAT TG (SEQ ID NO: 156) | BHQ-1 | GOA | hVH3-23 promoter(202-296) |
| UHC-h1b | CCCAGCAGCCACTATGTC (SEQ ID NO: 157) | TCCCACTGATGTCTTCAGCTTCCT C (SEQ ID NO: 158) | CCCTCAGGAATAACAGACT CATC (SEQ ID NO: 159) | BHQ-1 | GOA | hVH3-23 promoter(368-474) |
| UHC-h2a | AAGGGCGGTTCCACCATCT (SEQ ID NO: 160) | CCAGAGACAATCCAAGAACACGC TG (SEQ ID NO: 161) | CGGGTCTCAGGCTGTTCA (SEQ ID NO: 162) | BHQ-1 | GOA | hVH3-23 exon(2592-2664) |
| UHC-h2b | GCAGCCTCTGGATTCACCTT (SEQ ID NO: 163) | AGCAACTCTCCAATGAGCTGGGTC (SEQ ID NO: 164) | TCACGGAGTCTGCGTAGAA TG (SEQ ID NO: 165) | BHQ-1 | GOA | hVH3-23 exon(2466-2592) |
| mlgHA1 | CTCAGTGATTCTGGCCCTGC (SEQ ID NO: 166) | TGGTCCACAGTACAAACCCCTTC CTATAATG (SEQ ID NO: 167) | GGATGATGGCTCAGCAC AGAG (SEQ ID NO: 168) | | GOA | mAdam6a |
| neo | GGTGGAGAGGCTATTCGGC (SEQ ID NO: 169) | TGGGCACAACAGACAATCGGCTG (SEQ ID NO: 170) | GAACACGGCGGCATCAG (SEQ ID NO: 171) | BHQ-1 | GOA | |
| mlgHd10 | GGTGTGCGATGTACCCTCTGA AC (SEQ ID NO: 172) | CTAAAAATGCTACACCTGGGGCAA AACACCTG (SEQ ID NO: 173) | TGTGGCAGTTTAATCCAGC TTTATC (SEQ ID NO: 174) | | parental | mIgH distal V |
| 887.10 | GATGGGAAGAGACTGGTAACA TTTGTAC (SEQ ID NO: 175) | CCTCCACTGTGTTAATGGCTGCCA CAA (SEQ ID NO: 176) | TTCCTCTATTCACTCTTTG AGGCTC (SEQ ID NO: 177) | | parental | mIgH V |
| mlgHA7 | TGGTCACCTCCAGGAGCCTC (SEQ ID NO: 178) | AGTCTCTGCTTCCCCTTGTGCCT ATGAGC (SEQ ID NO: 179) | GCTGCAGGGTGTATCAGG TGC (SEQ ID NO: 180) | BHQ-1 | parental | mAdam6b |
| mlgHp2 | GCCATGCAAGGCCAAGC (SEQ ID NO: 181) | CCAGGAAAATGCTGCCAGAGCCTG (SEQ ID NO: 182) | AGTTCTTGAGCTTAGGGT GCTAG (SEQ ID NO: 183) | BHQ-1 | parental | mIgH D-J |

FIG. 8

FIG. 16 hVH3-23(D4-4_RF2)JH6.opt.nucl Text View
Thu, Jan 20, 2011 9:48 AM

Sequence: hVH3-23(D4-4_RF2)JH6.opt Range: 1 to 448    (SEQ ID NO: 146)

>/note=XhoI                                                                                                    >/note=hVH3-23
```
         10         20         30         40         50         60         70         80         90
CTCGAGCCAC CATGGAGTTC GGGCTGTCCT GGCTTTTTCT TGTGGCCATT CTGAAGGGTG TGCAATGTGA AGTGCAGTTG CTGGAGTCCG
GAGCTCGGTG GTACCTCAAG CCCGACAGGA CCGAAAAAGA ACACCGGTAA GACTTCCCAC ACGTTACACT TCACGTCAAC GACCTCAGGC
                                a                                         a
         M  E  F  G  L  S  W  L  F  L  V  A  I  L  K  G  V  Q  C  E  V  Q  L  L  E  S
                     b                                         b                                       b
                    /NOTE=hVH3-23 SIGPEP_a
                                         /NOTE=CDS_b
        100        110        120        130        140        150        160        170        180
GGGGGGGCCT TGTGCAGCCT GGAGGATCAC TCCGGCTGAG CTGGCCAGCC AGTGGTTTCA CGTTCAGTAG TTATGCTATG TCTTGGGTGC
CCCCCCCGGA ACACGTCGGA CCTCCTAGTG AGGCCGACTC GACCGGTCGG TCACCAAAGT GCAAGTCATC AATACGATAC AGAACCACG
 G  G  G  L  V  Q  P  G  G  S  L  R  L  S  C  A  A  S  G  F  T  F  S  S  Y  A  M  S  W  V
                   b                                         b                                       b
                                                                                       /NOTE=CDS_b
        190        200        210        220        230        240        250        260        270
GCCAGGCCCC TGGTAAGGGG CTGGAGTGGG TGTCAGCTAT TTCCGGCAGC GGCGGATCTA CTTATTACGC TGATAGCGTG AAGGGACGCT
CGGTCCGGGG ACCATTCCCC GACCTCACCC ACAGTCGATA AAGGCCGTCG CCGCCTAGAT GAATAATGCG ACTATCGCAC TTCCCTGCGA
 R  Q  A  P  G  K  G  L  E  W  V  S  A  I  S  G  S  G  G  S  T  Y  Y  A  D  S  V  K  G  R
                   b                                         b                                       b
        280        290        300        310        320        330        340        350        360
TCACAATCTC TCGGGACAAC TCCAAAAACA CCCTCTATCT TCAGATGAAT AGTCTACTTA AGCCTCGCG GACTCGTGTG CGCTGTTTAT TACTGCGCCA
AGTGTTAGAG AGCCCTGTTG AGGTTTTTGT GGGAGATAGA AGTCTACTTA TCGGAGCGGC CTGAGGCAC GACTCGTGTG GGGACAAATA ATGACGCGGT
 F  T  I  S  R  D  N  S  K  N  T  L  Y  L  Q  M  N  S  L  R  A  E  D  T  A  V  Y  Y  C  A
                   b                                         b                                       b
                                                                                       /NOTE=CDS_b
        370        380        390        400        410        420        430        440
AAGATTATTC TACTACTAC AAATTATTAT ATGGCATGGA CGTCTGGGGT CAGGGAACAA CCGTCACCGT GTCCAGGCGC TGAAGAGC
TTCTAATAAG ATGATGATG TTTAATAATA TACCGTACCT GCAGACCCCA GTCCCTTGTT GGCAGTGGCA CAGGTCGCCG ACTTCTCG
 K  D  Y  S  N  Y  Y  Y  Y  Y  Y  G  M  D  V  W  G  Q  G  T  T  V  T  V  S  S
                   b                                         b                           c
      /NOTE=CDS_b
                                         366 TO 425 OF hVH3-23(D-)JH6_OPTIMIZED
```
>/note=D4-4_RF2    >/note=hJH6                                                                         </note=Sap

FIG. 17

Sequence: hVH3-23(D4-4_RF3)JH4.opt Range: 1 to 430 (SEQ ID NO: 147)

```
>/note=XhoI                                                                >/note=hVH3-23
     |----+----|----+----|----+----|----+----|----+----|----+----|----+----|----+----|----+----|
          10        20        30        40        50        60        70        80        90
     CTGAGCCAC CATGGAGTTC GGGCTGTCC GGCTTTTTCT TGTGGCCATT CTGAAGGGTG TGCAATGTGA AGTGCAGTTG CTGGAGTCCG
     GAGTCGGGTG GTACCTCAAG CCCGACAGGA CCGAAAAAGA ACACCGGTAA GACTTCCCAC ACGTTACACT TCACGTCAAC GACCTCAGGC
                           a                                           a
                         M  E  F  G  L  S  W  L  F  L  V  A  I  L  K  G  V  Q  C  E  V  Q  L  L  E  S
                                        /NOTE=HVH3-23 SIGPEP_a
                                                                          /NOTE=CDS_b 100       110       120       130       140       150       160       170       180
     GGGGGGGCCT TGTGCAGCCT GGAGGATCCT CTGGGATCAC TCCGGCTGAG CTGCGCAGCC AGTGGTTTCA CGTTCAGTAG TTATGCTATG TCTTGGGTGC
     CCCCCCGGA ACACGTCGGA CCTCCTAGGA GACCCTAGTG AGGCCGACTC GACGCGTCGG TCACCAAAGT GCAAGTCATC AATACGATAC AGAACCCACG
                           a                                                                              b
      G  G  G  L  V  Q  P  G  G  S  L  R  L  S  C  A  A  S  G  F  T  F  S  S  Y  A  M  S  W  V
                                         /NOTE=CDS_b 190       200       210       220       230       240       250       260       270
     GCCAGGCCCC TGGTAAGGGG CTGGAATGGG TGTCAGCTAT TTCCGGCAGC GGGGATCTA AAGGCCGTCG CCGCCTAGAT GATAGCGTG AAGGGACGCT
     CGGTCCGGGG ACCATTCCCC GACCTTACCC ACAGTCGATA AAGGCCGTCG CCCTAGAT CTTATTACGC GATAAATGCG ACTATCGCAC TTCCCTGCGA
      R  Q  A  P  G  K  G  L  E  W  V  S  A  I  S  G  S  G  G  S  T  Y  Y  Y  A  D  S  V  K  G  R
                                          /NOTE=CDS_b 280       290       300       310       320       330       340       350       360
     TCACAATCTC TCGGGACAAC TCCAAAAACA CCCTCTATCT TCAGATGAAT AGTCTACTTA TCGGAGGCGC TGGAGGACAC CGGTGTCGCCA TACTGCGGCA ATGACGCGGT
     AGTGTTAGAG AGCCCTGTTG AGGTTTTTGT GGGAGATAGA AGTCTACTTA TCGAGATGAAT AGCCTCCGCG GACCTCCTGTG GCCACAAATA ATGACGCCGT TACTGCGCCA
      F  T  I  S  R  D  N  S  K  N  T  L  Y  L  Q  M  N  S  L  R  A  E  D  T  A  V  Y  Y  C  A
                                          /NOTE=CDS_b >/note=D4-4_RF3               >/note=JH4
     |----+----|----+----|----+----|----+----|----+----|----+----|----+
          370       380       390       400       410       420       430
     AAACCACAGT GACATACTTT GATTACTGGG GACAGGGGAC CCTCGTCACC GTCTCTTCTG CCTGAAGAGC
     TTTGGTGTCA CTGTATGAAA CTAATGACCC CTGTCCCCTG GGAGCAGTGG CAGAGAAGAC GGACTTCTCG
      K  T  T  V  F  D  Y  W  G  Q  G  T  L  V  T  V  S  S
                                          /NOTE=CDS
```

FIG. 18 hVH3-23(D4-4_RF2)JH4.opt.nucl Text View
Thu, Jan 20, 2011 9:49 AM

Sequence: hVH3-23(D4-4_RF2)JH4.opt Range: 1 to 433    (SEQ ID NO: 148)

>/note=XhoI
                                                                                              >/note=hVH3-23
      |----|----|----|----|----|----|----|----|----|
       10        20        30        40        50        60        70        80        90
CTCGAGCCAC CATGGAGTTC GGGCTGTCCT GGCTTTTTCT TGTGGCCATT CTGAAGGGTG TGCAATGTGA AGTGCAGTTG CTGGAGTCCG
GAGCTCGGTG GTACCTCAAG CCCGACAGGA CCGAAAAAGA ACACCGGTAA GACTTCCCAC ACGTTACACT TCACGTCAAC GACCTCAGGC
                          a                                                a
                      M  E  F  G  L  S  W  L  F  L  V  A  I  L  K  G  V  Q  C  E  V  Q  L  L  E  S
                         /NOTE=HVH3-23 SIGPEP_a                   b          /NOTE=CDS_b 100       110       120       130       140       150       160       170       180
GGGGGGCCT  TGTGCAGCCT GGAGGATCAC TCCGGCTGAG CTGCCAGCC AGTGGTTTCA CGTTCAGTAG TTATGCTATG TCTTGGGTGC
CCCCCCGGA  ACACGTCGGA CCTCCTAGTG AGGCCGACTC GACGGTCGG TCACCAAAGT GCAAGTCATC AATACGATAC AGAACCCACG
 G  G  G   L  V  Q  P  G  G  S    L  R  L  S  C  A  A  S  G  F  T  F  S  S  Y  A  M  S  W  V
                                                        /NOTE=CDS_b 190       200       210       220       230       240       250       260       270
GCCAGGCCCC TGGTAAGGGG CTGGAATGGG TGTCAGCTAT TTCCGGCAGC GGCGGATCTA CTTATTACGC TGATAGCGTG AAGGGACGCT
CGGTCCGGGG ACCATTCCCC GACCTTACCC ACAGTCGATA AAGGCCGTCG CCGCCTAGAT GAATAATGCG ACTATCGCAC TTCCTGCGA
 R  Q  A  P  G  K  G   L  E  W   V  S  A  I   S  G  S   G  G  S  T  Y  Y  A  D  S  V  K  G  R
                                                        /NOTE=CDS_b 280       290       300       310       320       330       340       350       360
TCACAATCTC TCGGGACAAC TCCAAAAACA CCCTCTATCT TCAGATGAAT AGCCTCCGCG CTGAGGACAC CGCTGTGTAT TACTGCGCCA
AGTGTTAGAG AGCCCTGTTG AGGTTTTTGT GGGAGATAGA AGTCTACTTA TCGGAGGGCG GACTCCTGTG GCGACACATA ATGACGCGGT
 F  T  I  S  R  D  N   S  K  N   T  L  Y  L   Q  M  N   S  L  R  A  E  D  T  A  V  Y  Y  C  A
                                                        /NOTE=CDS_b >/note=D4-4_RF2      >/note=JH4                                                    </note=SapI
      |----|
      370       380       390       400       410       420       430
AAGATTATTC AAATTACTAC TTTGATTACT GGGGACAGGG GACCCTGGTC ACCGTCTCTT CTGCCTGAAG AGC
TTCTAATAAG TTTAATGATG AAACTAATGA CCCCTGTCCC CTGGGAGCAG TGGCAGAGAA GACGGACTTC TCG
 K  D  Y  S  N  Y  Y   F  D  Y  W  G  Q  G   T  L  V  T  V  S  S
                         /NOTE=CDS_b                            c

FIG. 19

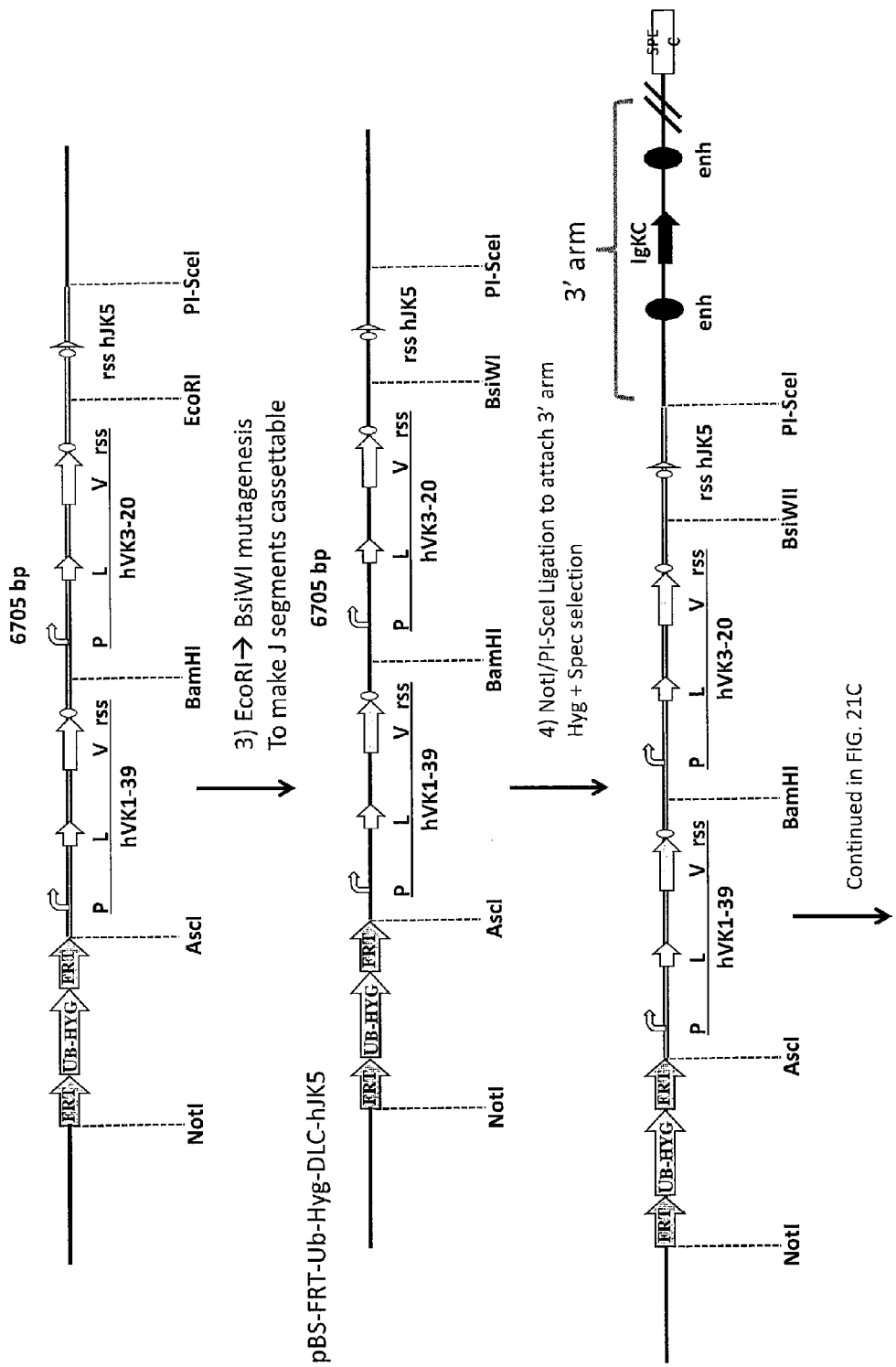

DLC-1J
SEQ ID NO:82

```
GCACCACTTCGTCGCAGCGCAGGCTTTGGTCTCCCTGTCCGTGCGGCCACGCCCACCGAGTTTACGCACCAGCACCACCGAGGTCTGGTTACCG
AAGTTCCTATTCCGAAGTTCCTAGGAAGTAGGAACTTCGCGCGTCTGGCCTCCGAGGCCTCCGATCCTTCCGCCCGACTCTTCCGCCGCCTCCCGCG
GGGCGCCCCCTCCTCACGCGCGAGCGCTGCCACGTCAGCGAAGGGCGCAGCGAGCGTCCGAGCACTTTTAGGACGGGACATTTTAGGACACTGGTTTCTTCCAGAGAGCG
CTCATAAGACTCGGCCTTAGAACCCCAGTATCAGCAGAAGGAGACATTTAGGACACTGGGTGACTCTCCGTTGGGTGACTCGGTGAACGCCGATGATTATATAAGAGCGCCGGGTGTG
GAACAGGCGAGGAAAGTAGTCCCTTCGCCAGCCGGATTTGGGTCGCAGTCGCTCGATCGTCACTTGGTGAGTAGTCTGGGTCCCGCGAGCAAGGTTGCCCTGAAC
GCACAGCTAGTTCGTGGCCGCGGGCGCTCGGTGGGACGGAAGCGTGTGAGAGACCCGCCAAGGCTGTAGTCTCTGAGGCGGCGTGATGGCCTGTCGTTGAAACAAGGTGG
GGGCTTTCGTGGTGGGGAGCGCAAGAACCAAGCTCTTGAGGCTTCGCTAATGCGGGAAAGCTCTTATTCCGGTGAGATGGCTGGGCAGTGCCAGTGCCATCTGGGACC
CTTCCCTGAAGTTGTCACTGACTGGAACTCGGTTGTCACCGTTCGTCGACTGTCGTCCTGGTATAATGCAGGGTGGGGCCAGTTATGCGGTGCCCGTGCCGGTAGGCTACCTTT
GGGAGCCGCGCAGCCCTTCGTCCGTCGACTGTCGTCCTGGTATAATGCAGGGTGGGGCCACCTCGGTGAGGGAGGAGATAACTCACGCGTCAGTTTC
CCGTCGCAGGACGCAGGTTCGGAGCTAGGCTCTCCGTGAAATGCAGGACGCCTCTGGTGAGGGAGGAGATAACTCACGCGTCAGTTTC
TTTGTCGGTTTTATGTATACCTACCTCTTAAGTAGTCGAAGCTCCGGTTTGAACATTGTGACAATTAATCGGCTATAATCGGTATAATCACGTGAAGTTTTGTT
GCACCTTTTGAAATGTAATCATTTGGGTGAATTAATGCTTCTCAGTGTTTAGACTAGTAATGTCCGCTAAATTGTGACAATTAATCGGCTATAATCATCGGCTATTCGGCTTGAAGTGAGG
AGACGTCGAGCTCTAGATTGGGAACCCGGGTCTTGGAACCCGAACAAGATGATTGAACAGATGCACCGAGGCGTTCCGGTGCCCTGAATGAACTG
CAATCGGCTGCTCTGATGCCGCCGTGTTCCGCTGGCTGGCTGGCCTGGCACGAACAAGATGATTGAACAGATGCACCGAGGCGTTCCGGTGCCCTGAATGAACTG
CAGGACGAGGCAGCGCAGGATCGTGGCGGGACAATCCCTGTCATCTCCAACCTTGTGCCCAGCTGTGTCTTGCTCGAGAAAGTATCATCATGGCTACTCGAGCCGGATCCTGTTGCATGCATGCTGCATACGC
ATTGGGCGAAGTGCCAGGACTACCTGGCCAGCCAATTCGACAGACATCAGGAGAAACATGGCAAGACACTGGGTCTTGTCAGTCCGGATCTCGCCGCTATCAGGGGATCTG
GACGAAGCATCAGGGCATCCGGCCCATTCGACAGATCGAGAAATCGCCGCTTCATCGGCTTATCGGCGGAACCCGTGCCCTCCCAGATCAGTCCCGCTATCCGGATCTGACCATGGCAGTTGG
CTGCCTTGCCCACCGTGATATTGCTGACGAGTTCTTCTGAAGAGCTTGGCGGGGAATGCCGCTGTAAGTGTGGCTACCATCAGCCGCAGTCCAAAATGGAAGCTT
TATCCGCCTTCATCATTTTGTTAAGAAGGTGAAGGTGACAGAATCCGGTACCACATTTTGAATGAAGGATTGGAGCTACGGGTGGGTGGGATTAGAATAA
ATGCCTGCTCTTCCCACCTACTGAAGCTCTTTACTATTGCTTTATGATAAAATGTTTCATGATGTTTTCTTCATTCTCATTCCTTGTTGGTTGCCAGTTGTTGGATTAGGGCCA
GCTCATTCCTCCCCATCATGATGATCTATAGATTTCCCAGCCAAGAAGTTCCTATTCCAGCCAAGATCAGACTTCTATTCCTAGAAAGTATAGGAACTTCCTAGGTTCACCGGTGGCGCCC
TCAGAATGCCTCGACCTGCAGCCCCCTAGAGAAGAAGTACCGATACCGGAGAACGAGATCAGACCTATTCCAGCAAGATCAGCTACACACCTCCGTCCCCGTCCCTGTCCACATACACCTCCGTCCCAGGGAAGTAAGGGCA
GAGAGCAAAGAGAGATTTCCACCTAAGAAGGGAGGAGTATGTATACACCTCCGTCCCTGTCCCACTTCCGAGAGATGCTCATTCC
GTCTCAGTATTTTCCACCTAAGAAGGGAGGAGTATGTATACACCTCCGTCCCTGTCCCACTTCCGAGAGATGCTCATTCC
AGTTGCTGATAGGCCATGTGTACAGGCAGGGCTGCCTTCTCCAGTTCAGATAGAAGAAAGATATGGCCATGGGGTCAGCAGAAGT
ACAGCAAAGGGAAAAGGAGCAAGTGACAAGAGTAGCAAAGGAGTGACAAATATTCACCCCCACACACAACACACGAAATTGTATTGCAATCCAG
AACTGCTTCTCTGAACCTAAATCTTAGCAAGCAGTTTACCAGTAACTGCCCTTGAAATTCAGCCCTCTGAAATTCACCAGGAGCAGGGGGTTGTCTACAGGC
```

FIG. 22A

DLC-1J

SEQ ID NO:82 continued

```
TATACCACAGAGCAGTCTGCCCACCCTTAGTGATGCATGAGTAATGCTCCCTGGACTCCCCAGTTCTAGTCTTCTCATGTCAGTAGTTGATTCCACT
TCCCTGCTGCACAACCAGCTGGGATGCCTGGGCAGGAGATGGAGACTCTCTTTCCCTGAGTGTGGGTTCAAATCTGTTTCCAAGTTTATCCAGCTTCAAAGC
ATTTCTCCGTGTACATGAGCCGGTGCCTTGACAGGAGATGGAGACTCTCTTCCCTGAGTGTGAGGCAGGAGCCAGGCGTCTGAGTCAGGATGATGTCC
CTACTCACTGCTAAAGACAAGTGCTTTGATGTGCAGGCAGGAAATGCACCTGAGTGGTCGCCACCCTGAACACTCACAGAAACATTATGGTGGAAAAG
TGGCCTTTCCCCAGGGCCTCTCCCTCCATTGCTTCTCTTCCCTTGGACAATTGATGTGGACATTAGACATTAACAAGAGTTTGACCCAGAGTTTCAAGTTTATCC
CAGATCAGAGCATTAGGCAAGTGCATTGCATTACCTTGGCTCATTACCTTGGACCATGCTAGACATTAGACAGATGTTTTTGAAGTAAACAGAATTGAATACTGATGAACCTATGG
TGATTCAGGCTTCAACAGCTGGAGGAAGAAACAGAACAGATGTTTTGAAGTAAACAGATTAGCATTACAAGCATGAAGATGGACTGCTGCCATTGAGACCCTGGGTATTACAGAGCCT
GAAATAATACCCAAGGGCAGAAAAATGGGCAGAATAATACTTTGGACAGCGCCTGAGTGTTATACAGCCATCATTATCGTGCATCGACATGGAATGCTTGTAAATATACTG
ATAGCTCTGGATAATGGAAGATCTATGAGTTAAGGTCACTACAAATATTTGGACGTGTATTACATCCCCAATACAAACTCTAAAATATATATTATTATCTCCACATGTCCCTAAGAGATG
GTAATTACAAATGTTAAGGTCACTACAAATATTTGGACGTGTATTACATCCCCAATACAAACTCTAAAATATATATTATTATCTCCACATGTCCCTAAGA
GTGACAATCACAGAGGTGTTGTTACTATAGCAAAAGGATTGTTACTCCCACATCCCTTAAGTAACTTGAAGGCCTGATAGACCTAGGTTTGTATTAA
CTTCATTAGACATTCCCTACGAATGGTTATACTCTCGTATATCCTGTGAGTTACTAAGATGAGCCAGCCTGCTGCAGCCCTGCAGCTCTGTGCTGATTGCAT
AGTTTGACTTTTTCCTTCAAAATATCTCTTCCTCAAAATATCTCTTGCTGAGTTACTAAGATGAGCCAGCCTGCTGCAGCCCTGCAGCTCTGTGCTGATTGCAT
TGGGACCTGGGACATTGCCCCTGCCCTGAGACATTTGCCCCTGCCCTGAGTCTGCAGGAGTCAGTCTGCAGGAGAACACTAGGAATTTACTGCCACAGTGCCCTCAGTCAGAAGTACTCAGTGACATGAGG
GTCCAGAGACACAGCCCCCTGCCCCTGCCCTGGGGCTCCTGGGGGCTCCTCGGGGCTCCTCTGATAACATGATTAATAGTAACAGATAATTTGTTTTATGTTTCCAATCTCAGGTGCCAGATGTGACATCCAGATGAC
AACTTCAGGAAGTTCTCCATCCTCCCTGTCTGCAGCATCTGTAGGAGACAGAGTCACCATCACTTGCCGGGCAAGTCAGAGCATTAGCA
CCAGTCTCCATCCTCCCTGTCTGCAGCATCTGTAGGAGACAGAGTCACCATCACTTGCCGGGCAAGTCAGAGCATTAGCA
GCTATTTAAATTGGTATCAGCAGAAACCAGGGAAAGCCCCTAAGCTCCTGATCTCCTGATCTGCATCCAGTTTGCAAAGT
GGGGTCCCATCAAGGTTCAGTGGCAGTGGATCTGGGACAGATTTCACTCTCACCATCAGCAGTCTGCAACCTGAAGA
TTTTGCAACTTACTGTCAACAGAGTTACAGTAGTACCCCCTCC CACAGTGTTACAAGTCATAACATAACTCCAAGGAAGCAGATG
TGTGAGGACGAGCCACCCAGATGCTCCTCTGAGATGCTCCTCTGAGATGCAGCATTTCAAACTCAGTTGGAGACTTT
TGTAGAGGGACCAGGAGGCTCCTGCAACTCTAAGCCTCTTTTGCCCGATCCCGATCAGGAAATAGCAACCGAGTGACTATTAAAGCAT
CCCCTCTGTGGAGAAAAGACTATGGAGATGTTTTGACCTTGCCACTGCAACAGCTTGCTTGACCTGAGAACAAATCAGTCTGATGTCTGGGGTCTACCATGACCACCCTTGA
GATGAACTTATGCCATGTTTTGGATGCCATGTTTTCCATACACCTTGTAGAGATGGAGTGTGTACCCCATCTGTTATCCAAATGACTCAGAACTGCTTCTTACTGCCAAATGACACCTCACGGCAACTGAAGAGTGTACA
GGGACACATGATGGATTTCCATACACCTTGTAGAGATGGAGTGTGTACCCCATCTGTTATCCAAATGACTCAGAACTGCTTCTTACTGCCAAATGACACCTCACGGCAACTGAAGAGTGTACA
TCAGGCAACCTGCTAGTAGAGTGAGTGAGTGAAGAAGAAGTTGGGCAAGCCAGTTGGGCAAGTTGCCACCACCAGGCCTGCCACTGCAGAGCTGCCACTGTGCCAAATCCAAAATCAGTGTTTCCAATC
AGGTTGAAAAACACTGAGTTGAGTGAGATGTTCTTGGGGGTGTTGCAGTTTGGGGTGTTGCAGTTGGCCAGTTGGCCAGGAGAAGAAGTTGGGCAAGCCAGTTGGGCAAGTTGCCACCACCAGGCCTGCCACTGCAGAGCTGCCACTGTGCCAAATCCAAAATCAGTGTTTCCAATC
ATTTTTTCCTTTTATAGTGATGTTCTTGCACAGATCAAGAAATATCAGGTTGTTTAATTTCCTTCTGCTGGTAGGAGGGTCATCATCGATTCCTCATTAGGGT
CCCTGGGTGCCTTCTATGGGTTCTACAGACATGTCAATTTCTACAGTACTTTGACCTGCCTTCTAGAACTGGAACAGATCTAGAAGGACTGAAGGACTGGATCAAGCAACAATGCC
GGATGACGTTATCAGACATGTCAATTTCTACAGTACTTTGACCTGCCTTCTAGAACTGGAACAGATCTAGAAGGACTGAAGGACTGGATCAAGCAACAATGCC
AATGGGTGCCCAAAGAGCTAGTAGTCTCAGAAACAGGGAGAGAACAGAAGACTCAGCCCCCTCCACTAACTCAGCCACCTAACTCAGCCCCTCCACTAACTCAGCCACCTGTGATGAGTGAGTAGGGATGCC
```

FIG. 22B

DLC-1J

SEQ ID NO:82 continued

```
TGAGATCCTGGGGTGGATGGCGAGGTGGGGCACTGATCTGTCAATCTGTCTTTTCTTCAAGGATCAGGCAGCAGAGACCCAGAAGCTTCATGTCTTTGT
AAGGCTCTTCCAAGCCAACACAGATAATTTGACAAAACACTGTATCTGCATCCAGAGACCTCACCCTGTCACACTGAAGTGGTTGTTCATCCTACT
AGGGTAAACTATACCAGCTATCACTACCCTGAGGATTTGGAGCACAGCTTCTGGAGTCTCTGCAGTTGTGAAAGTCCTCACACCCACAGTGCTGAGGT
TGTCTTTAGGGAAATGTTACTCTTTTAATTTCTGCAAAGAATGAGAGACAGCTTCTGGACCCTCAGGAAAGATCACTAACAAGTAATACAAGTATATCCGAAGA
TAAAGTTGTAATAGACTCTTCCTTTCAACAGACTTGTACCAAAACATTCTGTGGCTCAATCTAGGTGAGCATTTAGGGAGCTGACTGGAGCAGAACCACA
GCCTTCTATTTGTTTCTTCTAACAGACTTGTACCAAAACATTCTGTGGCTCAATCTAGGTGAGCATTTAGGGAGCTGACTGGAGCAGAATGTCTGCC
GCAGGGGAGAAGTTCTACCCTCAGACTGAGCCAACGGCCCTTTCTGCCTGATCACCTGGCATGGCCTGCTGAGACCCAGAAGGGGAGCAGATTGT
CTCTGCAGTCGCAAGCTGCACACCCGCCACCCAGCTGCTCTTTGCATGTCCCTCCCAGCTGCCCCTGCAGTCCAGAGCCCATATCAATGCTGGGTCAGAGCT
CTGGAGAAGACTGCTCAGTTGGACCCAGAGAGGAACCATGGAAACCCTCTCAAGTCCCTGTTACCTGCGTCAGCAACTCTGCAGCTCCTTCCTTCTGGCTACTCTGGCTCCCAGGTGAGGGAAC
ATGGGATGGTTTGCATGTCAGTGAAGACAATGGGTTTGATTTAGATTACATGGGTGACTTTCGTTTTATTCCAATCTCAGATACCACCGA|GAAATTG
AATTCTGGCTCTTCTGGGAAGACAATGGGTTTGATTTAGATTACATGGGTGACTTTCGTTTTATTCCAATCTCAGATACCACCGA
TGTTTGACGCAGTCTCCAGGCACCCTGTCTTTTGTCTCCAGGGAAAAGAGCCACCCTCTCCTCCTGCAGGGCCACTGGTGCAGT
GTTAGCAGCAGCTACTTAGCCTGGTACCAGCAGAAACCTGGCCAGGCTCCCAGGCTCCCTCATTCTATGGTGCATCCAG
CAGGGGCCACTGGCCATCCCAGACAGCAGTTCAGTGGCAGCAGTTCAGCAGTATGGTAGCTCACCTCC|CACAGTGATTCAGCTTGAACATCTCTCCTCTGCTTGGC
AGCCTGAAGATTTTGCAGTGTATTACTGTCAGCAGTATGGTAGCTCACCTCC
GCAAGACCTTCATTGTTTACTAGATTATACCAGCTGCTTCCTTTACAGATAGCTGCTGCAATGACAACTCAATTTTAGCATCTCTCCTCTGCTTGGGC
ATTTTTGGGGATCTTAAAAAGTAATCCTTTGATATATTTTGACTCTGAATTCCCTGATTCCTCAGACCAAGATGGACAGCCAGGTTAAGCACAG
TTTCACAGTAATGGCCACTGCAGTCAGATTTACATCAGTGGATGTCAGTAAAGTCCAACCAGACCCATAAGGCACAACAATAGCAACAAATAATCA
AAATTGGAAGAGAATAAAGCTGTCAATAAAGTCACTGAGAATTAATTCACTGTAAATTCATTTCTGCATAATAAATACTAAAATCAATACTAAAATTGA
CATGAGAAAATAAAAACAAACAACACACCATTTACAAAGAACAATCATTAGAGAATATCAATAATTCAGTTCAAAATTCATACACTGACGTCTCAAGAAAATGCTAAAAATTA
AAAAATAAAATAAGAAAATCAAATCCTAAGTAAATAGAATCTAAAAATCTAAATATTAAAGACTCAATTTAAATTAAGAAGCTAATCTAAAATATTATATGGAATGTCAAGGATGCTAGAATAGCCA
TACATATAAGAAACCTGAAGAAAACACCAAATGAGAACTTCCAGTGCCTGAATACTGTGAATAAGCTGAATATGTGGGTGGCAGTATGGTGATGGCTGAGATCAGAAGTTT
AAAAAAATTTGCAAACGTGCTTATTTTGGAAATAATCACTACGCAGATAGCCAAACCCTCTTAAGACAACAGCCAAGCGCTAGCCAGTTAAGTGAGGCATCTCAAT
TACCAGATTCTTTCAAAAGTCAGATGAGTAAGGATAGAATTAACAGCGAAAAGAGATTTTGTTAAGGGGAAAGATTTTTGTTAAGGGGAAAGATTTTGTCTTCTGAAATTTGGGTCTGATGGCTGAGGCATCTCAAT
TGCAAGATTTTCTCTGCATCGGTCAGTTGCTCAGTTAGTGACTGGAGATTAAAAC|GTAAGTAATTTTCACTATTGTCTTCTGAAATTTGGGTCTGATGGCTGAGCTGTTAGTACTGT
TTTAGAGGCTTAAATAGGAGTTTTGCTAAGATTGGTAAATGAGGCATTAAAGATTTGCCATGGTTGCAAAAAGGAAAGGTAACTAAAGGAACTGGAAAATGGAATGAAGATAAT
TGGAGAAAAAAAGATTAAAATTGCTCTAAACTGAATGACACAAAGTAACTAAAAAGGAACCCTGTATTTCTTAAGGAGCAAAA
GTAAATTTATTTGTTCACTCTGCCAAATATTGTATTGGTTGTTGCTGATTATGCATGATACGAGAAAATACATTTTTAGTCTTTCT
```

V<sub>K</sub>3-20

DLC-1J
SEQ ID NO:82 continued

CCCTTTTGTTTGATAAATTATTTTGTCAGACAACAATAAAAATCAATAGCACGCCCTAAGATCTAGATGCATGCTCGAGTGCCATTTCATTTACCTCTT
TCTCCGCACCCGACATAGATAAGCTTATCGATATCCGTCGACCTCGAGGGGGGGCCCGGTACCC*CGTGGCATACAGTGTCAGATTTTCTGTTTATCAAG*
*CTAGTGAGATTAGGGGCAAAAA*

Sequences of Vk1-39, Vk3-20, and Jk5 are in large font and boxed
Mouse sequences italicized
Human sequences in regular font
Restriction enzyme sites in bold
Neo Cassette sequences underlined
FRT sites double underlined

FIG. 22D

DLC-5J
SEQ ID NO:83

```
GCACCACTTCGTCGCCAGCCGCCAGGCTTTGGTCTCCCTTGTCCGTGGGCCGCACGCCCACCAGCACACCGAGTTCGGTGGTACCG
AAGTTCCTATTCCGAAGTTCCTATTCTCTAGAAAGTATAGGAACTTCTCGCGCGTCTGAGGCCTCCGCCGGGTTTTGGCGCCTCCCGCG
GGCGCCCCCTCCTCACGGCGAGCCGCCCACGTAGAACCCCAGTATCAGCAGAAGGACATTTAGGACGGACTTGGTGACTCCAGAGCG
CTCATAAGACTCGGCTTGAGAACGTCCCTTCTCGGCGATTCTGGGAGGATCTCCGGTTCTTGTTGTGAGAGACCCGCCAAGTTGGGG
GAACAGGCGAGGAAAAGTAGTCCCAGCCGGGCCCGGGGCTCGGTGGACGAAGCCAGCAAAATGGCGGCGTTCCCGAGTCTGGAAGGG
GCACAGCTAGTTCGTGGCCGCCGGGCCTCGGTGGGACGAAGCCAGCAAATGGCGGCGTTCCCGAGTCTGGAAGGGGGTCGTTGGAGGG
TGGGGGGGGCGGCGAGCCAGAACCCAAGGTCTTGAGGCCTGTTCCGAGTCGTTGGCCCGAGTCGTGTGAAGATGGCGGGGGTCCGGTACC
GGGCATGGTGGCAAGTTTGTCACTGACGTGTCCCCGCGCGCTCACCGTTCGCCCGCCCTCGTTGAGACGCCCCTAGCGGGAGGACCCTGT
CCGTCGCAGGACGCAGGTTTCGGAACGCTAGCCAGATGGTCGTCCTATAAATAATGCGCCTATTAATTGGCATGCCTGGGGGGTCACCGA
ACGACTTTTGAATGTATCATGGGAACCCGGCTCTTAAGAAGTAGCTGAAAATTTTCCAGTGTTGACAGCTAGTGAAATCGGCATAGTATATGGCCATATGGCTATATCGCCTATTCGACCTGTCCCCGGGCTGGCGGAATCTGG
CAATCGGCTCTGATTCCGCCGTGTTCCGGCTGTGCCGTAGCCAGTTCGGCGCACGAGGCGCCTATCGTGGCCACGACGGGATCTCCCATGTCATGACTTCACTGAAGCGGCGGACTGGCTGCT
CAGGACGAGGCAGCGCGCTATCGTGCCAGGATCTCCGTCATCCACCAAGCGAAACATCGAGCGAGGCAAGCGTACTGCCCAGGCCATGGCCGCGAGGATCTCGTCGTGACCATGCGATGC
ATTGGGGAAGTCAATCGCCAGTTCCTGATTGGCCCATTCGGGCAATCGCGCCATTCGGCAGGCTCACTGTTTCGGGATTCATGCCGACTGTGCCCGGGCCTGTGGCGACCGCTATCAGGACACATAGCGTTGG
TTGATCGGCTACCTGCCATTCAGGGCTCTCGGCCAACATGAAATGGCCGCTTTTCTGGATTCATGCGACTGTGTGCCGCCTCCCGATTCGCCAGCGCATCGCCTTC
CTGCTTGCCGAATATCATGGTGAAATATGGTCTGATCTGCGCATTGAAGAGCTTCCATCATTGGAAGCGTAGCGGGGTGGGATTAGATAA
TATCCCGTGATATTGCTGACGAGTTCTTCTGAAGATCCGCTCTGAAGTCTGCAGAATTCTGATGATCTATTAATAGATGTCCACTAAAATGGAAAGTTTT
TCCTGTGCATCACTTTGTTACGAAGAGGCTCTTTACTGAAGCCGTTCATGTTATGAAGTTTATAGATATCTGGTACACTAGTGGATAGAAGCAAACAATTAACATACGTTGTT
TCGAATGTCAGATGTTGCCAATGGCCATGTGTACAGGCAGGGGCTGCCTTTCAGCCTAACACTTCATTCTCAGTATTGTTTTGCCAAGTTCTAATTCA
TCAGACCTCGACCTGCAGCCCCTGAGAGGTTCTTCTGAAGATCCGAAGTTCCTATTCTCTAGAAAGTATAGGAACTTCACCGGTTTCACCGGTGGCGCCC
GAGAGAAGAGAACATTCCAAGCCGATACCGAAAAGTCCTCAGCGAGAAGTACCACAGAGAGATGAATGGAGATCAAGCCCACGTGGAAACATGGGAAAAT
GTCTCAGTATTTCACCTAAGAAGGAGGAGATGGGTATGTATACACCTCCCTGTCCTGCACTGATTCAGGGCTTTTCCAGAGGATGCTCATTCC
AGGTGCTGTGATAGGCCATGTGTACAGGCAGGGCTGCCTTTCAGCTTCAGATAGAAAGATATATGGGGGGTCAGCGAAGT
ACAGCAAGGGAAAGGAAAGGGTAGCAAGATGACAAGAGTGACAACTATAATTCACCCCCCACACACAGTACACACACACGAATTGTGTATTGCAAT
```

FIG. 24A

DLC-5J
SEQ ID NO:83 continued

```
CCAGAACTGCTTCTCTCTGAACCTAAATCTTAGCAAGCAGTTACCAGTAACTGCCCTGAAATTCAGGCCCCTGAGCCCCTGTGTAC
AGGCTATACCACAGACAGTCTGCCACAACCAGGCTGGGATGCCTGGGACAGAGCCAGACATGAGTAATGCTCCCCAGTTCTATCCATGTCTTCTCATGTCGATGTAGTTGATTC
CACTTCCCTTGCTGCACAAGCAGGCTGGGATGCCTGGGACAGAGCCAGACATGTGAGTATAGGGGTTCAAATCTGTTTCCAAGTTTTATCCAGCTTCA
AAGCATTTCTCCGTGTACATGAGCGGTGGCTTGCTTCCTGGATGTGCAGGGCGAAATGCACTGAGTGGTGCGCACCCTCACAGGAGGCAGGCGTCGAGTCAGGATGAT
GTCCCTACTCACTGCTAAAGAGAAAATGGCTTTGATGGTGCAGGGCAGAAATGCCATGATTTTTGAGACAATGATGTGGGTTCTAGATTGACCAGAGTTTCAAGTTT
GACCTGGCCTTTCCCCAGGCCTTCAACAGCTGCAAGTTGCATTACCTTGGCCCTTCTCCTTTTCCTTTGAACACCTGGGGTTCTAGATTGACCCAGAGTTTCAAGTTT
AAAGCAGATCAGAGCATTAGGACAAGTTGCATTACCTTGGCCTTCTCCTTTTCCTTTGAAGACAATTGATGTGGGGTTCTAGATTGACCAGAGTTTCAAGTTT
ATCCTGATTCAGGCTTCAACAGCTGGAGAGAAACAGAGATGTTTTTGAAGTAAACAGTAAACAGTAAACCAAGAGAGTCTCTACCTCATGACCTT
ATGGGAAATAATACCCAAGGGCAGAAAAATGGCAGAAGGAGCCCAAAACCAAGAGAAGCAGACGACATCAGCAGAAGCAGTCAGATTGCTGCCCATTGAGACCCTGGTATTACAGAG
ACCTATAGCTCTGATAATGCTTAAGTCACTACAAATATCTTGGAGTGTTATTAAAGTCTTCACACATATCGCCACATCCCCTTTAAGTAACTTAACTATAGAACCACCCTCT
AAGACTTCATTAGACATTCCCTACGAATGTTATATCTCTGTCAAAATATCTCTGTCAGTTACTACGACGGCTCTAGAATGAGCCAGGCTACTAAGATGAGAACCTGTGCTCAGTCTATCTGTCAGCATCTATCGACCCTGCTGCGCTGGTCT
TTAAAGTTGACTTTTTCCTTCACACAGACATTCCCTGGGACATTCCCCCCCTGCCCCTGGGGACATTGCCCCTGTCAGTTACTACAAGATGAGCCGGGCTACTAAGATGAGAACCTGTGCTCAGTCTAGAATGAGCCAGCCTGATTGATTT
GACCTGGGACACAGCCTCAGCTCCTCGGGACTTCTCAGAGACACAGCCTCTCAGCTCCTCCGGGGACTTCTCAGAGACACAGCCTCCTCAGCTCCTCCGGGGACTTCTCAGAGACACACACCTGTGTTCCAATCTGTTCCAATCTCCAGTGCCAGATGTGACATCCAGAT
CTGGAACTTCAGGGAAGTTCTGATAACATGATTAATAGTAAGAATATTGTTTTATGTTTTCCAATCTCCAGTGCCAGATGTCGCCGGGCAAGTCAGAGCATTA
GACCCAGTCTCCATCCTCCCTGTCTGCATCTGTAGGAGACAGAGTCACCACTTGCCGGGCAAGTCAGAGCATTA
GCAGCTATTTAAATTGGTATCAGCAGAAACCAGGGAAAGCCCCTAAGCTCCTGATCTATGCTGCATCCAGTTTGCAA
AGTGGGGTCCCATCAAGGTTCAGTGGCAGTGGATCTGGGACAGTGGCAGTGGATCTGGGACAGTGGATCTGGGACAGAGTTCACTCTCACCATCAGCAGTCTGCAACCTGA
AGATTTTGCAACTTACTACTGTCAACAGAGTTACAGTACCCCTCCCACAGTGTACAAGTCATAACATAAACCTCCAAGGAAGCA
GATGTGTGAGGACGAGCACCCCAGATGCTCCTCCGTGCCTCATCTGCTGAGAGCATTTCTCAAACTCAGTGAGCATTTGAAAGTCATTGGGAGA
CTTTTGTAGAGGGAGGGGACCAGGGAGGCTCCTCTGAACTCTAAGCCTCTTTTGCCCGGATCCGATCAGGAAAATAGCAACCGAGTGACTATTAAA
GGATCCCCTCTGTGAGAAAAGGACTATGGCAACAGCTTGCCACCTATAAGACAACAGCCGATCAGGAAAATAGCAACCGAGTGACTATTAAA
TTCGAGATGAACTTATGCCATGTTTTTGGATGCCCACTGAGACTTGTTTACTGCCCAAGGAAAGTCTTTATGAACAGCTGACTCAGGAACAGCTGAACAGCTGAACGACTCACCGCACTGAAGAGTG
TCATGGGACATGATGATTTTCCATACATCGTTGTTATCATTAATACCTTGTTATCCAAGCCAATGGACAATTAAACACTGCCACTGTTCCTGATAGAACCTCGATGAAAACACTGCCACTGAAGAGTG
GTGCAGGTTGAAAAACACTGAGTTGAGTAGTATGTGAGTTCTCTTGGGGGTTCTGCATGTTTCAGTTAGGCCCAAGGCCAGCCAGTGTAAAATCCCAAACTCAGTGTTCC
AATCATTTTTTCCTTTATAGTACATGTCGTTTCTCTTGGGGTTCTGCATGTTTCAGTTAGGCCCAAGGCCAGCCAGTGTAAAATCCCAAACTCAGTGTTCC
AATCATTTTTTCCTTTATAGTACATGTCGTTTCAGATGACAGCCAGACAAAGATCAAGAATCAAGAAATATCCTTCTCCTTCTGTGTGAAGGTCATCGATTCGATCGATTCATTGATGAAT
GATCCCCCTGGGCCTTCTATGGGTTCCACAGATCAAGAAATATCCTTCTCCTTCTGTGTGAAGGTCATCGATTCCATTA
```

FIG. 24B

DLC-5J
SEQ ID NO:83 continued

FIG. 24C

DLC-5J
SEQ ID NO:83 continued

```
CATTTTCTTTGAAGAGCAAGATTCAGTCATTGGGTGAGAATAACTTGTCTAAGTAATAGCTTCAGAAATGTCCTGGGAACATAACATGTT
CTGGACAGAGCCTTGGTCAGTCAATTGTGTGAGATAGGAGTTTTGTATAGGAGGAAGTTAAGAGAACCATTGTGTGTACACTTTTGGCCAGG
GGACCAAGCTGGAGATCAAACGTAAGTACTTTTTTCCACTGTTCTTCACTGTTGCTAATTAGTTTACTTTGTGTTCCTTTGTGTGGAT
TTTCATTAGTCGGATGCCAGGGATCTAAATCAAACTTCATTCCCAGGTTAGGTACAGAGAGGAGGGGAAATTGTTCCACAGGAAGCTAGCTTGTGCTA
ATTTTTAAGATTTCTAAATCAAATAACTTCATTGGGGAAGAGAGGCTTGCTGAGCTTTCAGGGAGGTTTTTGTAAAGGGAAAAGTTAAGACGAA
TCACTGTGATTCACTTTTCGCAGCCCCTGGGACCCAAAGTGGATATCAAACGTAAGTACATCTGTCTCAATTATTCGTGAGATTTAGT
GCCATTGTATCATTTGTGCAAGTTTGTTGAATAAACCTGGTGACCCAGAAGTAAATAGCAGGACACCAGAAATGAACTTAAA
AAGCTGAGCAAATAGACGAATCATTGGGTTTGAGAGAGAATAGGATTCATGGGGAAATGGGAAGGGAAGCTAGATTTTCCTGAACAAGC
AGCCTATCTCATATGATTGGCTTCAAGAGAGGTTTTGTGAGGGAAAGGTGAGATCCCTCACTGTCGCTCACTTTCGGCGGAGGGA
CCAAGGTGGAGATCAAACGTAAGTGCACTTCTTCCTAATGCTTTTCTTAAGGTTTTTAAATTTGGAGCGTTTTTAAATTTAGTTCATCTTAAGGAACAGCCAAGCGCTAG
CTCAGGTCAATTCCAAAGAGTACCAGATTCTTCAAAAGTCAGATGAGTAAGGATAGAAAATTAGTTCATCTTAAGGAACAGCCAAGCGCTAG
CCAGTTAAGTGAGGCATCCCAATTGCAAGATTTCTCTGCATCGGTCAGGTAGTGATATTAACAGCGAAAAGAGATTTTTGTTAAGGGAAAGT
AATTAAGTTAACACTGTGGATCACCTTCGGCCAAGGGACACGACTGGAGATTAAACGTAAGTAATTTTCACTATTGTCTTCTG
AAATTTGGGTCTGATGGCCAGTCCAGTCTTCACGATTCTTAGAGAGCTTAAATGGAATTTGGAGAGAAAAGATTAAATTGCTCTAAACTGAATGACACAAAGTAAACAAAGTGTAAC
TGCAAAGTTAAACTCAGCTTCAGTCTATTCTAAGGACAAAGTAAATTTATTTTGTTCACTCTTGCCAATATTGTATTGGTTGTTGCTGATTATGCATGA
TACAGAAAAGTGGAAAAATACATTTTAGTCTTCTCCCTTTGTTTGATAAATTATTTTGTCAGACAACATAGAATCAATAGCACGCCCTA
AGATCTAGATGCATGCTGAGTGCCATTCATTACTGTCAGATTTCGTTTATCAAGCTAGTGAGATTAGGGGCAAAA
CCGGTACCACGTGGCATACAGTGTCAGATTTCGTTTATCAAGCTAGTGAGATTAGGGGCAAAA
```

Sequences of Vk1-39, Vk3-20, Jk1, Jk2 Jk3, Jk4, and Jk5 are in large font and boxed
Mouse sequences italicized
Human sequences in regular font
Restriction enzyme sites in bold
Neo Cassette sequences underlined
FRT sites double underlined

FIG. 24D

Site-directed Mutagenesis Primers for 4 Histidine Substitutions in CDR3s of each VK of DLC-JK1-5 Plasmid

| Primer name | | Sequence | %GC | N | mismatches | Tm |
|---|---|---|---|---|---|---|
| GERMLINE hVK1-39 | | CAACTTACTACTGTCAACAGAGTTACAGTACCCCTCCCACAGTGTTACAAG | | | | |
| hVk1-39 HDLC(Q105H/Q106H/Y108H/P111H) | F | CAACTTACTACTGTCACCATAGTCACAGTACCCATCCCACAGTGTTACAAG | 45 | 51 | 4 | 79 |
| hVk1-39 HDLC(Q105H/Q106H/Y108H/P111H) | R | CTTGTAACACTGTGGGATGGGTACTGTGACTATGGTGACAGTAGTAAGTTG | 45 | 51 | 4 | 79 |
| GERMLINE hVk3-20 | | GCAGTGTATTACTGTCAGCAGTATGGTAGCTCACCTCCCAC | | | | |
| hVk3-20 HDLC(Q105H/Q106H/Y107H/S109H) | F | AGATTTGCAGTGTATTACTGTCACCATCATGGTCACTCCCACAGTGATTCAGCT | 45 | 60 | 5 | 82 |
| hVk3-20 HDLC(Q105H/Q106H/Y107H/S109H) | R | AGCTGAATCACTGTGGGAGTGACCATGATGGTGACAGTAATACACTGCAAATCT | 45 | 60 | 5 | 82 |

| Primer | SEQ ID NO |
|---|---|
| GERMLINE hVK1-39 | 105 |
| hVk1-39 HDLC (Q105H/Q106H/Y108H/P111H) F | 106 |
| hVk1-39 HDLC (Q105H/Q106H/Y108H/P111H) R | 107 |
| GERMLINE hVk3-20 | 108 |
| hVk3-20 (Q105H/Q106H/Y107H/S109H) F | 109 |
| hVk3-20 (Q105H/Q106H/Y107H/S109H) R | 110 |

FIG. 34

Site-Directed Mutagenesis Primers for 3 Histidine Substitutions in CDR3s of each VK of DLC-JK1-5 plasmid

| Primer name | Sequence | %GC | N | mismatches | Tm |
|---|---|---|---|---|---|
| GERMLINE hVK1-39 | CAACTTACTGTCAACAGAGTTACAGTACCCCTCCACAGTGTTACAAG | | | | |
| hVK1-39 HDLC (Q106H/Y108H/P111H) F | ATTTTGCAACTTACTGTCAACATAGTAGTCACAGTGTTAC | 40.7 | 54 | 3 | 73 |
| hVK1-39 HDLC (Q106H/Y108H/P111H) R | GTAACACTGTGGGATGGTACGTACTATGTTGACAGTAGTAAGTTGCAAAAT | 40.7 | 54 | 3 | 73 |
| GERMLINE hVK3-20 | GCAGTGTATTACTGTCAGCAGTATGGTAGCTCACCTCCCAC | | | | |
| hVK3-20 HDLC (Q105H/Q106H/S109H) F | ATTTTGCAGTGTATTACTGTCACCATTATGGTCACTCACCTCCCACAGTGATTCAG | 42.9 | 56 | 4 | 75 |
| hVK3-20 HDLC (Q105H/Q106H/S109H) R | CTGAATCACTGTGGGAGGTGAGTGACCATAATGGTGACGTAATACACTGCAAAAT | 42.9 | 56 | 4 | 75 |

| Primer | SEQ ID NO |
|---|---|
| GERMLINE hVK1-39 | 117 |
| hVK1-39 HDLC (Q106H/Y108H/P111H) F | 118 |
| hVK1-39 HDLC (Q106H/Y108H/P111H) R | 119 |
| GERMLINE hVk3-20 | 120 |
| hVk3-20 (Q105H/Q106H/S109H) F | 121 |
| hVk3-20 HDLC (Q105H/Q106H/S109H) R | 122 |

FIG. 36

|  | FR1 | CDR1 | FR2 | CDR2 |
|---|---|---|---|---|
| IGKV3-20*01 F | EIVLTQSPGTLSLSPGERATLSCRAS | QSVSSSY | LAWYQQKPGQAPRLLIY | GAS |
|  | EIVLTQSPGTLSLSPGERATLSCRAS | QSVSSSY | LAWYQQKPGQAPRLLIY | GAS |

|  | FR3 | CDR3 |  |
|---|---|---|---|
| IGKV3-20*01 F | SRATGIPDRFSGSGSGTDFTLTISRLEPEDFAVYYC | HHYGHSHH H | SEQ ID NO:131 |
|  | SRATGIPDRFSGSGSGTDFTLTISRLEPEDFAVYYC | QQYGSSP | SEQ ID NO:132 |

FIG. 38A

```
              FR1                              CDR1         FR2                CDR2
IGKV1-39*01 F  DIQMTQSPSSLSASVGDRVTITCRAS QSISSY LNWYQQKPGKAPKLLIY AAS
               DIQMTQSPSSLSASVGDRVTITCRAS QSISSY LNWYQQKPGKAPKLLIY AAS

FR3                                     CDR3
IGKV1-39*01 F  SLQSGVPSRFSGSGSGTDFTLTISSLQPEDFATYYC QHSHSTH      SEQ ID NO:133
               SLQSGVPSRFSGSGSGTDFTLTISSLQPEDFATYYC QQSYSTP      SEQ ID NO:134
                                                      H H
                                                        H
```

```
              FR1                              CDR1         FR2                CDR2
IGKV1-39*01 F  DIQMTQSPSSLSASVGDRVTITCRAS QSISSY LNWYQQKPGKAPKLLIY AAS
               DIQMTQSPSSLSASVGDRVTITCRAS QSISSY LNWYQQKPGKAPKLLIY AAS

FR3                                     CDR3
IGKV1-39*01 F  SLQSGVPSRFSGSGSGTDFTLTISSLQPEDFATYYC QHSHSTK      SEQ ID NO:135
               SLQSGVPSRFSGSGSGTDFTLTISSLQPEDFATYYC QQSYSTP      SEQ ID NO:134
                                                      H H
```

FIG. 38B

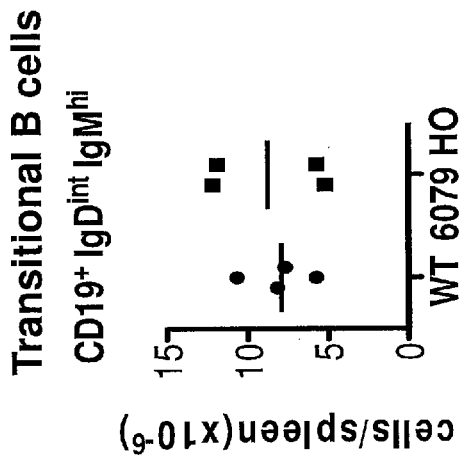
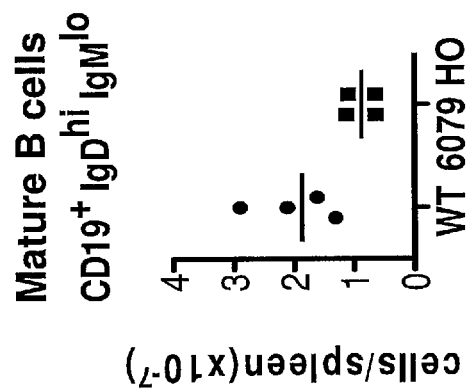
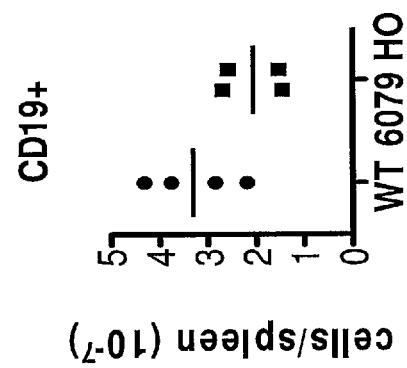
FIG. 53B

NON-HUMAN ANIMALS WITH MODIFED IMMUNOGLOBULIN HEAVY CHAIN SEQUENCES

CROSS-REFERENCE TO RELATED APPLICATIONS

This application is a continuation application of U.S. application Ser. No. 14/185,679, filed on Feb. 20, 2014, and claims the benefit of priority to U.S. Provisional Patent Application No. 61/766,765, filed Feb. 20, 2013, and to U.S. Provisional Patent Application No. 61/879,338, filed Sep. 18, 2013, all of which are hereby incorporated herein by reference in their entireties.

SEQUENCE LISTING

The official copy of the sequence listing is submitted electronically via EFS-Web as an ASCII formatted sequence listing with a file named 451790SEQLIST.TXT, created on Sep. 26, 2014, and having a size of 85 kilobytes, and is filed concurrently with the specification. The sequence listing contained in this ASCII formatted document is part of the specification and is herein incorporated by reference in its entirety.

FIELD OF THE INVENTION

Genetically modified non-human animals, e.g., rodents such as mice and rats, comprising a rearranged human heavy chain variable region nucleic acid sequence (i.e., a rearranged heavy chain VDJ sequence) operably linked to a constant region nucleic acid sequence. In some embodiments, the animals are genetically engineered to have an immunoglobulin locus comprising a rearranged heavy chain variable region (a VDJ sequence) nucleic acid sequence operably linked to an immunoglobulin constant region gene sequence, wherein the VDJ sequence is a human VDJ sequence, and the constant region gene sequence is human or non-human. In some embodiments, the non-human animals containing a genetically modified immunoglobulin locus comprise: (1) a first nucleotide sequence that encodes a rearranged heavy chain variable domain (i.e., where the first nucleotide sequence is a rearranged human immunoglobulin heavy chain variable region nucleotide sequence), wherein the first nucleotide sequence is operably linked to a light chain (e.g., a κ or λ light chain) constant region gene sequence; and (2) a second nucleotide sequence that encodes a human or non-human light chain (e.g., a κ or λ light chain) variable domain (i.e., where the second nucleotide sequence is an unrearranged human immunoglobulin light chain variable nucleotide sequence), wherein the second nucleotide sequence is operably linked to a heavy chain constant region gene sequence. In some embodiments, the non-human animals comprise a genetically modified immunoglobulin heavy chain locus comprising a rearranged human immunoglobulin heavy chain variable region nucleotide sequence, wherein the rearranged heavy chain variable domain comprises a heavy chain Vgene segment ($V_H$) sequence operably linked, via a spacer, to a heavy chain J gene segment ($J_H$) sequence, and wherein the spacer comprises at least one amino acid residue. Genetically modified non-human animals, e.g., rodents such as mice and rats, are provided comprising in their genomes: (i) a rearranged human heavy chain variable region nucleic acid sequence operably linked to a constant region nucleic acid sequence; and (ii) an immunoglobulin light chain locus comprising one or more but less than the wild type number of human light chain variable region gene segments. Genetically modified non-human animals are provided comprising in their genomes: (i) a rearranged human heavy chain variable region nucleic acid sequence operably linked to a constant region nucleic acid sequence; and (ii) an immunoglobulin light chain locus comprising one or more but less than the wild type number of human immunoglobulin light chain variable region gene segments. In some embodiments, at least one of the variable region gene segments encodes one or more histidine residues that is/are not encoded by a corresponding human germline light chain variable region gene segment. Methods of making the genetically modified non-human animals described herein are provided. Methods for producing immunoglobulin light chain (e.g., a κ or λ light chain) variable region sequences that can bind an antigen in the absence of a heavy chain, and/or can be associated with a rearranged heavy chain variable domain and/or exhibit pH-dependent antigen binding characteristics, are provided, which are useful for producing bispecific antibodies.

BACKGROUND

Bispecific antibodies are multifunctional antibodies that comprise antigen-binding sites that can bind two distinct antigenic determinants and have emerged as one of the major therapeutic biologics for treating many diseases, including cancer. While a variety of bispecific antibodies with dual antigen-binding properties have been developed recently, the specificity and affinity of immunoglobulin light chain or heavy chain variable domains in the conventional bispecific antibodies had to be sacrificed to some extent because, in the conventional bispecific antibodies, either only a heavy chain or a light chain variable domain contributes to binding to each antigenic determinant, whereas, in regular antibodies, both light and heavy chain variable regions can contribute to binding to the same antigenic determinant. In addition, in achieving a desirable level of efficacy, therapeutic antibodies, e.g., bispecific therapeutic antibodies, often require high or multiple doses of antibodies due to their limited recyclability in vivo.

Most antigen-binding proteins that target two antigens or epitopes developed so far comprise two antigen-binding arms: (i) a first antigen-binding arm comprising an immunoglobulin heavy-light chain variable domain pair that contributes to binding to a first antigen or epitope; and (ii) a second antigen-binding arm comprising a second heavy-light chain variable domain pair that contributes to binding to a second antigen or epitope. These antigen-binding proteins, though bispecific in the context of the whole antigen-binding protein, are not necessarily bispecific within each antigen-binding arm, limiting the use of the antigen-binding proteins in multi-specific formats, e.g., tri-specific antigen-binding proteins. As disclosed herein, a non-human animal that expresses a universal heavy chain variable domain may be employed as a general tool for making antigen-binding proteins for use in many different formats of antigen-binding proteins.

SUMMARY

There is a need in the art to generate immunoglobulin light chain variable domain sequences in which antigen specificity and affinity results solely or primarily from, and/or resides solely or primarily in, immunoglobulin light chain variable domain diversity. Such sequences would be extremely useful in designing antigen-binding proteins, e.g., bispecific antibodies, in which each variable domain is separately responsible for distinct antigen-specific binding. Various aspects and embodiments described herein are based in part on the surprising discovery that genetically modified non-human animals comprising immunoglobulin heavy chain variable domains encoded by a rearranged heavy chain variable gene sequence (e.g., a rearranged heavy chain VDJ sequence) can meet this need. Non-human animals encoding a rearranged immunoglobulin heavy chain variable domain (i.e., a universal heavy chain variable domain) focus the mechanisms of antibody diversification on unrearranged (i.e., diversifiable) antibody light chain variable domain(s). Non-human animals include, e.g., mammals and, in particular embodiments, rodents (e.g., mice, rats, or hamsters).

Genetically modified non-human animals are provided that, upon stimulation with an antigen of interest, produce antibodies with antigen-binding specificity residing solely or primarily in the antibody light chain variable domains. Light chain antibody variable domain amino acids and corresponding nucleic acid sequences can be identified from antibodies produced by such genetically modified animals, and the sequences can be utilized in recombinant antibodies or other antigen-binding proteins to develop light chain variable domains that bind an antigenic determinant independently (and with sufficient specificity and affinity) from heavy chain variable domains. Moreover, the utility of genetically modified animals comprising a rearranged heavy chain variable domain (i.e., comprising a prearranged heavy chain variable domain gene sequence) can be applied by placing a nucleotide sequence encoding the rearranged heavy chain variable domain in a variety of genomic contexts, e.g., in different immunoglobulin loci. Rearranged heavy chain variable domain gene sequences can be targeted to a heavy chain locus or a light chain locus such that the rearranged heavy chain variable domain sequences can be operably linked to a heavy or light chain constant sequence, either human or non-human. Rearranged heavy chain variable domain gene sequences can be placed anywhere in the genome in operable linkage with human, non-human, or mixed human/non-human immunoglobulin constant region sequences. Furthermore, non-human animals comprising a nucleotide sequence encoding a rearranged heavy chain variable domain can be combined with additional genetic modifications of immunoglobulin loci (e.g., crossbred to animals comprising additional genetic modifications of immunoglobulin loci). For example, the focused diversification imparted by a rearranged heavy chain variable domain gene sequence targeted to a light chain locus can be paired with a light chain variable domain gene sequence inserted into a heavy chain locus, thereby generating animals that fully utilize the timing and diversification of a genomic context of choice (e.g., the diversification mechanisms of the heavy chain locus) to increase diversity of antibody variable gene sequence of choice (e.g., antibody light chain variable gene sequences). In addition, by utilizing mice that have a restricted (limited) light chain variable region gene segment repertoire (e.g., a restricted number of light chain variable gene sequences that comprise one or more but less than the wild type number of human $V_L$ gene segments in combination with the single rearranged heavy chain sequence described above), an immunoglobulin light chain variable domain that can more efficiently pair with an immunoglobulin heavy chain variable domain can be produced.

Thus, genetically modified non-human animals (e.g., rodents such as mice, rats, or hamsters) are provided that comprise an immunoglobulin locus comprising a rearranged human immunoglobulin heavy chain variable region (i.e., a nucleotide sequence that encodes a rearranged heavy chain variable domain; i.e., a rearranged heavy chain VDJ sequence).

In various aspects, the only genomic heavy chain variable domain-encoding nucleic acid sequence expressed by the genetically modified non-human animals is the rearranged heavy chain variable domain. Accordingly, the diversity of antibody heavy chain variable domains produced by the genetically modified non-human animals is extremely restricted.

In some embodiments, genetically modified non-human animals are provided that have in their genome an immunoglobulin locus that has been genetically modified so that its variable region sequences consist essentially of a single rearranged human heavy chain variable region. It is understood that different cells in such genetically modified non-human animals may not always have completely identical sequences in the single rearranged human heavy chain variable region (e.g., due to replication errors, somatic hypermutation, or other mechanisms), but regardless, such genetically modified non-human animals show dramatically restricted diversity of antibody heavy chain variable domains as compared with animals having unrearranged heavy chain variable sequences, and/or animals whose genomes include multiple heavy chain variable region gene segments (e.g., multiple V, D, and/or J segments, particularly if unrearranged).

In various aspects, a genetically modified immunoglobulin heavy chain locus is provided comprising a rearranged human immunoglobulin heavy chain variable region nucleotide sequence (i.e., comprising a nucleotide sequence that encodes a rearranged heavy chain variable domain). In various aspects, the rearranged human immunoglobulin heavy chain variable region nucleotide sequence and the rearranged heavy chain variable domain it encodes are derived from a human V, D, and J gene segment. In various aspects, the rearranged human immunoglobulin heavy chain variable region nucleotide sequence and the rearranged heavy chain variable domain it encodes are derived from a human $V_H$ gene and a human $J_H$ segment. In various aspects, the rearranged human immunoglobulin heavy chain variable region nucleotide sequence is operably linked to a heavy chain constant region region gene sequence. In various aspects, the rearranged human immunoglobulin heavy chain variable region nucleotide sequence is operably linked to a light chain constant region region gene sequence. In various aspects, the genetically modified immunoglobulin locus is present in the germline of a non-human animal. In various aspects, the genetically modified non-human animals comprise the full complement of unrearranged light chain variable gene segments capable of rearranging to form a light chain gene in operable linkage with a light chain constant region gene sequence. In other aspects, the genetically modified non-human animals comprise a plurality but less than a full complement (i.e., less than a wild type number) of unrearranged light chain variable gene segments. In various aspects, the unrearranged light chain variable gene segments are operably linked to a heavy chain constant region gene sequence. In specific aspects, the non-human animal is a rodent, e.g., a mouse, rat, or hamster. In another aspect, a nucleic acid construct is provided comprising a rearranged human immunoglobulin heavy chain variable region (i.e., comprising a nucleotide sequence that encodes a rearranged heavy chain variable domain; i.e., a pre-rearranged heavy chain VDJ sequence) as described herein.

Numerous variations of genetically modified non-human animals with an immunoglobulin locus comprising a rearranged human immunoglobulin heavy chain variable region nucleotide sequence (i.e., with an immunoglobulin locus comprising a nucleotide sequence that encodes a rearranged heavy chain variable domain) are disclosed herein. Each variation has the capability to focus the mechanisms of antibody diversification on immunoglobulin light chain variable region nucleotide sequences.

In various aspects, a nucleotide sequence that encodes a rearranged heavy chain variable domain (i.e., a heavy chain variable domain encoded by a rearranged human immunoglobulin heavy chain variable region nucleotide sequence) is operably linked to a human or non-human heavy chain constant region gene sequence (e.g., a heavy chain constant region gene sequence that encodes an immunoglobulin isotype selected from IgM, IgD, IgA, IgE, IgG, and combinations thereof). For example, genetically modified non-human animals are provided comprising immunoglobulin loci in which: (a) a first nucleotide sequence encodes a rearranged heavy chain variable domain (i.e., where the first nucleotide sequence is a rearranged human immunoglobulin heavy chain variable region nucleotide sequence), wherein the first nucleotide sequence is operably linked to a human or non-human (or mixed human/non-human) heavy chain constant region gene sequence; and (b) a second nucleotide sequence encodes a light chain variable domain (i.e., where the second nucleotide sequence is an unrearranged human immunoglobulin light chain variable nucleotide sequence), wherein the second nucleotide sequence is operably linked to a human or non-human light chain constant region gene sequence.

In another aspect, modified non-human animals are provided in which the animals comprise a rearranged nucleotide sequence that encodes a heavy chain variable domain, wherein the heavy chain variable domain comprises a heavy chain variable ($V_H$) sequence that is operably linked, via a spacer, to a heavy chain J segment ($J_H$) sequence, wherein the spacer encodes at least one amino acid residue.

In another aspect, a non-human animal is provided comprising a genetically modified immunoglobulin locus that comprises a rearranged human immunoglobulin heavy chain variable region nucleotide sequence (i.e., comprise a nucleic acid sequence encoding a rearranged heavy chain variable domain; i.e., a rearranged heavy chain VDJ sequence), wherein the genetically modified immunoglobulin locus is present in the germline of the non-human animal. In some embodiments, the genetically modified immunoglobulin locus is a heavy chain locus. In some embodiments, the genetically modified immunoglobulin locus is a light chain locus In another aspect, genetically modified non-human animals (e.g., rodents such as mice, rats, or hamsters) are provided having a genetically modified immunoglobulin genomic locus a rearranged human immunoglobulin heavy chain variable region nucleotide sequence, wherein the nucleotide sequence is operably linked to a human or non-human light chain (e.g., κ or λ light chain) constant region gene sequence.

In another aspect, a non-human animal comprising a genetically modified immunoglobulin locus is provided comprising: (a) a rearranged human immunoglobulin heavy chain variable region nucleotide sequence operably linked to a light chain constant region gene sequence; and (b) a unrearranged human or non-human light chain (e.g., κ or λ light chain) variable region nucleotide sequence operably linked to a human or non-human heavy chain constant region gene sequence (e.g., a heavy chain constant region gene sequence that encodes an immunoglobulin isotype selected from IgM, IgD, IgA, IgE, IgG, and a combination thereof).

In another aspect, a genetically modified non-human animal is provided with an immunoglobulin locus comprising:
(a) a first allele comprising:
(i) a first nucleotide sequence that encodes a rearranged heavy chain variable domain (i.e., where the first nucleotide sequence is a rearranged human immunoglobulin heavy chain variable region nucleotide sequence) operably linked to a heavy chain constant region gene sequence, and
(ii) a second nucleotide sequence that encodes a light chain variable domain (i.e., where the second nucleotide sequence is an unrearranged human immunoglobulin light chain variable nucleotide sequence) operably linked to a light chain constant region gene sequence; and
(b) a second allele comprising
(i) a third nucleotide sequence that encodes a light chain variable domain (i.e., where the third nucleotide sequence is an unrearranged human immunoglobulin light chain variable nucleotide sequence) operably linked to a heavy chain constant region gene sequence, and
(ii) a fourth nucleotide sequence that encodes the rearranged heavy chain variable domain (i.e., where the fourth nucleotide sequence is a rearranged human immunoglobulin heavy chain variable region nucleotide sequence) operably linked to a light chain constant region gene sequence.

In various aspects, genetically modified non-human animals with unrearranged light chain variable region gene sequences or loci are provided. In some embodiments, the genetically modified non-human animals comprise a wild type number (i.e., all or substantially all) of human immunoglobulin light chain variable region gene segments (i.e., sequences). In other aspects, the non-human animals described herein comprises a limited repertoire of light chain variable gene segments, e.g., (i) one, two or more but less than the wild type number of human $V_L$ gene segments; and (ii) one or more human $J_L$ gene segments, operably linked to a non-human light chain constant region nucleic acid sequence. The heavy chain nucleic acid sequence and/or the light chain segments may be present, e.g., in a transgene or at an endogenous immunoglobulin locus.

In various aspects, genetically modified non-human animals are provided, wherein all immunoglobulin heavy chain variable domains of the animal are derived from the same rearranged variable heavy chain gene sequence, and wherein said variable domains are expressed cognate with a light chain variable domain derived from one of at least one, two, or three or more $V_L$ gene segments and at least one, two, or three or more $J_L$ gene segments. Additionally, genetically modified non-human animals (e.g., rodents, such as mice and rats) are provided comprising in their genomes: (i) an immunoglobulin heavy chain locus that comprises a rearranged human heavy chain variable region nucleic acid sequence operably linked to a human or non-human heavy chain constant region nucleic acid sequence; and (ii) an immunoglobulin light chain locus comprising one or more but less than the wild type number of human immunoglobulin light chain variable region gene segments (e.g., two human $V_\kappa$ gene segments and one or more human $J_\kappa$ gene segments), operably linked to a human or non-human light chain constant region nucleic acid sequence. In some embodiments, the light chain constant region is a rat or a mouse constant region, e.g., a rat or a mouse Cκ constant region.

In another aspect, the genetically modified non-human animals as described herein, upon stimulation with an antigen of interest, express an antigen-binding protein comprising an immunoglobulin heavy chain and a light chain amino acid sequence, wherein the heavy chain amino acid sequence is derived from a genetically modified heavy chain locus comprising a rearranged human heavy chain variable region nucleic acid sequence operably linked to a heavy chain constant region nucleic acid sequence. In certain aspects, the light chain amino acid sequence is derived from a genetically modified immunoglobulin light chain locus comprising one or more but less than the wild type number of human $V_L$ gene segments and (ii) two or more human $J_L$ gene segments, operably linked to a non-human light chain constant region nucleic acid sequence.

Genetically modified non-human animals are provided comprising in their genomes a rearranged human immunoglobulin heavy chain variable region nucleic acid sequence that comprises a heavy chain V gene segment ($V_H$) that is operably linked, via a spacer, to a heavy chain J gene segment ($J_H$) sequence, wherein the spacer encodes at least one amino acid (e.g., 2 amino acids, 3 amino acids, or 4 amino acids) and/or a modified D gene segment. In various embodiments, the rearranged heavy chain variable region nucleic acid sequence is operably linked to a human or non-human heavy chain constant region nucleic acid sequence. In various embodiments, the non-human animals further comprise in their genomes a genetically modified immunoglobulin light chain locus comprising one or more but less than the wild type number of human immunoglobulin light chain variable region gene segments, e.g., two human $V_\kappa$ gene segments and one or more human $J_\kappa$ gene segments, operably linked to a human or non-human light chain constant region nucleic acid sequence.

Methods of making and using the genetically modified non-human animals described herein are also provided. Methods are provided for placing a rearranged human heavy chain variable region nucleic acid sequence in operable linkage with an immunoglobulin heavy or light chain constant region nucleic acid sequence in the genome of a non-human animal.

In another aspect, methods are provided for obtaining an immunoglobulin light chain variable region ($V_L$) amino acid sequence capable of binding an antigen independently from a heavy chain variable region amino acid sequence.

In another aspect, a genetically modified immunoglobulin locus obtainable by any of the methods as described herein is provided.

In various aspects, antigen-binding proteins (e.g., antibodies) produced by or derived from the genetically modified non-human animals described herein are provided. Also provided are methods for making antigen-binding proteins, including multispecific (e.g., bispecific or trispecific) antigen-binding proteins. Also provided are methods for making an effector light chain immunoglobulin variable domains.

In another aspect, a pluripotent cell, induced pluripotent, or totipotent stem cells derived from a non-human animal comprising the various genomic modifications described herein are provided. Cells that comprise a nucleus containing a genetic modification as described herein are also provided, e.g., a modification introduced into a cell by pronuclear injection.

In various aspects, a non-human animal embryo comprising a cell whose genome comprises an immunoglobulin heavy chain locus comprising a rearranged human heavy chain variable region nucleic acid sequence operably linked to a constant region nucleic acid sequence is provided. In certain aspects, the non-human animal embryo further comprises an immunoglobulin light chain locus comprising two or more but less than the wild type number of human immunoglobulin light chain variable region gene segments, operably linked to a light chain constant region nucleic acid sequence.

Also provided are methods for making nucleic acid sequences that encode an immunoglobulin light chain variable region ($V_L$) amino acid sequence capable of binding an antigen or an epitope thereof independently from a heavy chain variable domain, comprising: (a) immunizing a non-human animal with an antigen of interest or an immunogen thereof, wherein the non-human animal comprises in its genome (i) a rearranged human immunoglobulin heavy chain variable region nucleic acid sequence operably linked to a heavy chain constant region nucleic acid sequence, and (ii) an unrearranged human immunoglobulin light chain variable region nucleic acid sequence operably linked to a light chain constant region nucleic acid sequence; (b) allowing the non-human animal to mount an immune response; (c) isolating from the immunized non-human animal a cell comprising a nucleic acid sequence that encodes a light chain variable domain that can bind the antigen; and (d) obtaining from the cell a nucleic acid sequence that encodes the light chain variable domain ($V_L$ domain) that can bind the antigen. In various embodiments, the cell is a lymphocyte, including, but not limited to, natural killer cells, T cells, and B cells. In various embodiments, the method further comprises (c)' fusing the lymphocyte with a cancer cells, e.g., a myeloma cell.

Also provided are methods for making nucleic acid sequences that encode an immunoglobulin light chain variable region ($V_L$) amino acid sequence capable of binding an antigen or an epitope thereof independently from a heavy chain variable domain, comprising: (a) immunizing a non-human animal with an antigen of interest or an immunogen thereof, wherein the non-human animal comprises in its genome (i) a rearranged human immunoglobulin heavy chain variable region nucleic acid sequence operably linked to a heavy chain constant region nucleic acid sequence, and (ii) two or more but less than the wild type number of human immunoglobulin light chain variable region gene segments ($V_L$ and $J_L$) operably linked to a light chain constant region nucleic acid sequence; (c) isolating from the immunized non-human animal a cell comprising a nucleic acid sequence that encodes a light chain variable domain that can bind the antigen; and (d) obtaining from the cell a nucleic acid sequence that encodes the light chain variable domain ($V_L$ domain) that can bind the antigen. In various embodiments, the cell is a lymphocyte, including, but not limited to, natural killer cells, T cells, and B cells. In various embodiments, the method further comprises (c)' fusing the lymphocyte with a cancer cells, e.g., a myeloma cell.

Also provided are methods for making nucleic acid sequences that encode an immunoglobulin light chain variable region ($V_L$) amino acid sequence capable of binding an antigen or an epitope thereof independently from a heavy chain variable domain, comprising: (a) immunizing a non-human animal with an antigen of interest or an immunogen thereof, wherein the non-human animal comprises in its genome: (i) a rearranged human immunoglobulin heavy chain variable region nucleic acid sequence operably linked to a light chain constant region nucleic acid sequence, and (ii) human immunoglobulin light chain variable region gene segments ($V_L$ and $J_L$) operably linked to a heavy chain constant region nucleic acid sequence; (c) isolating from the immunized non-human animal a cell comprising a nucleic acid sequence that encodes a light chain variable domain that can bind the antigen; and (d) obtaining from the cell a nucleic acid sequence that encodes the light chain variable domain ($V_L$ domain) that can bind the antigen. In various embodiments, the cell is a lymphocyte, including, but not limited to, natural killer cells, T cells, and B cells. In various embodiments, the method further comprises (c)' fusing the lymphocyte with a cancer cells, e.g., a myeloma cell.

Also provided are methods for making antigen-binding proteins, comprising:
(a) immunizing a non-human animal with a first antigen that comprises a first epitope or immunogenic portion thereof, wherein the non-human animal comprises in its genome: (i) a rearranged human immunoglobulin heavy chain variable region nucleic acid sequence operably linked to a heavy chain constant region nucleic acid sequence, and (ii) an unrearranged human immunoglobulin light chain variable region nucleic acid sequence operably linked to a light chain constant region nucleic acid sequence;
(b) allowing the non-human animal to mount an immune response to the first epitope or immunogenic portion thereof;
(c) isolating from the non-human animal a cell comprising a nucleic acid sequence that encodes a light chain variable domain that specifically binds the first epitope or immunogenic portion thereof;
(d) obtaining from the cell of (c) the nucleic acid sequence that encodes a light chain variable domain that specifically binds the first epitope or immunogenic portion thereof;
(e) employing the nucleic acid sequence of (c) in an expression construct, fused to a human immunoglobulin constant region nucleic acid sequence; and
(f) expressing the nucleic acid sequence of (c) in a production cell line that expresses a human immunoglobulin heavy chain that specifically binds a second antigen or epitope thereof to form an antigen-binding protein whose light chain is encoded by the nucleic acid of (c) and that binds the first epitope or immunogenic portion thereof independently from the heavy chain, and whose heavy chain specifically binds the second antigen or epitope.

Also provided are methods for making antigen-binding proteins, comprising:
(a) immunizing a non-human animal with a first antigen that comprises a first epitope or immunogenic portion thereof, wherein the non-human animal comprises in its genome: (i) a rearranged human immunoglobulin heavy chain variable region nucleic acid sequence operably linked to a heavy chain constant region nucleic acid sequence, and (ii) two or more but less than the wild type number of human immunoglobulin light chain variable region gene segments ($V_L$ and $J_L$) operably linked to a light chain constant region nucleic acid sequence;
(b) allowing the non-human animal to mount an immune response to the first epitope or immunogenic portion thereof;
(c) isolating from the non-human animal a cell comprising a nucleic acid sequence that encodes a light chain variable domain that specifically binds the first epitope or immunogenic portion thereof;
(d) obtaining from the cell of (c) the nucleic acid sequence that encodes a light chain variable domain that specifically binds the first epitope or immunogenic portion thereof;
(e) employing the nucleic acid sequence of (c) in an expression construct, fused to a human immunoglobulin constant region nucleic acid sequence; and
(f) expressing the nucleic acid sequence of (c) in a production cell line that expresses a human immunoglobulin heavy chain that specifically binds a second antigen or epitope thereof to form an antigen-binding protein whose light chain is encoded by the nucleic acid of (c) and that binds the first epitope or immunogenic portion thereof independently from the heavy chain, and whose heavy chain specifically binds the second antigen or epitope.

Also provided are methods for making antigen-binding proteins, comprising:
(a) immunizing a non-human animal with a first antigen that comprises a first epitope or immunogenic portion thereof, wherein the non-human animal comprises in its genome: (i) a rearranged human immunoglobulin heavy chain variable region nucleic acid sequence operably linked to a light chain constant region nucleic acid sequence, and (ii) human immunoglobulin light chain variable region gene segments ($V_L$ and JO operably linked to a heavy chain constant region nucleic acid sequence;
(b) allowing the non-human animal to mount an immune response to the first epitope or immunogenic portion thereof;
(c) isolating from the non-human animal a cell comprising a nucleic acid sequence that encodes a light chain variable domain that specifically binds the first epitope or immunogenic portion thereof;
(d) obtaining from the cell of (c) the nucleic acid sequence that encodes a light chain variable domain that specifically binds the first epitope or immunogenic portion thereof;
(e) employing the nucleic acid sequence of (c) in an expression construct, fused to a human immunoglobulin constant region nucleic acid sequence; and
(f) expressing the nucleic acid sequence of (c) in a production cell line that expresses a human immunoglobulin heavy chain that specifically binds a second antigen or epitope thereof to form an antigen-binding protein whose light chain is encoded by the nucleic acid of (c) and that binds the first epitope or immunogenic portion thereof independently from the heavy chain, and whose heavy chain specifically binds the second antigen or epitope.

In various aspects, a non-human animal is provided comprising in its germline genome an immunoglobulin heavy chain locus that comprises a rearranged human immunoglobulin heavy chain variable region nucleotide sequence. In some embodiments, the non-human animal is a mammal. In some embodiments, the mammal is a rodent. In some embodiments, the rodent selected from the group consisting of a mouse, a rat, and a hamster. In some embodiments, the non-human animal is homozygous for the rearranged human immunoglobulin heavy chain variable region nucleotide sequence. In some embodiments, the rearranged human immunoglobulin heavy chain variable region nucleotide sequence is operably linked to a non-human heavy chain constant region gene sequence. In certain embodiments, the non-human heavy chain constant region gene sequence encodes an Fc. In particular embodiments, the non-human heavy chain constant region gene sequence is a mouse or a rat heavy chain constant region gene sequence. In some embodiments, the non-human animal is a rodent, and the rearranged human immunoglobulin heavy chain variable region nucleotide sequence is operably linked to a human heavy chain constant region gene sequence. In particular embodiments, the heavy chain constant region gene sequence is selected from a $C_H1$, a hinge, a $C_H2$, a $C_H3$, and a combination thereof. In some embodiments, the rearranged human immunoglobulin heavy chain variable region nucleotide sequence is derived from a human heavy chain $V_H$ gene segment, a human heavy chain D gene segment, and a human heavy chain $J_H$ gene segment. In certain embodiments, the rearranged human immunoglobulin heavy chain variable region nucleotide sequence is derived from a human germline heavy chain $V_H$ segment, a human germline heavy chain D segment, and a human germline heavy chain $J_H$ segment. In some embodiments, the rearranged human immunoglobulin heavy chain variable region nucleotide sequence encodes the sequence of human $V_H3$-23/GY/$J_H4$-4. In some embodiments, substantially all endogenous functional $V_H$, D, and $J_H$ gene segments are deleted from the immunoglobulin heavy chain locus of the non-human animal or rendered non-functional. In some embodiments, the non-human animal comprises a modification that deletes or renders non-functional endogenous functional $V_H$, D, and $J_H$ gene segments; and the non-human animal comprises the rearranged human immunoglobulin heavy chain variable region nucleotide sequence, wherein the rearranged human immunoglobulin heavy chain variable region nucleotide sequence is present ectopically. In some embodiments, an immunoglobulin heavy chain variable domain encoded by the rearranged heavy chain variable region nucleotide sequence is not immunogenic to the non-human animal. In some embodiments, the non-human animal comprises an Adam6a gene, an Adam6b gene, or both. In some embodiments, the non-human animal further comprises a nucleotide sequence encoding an unrearranged human immunoglobulin light chain ($V_L$) gene segment and an unrearranged human immunoglobulin light chain J gene segment. In certain embodiments, the nucleotide sequence encoding the unrearranged light chain V gene segment ($V_L$) and the unrearranged light chain ($J_L$) gene segment is operably linked to an immunoglobulin light chain constant region gene sequence. In particular embodiments, the light chain constant region gene sequence is selected from a rodent and a human constant region gene sequence. In yet more particular embodiments, the rodent is selected from a mouse, a rat, and a hamster. In certain embodiments, the unrearranged human immunoglobulin light chain ($V_L$) gene segment and the unrearranged human immunoglobulin ($J_L$) gene segment are operably linked, at an endogenous rodent locus, to a rodent immunoglobulin constant region gene sequence. In some embodiments, the immunoglobulin heavy chain locus comprises a plurality of copies of the rearranged human immunoglobulin heavy chain variable region nucleotide sequence.

In additional aspects are provided a non-human immunoglobulin heavy chain locus in a genome of a non-human germ cell comprising a rearranged human immunoglobulin heavy chain variable region nucleotide sequence operably linked to a heavy chain constant region gene sequence, wherein the constant region gene sequence comprises a non-human sequence, a human sequence, or a combination thereof. In some embodiments, the rearranged human immunoglobulin heavy chain variable region nucleotide sequence is operably linked to an endogenous non-human immunoglobulin constant region gene sequence. In certain embodiments, the endogenous non-human immunoglobulin constant region gene sequence is a mouse or rat heavy chain constant region gene sequence.

In additional aspects, methods are provided for making a non-human animal, the methods comprising:
(a) modifying a genome of a non-human animal to delete or render non-functional endogenous functional immunoglobulin heavy chain $V_H$, D, and $J_H$ gene segments; and
(b) placing in the genome a rearranged human immunoglobulin heavy chain variable region nucleotide sequence.

In some embodiments, the rearranged human immunoglobulin heavy chain variable region nucleotide sequence is operably linked to a non-human immunoglobulin heavy chain constant region gene sequence. In certain embodiments, the non-human immunoglobulin heavy chain constant region gene sequence is a mouse or rat immunoglobulin heavy chain constant region gene sequence. In some embodiments, the rearranged human immunoglobulin heavy chain variable region nucleotide sequence is placed at an endogenous immunoglobulin heavy chain locus in the genome. In some embodiments, the rearranged human immunoglobulin heavy chain variable region nucleotide sequence is present in a germline genome of the non-human animal. In some embodiments, the rearranged human immunoglobulin heavy chain variable region nucleotide sequence is present at an ectopic locus in the genome. In some embodiments, the non-human animal comprises a plurality of copies of the rearranged human immunoglobulin heavy chain variable region nucleotide sequence. In some embodiments, the non-human animal comprises an Adam6a gene, an Adam6b gene or both. In some embodiments, the non-human animal is a rodent selected from the group consisting of a mouse, a rat, or a hamster. In some embodiments are provided a non-human animal that is heterozygous for the immunoglobulin heavy chain locus as described herein, wherein the non-human animal expresses the rearranged human immunoglobulin heavy chain variable region nucleotide sequence predominantly from the immunoglobulin heavy chain locus.

In additional aspects are provided non-human animals comprising a genetically modified immunoglobulin locus comprising:
(a) a rearranged human immunoglobulin heavy chain variable region nucleotide sequence that is operably linked to a light chain constant region gene sequence; and
(b) an unrearranged human immunoglobulin light chain variable region nucleotide sequence that is operably linked to a heavy chain constant region gene sequence.

In some embodiments, the non-human animal is a mammal. In particular embodiments, the mammal is selected from the group consisting of a mouse, a rat, and a hamster. In some embodiments, the rearranged human immunoglobulin heavy chain variable region nucleotide sequence is operably linked to a κ light chain constant region gene sequence. In some embodiments, the rearranged human immunoglobulin heavy chain variable region nucleotide sequence is operably linked to a λ light chain constant region gene sequence. In some embodiments, the light chain constant region gene sequence is a mouse or a rat light chain constant region gene sequence. In some embodiments, the light chain constant region gene sequence is a human light chain constant region gene sequence. In some embodiments, the heavy chain constant region gene sequence is a mouse or a rat heavy chain constant region gene sequence. In some embodiments, the heavy chain constant region gene sequence is a human heavy chain constant region gene sequence. In some embodiments, the heavy chain constant region gene sequence encodes a sequence selected from a CH1, a hinge, a CH2, a CH3, and a combination thereof. In some embodiments, the unrearranged human immunoglobulin light chain variable region nucleotide sequence comprises a human κ light chain variable domain gene sequence. In some embodiments, the unrearranged human immunoglobulin light chain variable region nucleotide sequence comprises a human λ light chain variable domain gene sequence. In some embodiments, the rearranged human immunoglobulin heavy chain variable region nucleotide sequence is derived from a human heavy chain $V_H$ gene segment, a human heavy chain D gene segment, and a human heavy chain $J_H$ gene segment. In certain embodiments, the rearranged human immunoglobulin heavy chain variable region nucleotide sequence is derived from a human germline heavy chain $V_H$ segment, a human germline heavy chain D segment, and a human germline heavy chain $J_H$ segment. In certain embodiments, the human $V_H$ gene segment is selected from the group consisting of $V_H$1-2, $V_H$1-3, $V_H$1-8, $V_H$1-18, $V_H$1-24, $V_H$1-45, $V_H$1-46, $V_H$1-58, $V_H$1-69, $V_H$2-5, $V_H$2-26, $V_H$2-70, $V_H$3-7, $V_H$3-9, $V_H$3-11, $V_H$3-13, $V_H$3-15, $V_H$3-16, $V_H$3-20, $V_H$3-21, $V_H$3-23, $V_H$3-30, $V_H$3-30-3, $V_H$3-30-5, $V_H$3-33, $V_H$3-35, $V_H$3-38, $V_H$3-43, $V_H$3-48, $V_H$3-49, $V_H$3-53, $V_H$3-64, $V_H$3-66, $V_H$3-72, $V_H$3-73, $V_H$3-74, $V_H$4-4, $V_H$4-28, $V_H$4-30-1, $V_H$4-30-2, $V_H$4-30-4, $V_H$4-31, $V_H$4-34, $V_H$4-39, $V_H$4-59, $V_H$4-61, $V_H$5-51, $V_H$6-1, $V_H$7-4-1, $V_H$7-81, and a polymorphic variant thereof. In certain embodiments, the human D gene segment is selected from the group consisting of D1-1, D1-7, D1-14, D1-20, D1-26, D2-2, D2-8, D2-15, D2-21, D3-3, D3-9, D3-10, D3-16, D3-22, D4-4, D4-11, D4-17, D4-23, D5-12, D5-5, D5-18, D5-24, D6-6, D6-13, D6-19, D6-25, D7-27, and a polymorphic variant thereof. In certain embodiments, the human $J_H$ gene segment is selected from the group consisting of $J_H$1, $J_H$2, $J_H$3, $J_H$4, $J_H$5, $J_H$6, and a polymorphic variant thereof. In some embodiments, wherein the rearranged human immunoglobulin heavy chain variable region nucleotide sequence encodes the sequence of human $V_H$3-23/GY/$J_H$4-4 (SEQ ID NO: 137). In some embodiments, the genetically modified immunoglobulin locus is present in the germline of the non-human animal. In some embodiments, substantially all endogenous functional $V_H$, D, and $J_H$ gene segments are deleted from the immunoglobulin heavy chain locus of the non-human animal or rendered non-functional. In some embodiments, the non-human animal comprises a modification that deletes or renders non-functional endogenous functional $V_H$, D, and $J_H$ gene segments; and the non-human animal comprises the rearranged human immunoglobulin heavy chain variable region nucleotide sequence that is operably linked to the light chain constant region gene sequence, wherein the rearranged human immunoglobulin heavy chain variable region nucleotide sequence is present at an ectopic locus in the genome. In some embodiments, the non-human animal comprises an Adam6a gene, an Adam6b gene or both. In some embodiments, a heavy chain variable domain encoded by the rearranged human immunoglobulin heavy chain variable region nucleotide sequence is not immunogenic to the non-human animal. In some embodiments, the genetically modified immunoglobulin locus comprises a plurality of copies of the rearranged human immunoglobulin heavy chain variable region nucleotide sequence that is operably linked to the light chain constant region gene sequence.

Additional aspects provide an immunoglobulin locus in a germline genome of a non-human animal comprising:

(1) a rearranged human immunoglobulin heavy chain variable region nucleotide sequence that is operably linked to a light chain constant region gene sequence, and (2) an unrearranged human immunoglobulin light chain variable region nucleotide sequence that is operably linked to a heavy chain constant region gene sequence.

In some embodiments, the light chain constant region gene sequence is a κ light chain constant region gene sequence. In some embodiments, the light chain constant region gene sequence is a λ light chain constant region gene sequence. In some embodiments, the light chain constant region gene sequence is a mouse or rat light chain constant region gene sequence.

Additional aspects provide methods of making a non-human animal that comprise a modified immunoglobulin locus, the methods comprising:

(a) modifying a genome of a non-human animal to delete or render non-functional:
  (i) endogenous functional immunoglobulin heavy chain V, D, and J gene segments, and
  (ii) endogenous functional immunoglobulin light chain V and J gene segments; and
(b) placing in the genome:
  (i) a rearranged human immunoglobulin heavy chain variable region nucleotide sequence that is operably linked to a light chain constant region gene sequence, and
  (ii) an unrearranged human immunoglobulin light chain variable region nucleotide sequence that is operably linked to a heavy chain constant region gene sequence.

In some embodiments, the unrearranged human immunoglobulin light chain variable region nucleotide sequence encodes a κ light chain variable domain. In some embodiments, the unrearranged human immunoglobulin light chain variable region nucleotide sequence encodes a λ light chain variable domain. In some embodiments, the heavy chain constant region gene sequence is a non-human immunoglobulin heavy chain constant region gene sequence. In certain embodiments, the non-human immunoglobulin heavy chain constant region gene sequence is a mouse or a rat heavy chain constant region gene sequence. In particular embodiments, the heavy chain constant region gene sequence encodes a sequence selected from a CH1, a hinge, a CH2, a CH3, and a combination thereof. In some embodiments, the non-human animal is a rodent selected from the group consisting of a mouse, a rat, or a hamster. In some embodiments, the modified immunoglobulin locus is present in a germline genome of the non-human animal. In some embodiments, the non-human animal comprises an Adam6a gene, an Adam6b gene or both.

Also provided are non-human animals comprising a modified immunoglobulin heavy chain locus that comprises a rearranged human immunoglobulin heavy chain variable region nucleotide sequence comprising a heavy chain V segment ($V_H$) sequence that is operably linked, via a spacer, to a heavy chain J segment ($J_H$) sequence, wherein the spacer comprises at least one amino acid residue. In some embodiments, the non-human animal is a rodent. In some embodiments, the rodent is selected from the group consisting of a mouse, a rat, and a hamster. In some embodiments, the rearranged human immunoglobulin heavy chain variable region nucleotide sequence is operably linked to a non-human heavy chain constant region gene sequence. In some embodiments, the non-human heavy chain constant region gene sequence is a mouse or a rat constant region gene sequence. In some embodiments, the rearranged human immunoglobulin heavy chain variable region nucleotide sequence is operably linked to a human heavy chain constant region gene sequence. In certain embodiments, the heavy chain constant region gene sequence encodes a sequence selected from a $C_H$1, a hinge, a $C_H$2, a $C_H$3, and a combination thereof. In some embodiments, the $V_H$ sequence and the $J_H$ sequence are derived from a human $V_H$ gene segment and a human $J_H$ gene segment. In certain embodiments, wherein the human $V_H$ gene segment is selected from the group consisting of $V_H$1-2, $V_H$1-3, $V_H$1-8, $V_H$1-18, $V_H$1-24, $V_H$1-45, $V_H$1-46, $V_H$1-58, $V_H$1-69, $V_H$2-5, $V_H$2-26, $V_H$2-70, $V_H$3-7, $V_H$3-9, $V_H$3-11, $V_H$3-13, $V_H$3-15, $V_H$3-16, $V_H$3-20, $V_H$3-21, $V_H$3-23, $V_H$3-30, $V_H$3-30-3, $V_H$3-30-5, $V_H$3-33, $V_H$3-35, $V_H$3-38, $V_H$3-43, $V_H$3-48, $V_H$3-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, $V_H7$-81, and a polymorphic variant thereof. In particular embodiments, the human $V_H$ gene segment is $V_H3$-23 or a polymorphic variant thereof. In some embodiments, the spacer encodes a sequence derived from a human D gene segment. In particular embodiments, the human D gene segment is selected from the group consisting of D1-1, D1-7, D1-14, D1-20, D1-26, D2-2, D2-8, D2-15, D2-21, D3-3, D3-9, D3-10, D3-16, D3-22, D4-4, D4-11, D4-17, D4-23, D5-12, D5-5, D5-18, D5-24, D6-6, D6-13, D6-19, D6-25, D7-27, and a polymorphic variant thereof. In particular embodiments, the spacer encodes the sequence of D4-4 or a polymorphic variant thereof. In certain embodiments, the human $J_H$ gene segment is selected from the group consisting of $J_H1$, $J_H2$, $J_H3$, $J_H4$, $J_H5$, $J_H6$, and a polymorphic variant thereof. In certain embodiments, the human $J_H$ segment is $J_H4$-4 or a polymorphic variant thereof. In some embodiments, the rearranged immunoglobulin heavy chain variable region nucleotide sequence encodes the sequence of human $V_H3$-23/GY/$J_H4$-4 (SEQ ID NO: 137). In some embodiments, substantially all endogenous functional $V_H$, D, and $J_H$ gene segments are deleted from the immunoglobulin heavy chain variable locus of the non-human animal or rendered non-functional. In some embodiments, the non-human animal comprises a modification that deletes or renders non-functional endogenous functional $V_H$, D, and $J_H$ gene segments; and the non-human animal comprises the rearranged human immunoglobulin heavy chain variable region nucleotide sequence at an ectopic locus of its genome. In some embodiments, a heavy chain variable domain encoded by the rearranged human immunoglobulin heavy chain variable region nucleotide sequence is not immunogenic to the non-human animal. In some embodiments, the non-human animal comprises an Adam6a gene, an Adam6b gene, or both.

Additional aspects provide an immunoglobulin heavy chain locus in a germline genome of a non-human animal, comprising a rearranged human immunoglobulin heavy chain variable region nucleotide sequence comprising a heavy chain variable gene segment ($V_H$) that is operably linked, via a spacer, to a heavy chain J gene segment ($J_H$), wherein the spacer encodes at least one amino acid residue. In some embodiments, the rearranged human immunoglobulin heavy chain variable region nucleotide sequence is operably linked to a non-human heavy chain constant region gene sequence. In certain embodiments, the non-human heavy chain constant region gene sequence is a mouse or a rat heavy chain constant region gene sequence. In some embodiments, the immunoglobulin locus comprises a plurality of copies of the rearranged heavy chain variable region nucleotide sequence.

In additional aspects are provided methods of making a non-human animal comprising a modified immunoglobulin heavy chain locus, the methods comprising:
(a) modifying a genome of a non-human animal to delete or render non-functional endogenous functional immunoglobulin heavy chain $V_H$, D, and $J_H$ gene segments; and
(b) placing in the genome a rearranged human immunoglobulin heavy chain variable region nucleotide sequence comprising a heavy chain variable gene segment ($V_H$) that is operably linked, via a spacer, to a heavy chain J gene segment ($J_H$), wherein the spacer comprises at least one amino acid residue.

In some embodiments, the rearranged human immunoglobulin heavy chain nucleotide sequence is operably linked to a non-human immunoglobulin heavy chain constant region gene sequence. In certain embodiments, the non-human immunoglobulin heavy chain constant region gene sequence is a mouse or a rat heavy chain constant region gene sequence. In some embodiments, the rearranged human immunoglobulin heavy chain variable region nucleotide sequence is placed at an endogenous immunoglobulin heavy chain locus in the genome. In some embodiments, the rearranged human immunoglobulin heavy chain variable region nucleotide sequence is present at an ectopic locus in the genome. In some embodiments, the modified heavy chain locus comprises a plurality of copies of the rearranged human immunoglobulin heavy chain variable region nucleotide sequence. In some embodiments, the non-human animal is a rodent selected from the group consisting of a mouse, a rat, or a hamster. In some embodiments, the non-human animal comprises an Adam6a gene, an Adam6b gene or both. In some embodiments, the modified immunoglobulin heavy chain locus is present in a germline genome of the non-human animal.

Additional aspects provide a modified non-human animal comprising in its genome:
(a) an immunoglobulin heavy chain locus that comprises a rearranged human heavy chain variable region nucleic acid sequence operably linked to a heavy chain constant region nucleic acid sequence; and
(b) an immunoglobulin light chain locus comprising one or more but less than the wild type number of human immunoglobulin light chain $V_L$ and $J_L$ gene segments, operably linked to a light chain constant region nucleic acid sequence.

In some embodiments, the non-human animal is a mammal. In certain embodiments, the mammal is a rodent. In particular embodiments, the rodent is selected from the group consisting of a mouse, a rat, and a hamster. In some embodiments, the heavy chain constant region nucleic acid sequence is a rodent constant region sequence that encodes an immunoglobulin isotype selected from IgM, IgD, IgG, IgE, IgA, and a combination thereof. In some embodiments, the light chain constant region nucleic acid sequence is a rodent κ or λ constant region nucleic acid sequence. In some embodiments, the rearranged human heavy chain variable region nucleic acid sequence is selected from a human germline $V_H$ segment, a human germline D segment, and a human germline $J_H$ segment. In some embodiments, the rearranged human heavy chain variable region nucleic acid sequence is operably linked to the constant region nucleic acid sequence at an endogenous locus. In some embodiments, the one or more but less than the wild type number of human immunoglobulin light chain $V_L$ and $J_L$ gene segments are operably linked to the light chain constant region nucleic acid sequence at an endogenous locus. In some embodiments, the non-human animal comprises no more than two human immunoglobulin unrearranged $V_L$ gene segments, and one, two, or three or more human unrearranged $J_L$ gene segments. In some embodiments, the rearranged heavy chain variable region nucleic acid sequence is derived from a human germline $V_H$ gene segment selected from the group consisting of $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H3$-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, $V_H7$-81, and a polymorphic variant thereof. In certain, the rearranged heavy chain variable region nucleic acid sequence is derived from a human germline $V_H3$-23 gene segment. In some embodiments, the rearranged heavy chain variable region nucleic acid sequence encodes the sequence of human $V_H3$-23/GY/$J_H4$-4 (SEQ ID NO: 137). In some embodiments, the rearranged heavy chain variable region nucleic acid sequence encodes the sequence of $V_H3$-23/$X_1X_2$/J, wherein $X_1$ is any amino acid, and $X_2$ is any amino acid. In certain embodiments, $X_1$ is Gly and $X_2$ is Tyr. In some embodiments, the immunoglobulin heavy chain locus comprises a functional Adam6a gene, Adam6b gene, or both. In certain embodiments, the Adam6a gene, Adam6b gene, or both are endogenous Adam6 genes. In some embodiments, the genetically modified non-human animal comprises an Adam6a gene, Adam6b gene, or both at an ectopic locus of the genome. In some embodiments, the human variable region $V_L$ and $J_L$ gene segments are capable of rearranging and encoding a human immunoglobulin light chain variable domain. In some embodiments, the immunoglobulin light chain locus comprises two human $V_L$ gene segments, Vκ1-39 and Vκ3-20. In certain embodiments, the gene segments are germline gene segments. In certain embodiments, the non-human animal comprises Jκ1, Jκ2, Jκ3, Jκ4, and Jκ5 gene segments. In some embodiments, two or more, three or more, four or more, or five or more human $V_L$ gene segments and two or more human $J_L$ gene segments are present at an endogenous light chain locus. In some embodiments, at least one of the human light chain $V_L$ or $J_L$ gene segments encode one or more histidine codons that are not encoded by a corresponding human germline light chain variable gene segment. In some embodiments, at least one of the $V_L$ gene segments comprises an addition or substitution of at least one non-histidine codon encoded by the corresponding human germline $V_L$ segment sequence with a histidine codon. In certain embodiments, the added or substituted histidine codon is present in CDR3. In some embodiments, the human $V_L$ gene segments are human Vκ1-39 and Vκ3-20 gene segments, and each of the human Vκ1-39 and Vκ3-20 gene segments comprises a substitution of at least one non-histidine codon encoded by a corresponding human germline $V_L$ gene segment with the histidine codon. In certain embodiments, the substitution is of three non-histidine codons of the human Vκ1-39 gene segment, wherein the substitution is designed to express histidines at positions 106, 108, and 111. In particular embodiments, the substitution is of four non-histidine codons of the human Vκ1-39 gene segment, and the substitution is designed to express histidines at positions 105, 106, 108, and 111. In particular embodiments, the substitution is of three non-histidine codons of the human Vκ3-20 gene segment, and the substitution is designed to express histidines at positions 105, 106, and 109. In particular embodiments, the substitution is of four non-histidine codons of the human Vκ3-20 gene segment, and the substitution is designed to express histidines at positions 105, 106, 107, and 109. In some embodiments, non-human animal of claim 107, wherein the non-human animal, upon stimulation by an antigen of interest, expresses an antigen-binding protein that specifically binds the antigen, wherein the antigen-binding protein comprises an amino acid sequence derived from the human $V_L$ and $J_L$ gene segments, and wherein the antigen-binding protein comprises at least one histidine residue at an amino acid position encoded by the human $V_L$ gene segment. In some embodiments, the non-human animal expresses a population of antigen-binding proteins in response to an antigen, wherein all antigen-binding proteins in the population comprise: (a) immunoglobulin heavy chains comprising human heavy chain variable domains derived from the rearranged human variable region nucleic acid sequence; and (b) immunoglobulin light chains comprising immunoglobulin light chain variable domains derived from a rearrangement of the human $V_L$ gene segments and the $J_L$ gene segments in the genome of the non-human animal, and wherein at least one of the human $V_L$ gene segments encodes one or more histidine codons that are not encoded by the corresponding human germline $V_L$ gene segment.

Additional aspects provide methods for making a non-human animal comprising a modified immunoglobulin locus, comprising:

(a) modifying a genome of a non-human animal to delete or render non-functional:
(i) endogenous functional immunoglobulin heavy chain $V_H$, D, and/or $J_H$ gene segments, and
(ii) endogenous functional immunoglobulin light chain $V_L$ and $J_L$ gene segments; and (b) placing in the modified genome of the non-human animal:
(i) a rearranged human immunoglobulin heavy chain variable region nucleic acid sequence in operable linkage to an immunoglobulin heavy chain constant region nucleic acid sequence; and
(ii) one or more but less than the wild type number of human immunoglobulin light chain $V_L$ and $J_L$ gene segments in operable linkage to an immunoglobulin light chain constant region nucleic acid sequence.

In some embodiments, the non-human animal is a rodent. In certain embodiments, the rodent is a mouse, a rat, or a hamster. In some embodiments, the rearranged human immunoglobulin heavy chain variable region nucleic acid sequence is operably linked to a mouse or rat heavy chain constant region gene sequence selected from a CH1, a hinge, a CH2, a CH3, and a combination thereof. In some embodiments, the rearranged human immunoglobulin heavy chain variable region nucleic acid sequence and the human immunoglobulin light chain $V_L$ and $J_L$ gene segments are placed at or near a corresponding nucleotide sequence of the wild type non-human animal. In some embodiments, the rearranged immunoglobulin human heavy chain variable region nucleic acid sequence and the human immunoglobulin light chain $V_L$ and $J_L$ gene segments are placed at an ectopic locus in the genome. In some embodiments, the non-human animal comprises an immunoglobulin heavy chain locus comprising an endogenous Adam6a gene, Adam6b gene, or both. In some embodiments, the non-human animal comprises an Adam6a gene, Adam6b gene, or both at an ectopic locus of the genome. In some embodiments, the rearranged human immunoglobulin heavy chain variable region nucleic acid sequence encodes the sequence of human $V_H3$-23/GY/$J_H4$-4 (SEQ ID NO: 137). In some embodiments, the immunoglobulin light chain constant region nucleic acid sequence is a rat or a mouse Cκ constant region nucleic acid sequence. In some embodiments, the human immunoglobulin light chain $V_L$ and $J_L$ gene segments are capable of rearranging and encoding a human immunoglobulin light chain variable domain. In some embodiments, the non-human animal comprises an immunoglobulin light chain locus comprising two human $V_L$ gene segments, Vκ1-39 and Vκ3-20. In certain embodiments, the non-human animal comprises Jκ1, Jκ2, Jκ3, Jκ4, and Jκ5 gene segments. In some embodiments, two or more, three or more, four or more, or five or more human $V_L$ gene segments and two or more human $J_L$ gene segments are present at an endogenous light chain locus. In some embodiments, at least one of the human immunoglobulin light chain $V_L$ or $J_L$ gene segments encode one or more histidine codons that are not encoded by a corresponding human germline light chain variable gene segment. In some embodiments, at least one of the $V_L$ gene segments comprises an addition or a substitution of at least one non-histidine codon encoded by the corresponding human germline $V_L$ segment sequence with a histidine codon. In certain embodiments, the added or substituted histidine codon is present in CDR3. In certain embodiments, the human $V_L$ gene segments are human Vκ1-39 and Vκ3-20 gene segments, and each of the human Vκ1-39 and Vκ3-20 gene segments comprises the substitution of at least one non-histidine codon encoded by a corresponding human germline $V_L$ gene segment with the histidine codon. In particular embodiments, the substitution is of three non-histidine codons of the human Vκ1-39 gene segment, and wherein the substitution is designed to express histidines at positions 106, 108, and 111. In particular embodiments, the substitution is of four non-histidine codons of the human Vκ1-39 gene segment, and wherein the substitution is designed to express histidines at positions 105, 106, 108, and 111. In particular embodiments, the substitution is of three non-histidine codons of the human Vκ3-20 gene segment, and wherein the substitution is designed to express histidines at positions 105, 106, and 109. In particular embodiments, the substitution is of four non-histidine codons of the human Vκ3-20 gene segment, and the substitution is designed to express histidines at positions 105, 106, 107, and 109.

Additional aspects provide methods for obtaining a nucleic acid sequence that encodes an immunoglobulin light chain variable domain ($V_L$) capable of binding an antigen independently from a heavy chain variable domain, comprising:
(a) immunizing a non-human animal with an antigen of interest or an immunogen thereof, wherein the non-human animal comprises in its genome (i) a rearranged human immunoglobulin heavy chain variable region nucleic acid sequence operably linked to a heavy chain constant region nucleic acid sequence; and (ii) two or more but less than the wild type number of human immunoglobulin light chain variable region gene segments ($V_L$ and $J_L$) operably linked to a light chain constant region nucleic acid sequence;
(b) allowing the non-human animal to mount an immune response;
(c) isolating from the immunized non-human animal a cell comprising a nucleic acid sequence that encodes a light chain variable domain that can bind the antigen; and
(d) obtaining from the cell a nucleic acid sequence that encodes the light chain variable domain ($V_L$ domain) that can bind the antigen.

In some embodiments, the isolating step (c) is carried out via fluorescence-activated cell sorting (FACS) or flow cytometry. In some embodiments, the cell comprising the nucleic acid sequence that encodes the light chain variable domain that bind the antigen is a lymphocyte. In certain embodiments, the lymphocyte comprises natural killer cells, T cells, or B cells. In some embodiments, the method further comprises a step of (c)' fusing the lymphocyte with a cancer cell. In certain embodiments, the cancer cell is a myeloma cell. In some embodiments, the nucleic acid sequence of (d) is fused with a nucleic acid sequence encoding an immunoglobulin constant region nucleic acid sequence. In some embodiments, the light chain constant region nucleic acid sequence is a human kappa sequence or a human lambda sequence. In some embodiments, the heavy chain constant region nucleic acid sequence is a human sequence selected from a CH1, a hinge, a CH2, a CH3, and a combination thereof. In some embodiments, the nucleic acid sequence of (d) comprises one or more histidine codon substitutions or insertions that are derived from the unrearranged $V_L$ gene segment in the genome of the animal.

Additional aspects provide methods for making an antigen-binding protein that comprises an immunoglobulin light chain variable domain that can bind an antigen independently from a heavy chain variable domain, comprising:
(a) immunizing a genetically modified non-human animal with a first antigen that comprises a first epitope or immunogenic portion thereof, wherein the non-human animal comprises in its genome:
(i) a rearranged human heavy chain variable region nucleic acid sequence operably linked to a heavy chain constant region nucleic acid sequence; and
(ii) two or more but less than the wild type number of human immunoglobulin light chain variable region gene segments ($V_L$ and $J_L$) operably linked to an immunoglobulin light chain constant region nucleic acid sequence;
(b) allowing the non-human animal to mount an immune response to the first epitope or immunogenic portion thereof;
(c) isolating from the non-human animal a cell comprising a nucleic acid sequence that encodes a light chain variable domain that specifically binds the first epitope or immunogenic portion thereof;
(d) obtaining from the cell of (c) the nucleic acid sequence that encodes the light chain variable domain that specifically binds the first epitope or immunogenic portion thereof;
(e) employing the nucleic acid sequence of (d) in an expression construct, fused to a human immunoglobulin constant region nucleic acid sequence; and
(f) expressing the nucleic acid sequence of (d) in a production cell line that expresses a human immunoglobulin heavy chain that specifically binds a second antigen or epitope to form an antigen-binding protein whose light chain is encoded by the nucleic acid of (d) and that binds the first epitope or immunogenic portion thereof independently from the heavy chain, and whose heavy chain specifically binds the second antigen or epitope.

In some embodiments, at least one of the human light chain $V_L$ or $J_L$ gene segments encode one or more histidine codons that are not encoded by a corresponding human germline light chain variable gene segment. In some embodiments, the first epitope is derived from a cell surface receptor. In particular embodiments, the cell surface receptor is an Fc receptor. In yet more particular embodiments, the Fc receptor is FcRn. In some embodiments, the second antigen or epitope is derived from a soluble antigen. In some embodiments, the second antigen or epitope is derived from a cell surface receptor. In some embodiments, the first antigen is an Fc receptor, the second antigen is a soluble protein, and the antigen-binding protein comprises one or more histidine substitutions and insertions derived from the $V_L$ gene segment in the genome of the non-human animal.

Additional aspects provide methods for obtaining a nucleic acid sequence that encodes an immunoglobulin light chain variable domain ($V_L$) capable of binding an antigen independently from a heavy chain variable domain, comprising:
(a) immunizing a non-human animal with a first antigen that comprises a first epitope or immunogenic portion thereof, wherein the non-human animal comprises in its genome: (i) a rearranged human immunoglobulin heavy chain variable region nucleic acid sequence operably linked to a heavy chain constant region nucleic acid sequence, and (ii) an unrearranged human immunoglobulin light chain variable region nucleic acid sequence operably linked to a light chain constant region nucleic acid sequence;
(b) allowing the non-human animal to mount an immune response;

(c) isolating from the immunized non-human animal a cell comprising a nucleic acid sequence that encodes a light chain variable domain that can bind the antigen; and (d) obtaining from the cell a nucleic acid sequence that encodes the light chain variable domain ($V_L$ domain) that can bind the antigen.

In some embodiments, the isolating step (c) is carried out via fluorescence-activated cell sorting (FACS) or flow cytometry. In some embodiments, the cell comprising the nucleic acid sequence that encodes the light chain variable domain that binds the antigen is a lymphocyte. In certain embodiments, the lymphocyte comprises natural killer cells, T cells, or B cells. In some embodiments, the method further comprises: (c)' fusing the lymphocyte with a cancer cell. In certain embodiments, the cancer cell is a myeloma cell. In some embodiments, the nucleic acid sequence of (d) is fused with a nucleic acid sequence encoding an immunoglobulin constant region nucleic acid sequence. In some embodiments, the light chain constant region nucleic acid sequence is a human kappa sequence or a human lambda sequence. In some embodiments, the heavy chain constant region nucleic acid sequence is a human sequence selected from a CH1, a hinge, a CH2, a CH3, and a combination thereof. In some embodiments, the nucleic acid sequence of (d) comprises one or more histidine codon substitutions or insertions that are derived from the unrearranged $V_L$ gene segment in the genome of the animal.

Additional aspect provide methods for obtaining a nucleic acid sequence that encodes an immunoglobulin light chain variable domain ($V_L$) capable of binding an antigen independently from a heavy chain variable domain, comprising:

(a) immunizing a non-human animal with a first antigen that comprises a first epitope or immunogenic portion thereof, wherein the non-human animal comprises in its genome: (i) a rearranged human immunoglobulin heavy chain variable region nucleic acid sequence operably linked to a light chain constant region nucleic acid sequence, and (ii) human immunoglobulin light chain variable region gene segments ($V_L$ and $J_L$) operably linked to a heavy chain constant region nucleic acid sequence;

(b) allowing the non-human animal to mount an immune response;

(c) isolating from the immunized non-human animal a cell comprising a nucleic acid sequence that encodes a light chain variable domain that can bind the antigen; and (d) obtaining from the cell a nucleic acid sequence that encodes the light chain variable domain ($V_L$ domain) that can bind the antigen.

In some embodiments, the isolating step (c) is carried out via fluorescence-activated cell sorting (FACS) or flow cytometry. In some embodiments, the cell comprising the nucleic acid sequence that encodes the light chain variable domain that binds the antigen is a lymphocyte. In certain embodiments, the lymphocyte comprises natural killer cells, T cells, or B cells. In some embodiments, the method further comprises: (c)' fusing the lymphocyte with a cancer cell. In certain embodiments, the cancer cell is a myeloma cell. In some embodiments, the nucleic acid sequence of (d) is fused with a nucleic acid sequence encoding an immunoglobulin constant region nucleic acid sequence. In some embodiments, the light chain constant region nucleic acid sequence is a human kappa sequence or a human lambda sequence. In some embodiments, the heavy chain constant region nucleic acid sequence is a human sequence selected from a CH1, a hinge, a CH2, a CH3, and a combination thereof. In some embodiments, the nucleic acid sequence of (d) comprises one or more histidine codon substitutions or insertions that are derived from the unrearranged $V_L$ gene segment in the genome of the animal.

Additional aspect provided methods for making an antigen-binding protein that comprises an immunoglobulin light chain variable domain that can bind an antigen independently from a heavy chain variable domain, comprising:

(a) immunizing a genetically modified non-human animal with a first antigen that comprises a first epitope or immunogenic portion thereof, wherein the non-human animal comprises in its genome:
   (i) a rearranged human heavy chain variable region nucleic acid sequence operably linked to a heavy chain constant region nucleic acid sequence; and
   (ii) unrearranged human immunoglobulin light chain variable region gene segments ($V_L$ and $J_L$) operably linked to a light chain constant region nucleic acid sequence;

(b) allowing the non-human animal to mount an immune response to the first epitope or immunogenic portion thereof;

(c) isolating from the non-human animal a cell comprising a nucleic acid sequence that encodes a light chain variable domain that specifically binds the first epitope or immunogenic portion thereof;

(d) obtaining from the cell of (c) the nucleic acid sequence that encodes the light chain variable domain that specifically binds the first epitope or immunogenic portion thereof;

(e) employing the nucleic acid sequence of (d) in an expression construct, fused to a human immunoglobulin constant region nucleic acid sequence; and (f) expressing the nucleic acid sequence of (d) in a production cell line that expresses a human immunoglobulin heavy chain that specifically binds a second antigen or epitope to form an antigen-binding protein whose light chain is encoded by the nucleic acid of (d) and that binds the first epitope or immunogenic portion thereof independently from the heavy chain, and whose heavy chain specifically binds the second antigen or epitope.

In some embodiments, at least one of the human light chain $V_L$ or $J_L$ gene segments encode one or more histidine codons that are not encoded by a corresponding human germline light chain variable gene segment. In some embodiments, the first epitope is derived from a cell surface receptor. In certain embodiments, the cell surface receptor is an Fc receptor. In particular embodiments, the Fc receptor is FcRn. In some embodiments, the second antigen or epitope is derived from a soluble antigen. In some embodiments, the second antigen or epitope is derived from a cell surface receptor. In some embodiments, the first antigen is an Fc receptor, the second antigen is a soluble protein, and the antigen-binding protein comprises one or more histidine substitutions and insertions derived from the $V_L$ gene segment in the genome of the non-human animal.

Additional aspects provided methods for making an antigen-binding protein that comprises an immunoglobulin light chain variable domain that can bind an antigen independently from a heavy chain variable domain, comprising:

(a) immunizing a genetically modified non-human animal with a first antigen that comprises a first epitope or immunogenic portion thereof, wherein the non-human animal comprises in its genome:
   (i) a rearranged human heavy chain variable region nucleic acid sequence operably linked to a light chain constant region nucleic acid sequence; and (ii) unrearranged human immunoglobulin light chain variable region gene segments ($V_L$ and $J_L$) operably linked to a heavy chain constant region nucleic acid sequence;

(b) allowing the non-human animal to mount an immune response to the first epitope or immunogenic portion thereof;

(c) isolating from the non-human animal a cell comprising a nucleic acid sequence that encodes a light chain variable domain that specifically binds the first epitope or immunogenic portion thereof;

(d) obtaining from the cell of (c) the nucleic acid sequence that encodes the light chain variable domain that specifically binds the first epitope or immunogenic portion thereof;

(e) employing the nucleic acid sequence of (d) in an expression construct, fused to a human immunoglobulin constant region nucleic acid sequence; and (f) expressing the nucleic acid sequence of (d) in a production cell line that expresses a human immunoglobulin heavy chain that specifically binds a second antigen or epitope to form an antigen-binding protein whose light chain is encoded by the nucleic acid of (d) and that binds the first epitope or immunogenic portion thereof independently from the heavy chain, and whose heavy chain specifically binds the second antigen or epitope.

In some embodiments, at least one of the human light chain $V_L$ or $J_L$ gene segments encode one or more histidine codons that are not encoded by a corresponding human germline light chain variable gene segment. In some embodiments, the first epitope is derived from a cell surface receptor. In certain embodiments, the cell surface receptor is an Fc receptor. In particular embodiments, the Fc receptor is FcRn. In some embodiments, the second antigen or epitope is derived from a soluble antigen. In some embodiments, the second antigen or epitope is derived from a cell surface receptor. In some embodiments, the first antigen is an Fc receptor, the second antigen is a soluble protein, and the antigen-binding protein comprises one or more histidine substitutions and insertions derived from the VL gene segment in the genome of the non-human animal.

BRIEF DESCRIPTION OF THE DRAWING

FIG. 5 shows a list of antibodies in the ASAP database of Regeneron Pharmaceuticals that contain CDR3 sequences similar to the UHC CDR3 sequence (AK<u>DYSNY</u>YFDY; SEQ ID NO: 143).

FIG. 7 shows a list of primers and probes used to confirm a loss of allele (LOA), a gain of allele (GOA), or a parental allele (parental) in the screening assays.

FIG. 8 shows sequences of primers and probes used in the screening assays.

Figure 16:
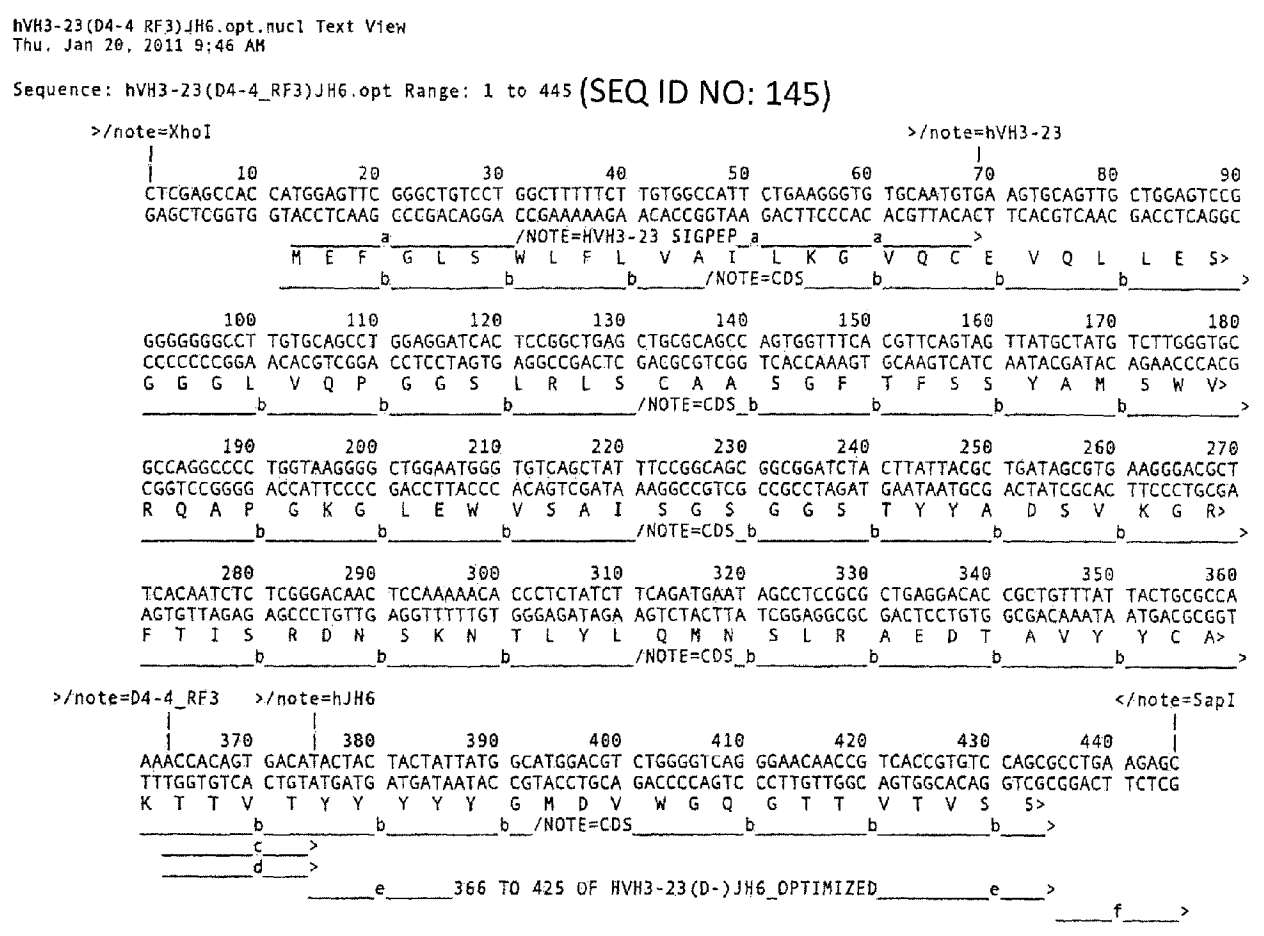

FIG. 16 shows codon-optimized nucleotide sequence and deduced amino acid sequence of hV$_H$3-23(D4-4_Reading Frame 3)J$_H$6 (SEQ ID NO: 145).

FIG. 17 shows codon-optimized nucleotide sequence and deduced amino acid sequence of hV$_H$3-23(D4-4_Reading Frame 2)J$_H$6 (SEQ ID NO: 146).

FIG. 18 shows codon-optimized nucleotide sequence and deduced amino acid sequence of hV$_H$3-23(D4-4_Reading Frame 3)J$_H$4 (SEQ ID NO: 147).

FIG. 19 shows codon-optimized nucleotide sequence and deduced amino acid sequence of hV$_H$3-23(D4-4_Reading Frame 2)J$_H$4 (SEQ ID NO: 148).

FIGS. 21A-21C show a general strategy for construction of a targeting vector for the engineering of an immunoglobulin kappa locus comprising two human Vκ segments (hVκ1-39 and hVκ3-20) and one human Jκ segment (Jκ5), as well as mouse enhancers and IgκC arm.

FIG. 21D shows introduction of this targeting vector into ES cells and generation of heterozygous mice with the same; while

FIGS. 22A-22D show the nucleotide sequence (SEQ ID NO:82) of the engineered portion of immunoglobulin κ locus comprising two human Vκ segments (hVκ1-39 and hVκ3-20) and one human Jκ segment; the nucleotide sequence spans the engineered human sequence and comprising 100 base pairs of endogenous mouse sequence at both the 5' and the 3' end. Bottom of FIG. 22D explains different fonts used to depict various sequences.

FIG. 23C shows introduction of this targeting vector into ES cells and generation of heterozygous mice with the same; while

Figure 24C:
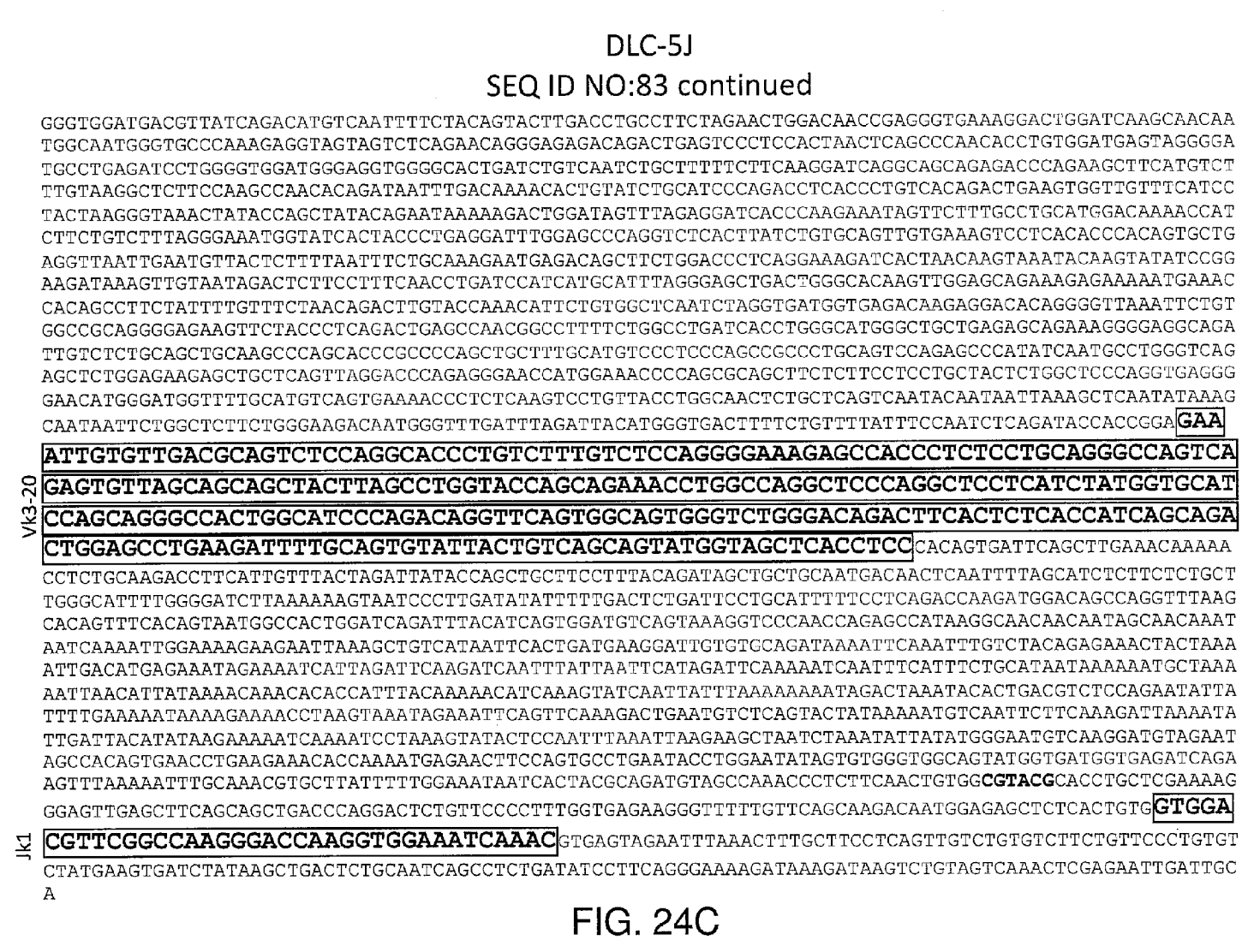

FIGS. 24A-24D show the nucleotide sequence (SEQ ID NO:83) of the engineered immunoglobulin κ locus comprising two human Vκ segments (hVκ1-39 and hVκ3-20) and five human Jκ segments; the nucleotide sequence spans the engineered sequence and 100 base pairs of endogenous mouse sequence at both the 5' and the 3' end. Bottom of FIG. 24D explains different fonts used to depict various sequences.

FIG. 34 shows the sequence and properties (% GC content, N, % mismatch, Tm) of selected mutagenesis primers used to engineer four histidine residues into CDR3's of human Vκ1-39 and Vκ3-20 light chain sequence. SEQ ID NOs for these primers used in the Sequence Listing are included in the Table below. F=forward primer, R=reverse primer.

FIG. 35A shows introduction of a targeting vector comprising two human Vκ light chain segments each substituted with four histidine residues and five human Jκ into ES cells and generation of heterozygous mice with the same; while

FIG. 36 shows the sequence and properties (% GC content, N, % mismatch, Tm) of selected mutagenesis primers used to engineer three histidine residues into CDR3's of human Vκ1-39 and Vκ3-20 light chain sequence. SEQ ID NOs for these primers used in the Sequence Listing are included in the Table below. F=forward primer, R=reverse primer.

FIG. 37A shows introduction of a targeting vector comprising two human Vκ light chain segments each substituted with three histidine residues and five human Jκ into ES cells and generation of heterozygous mice with the same; while

FIG. 38A shows alignment of amino acid sequence encoded by human germline Vκ3-20 sequence (bottom sequence) with exemplary amino acid translation of IgM light kappa chain variable sequence expressed in a mouse comprising two V kappa segments (Vκ3-20 and Vκ1-39), each substituted with 3 histidine residues in CDR3 sequence (top sequence); the alignment shows IgM kappa chain variable sequence expressed in a mouse that retained all three histidine substitutions introduced into the germline sequence. FIG. 38B shows alignment of amino acid sequence encoded by human germline Vκ1-39 sequence (bottom sequence in each alignment) with exemplary amino acid translation of IgM light kappa chain variable sequence expressed in a mouse comprising two V kappa segments (Vκ3-20 and Vκ1-39), each substituted with 3 histidine residues in CDR3 sequence (top sequence in each alignment); top alignment shows IgM kappa chain variable sequence expressed in a mouse that retained all three histidine modifications introduced into the germline sequence, the bottom alignment shows IgM kappa chain variable sequence expressed in a mouse that retained two out of three histidine modifications introduced into the germline sequence. In some embodiments, histidine introduced into the last position of the Vκ may be lost during V-J rearrangement.

FIG. 53B shows the total number of CD19$^+$ B cells, mature B cells (CD19$^+$IgM$^{lo}$IgD$^{hi}$) and transitional B cells (CD19$^+$IgM$^{hi}$IgD$^{int}$) in harvested spleens from wild type mice (WT) and mice homozygous a rearranged heavy chain variable region nucleic acid sequence (hV$_H$3-23/D/J$_H$4) in the kappa light chain locus.

DETAILED DESCRIPTION

Figure 1:
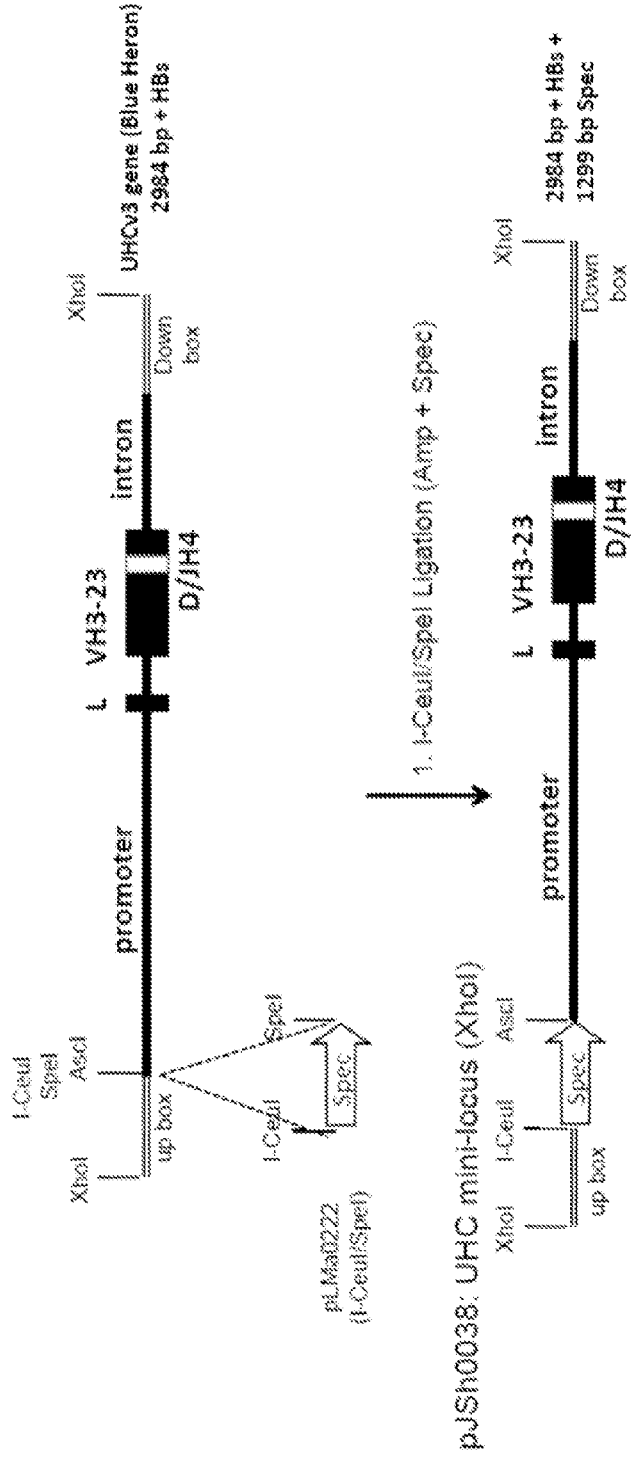
FIG. 1 illustrates schemes for constructing a rearranged heavy chain variable domain mini-locus ("UHC mini-locus") comprising a rearranged human immunoglobulin variable region nucleotide sequence ($V_H3$-23/D/$J_H4$; SEQ ID NO: 136) and an intron of $J_H4$ (SEQ ID NO: 140), which are operably linked to a human $V_H3$-23 promoter (SEQ ID NO: 139). The UHC mini-locus was flanked 5' and 3' by mouse homology arms. In Step 1 (I-CeuI/SpeI Ligation (Amp+Spec)), a spectinomycin selection cassette was introduced into the upstream of the promoter between the I-CeuI and SpeI sites to generate pJSh0038 (UHC mini-locus;).
Figure 2:
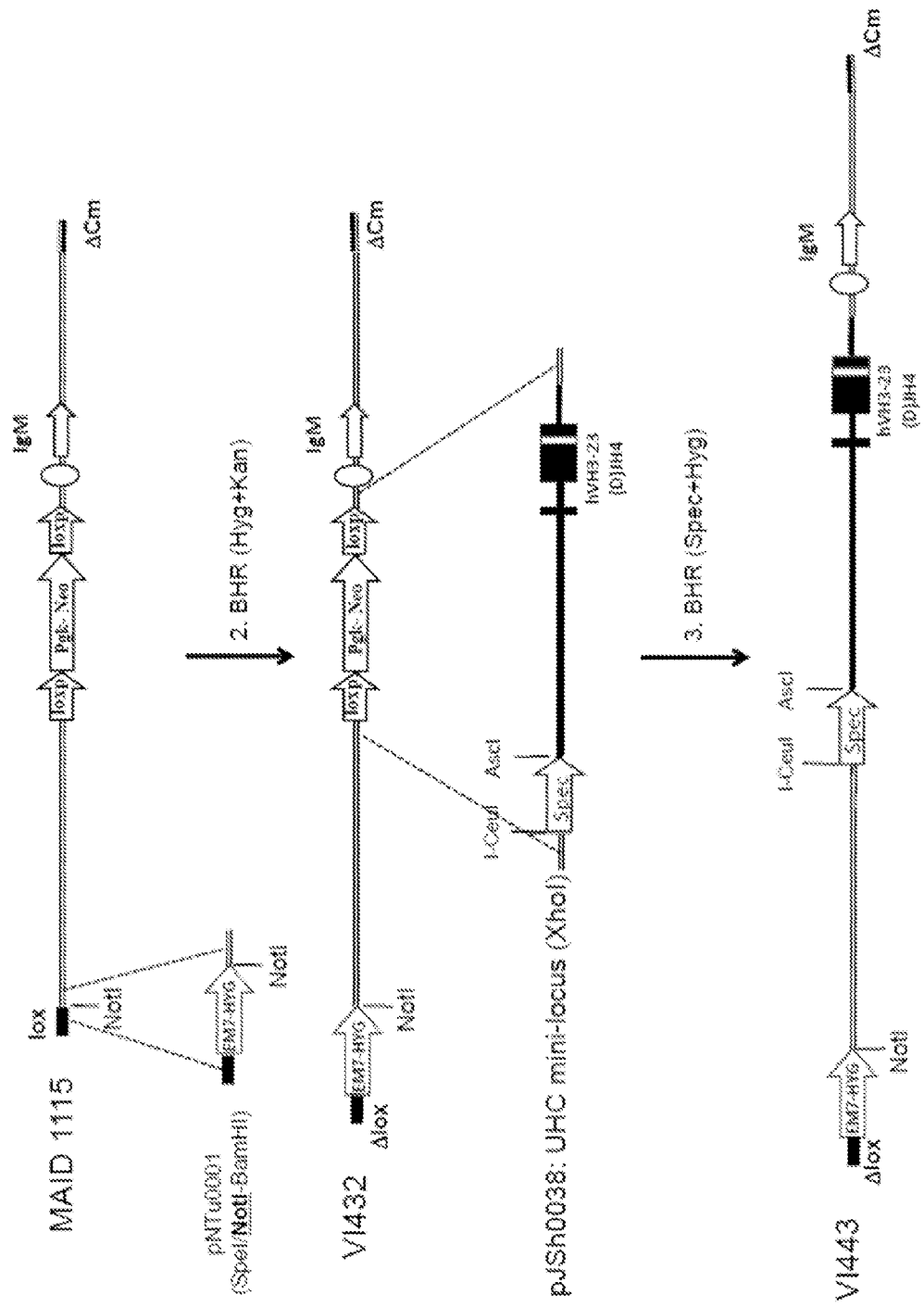
FIG. 2 illustrates schemes for (A) targeting a hygromycin selection cassette (EM7-HYG) into the 5' end of the MAID 1115 BAC clone (2. BHR (Hyg+Kan)); and (B) targeting the UHC mini-locus (pJSh0038) into the upstream of the IgM locus in the VI432 BAC clone (3. BHR (Spec+Hyg)).

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned are hereby incorporated by reference.

The term "antibody", as used herein, includes immunoglobulin molecules comprising four polypeptide chains, two heavy (H) chains and two light (L) chains inter-connected by disulfide bonds. Each heavy chain comprises a heavy chain variable domain and a heavy chain constant region ($C_H$). The heavy chain constant region comprises three domains, $C_H1$, $C_H2$ and $C_H3$. Each light chain comprises a light chain variable domain and a light chain constant region (CO. The heavy chain and light chain variable domains can be further subdivided into regions of hypervariability, termed complementarity determining regions (CDR), interspersed with regions that are more conserved, termed framework regions (FR). Each heavy and light chain variable domain comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3). The term "high affinity" antibody refers to an antibody that has a $K_D$ with respect to its target epitope about of $10^{-9}$ M or lower (e.g., about $1 \times 10^{-9}$ M, $1 \times 10^{-10}$ M, $1 \times 10^{-11}$ M, or about $1 \times 10^{-12}$ M). In one embodiment, $K_D$ is measured by surface plasmon resonance, e.g., BIACORE™; in another embodiment, $K_D$ is measured by ELISA.

The phrase "bispecific antibody" includes an antibody capable of selectively binding two or more epitopes. Bispecific antibodies generally comprise two nonidentical heavy chains, with each heavy chain specifically binding a different epitope—either on two different molecules (e.g., different epitopes on two different immunogens) or on the same molecule (e.g., different epitopes on the same immunogen). If a bispecific antibody is capable of selectively binding two different epitopes (a first epitope and a second epitope), the affinity of the first heavy chain for the first epitope will generally be at least one to two or three or four or more orders of magnitude lower than the affinity of the first heavy chain for the second epitope, and vice versa. Epitopes specifically bound by the bispecific antibody can be on the same or a different target (e.g., on the same or a different protein). Exemplary bispecific antibodies include those with a first heavy chain specific for a tumor antigen and a second heavy chain specific for a cytotoxic marker, e.g., an Fc receptor (e.g., FcγRI, FcγRII, FcγRIII, etc.) or a T cell marker (e.g., CD3, CD28, etc.). Further, the second heavy chain variable domain can be substituted with a heavy chain variable domain having a different desired specificity. For example, a bispecific antibody with a first heavy chain specific for a tumor antigen and a second heavy chain specific for a toxin can be paired so as to deliver a toxin (e.g., saporin, vinca alkaloid, etc.) to a tumor cell. Other exemplary bispecific antibodies include those with a first heavy chain specific for an activating receptor (e.g., B cell receptor, FcγRI, FcγRIIA, FcγRIIIA, FcαRI, T cell receptor, etc.) and a second heavy chain specific for an inhibitory receptor (e.g., FcγRIIB, CD5, CD22, CD72, CD300a, etc.). Such bispecific antibodies can be constructed for therapeutic conditions associated with cell activation (e.g. allergy and asthma). Bispecific antibodies can be made, for example, by combining heavy chains that recognize different epitopes of the same immunogen. For example, nucleic acid sequences encoding heavy chain variable sequences that recognize different epitopes of the same immunogen can be fused to nucleic acid sequences encoding the same or different heavy chain constant regions, and such sequences can be expressed in a cell that expresses an immunoglobulin light chain. A typical bispecific antibody has two heavy chains each having three heavy chain CDRs, followed by (N-terminal to C-terminal) a $C_H1$ domain, a hinge, a $C_H2$ domain, and a $C_H3$ domain, and an immunoglobulin light chain that either does not confer epitope-binding specificity but that can associate with each heavy chain, or that can associate with each heavy chain and that can bind one or more of the epitopes bound by the heavy chain epitope-binding regions, or that can associate with each heavy chain and enable binding of one or both of the heavy chains to one or both epitopes. Similarly, the term "trispecific antibody" includes an antibody capable of selectively binding three or more epitopes.

The term "cell" includes any cell that is suitable for expressing a recombinant nucleic acid sequence. Cells include those of prokaryotes and eukaryotes (single-cell or multiple-cell), bacterial cells (e.g., strains of E. coli, Bacillus spp., Streptomyces spp., etc.), mycobacteria cells, fungal cells, yeast cells (e.g., S. cerevisiae, S. pombe, P. pastoris, P. methanolica, etc.), plant cells, insect cells (e.g., SF-9, SF-21, baculovirus-infected insect cells, Trichoplusia ni, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, W138, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g. a retinal cell that expresses a viral gene (e.g., a PER.C6™ cell).

The phrase "complementarity determining region," or the term "CDR," includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naive or a mature B cell or a T cell. A CDR can be somatically mutated (e.g., vary from a sequence encoded in an animal's germline), humanized, and/or modified with amino acid substitutions, additions, or deletions. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The term "conservative," when used to describe a conservative amino acid substitution, includes substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a variable region to specifically bind a target epitope with a desired affinity. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be substitution of any native residue in a protein with alanine, as used in, for example, alanine scanning mutagenesis. In some embodiments, a conservative substitution is made that has a positive value in the PAM250 log-likelihood matrix disclosed in Gonnet et al. (1992) Exhaustive Matching of the Entire Protein Sequence Database, Science 256:1443-45, hereby incorporated by reference. In some embodiments, the substitution is a moderately conservative substitution wherein the substitution has a nonnegative value in the PAM250 log-likelihood matrix.

In some embodiments, residue positions in an immunoglobulin light chain or heavy chain differ by one or more conservative amino acid substitutions. In some embodiments, residue positions in an immunoglobulin light chain or functional fragment thereof (e.g., a fragment that allows expression and secretion from, e.g., a B cell) are not identical to a light chain whose amino acid sequence is listed herein, but differs by one or more conservative amino acid substitutions.

The phrase "epitope-binding protein" includes a protein having at least one CDR and that is capable of selectively recognizing an epitope, e.g., is capable of binding an epitope with a $K_D$ that is at about one micromolar or lower (e.g., a $K_D$ that is about $1 \times 10^{-6}$ M, $1 \times 10^{-7}$ M, $1 \times 10^{-9}$ M, $1 \times 10^{-9}$ M, $1 \times 10^{-10}$ M, $1 \times 10^{-11}$ M, or about $1 \times 10^{-12}$ M). Therapeutic epitope-binding proteins (e.g., therapeutic antibodies) frequently require a $K_D$ that is in the nanomolar or the picomolar range.

The phrase "functional fragment" includes fragments of epitope-binding proteins that can be expressed, secreted, and specifically bind to an epitope with a $K_D$ in the micromolar, nanomolar, or picomolar range. Specific recognition includes having a $K_D$ that is at least in the micromolar range, the nanomolar range, or the picomolar range.

The term "germline" in reference to an immunoglobulin nucleic acid sequence includes a nucleic acid sequence that can be passed to progeny.

The phrase "heavy chain," or "immunoglobulin heavy chain" includes an immunoglobulin heavy chain sequence, including immunoglobulin heavy chain constant region sequence, from any organism. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a $C_H1$ domain, a hinge, a $C_H2$ domain, and a $C_H3$ domain. A functional fragment of a heavy chain includes a fragment that is capable of specifically recognizing an epitope (e.g., recognizing the epitope with a $K_D$ in the micromolar, nanomolar, or picomolar range), that is capable of expressing and secreting from a cell, and that comprises at least one CDR. A heavy chain variable domain is encoded by a variable region gene sequence, which generally comprises $V_H$, $D_H$, and $J_H$ segments derived from a repertoire of $V_H$, $D_H$, and $J_H$ segments present in the germline. Sequences, locations and nomenclature for V, D, and J heavy chain segments for various organisms can be found in IMGT database, www.imgt.org.

The term "identity" when used in connection with a sequence, includes identity as determined by a number of different algorithms known in the art that can be used to measure nucleotide and/or amino acid sequence identity. In some embodiments described herein, identities are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008). The length of the sequences compared with respect to identity of sequences will depend upon the particular sequences, but in the case of a light chain constant domain, the length should contain sequence of sufficient length to fold into a light chain constant domain that is capable of self-association to form a canonical light chain constant domain, e.g., capable of forming two beta sheets comprising beta strands and capable of interacting with at least one $C_H1$ domain of a human or a mouse. In the case of a $C_H1$ domain, the length of sequence should contain sequence of sufficient length to fold into a $C_H1$ domain that is capable of forming two beta sheets comprising beta strands and capable of interacting with at least one light chain constant domain of a mouse or a human.

The phrase "immunoglobulin molecule" includes two immunoglobulin heavy chains and two immunoglobulin light chains. The heavy chains may be identical or different, and the light chains may be identical or different.

The phrase "light chain" includes an immunoglobulin light chain sequence from any organism, and unless otherwise specified includes human kappa and lambda light chains and a VpreB, as well as surrogate light chains. Light chain variable domains typically include three light chain CDRs and four framework (FR) regions, unless otherwise specified. Generally, a full-length light chain includes, from amino terminus to carboxyl terminus, a variable domain that includes FR1-CDR1-FR2-CDR2-FR3-CDR3-FR4, and a light chain constant region. A light chain variable domain is encoded by a light chain variable region gene sequence, which generally comprises $V_L$ and $J_L$ segments, derived from a repertoire of V and J segments present in the germline. Sequences, locations and nomenclature for V and J light chain segments for various organisms can be found in IMGT database, www.imgt.org. Light chains include those, e.g., that do not selectively bind either a first or a second epitope selectively bound by the epitope-binding protein in which they appear. Light chains also include those that bind and recognize, or assist the heavy chain with binding and recognizing, one or more epitopes selectively bound by the epitope-binding protein in which they appear. Common or universal light chains include those derived from a human Vκ1-39Jκ5 gene or a human Vκ3-20Jκ1 gene, and include somatically mutated (e.g., affinity matured) versions of the same. Dual light chains (DLC) include those derived from a light chain locus comprising no more than two human Vκ segments, e.g., a human Vκ1-39 gene segment and a human Vκ3-20 gene segment, and include somatically mutated (e.g., affinity matured) versions of the same.

The phrase "somatically hypermutated" includes reference to a nucleic acid sequence from a B cell that has undergone class-switching, wherein the nucleic acid sequence of an immunoglobulin variable region (e.g., nucleotide sequence encoding a heavy chain variable domain or including a heavy chain CDR or FR sequence) in the class-switched B cell is not identical to the nucleic acid sequence in the B cell prior to class-switching, such as, for example, a difference in a CDR or framework nucleic acid sequence between a B cell that has not undergone class-switching and a B cell that has undergone class-switching. "Somatically mutated" includes reference to nucleic acid sequences from affinity-matured B cells that are not identical to corresponding immunoglobulin variable region sequences in B cells that are not affinity-matured (i.e., sequences in the genome of germline cells). The phrase "somatically mutated" also includes reference to an immunoglobulin variable region nucleic acid sequence from a B cell after exposure of the B cell to an epitope of interest, wherein the nucleic acid sequence differs from the corresponding nucleic acid sequence prior to exposure of the B cell to the epitope of interest. The phrase "somatically mutated" refers to sequences from antibodies that have been generated in an animal, e.g., a mouse having human immunoglobulin variable region nucleic acid sequences, in response to an immunogen challenge, and that result from the selection processes inherently operative in such an animal.

The term "unrearranged," with reference to a nucleic acid sequence, includes nucleic acid sequences that exist in the germline of an animal cell.

The phrase "variable domain" includes an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4.

The term "operably linked" refers to a relationship wherein the components operably linked function in their intended manner. In one instance, a nucleic acid sequence encoding a protein may be operably linked to regulatory sequences (e.g., promoter, enhancer, silencer sequence, etc.) so as to retain proper transcriptional regulation. In one instance, a nucleic acid sequence of an immunoglobulin variable region (or V(D)J segments) may be operably linked to a nucleic acid sequence of an immunoglobulin constant region so as to allow proper recombination between the sequences into an immunoglobulin heavy or light chain sequence.

"Functional" as used herein, e.g., in reference to a functional polypeptide, includes a polypeptide that retains at least one biological activity normally associated with the native protein. In another instance, a functional immunoglobulin gene segment may include a variable gene segment that is capable of productive rearrangement to generate a rearranged immunoglobulin gene sequence.

"Neutral pH" includes pH between about 7.0 and about 8.0, e.g., pH between about 7.0 and about 7.4, e.g., between about 7.2 and about 7.4, e.g., physiological pH. "Acidic pH" includes pH of 6.0 or lower, e.g., pH between about 5.0 and about 6.0, pH between about 5.75 and about 6.0, e.g., pH of endosomal or lysosomal compartments.

The term "polymorphic variant" as used herein includes a sequence in which one or more nucleotides or amino acids have been substituted by a different nucleotides or amino acid as compared to the given sequence. Polymorphic alleles of the human immunoglobulin heavy chain variable gene segments ($V_H$ genes) have largely been the result of insertion/deletion of gene segments and single nucleotide differences within coding regions, both of which have the potential to have functional consequences on the immunoglobulin molecule. Examples of common polymorphic alleles of the human immunoglobulin $V_H$ genes are well known in the art (see, for example, U.S. Ser. No. 13/653,456, incorporated by reference herein in its entirety).

The term "substantial" or "substantially all" when used to refer to an amount of gene segments (e.g., "substantially all" V, D, or J gene segments) includes both functional and non-functional gene segments and includes, in various embodiments, e.g., 80% or more, 85% or more, 90% or more, 95% or more, 96% or more, 97% or more, 98% or more, or 99% or more of all V, D, or J gene segments. In various embodiments, "substantially all" gene segments include, e.g., at least 95%, 96%, 97%, 98%, or 99% of functional (i.e., non-pseudogene) gene segments).

Non-Human Animals Comprising a Rearranged Heavy Chain Variable Region Gene Sequence and Optionally a Limited Repertoire of Unrearranged Light Chain Variable Gene Segments While a variety of bispecific antibodies with dual antigen binding properties have been developed, the specificity and affinity of the light chain or heavy chain variable regions in conventional bispecific antibodies had to be sacrificed to some extent because, in conventional bispecific antibodies, either a heavy chain or a light chain variable region alone contributes to binding each separate antigenic determinant, whereas in regular antibodies, both light and heavy chain variable regions can contribute to binding the same antigenic determinant.

Therefore, generation of light chain variable regions that have an ability to bind an antigen independently from a heavy chain variable region can be useful for making light chain variable domains ($V_L$s) for use in antigen-binding molecules (e.g., bispecific binding molecules that comprise a heavy chain constant region (e.g., selected from a $C_H1$, a hinge, a $C_H2$, a $C_H3$, and a combination thereof) fused with $V_L$, particularly those that do not comprise a heavy chain variable domain, including heterodimers having the same or similar heavy chain constant region but $V_L$s with different specificities and/or affinities.

One approach to produce such light chain variable domains that can bind to an antigen independently from a heavy chain variable region is to apply a selective pressure on nucleotide sequences that encode a variable region or domain of a light chain ($V_L$) to generate light chain CDR3s with more diverse antigenic binding repertoire. As disclosed herein, this can be achieved by generating a genetically modified non-human animal that contains, in its genome, a rearranged human immunoglobulin heavy chain variable region nucleotide sequence. Since the heavy chain sequence is restricted to a common or universal (i.e., the same or a very similar) sequences in these animals, the light chain variable region nucleotide sequences (i.e., genes) will be forced to make light chain CDR3s with more diverse and efficient antigenic binding properties, which can bind an antigenic determinant independently from heavy chain variable regions. Furthermore, as disclosed herein, the precise replacement of germline variable region gene segments (e.g., by homologous recombination-mediated gene targeting) allows for making animals (e.g., mice) that have partly human immunoglobulin loci. Because the partly human immunoglobulin loci rearrange, hypermutate, and somatically mutate (e.g., class switch) normally, the partly human immunoglobulin loci generate antibodies in the animal that comprise human variable regions. These animals exhibit a humoral immune system that is substantially similar to wild type animals, and display normal cell populations and normal lymphoid organ structures—even where the animals lack a full repertoire of human variable region gene segments. Immunizing these animals (e.g., mice) results in robust humoral responses that display a wide diversity of variable gene segment usage. Nucleotide sequences that encode the variable regions can be identified and cloned, then fused (e.g., in an in vitro system) with any sequences of choice, e.g., any immunoglobulin isotype suitable for a particular use, resulting in an antibody or antigen-binding protein derived wholly from human sequences.

In addition, by utilizing animals (e.g., mice or rats) that have a restricted (limited) light chain variable region gene segment repertoire, e.g., a restricted light chain variable segment repertoire comprising one or more but less than the wild type number of human $V_L$ gene segments (e.g., a dual light chain or "DLC," US Patent Application Publication No. 2013/0198880, incorporated by reference herein in its entirety) in combination with the rearranged human immunoglobulin heavy chain variable region nucleotide sequence described above, an immunoglobulin light chain variable domain that can more efficiently pair with an immunoglobulin heavy chain variable domain can be produced. Furthermore, by introducing histidine codons, e.g., via addition of one or more histidine codons or substitution of one or more non-histidine codons with histidine codons, into the limited light chain variable gene segments in the genome of the non-human animals described herein, light chain variable region amino acid sequences that can confer improved pH-dependent recyclability to the antigen-binding proteins (e.g., bispecific or trispecific antibodies) can be generated.

In some embodiments, the genetically modified non-human animals as described herein provide a greater yield of antibodies, while limiting diversity at the same time, thereby increasing the probability of successful pairing of light chains with heavy chains generated in a non-human animal comprising a single rearranged light chain variable region (e.g., a Universal Light Chain ("ULC") mouse; see, e.g., U.S. pre-grant publication 2013/0185821, incorporated by reference herein). In some embodiments, the light chains may themselves exhibit antigen-binding properties. In some embodiments, the non-human animal may be induced to produce antigen-binding proteins exhibiting antigen specificity that resides in their light chains (e.g., by limiting a mouse or rat's immunoglobulin heavy chain repertoire; e.g., by replacing the mouse or rat heavy chain locus with a locus comprising a single rearranged human immunoglobulin heavy chain variable region nucleotide sequence). In some embodiments, antigen-binding proteins (e.g., antibodies) produced in such animals will be specific for a particular first epitope (e.g., effector antigens, cytotoxic molecules, Fc receptors, toxins, activating or inhibitory receptors, T cell markers, immunoglobulin transporters, etc.) through their light chain binding. Such epitope-specific human light chains derived from these non-human animals may be co-expressed with human heavy chains derived from a mouse with a limited light chain repertoire, e.g., a ULC mouse or rat, wherein the heavy chain is selected based on its ability to bind a second epitope (e.g., a second epitope on a different antigen).

In various aspects, a non-human animal is provided comprising in its germline genome an immunoglobulin heavy chain locus that comprises a rearranged human immunoglobulin heavy chain variable region nucleotide sequence (i.e., a rearranged heavy chain VDJ sequence). In some embodiments, the rearranged human immunoglobulin heavy chain variable region nucleotide sequence is operably linked to a human or a non-human heavy chain constant region sequence. In some embodiments, an immunoglobulin heavy chain variable domain encoded by the rearranged heavy chain variable region nucleotide sequence is not immunogenic to the non-human animal. In some embodiments, the non-human animal is modified to comprise a nucleotide sequence that encodes two copies, three copies, four copies or more of the rearranged heavy chain variable domain operably linked to a heavy chain constant domain. In some embodiments, the nucleotide sequence encodes a plurality of copies of the rearranged human immunoglobulin heavy chain variable region nucleotide sequence. For example, the nucleotide sequence can encode at least one, two, three, four, five copies of the rearranged human immunoglobulin heavy chain variable region nucleotide sequence. In some embodiments, the nucleotide sequence encodes 1, 2, 3, 4, 5, 6, 7, 8, 9, or 10 copies of the rearranged human immunoglobulin heavy chain variable region nucleotide sequence. In some embodiments, the locus comprises a plurality of copies of the rearranged human immunoglobulin heavy chain variable region nucleotide sequence operably linked to a heavy chain constant domain gene sequence.

In other aspects, a non-human animal is provided that is genetically engineered to contain an immunoglobulin light chain locus that encodes a rearranged heavy chain variable domain (i.e., a light chain locus that comprises a rearranged human immunoglobulin heavy chain variable region nucleotide sequence) operably linked to a human or a non-human light chain constant region gene sequence. For example, in some embodiments, a rearranged human immunoglobulin heavy chain variable region nucleotide sequence (i.e., a pre-designed VDJ region; i.e., a common or universal heavy chain sequence) can be operably linked to a light chain constant region gene sequence by targeting the rearranged heavy chain sequence into a mouse or rat light chain loci, either kappa or lambda. Thus, in some embodiments, the nucleotide sequence encoding the rearranged heavy chain variable domain is present in the germline genome of the non-human animal. In some embodiments, the rearranged heavy chain variable domain expressed by the genetically modified non-human animal is not immunogenic to the non-human animal. In some embodiments, the non-human animal is modified to comprise a nucleotide sequence that encodes two copies, three copies, four copies or more of the rearranged human immunoglobulin heavy chain variable region nucleotide sequence operably linked to a light chain constant domain. In some embodiments, the nucleotide sequence can encode a plurality of copies of the rearranged human immunoglobulin heavy chain variable region nucleotide sequence. For example, the nucleotide sequence encodes at least 1, 2, 3, 4, 5, 6, 7, 8, 9, or 10 copies of the rearranged human immunoglobulin heavy chain variable region nucleotide sequence. In some embodiments, the locus comprises a plurality of copies of the rearranged human immunoglobulin heavy chain variable region nucleotide sequence operably linked to a light chain constant domain gene sequence.

In various aspects, the immunoglobulin light chain locus of the non-human animals described herein comprises a limited repertoire of light chain variable gene segments, e.g., one or more but less than the wild type number of human $V_L$ gene segments; and one or more human $J_L$ gene segments, operably linked to a non-human light chain constant region nucleic acid sequence. Thus, genetically modified non-human animals are provided comprising in their genomes: (i) an immunoglobulin heavy chain locus that comprises a rearranged human heavy chain variable region nucleic acid sequence operably linked to a human or non-human heavy chain constant region nucleic acid sequence; and (ii) an immunoglobulin light chain locus comprising two or more but less than the wild type number of human immunoglobulin light chain variable $V_L$ and $J_L$ gene segments operably linked to a light chain constant region nucleic acid sequence. In some embodiments, the light chain constant region is a rat or a mouse constant region, e.g., a rat or a mouse Cκ constant region. In some embodiments, the human variable region gene segments are capable of rearranging and encoding human variable domains of an antibody, and the non-human animal does not comprise an endogenous $V_L$ gene segment. In some embodiments, the non-human animal comprises five human Jκ gene segments, e.g., Jκ1, Jκ2, Jκ3, Jκ4, and Jκ5 gene segments. In some embodiments, the immunoglobulin light chain locus comprises two human $V_L$ gene segments, Vκ1-39 and Vκ3-20. In some embodiments, one or more (e.g., 2, 3, 4, or 5) human $V_L$ gene segments and two or more human $J_L$ gene segments are present at an endogenous light chain locus, e.g., at an endogenous kappa light chain locus. In some embodiments, the mouse comprises a functional λ light chain locus. In some embodiments, the mouse comprises a non-functional λ light chain locus. In some embodiments, the one or more human $V_H$, one or more human $D_H$, and one or more human $J_H$ gene segments are operably linked to a mouse or a rat heavy chain constant region sequence.

In some embodiments, genetically modified mice comprising in their genomes (i) an immunoglobulin heavy chain locus that comprises a rearranged human heavy chain variable region nucleic acid sequence operably linked to a human or non-human heavy chain constant region nucleic acid sequence, and (ii) an immunoglobulin light chain locus comprising two or more but less than the wild type number of human immunoglobulin light chain variable $V_L$ and $J_L$ gene segments operably linked to a light chain constant region nucleic acid sequence, demonstrate CD19+B cell numbers and mature B cell numbers that are substantially the same as the numbers observed in wild type mice or mice containing other modifications of their immunoglobulin loci (i.e., genetically modified control mice; e.g., VELOCIMMUNE® mice, in which the humoral immune system of the mouse functions like that of a wild type mouse). In some embodiments, such mice demonstrate an increase in immature B cell numbers in the spleen compared to genetically modified control mice. In specific embodiments, such mice demonstrate about a 2-fold, about a 3-fold, about a 4-fold, or about a 5-fold or greater fold increase in immature B cell numbers in the spleen compared to genetically modified control mice. In some embodiments, such mice are also substantially similar to wild type mice or genetically modified control mice with respect to kappa and gamma light chain usage in splenic B cells. In some embodiments, such mice demonstrate increased surface IgM on splenic B cells (i.e., more IgM surface expression per cell) as compared to genetically modified control mice. In some embodiments, such mice demonstrate altered peripheral B cell development through various stages of B cell development in the splenic compartment compared to genetically modified control mice, for example an increase in immature, T1 and/or marginal zone B cells. In some embodiments, such mice demonstrate numbers of CD19+ B cells in the bone marrow compartment that are substantially similar to the numbers demonstrated in genetically modified control mice. In some embodiments, such mice demonstrate fewer pro-B cells in the bone marrow compared to genetically modified control mice. In specific embodiments, the numbers of pro-B cells in the bone marrow compartment are reduced by about 2-fold, about 5-fold, about 10-fold, about 15-fold, about 20-fold, about 25-fold or more compared to genetically modified control mice. In some embodiments, such mice demonstrate about 2-fold, about 3-fold, about 4-fold, about 5-fold, etc. fewer immature and/or mature B cells in the bone marrow compared to genetically modified control mice. In some embodiments, such mice exhibit a slight preference (e.g., 2-fold increase) in the bone marrow compartment for usage of lambda light chain genes compared to genetically modified control mice.

In another aspect, a non-human animal is provided comprising a genetically modified immunoglobulin locus comprising: (a) a first nucleotide sequence that encodes a rearranged heavy chain variable domain (i.e., where the first nucleotide sequence is a rearranged human immunoglobulin heavy chain variable region nucleotide sequence), wherein the first nucleotide sequence is operably linked to a light chain constant region gene sequence; and (b) a second nucleotide sequence that encodes a human light chain variable domain (i.e., where the second nucleotide sequence is an unrearranged human immunoglobulin light chain variable region nucleotide sequence), wherein the second nucleotide sequence is operably linked to a heavy chain constant region gene sequence. For example, in some embodiments, a rearranged heavy chain from a pre-designed VDJ region (i.e., a rearranged human immunoglobulin heavy chain variable region nucleotide sequence; i.e., a common or universal heavy chain sequence) can be operably linked to a light chain constant region gene sequence by targeting the rearranged heavy chain sequence into a mouse light chain loci, either kappa or lambda. Thus, as in other embodiments, this genetically engineered immunoglobulin locus may be present in the germline genome of the non-human animal. Genetically modified non-human animals comprising a human immunoglobulin light chain variable region nucleotide sequences in operable linkage with a heavy chain constant region gene sequences are described in U.S. pre-grant publication 2012/0096572, which is incorporated herein by reference. In some embodiments, the first nucleotide sequence that encodes the rearranged heavy chain variable domain is operably linked to a κ light chain constant region gene sequence. In some embodiments, the first nucleotide sequence that encodes the rearranged heavy chain variable domain is operably linked to a mouse or rat κ light chain constant region gene sequence. In some embodiments, the first nucleotide sequence that encodes the rearranged heavy chain variable domain is operably linked to a human κ light chain constant region gene sequence. In some embodiments, the first nucleotide sequence that encodes the rearranged heavy chain variable domain is operably linked to a λ light chain constant region gene sequence. In some embodiments, the first nucleotide sequence that encodes the rearranged heavy chain variable domain is operably linked to a mouse or rat λ light chain constant region gene sequence. In some embodiments, the first nucleotide sequence that encodes the rearranged heavy chain variable domain is operably linked to a human λ light chain constant region gene sequence.

In some embodiments, a genetically modified mouse comprising an immunoglobulin light chain locus containing a rearranged human immunoglobulin heavy chain variable region nucleotide sequence and an immunoglobulin heavy chain locus containing unrearranged human immunoglobulin light chain variable domain sequences (e.g., kappa light chain genes) presents CD19+ and pre-B cell frequencies in the bone marrow that are altered relative to a wild type mouse or a genetically modified mouse with other modifications at an immunoglobulin locus (i.e., genetically modified control mice; e.g., VELOCIMMUNE® mice, in which the humoral immune system of the mouse functions like that of a wild type mouse). In specific embodiments, the CD19+B cell and pre-B cell numbers in the bone marrow are 2-fold lower, 3-fold lower, 4-fold lower or 5-fold lower compared to a wild type mouse or a genetically modified immunoglobulin locus control mouse. In specific embodiments, the number of immature B cells in the bone marrow is 2-fold less, 3-fold less, 4-fold less or 5-fold less compared to a wild type mouse or a genetically modified immunoglobulin locus control mouse. In some embodiments, a genetically modified mouse comprising an immunoglobulin light chain locus containing a rearranged human immunoglobulin heavy chain variable region nucleotide sequence and an immunoglobulin heavy chain locus containing unrearranged human immunoglobulin light chain variable domain sequences (e.g., kappa light chain genes) does not express or essentially does not express lambda light chain genes in the bone marrow cells. In some embodiments, a genetically modified mouse comprising an immunoglobulin light chain locus containing a rearranged human immunoglobulin heavy chain variable region nucleotide sequence and an immunoglobulin heavy chain locus containing unrearranged human immunoglobulin light chain variable domain sequences (e.g., kappa light chain genes) has reduced levels of splenic B cells compared to a wild type mouse or a genetically modified immunoglobulin locus control mouse. In specific embodiments, the levels of splenic B cells and mature B cells are 2-fold lower, 3-fold lower, 4-fold lower or 5-fold lower compared to a wild type mouse or a genetically modified immunoglobulin locus control mouse. In some embodiments, a genetically modified mouse comprising an immunoglobulin light chain locus containing a rearranged human immunoglobulin heavy chain variable region nucleotide sequence and an immunoglobulin heavy chain locus containing unrearranged human immunoglobulin light chain variable domain sequences (e.g., kappa light chain genes) does not express or essentially does not express lambda light chain genes in splenic B cells. In specific embodiments, a genetically modified mouse comprising an immunoglobulin light chain locus containing a rearranged human immunoglobulin heavy chain variable region nucleotide sequence and an immunoglobulin heavy chain locus containing unrearranged human immunoglobulin light chain variable domain sequences (e.g., kappa light chain genes) has an increased frequency of cells in the T1 phase in the spleen compared to a wild type mouse or a genetically modified immunoglobulin locus control mouse.

In some embodiments, the non-human animal is a mammal. Although embodiments employing a rearranged human heavy chain variable domain in a mouse (i.e., a mouse with an immunoglobulin locus comprising a rearranged human immunoglobulin heavy chain variable region nucleotide sequence) are extensively discussed herein, other non-human animals that comprise a genetically modified immunoglobulin locus encoding a rearranged human heavy chain variable domain are also provided. Such non-human animals include any of those which can be genetically modified to express the rearranged human immunoglobulin heavy chain variable region nucleotide sequence as disclosed herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing somatic cell nuclear transfer (SCNT) to transfer the genetically modified genome to a suitable cell, e.g., an enucleated oocyte, and gestating the modified cell (e.g., the modified oocyte) in a non-human animal under suitable conditions to form an embryo. Methods for modifying a non-human animal genome (e.g., a pig, cow, rodent, chicken, etc. genome) include, e.g., employing a zinc finger nuclease (ZFN) or a transcription activator-like effector nuclease (TALEN) to modify a genome to include a rearranged human immunoglobulin heavy chain variable region nucleotide sequence.

In some embodiments, the non-human animal is a small mammal, e.g., of the superfamily Dipodoidea or Muroidea. In some embodiments, the genetically modified animal is a rodent. In some embodiments, the rodent is selected from a mouse, a rat, and a hamster. In some embodiments, the rodent is selected from the superfamily Muroidea. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, *Malagasy* rats and mice), Platacanthomyidae (e.g., spiny dormice), and Spalacidae (e.g., mole rats, bamboo rats, and zokors). In a specific embodiment, the genetically modified rodent is selected from a true mouse or rat (family Muridae), a gerbil, a spiny mouse, and a crested rat. In some embodiments, the genetically modified mouse is from a member of the family Muridae. In some embodiments, the animal is a rodent. In specific embodiments, the rodent is selected from a mouse and a rat. In some embodiments, the non-human animal is a mouse.

In some embodiments, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6N, C57BL/6NJ, C57BL/10, C57BL/10ScSn, C57BL/10Cr, and C57BL/Ola. In another embodiment, the mouse is a 129 strain. In some embodiments, the 129 strain is selected from the group consisting of 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al. (2000) Establishment and Chimera Analysis of 129/SvEv- and C57BL/6-Derived Mouse Embryonic Stem Cell Lines). In some embodiments, the genetically modified mouse is a mix of an aforementioned 129 strain and an aforementioned C57BL strain (e.g., a C57BL/6 strain). In another embodiment, the mouse is a mix of aforementioned 129 strains, or a mix of aforementioned C57BL/6 strains. In some embodiments, the 129 strain of the mix is a 129S6 (129/SvEvTac) strain. In another embodiment, the mouse is a mix of a 129/SvEv- and a C57BL/6-derived strain. In a specific embodiment, the mouse is a mix of a 129/SvEv- and a C57BL/6-derived strain as described in Auerbach et al. 2000 BioTechniques 29:1024-1032. In another embodiment, the mouse is a BALB strain, e.g., BALB/c strain. In another embodiment, the mouse is a mix of a BALB strain (e.g., BALB/c strain) and another aforementioned strain.

In some embodiments, the non-human animal is a rat. In some embodiments, the rat is selected from a Wistar rat, an LEA strain, a Sprague Dawley strain, a Fischer strain, F344, F6, ACI, and Dark Agouti (DA). In some embodiments, the rat strain is a mix of two or more of a strain selected from the group consisting of Wistar, LEA, Sprague Dawley, Fischer, F344, F6, ACI and Dark Agouti (DA).

In some embodiments, a genetically modified mouse comprising in its germline genome an immunoglobulin heavy chain locus that comprises a rearranged human immunoglobulin heavy chain variable region nucleotide sequence generates splenic mature and immature B cell populations that are essentially normal relative to a wild type mouse. In some embodiments, such a genetically modified mouse has a slight decrease in the usage of light chain lambda gene sequences relative to wild type in splenic B cells. In specific embodiments, such a genetically modified mouse uses light chain lambda gene sequences with a 2-fold, 3-fold, 4-fold or 5-fold lower frequency than wild type in splenic B cells. In some embodiments, such a genetically modified mouse has a slight decrease in T1 population splenic B cells and an increase in marginal zone splenic B cells relative to wild type. In some embodiments, such a genetically modified mouse has near normal B cell populations in the bone marrow. In some embodiments, such a genetically modified mouse uses lambda gene sequences with a frequency that is half or less than half of the frequency that lambda gene sequences are used in wild type.

In various embodiments, as described herein, the rearranged heavy chain variable domain (e.g., the rearranged human immunoglobulin heavy chain variable region nucleotide sequence) is derived from a human V, D, and J gene sequence or segment. In some embodiments, the rearranged heavy chain variable domain is derived from a human germline V segment, a human germline D segment, and a human germline J segment. In some embodiments, the human $V_H$ segment corresponds to observed variants in the human population.

In various embodiments, as described herein, the human V gene segment is selected from the group consisting of $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H3$-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, $V_H7$-81, and a polymorphic variant thereof. In some embodiments, the human V segment is $V_H3$-23 or polymorphic variant thereof. In various embodiments, as described herein, the human D gene segment is selected from the group consisting of D1-1, D1-7, D1-14, D1-20, D1-26, D2-2, D2-8, D2-15, D2-21, D3-3, D3-9, D3-10, D3-16, D3-22, D4-4, D4-11, D4-17, D4-23, D5-12, D5-5, D5-18, D5-24, D6-6, D6-13, D6-19, D6-25, D7-27, and a polymorphic variant thereof. In some embodiments, the human or non-human animal heavy chain constant region sequence comprises a sequence selected from a $C_H1$, a hinge, a $C_H2$, a $C_H3$, and a combination thereof. In specific embodiments, the constant region sequence comprises a $C_H1$, a hinge, a $C_H2$, and a $C_H3$. In various embodiments, as described herein, the human J gene segment is selected from the group consisting of $J_H1$, $J_H2$, $J_H3$, $J_H4$, $J_H5$, $J_H6$, and a polymorphic variant thereof. In some embodiments, the rearranged human immunoglobulin heavy chain variable region nucleotide sequence encodes the sequence of human $V_H3$-23/GY/$J_H4$-4 (SEQ ID NO: 137). In some embodiments, the rearranged heavy chain variable domain encoded by and expressed from the rearranged human immunoglobulin heavy chain variable region nucleotide sequence comprises the sequence of human $V_H3$-23/$X_1X_2$/J (wherein X1 is any amino acid, and X2 is any amino acid). In some embodiments, $X_1$ is Gly and $X_2$ is Tyr. In some embodiments, the rearranged heavy chain variable domain comprises the sequence of human $V_H3$-23/$X_1X_2$/$J_H4$-4 (wherein X1 is any amino acid, and $X_2$ is any amino acid). In some embodiments, $X_2$ is an amino acid comprising a phenyl group. In specific embodiments, $X_2$ is selected from Tyr and Phe.

In some embodiments, the rearranged human immunoglobulin heavy chain variable region nucleotide sequence comprises a human D segment that is not autoreactive (non-immunogenic) in the animal. In some embodiments, the nucleotide sequence comprises a human D segment that is capable of being expressed in a heavy chain variable sequence of a mature B cell of a mouse. In some embodiments, the D segment is a segment that has been expressed in a mouse that comprises a humanized immunoglobulin locus comprising a human $V_H$, a human D, and a human $J_H$ segment.

Various embodiments utilize or encompass features or sequence information derived from VELOCIMMUNE® humanized mice. VELOCIMMUNE® humanized mice contain a precise, large-scale replacement of germline variable regions of mouse immunoglobulin heavy chain (IgH) and immunoglobulin light chain (e.g., κ light chain, Igκ) with corresponding human immunoglobulin variable regions, at the endogenous loci (see, e.g., U.S. Pat. Nos. 6,596,541 and 8,502,018, the entire contents of which are incorporated herein by reference). In total, about six megabases of mouse loci are replaced with about 1.5 megabases of human genomic sequence. This precise replacement results in a mouse with hybrid immunoglobulin loci that make heavy and light chains that have a human variable regions and a mouse constant region. The precise replacement of mouse $V_H$-$D$-$J_H$ and Vκ-Jκ segments leave flanking mouse sequences intact and functional at the hybrid immunoglobulin loci. The humoral immune system of the mouse functions like that of a wild type mouse. B cell development is unhindered in any significant respect and a rich diversity of human variable regions is generated in the mouse upon antigen challenge. Moreover, VELOCIMMUNE® humanized mice display an essentially normal, wild-type response to immunization that differs only in one significant respect from wild type mice—the variable regions generated in response to immunization are fully human. VELOCIMMUNE® humanized mice are possible because immunoglobulin gene segments for heavy and κ light chains rearrange similarly in humans and mice.

Although the loci are not identical, they are similar enough that humanization of the heavy chain variable gene locus can be accomplished by replacing about three million base pairs of contiguous mouse sequence that contains all the $V_H$, D, and $J_H$ gene segments with about one million bases of contiguous human genomic sequence covering basically the equivalent sequence from a human immunoglobulin locus. For example, in some embodiments, the D segment is derived from a heavy chain expressed in a mature B cell of a VELOCIMMUNE® humanized mouse immunized with an antigen, wherein the D segment contributes no more than two amino acids to the heavy chain CDR3 sequence.

In particular embodiments, a VELOCIMMUNE® mouse comprising an immunoglobulin heavy chain locus encoding a rearranged heavy chain variable domain (i.e., comprising an immunoglobulin heavy chain locus that comprises a rearranged human immunoglobulin heavy chain variable region nucleotide sequence) is provided. A VELOCIMMUNE® mouse so modified comprises a replacement of mouse immunoglobulin heavy chain variable gene segments with a rearranged human immunoglobulin heavy chain variable region nucleotide sequence (i.e., a Universal Heavy Chain sequence at an endogenous heavy chain locus), and a replacement of mouse immunoglobulin κ light chain variable gene segments with at least 40 human Vκ gene segments and five human Jκ gene segments. In some embodiments, the human Vκ gene segments are selected from the group consisting of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1 D-8, Vκ1D-12, Vκ1 D-13, Vκ1 D-16, Vκ1 D-17, Vκ1 D-22, Vκ1 D-27, Vκ1D-32, Vκ1D-33, Vκ1 D-35, Vκ1D-37, Vκ1 D-39, Vκ1 D-42, Vκ1 D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2- 30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3. In some embodiments, the human Vκ gene segments comprise Vκ4-1, Vκ5-2, Vκ7-3, Vκ2-4, Vκ1-5, and Vκ1-6. In one embodiment, the Vκ gene segments comprise Vκ3-7, Vκ1-8, Vκ1-9, Vκ2-10, Vκ3-11, Vκ1-12, Vκ1-13, Vκ2-14, Vκ3-15 and Vκ1- 16. In some embodiments, the human Vκ gene segments comprise Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, and Vκ2-30. In some embodiments, the human Vκ gene segments comprise Vκ3-31, Vκ1-32, Vκ1-33, Vκ3-34, Vκ1-35, Vκ2-36, Vκ1-37, Vκ2-38, Vκ1-39, and Vκ2-40. In specific embodiments, the Vκ gene segments comprise contiguous human immunoglobulin κ gene segments spanning the human immunoglobulin κ light chain locus from Vκ4-1 through Vκ2-40, and the Jκ gene segments comprise contiguous gene segments spanning the human immunoglobulin κ light chain locus from Jκ1 through Jκ5. In some embodiments, the rearranged human heavy chain variable domain nucleotide sequence is operably linked to a mouse heavy chain constant region sequence. A VELOCIMMUNE® mouse comprising an immunoglobulin heavy chain locus encoding a rearranged heavy chain variable domain (i.e., comprising an immunoglobulin heavy chain locus that comprises a rearranged human immunoglobulin heavy chain variable region nucleotide sequence) can be used in any of the aspects, embodiments, methods, etc. described herein.

In various embodiments, the rearranged human immunoglobulin heavy chain variable region nucleotide sequence is operably linked to a human or mouse heavy chain constant region gene sequence (e.g., a heavy chain constant region gene sequence that encodes an immunoglobulin isotype selected from IgM, IgD, IgA, IgE, IgG, and combinations thereof). For example, genetically modified non-human animals are provided comprising immunoglobulin loci in which: (a) a first nucleotide sequence encodes a rearranged heavy chain variable domain (i.e., where the first nucleotide sequence is a rearranged human immunoglobulin heavy chain variable region nucleotide sequence), wherein the first nucleotide sequence is operably linked to a human or non-human heavy chain constant region gene sequence; and (b) a second nucleotide sequence encodes a light chain variable domain (i.e., where the second nucleotide sequence is an unrearranged human immunoglobulin light chain variable nucleotide sequence), wherein the second nucleotide sequence is operably linked to a human or non-human light chain constant region gene sequence. In some embodiments, the human heavy chain constant region gene sequence is selected from a $C_H1$, a hinge, a $C_H2$, a $C_H3$, and combinations thereof. In some embodiments, a mouse heavy chain constant region gene sequence is selected from a $C_H1$, a hinge, a $C_H2$, a $C_H3$, and combinations thereof. In some embodiments, further replacement of certain non-human animal constant region gene sequences with human gene sequences (e.g., replacement of mouse $C_H1$ sequence with human $C_H1$ sequence, and replacement of mouse $C_L$ sequence with human $C_L$ sequence) results in genetically modified non-human animals with hybrid immunoglobulin loci that make antibodies that have human variable regions and partly human constant regions, suitable for, e.g., making fully human antibody fragments, e.g., fully human Fab's. In some embodiments, the rearranged human immunoglobulin heavy chain variable region nucleotide sequence is operably linked to a rat heavy chain constant region gene sequence. In some embodiments, the rat heavy chain constant region gene sequence is selected from a $C_H1$, a hinge, a $C_H2$, a $C_H3$, and combinations thereof. In various embodiments, the genetically modified immunoglobulin heavy chain locus of the non-human animal comprises two copies, three copies, four copies or more of the rearranged human immunoglobulin heavy chain variable region nucleotide sequence operably linked to a heavy chain constant domain gene sequence. In particular embodiments, the locus comprises a plurality of copies of the rearranged human immunoglobulin heavy chain variable region nucleotide sequence operably linked to a heavy chain constant domain gene sequence.

In various embodiments, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0). In some embodiments, the heavy chain constant region nucleotide sequence encodes a human heavy chain constant region amino acid sequence comprising a modification at position 250 by EU numbering (263 by Kabat numbering) (e.g., E or Q); 250 by EU numbering (263 by Kabat numbering) and 428 by EU numbering (459 by Kabat numbering) (e.g., L or F); 252 by EU numbering (265 by Kabat numbering) (e.g., L/Y/F/W or T), 254 by EU numbering (267 by Kabat numbering) (e.g., S or T), and 256 by EU numbering (269 by Kabat numbering)(e.g., S/R/Q/E/D or T); or a modification at position 428 by EU numbering (459 by Kabat numbering) and/or 433 by EU numbering (464 by Kabat numbering) (e.g., L/R/S/P/Q or K) and/or 434 by EU numbering (465 by Kabat numbering) (e.g., H/F or Y); or a modification at position 250 by EU numbering (263 by Kabat numbering) and/or 428 by EU numbering (459 by Kabat numbering); or a modification at position 307 by EU numbering (326 by Kabat numbering) or 308 by EU numbering (327 by Kabat numbering) (e.g., 308F, V308F), and 434 by EU numbering (465 by Kabat numbering). In one embodiment, the modification comprises a 428L (e.g., M428L) and 434S (e.g., N434S) modification by EU numbering (a 459, e.g., M459L, and 465S (e.g., N465S) modification by Kabat numbering); a 428L, 259I (e.g., V259I), and 308F (e.g., V308F) modification by EU numbering (a 459L, 272I (e.g., V272I), and 327F (e.g., V327F) modification by Kabat numbering; a 433K (e.g., H433K) and a 434 (e.g., 434Y) modification by EU numbering (a 464K (e.g., H464K) and a 465 (e.g., 465Y) modification by Kabat numbering; a 252, 254, and 256 (e.g., 252Y, 254T, and 256E) modification by EU numbering (a 265, 267, 269 (e.g., 265Y, 267T, and 269E) modification by Kabat numbering; a 250Q and 428L modification (e.g., T250Q and M428L) by EU numbering (a 263Q and 459L modification, e.g., T263Q and M459L, by Kabat numbering); and a 307 and/or 308 modification (e.g., 307F or 308P) by EU numbering (326 and/or 327 modification, e.g., 326F or 308P, by Kabat numbering), wherein the modification increases the affinity of the heavy chain constant region amino acid sequence to FcRn in an acidic environment (e.g., in an endosome where pH ranges from about 5.5 to about 6.0). In some embodiments, the heavy chain constant region nucleotide sequence encodes a human $C_H2$ amino acid sequence comprising at least one modification between amino acid residues at positions 252 and 257 by EU numbering (i.e., at least one modification between amino acid positions 265 and 270 by Kabat numbering), wherein the modification increases the affinity of the human $C_H2$ amino acid sequence to FcRn in an acidic environment (e.g., in an endosome where pH ranges from about 5.5 to about 6.0). In some embodiments, the heavy chain constant region nucleotide sequence encodes a human $C_H2$ amino acid sequence comprising at least one modification between amino acid residues at positions 307 and 311 (i.e., at least one modification between amino acid positions 326 and 330 by Kabat numbering), wherein the modification increases the affinity of the $C_H2$ amino acid sequence to FcRn in an acidic environment (e.g., in an endosome where pH ranges from about 5.5 to about 6.0). In some embodiments, the heavy chain constant region nucleotide sequence encodes a human $C_H3$ amino acid sequence, wherein the $C_H3$ amino acid sequence comprises at least one modification between amino acid residues at positions 433 and 436 by EU numbering (i.e., at least one modification between amino acid residues at positions 464 and 467 by Kabat numbering), wherein the modification increases the affinity of the $C_H3$ amino acid sequence to FcRn in an acidic environment (e.g., in an endosome where pH ranges from about 5.5 to about 6.0). In some embodiments, the heavy chain constant region nucleotide sequence encodes a human heavy chain constant region amino acid sequence comprising a mutation selected from the group consisting of M428L by EU numbering (459 by Kabat numbering), N434S by EU numbering (465 by Kabat numbering), and a combination thereof. In some embodiments, the heavy chain constant region nucleotide sequence encodes a human heavy chain constant region amino acid sequence comprising a mutation selected from the group consisting of M428L by EU numbering (M459L by Kabat numbering), V259I by EU numbering (V272I by Kabat numbering), V308F by EU numbering (V327F by Kabat numbering), and a combination thereof. In some embodiments, the heavy chain constant region nucleotide sequence encodes a human heavy chain constant region amino acid sequence comprising an N434A mutation by EU numbering (an N465A mutation by Kabat numbering). In some embodiments, the heavy chain constant region nucleotide sequence encodes a human heavy chain constant region amino acid sequence comprising a mutation selected from the group consisting of M252Y by EU numbering (M265Y by Kabat numbering), S254T by EU numbering (S267T by Kabat numbering), T256E by EU numbering (T269E by Kabat numbering), and a combination thereof. In some embodiments, the heavy chain constant region nucleotide sequence encodes a human heavy chain constant region amino acid sequence comprising a mutation selected from the group consisting of T250Q by EU numbering (T263Q by Kabat numbering), M428L by EU numbering (M459L by Kabat numbering), or both. In some embodiments, the heavy chain constant region nucleotide sequence encodes a human heavy chain constant region amino acid sequence comprising a mutation selected from the group consisting of H433K by EU numbering (H464K by Kabat numbering), N434Y by EU numbering (N465Y by Kabat numbering), or both.

In some embodiments, a genetically modified immunoglobulin locus comprises: (1) a first allele, wherein the rearranged human immunoglobulin heavy chain variable region nucleotide sequence as described herein is operably linked to a first heavy chain constant region nucleotide sequence encoding a first $CH_3$ amino acid sequence of a human IgG selected from IgG1, IgG2, IgG4, and a combination thereof; and (2) a second allele, wherein the rearranged human immunoglobulin heavy chain variable region nucleotide sequence as described herein is operably linked to a second heavy chain constant region nucleotide sequence encoding a second $C_H3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, U.S. Pat. No. 8,586,713, which is incorporated by reference herein in its entirety). In some embodiments, the second $CH_3$ amino acid sequence comprises an H95R modification (by IMGT exon numbering; H435R by EU numbering). In one embodiment the second $CH_3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU). In some embodiments, the second $CH_3$ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU). In some embodiments, the second $CH_3$ amino acid sequence is from a modified human IgG2 and further comprises a mutation selected from the group consisting of N44S, K52N, and V82I (IMGT: N384S, K392N, and V422I by EU). In some embodiments, the second $CH_3$ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU). In some embodiments, the heavy chain constant region amino acid sequence is a non-human constant region amino acid sequence, and the heavy chain constant region amino acid sequence comprises one or more of any of the types of modifications described above.

In various embodiments, Fc domains are modified to have altered Fc receptor binding, which in turn affects effector function. In some embodiments, an engineered heavy chain constant region ($C_H$), which includes the Fc domain, is chimeric. As such, a chimeric $C_H$ region combines $C_H$ domains derived from more than one immunoglobulin isotype. For example, a chimeric $C_H$ region comprises part or all of a $C_H2$ domain derived from a human IgG1, human IgG2 or human IgG4 molecule, combined with part or all of a $C_H3$ domain derived from a human IgG1, human IgG2 or human IgG4 molecule. In some embodiments, a chimeric $C_H$ region contain a chimeric hinge region. For example, a chimeric hinge may comprise an "upper hinge" amino acid sequence (amino acid residues from positions 216 to 227 according to EU numbering; amino acid residues from positions 226 to 240 according to Kabat numbering) derived from a human IgG1, a human IgG2 or a human IgG4 hinge region, combined with a "lower hinge" sequence (amino acid residues from positions 228 to 236 according to EU numbering; amino acid positions from positions 241 to 249 according to Kabat numbering) derived from a human IgG1, a human IgG2 or a human IgG4 hinge region. In some embodiments, the chimeric hinge region comprises amino acid residues derived from a human IgG1 or a human IgG4 upper hinge and amino acid residues derived from a human IgG2 lower hinge.

In some embodiments, the Fc domain may be engineered to activate all, some, or none of the normal Fc effector functions, without affecting the Fc-containing protein's (e.g. antibody's) desired pharmacokinetic properties. For examples of proteins comprising chimeric $C_H$ regions and having altered effector functions, see U.S. Provisional Application No. 61/759,578, filed Feb. 1, 2013, which is herein incorporated in its entirety.

In various aspects, the genome of the non-human animals is modified (i) to delete or render nonfunctional (e.g., via insertion of a nucleotide sequence (e.g., an exogenous nucleotide sequence)) in the immunoglobulin locus or via non-functional rearrangement or inversion of all, or substantially all, endogenous functional immunoglobulin $V_H$, D, $J_H$ segments; and (ii) to comprise a rearranged human immunoglobulin heavy chain variable region nucleotide sequence, wherein the nucleotide sequence is present at an endogenous locus (i.e., where the nucleotide sequence is located in a wild type non-human animal). In some embodiments, the rearranged human immunoglobulin heavy chain variable region nucleotide sequence is at an ectopic locus in the genome (e.g., at a locus different from the endogenous immunoglobulin chain locus in its genome, or within its endogenous locus, e.g., within an immunoglobulin variable locus, wherein the endogenous locus is placed or moved to a different location in the genome). In some embodiments, e.g., about 80% or more, about 85% or more, about 90% or more, about 95% or more, about 96% or more, about 97% or more, about 98% or more, or about 99% or more of all endogenous functional heavy chain V, D, or J gene segments are deleted or rendered non-functional. In some embodiments, e.g., at least 95%, 96%, 97%, 98%, or 99% of endogenous functional heavy chain V, D, or J gene segments are deleted or rendered non-functional. In some embodiments, the rearranged human immunoglobulin heavy chain variable region nucleotide sequence is operably linked to a human or non-human heavy chain constant region gene sequence. In some embodiments, the rearranged human immunoglobulin heavy chain variable region nucleotide sequence is operably linked to a human or non-human light chain constant region gene sequence, either kappa or lambda.

In some embodiments, the genetically modified non-human animal comprises a modification that deletes or renders non-functional endogenous functional $V_H$, D, and $J_H$ heavy chain variable gene segments and endogenous functional light chain variable $V_L$ and $J_L$ gene segments; and comprises (i) a rearranged human immunoglobulin heavy chain variable region nucleotide sequence and (ii) a nucleotide sequence encoding unrearranged human immunoglobulin light chain V gene segments ($V_L$) and unrearranged human immunoglobulin light chain J gene segments ($J_L$) (i.e., where the nucleotide sequence is located in a wild-type non-human animal) or at an ectopic location (e.g., at a locus different from the endogenous immunoglobulin chain locus in its genome, or within its endogenous locus, e.g., within an immunoglobulin variable region locus, wherein the endogenous locus is placed or moved to a different location in the genome). In some embodiments, the genetically modified non-human animal comprises a modification that deletes or renders non-functional endogenous functional $V_H$, D, and $J_H$ heavy chain variable gene segments and endogenous functional light chain variable $V_L$ and $J_L$ gene segments; and comprises (i) a rearranged human immunoglobulin heavy chain variable region nucleotide sequence and (ii) one or more but less than the wild type number of human immunoglobulin light chain variable region gene segments ($V_L$ and $J_L$) at an endogenous location (i.e., where the nucleotide sequence is located in a wild-type non-human animal) or at an ectopic location (e.g., at a locus different from the endogenous immunoglobulin chain locus in its genome, or within its endogenous locus, e.g., within an immunoglobulin variable region locus, wherein the endogenous locus is placed or moved to a different location in the genome). In some embodiments, e.g., about 80% or more, about 85% or more, about 90% or more, about 95% or more, about 96% or more, about 97% or more, about 98% or more, or about 99% or more of all endogenous functional heavy chain V, D, or J gene segments are deleted or rendered non-functional. In some embodiments, e.g., at least 95%, 96%, 97%, 98%, or 99% of endogenous functional heavy chain V, D, or J gene segments are deleted or rendered non-functional. In some embodiments, the rearranged human immunoglobulin heavy chain variable region nucleotide sequence is operably linked to a human or non-human heavy chain constant region gene sequence. In some embodiments, the rearranged human immunoglobulin heavy chain variable region nucleotide sequence is operably linked to a human or non-human light chain constant region gene sequence, either kappa or lambda.

Various embodiments encompass light chain variable domains. Nucleic acid sequences encoding light chain variable domains may be used in making the genetically modified non-humans described herein, may be expressed by such animals, and/or may encode amino acids present in antibodies bodied produced by (or derived from sequences diversified by) such animals. In some embodiments, the light chain variable domain is a human κ light chain variable domain. In some embodiments, the light chain variable domain is a mouse κ light chain variable domain. In some embodiments, the light chain variable domain is a rat κ light chain variable domain. In some embodiments, the light chain variable domain is a human λ light chain variable domain. In some embodiments, the light chain variable domain is a mouse λ light chain variable domain. In some embodiments, the light chain variable domain is a rat λ light chain variable domain.

In various embodiments, the light chain variable domains produced by the genetically modified non-human animals described herein are encoded by one or more mouse or human immunoglobulin κ light chain variable gene segments. In some embodiments, the one or more mouse immunoglobulin κ light chain variable gene segments comprises about three megabases of the mouse immunoglobulin κ light chain locus. In some embodiments, the one or more mouse immunoglobulin κ light chain variable gene segments comprises at least 137 Vκ gene segments, at least five Jκ gene segments or a combination thereof of the mouse immunoglobulin κ light chain locus. In some embodiments, the one or more human immunoglobulin κ light chain variable gene segments comprises about one-half megabase of a human immunoglobulin κ light chain locus. In specific embodiments, the one or more human immunoglobulin κ light chain variable gene segments comprises the proximal repeat (with respect to the immunoglobulin κ constant region) of a human immunoglobulin κ light chain locus. In some embodiments, the one or more human immunoglobulin κ light chain variable gene segments comprises at least 40Vκ gene segments, at least five Jκ gene segments or a combination thereof of a human immunoglobulin κ light chain locus.

In particular embodiments, the genetically modified non-human animals further comprise a nucleotide sequence encoding an unrearranged human immunoglobulin light chain ($V_L$) gene segment and an unrearranged human immunoglobulin light chain ($J_L$) gene segment. In some embodiments, the nucleotide sequence encoding the unrearranged light chain V gene segment and the unrearranged light chain J gene segment is operably linked to an immunoglobulin light chain constant region gene sequence. In other embodiments, the nucleotide sequence encoding the unrearranged light chain V gene segment and the unrearranged light chain J gene segment is operably linked to an immunoglobulin heavy chain constant region gene sequence. In some embodiments, the unrearranged human immunoglobulin light chain V ($V_L$) gene segment and the unrearranged human immunoglobulin J ($J_L$) gene segment are operably linked, at an endogenous rodent locus, to a rodent immunoglobulin light chain constant region gene; e.g., a κ or λ light chain constant region gene.

In various embodiments, the unrearranged human variable region gene segments (e.g., human Vκ gene segments) are capable of rearranging and encoding human variable domains of an antibody. In some embodiments, the non-human animal does not comprise an endogenous $V_L$ gene segment. In some embodiments, the human Vκ gene segments expressed by the non-human animals are selected from the group consisting of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1 D-12, Vκ1 D-13, Vκ1 D-16, Vκ1 D-17, Vκ1 D-22, Vκ1 D-27, Vκ1D-32, Vκ1 D-33, Vκ1 D-35, Vκ1 D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2- 38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ1D-21, Vκ6D-41, and Vκ7-3. In some embodiments, the genetically modified non-human animals described herein express all functional human Vκ genes. In some embodiments, the human Vκ gene segments comprise Vκ4-1, Vκ5-2, Vκ7-3, Vκ2-4, Vκ1-5, and Vκ1-6. In some embodiments, the Vκ gene segments comprise Vκ3-7, Vκ1-8, Vκ1-9, Vκ2-10, Vκ3-11, Vκ1-12, Vκ1-13, Vκ2-14, Vκ3-15 and Vκ1-16. In some embodiments, the human Vκ gene segments comprise Vκ1-17, Vκ2-18, Vκ2-19, Vκ3-20, Vκ6-21, Vκ1-22, Vκ1-23, Vκ2-24, Vκ3-25, Vκ2-26, Vκ1- 27, Vκ2-28, Vκ2-29, and Vκ2-30. In some embodiments, the human Vκ gene segments comprise Vκ3-31, Vκ1-32, Vκ1-33, Vκ3-34, Vκ1-35, Vκ2-36, Vκ1-37, Vκ2-38, Vκ1-39, and Vκ2-40. In various embodiments, the non-human animal comprises five human Jκ gene segments, e.g., Jκ1, Jκ2, Jκ3, Jκ4, and Jκ5 gene segments. In specific embodiments, the Vκ gene segments comprise contiguous human immunoglobulin κ gene segments spanning the human immunoglobulin κ light chain locus from Vκ4-1 through Vκ2-40, and the Jκ gene segments comprise contiguous gene segments spanning the human immunoglobulin κ light chain locus from Jκ1 through Jκ5. In some embodiments, the immunoglobulin light chain locus comprises two human $V_L$ gene segments, Vκ1-39 and Vκ3-20. In some embodiments, one or more (e.g., 2, 3, 4, or 5) human $V_L$ gene segments and two or more human $J_L$ gene segments are present at an endogenous light chain locus, e.g., at an endogenous kappa light chain locus. In some embodiments, the genetically modified non-human animal is a mouse that comprises a functional λ light chain locus. In other embodiments, the mouse comprises a non-functional λ light chain locus. In some embodiments, the one or more human $V_H$, one or more human $D_H$, and one or more human $J_H$ gene segments are operably linked to a mouse or a rat heavy chain constant region sequence (i.e., the one or more human $V_L$ gene segments and two or more human $J_L$ gene segments are present at an endogenous heavy chain locus).

In some embodiments, a genetically modified non-human animal (e.g., mouse or rat) as described herein expresses a rearranged human immunoglobulin heavy chain variable region nucleotide sequence (i.e., produces an antigen-binding protein comprising a rearranged heavy chain variable domain) and one or more, two or more, three or more, four or more, five or more, etc. light chain variable domains encoded by Vκ genes selected from the group consisting of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1 D-8, Vκ1D-12, Vκ1 D-13, Vκ1 D-16, Vκ1 D-17, Vκ1 D-22, Vκ1D-27, Vκ1D-32, Vκ1D-33, Vκ1 D-35, Vκ1D-37, Vκ1 D-39, Vκ1 D-42, Vκ1 D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2- 30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, W4-1, Vκ5-2, W6-21, W6 D-21, Vκ6D-41, and Vκ7-3.

In various embodiments, at least one of the light chain variable region gene segments (e.g., human light chain variable region gene segments) encode one or more histidine codons that are not encoded by a corresponding human germline light chain variable gene segment. In some embodiments, the light chain variable domain as described herein exhibits a decrease in dissociative half-life ($t_{1/2}$) at an acidic pH as compared to neutral pH of at least about 2-fold, at least about 3-fold, at least about 4-fold, at least about 5-fold, at least about 10-fold, at least about 15-fold, at least about 20-fold, at least about 25-fold, or at least about 30-fold. In some embodiments, the decrease in $t_{1/2}$ at an acidic pH as compared to a neutral pH is about 30 fold or more. In some embodiments, at least one of the $V_L$ gene segments comprises a substitution of at least one non-histidine codon encoded by the corresponding human germline $V_L$ segment sequence with a histidine codon. In some embodiments, the substitution is of one, two, three, or four codons (e.g., three or four codons). In some embodiments, the substitution is in the CDR3 codon(s). In some embodiments, the human $V_L$ gene segments are human Vκ1-39 and Vκ3-20 gene segments, and each of the human Vκ1-39 and Vκ3-20 gene segments comprises a substitution of at least one non-histidine codon encoded by a corresponding human germline $V_L$ gene segment with the histidine codon. In some embodiments, each of the human Vκ1-39 and Vκ3-20 gene segments comprises a substitution of three or four histidine codons. In some embodiments, the three or four substitutions are in the CDR3 region. In some embodiments, the substitution is of three non-histidine codons of the human Vκ1-39 gene segment, wherein the substitution is designed to express histidines at positions 106, 108, and 111. In some embodiments, the substitution is of four non-histidine codons of the human Vκ1-39 gene segment, and the substitution is designed to express histidines at positions 105, 106, 108, and 111 (see, e.g., US 2013/0247234A1 and WO 2013/138680, incorporated by reference herein). In some embodiments, the substitution is of three non-histidine codons of the human Vκ3-20 gene segment, and the substitution is designed to express histidines at positions 105, 106, and 109. In yet additional embodiments, the substitution is of four non-histidine codons of the human Vκ3-20 gene segment, and the substitution is designed to express histidines at positions 105, 106, 107, and 109. In some embodiments, the immunoglobulin light chain locus comprises one or more but less than the wild type number of human $V_L$ gene segments and one or more, e.g., two or more, human $J_L$ gene segments, wherein each of the human $V_L$ gene segments comprises at least one histidine codon that is not encoded by the corresponding human germline $V_L$ gene segment. In various embodiments, the non-human animal comprising the genetically modified immunoglobulin loci as described herein, upon stimulation by an antigen of interest, expresses an antigen-binding protein comprising an amino acid sequence derived from the human $V_L$ gene segments, wherein the antigen-binding protein retains at least one histidine residue at an amino acid position encoded by the at least one histidine codon introduced into the human $V_L$ gene segment. In some embodiments, the animal expresses a population of antigen-binding proteins in response to an antigen, wherein all antigen-binding proteins in the population comprise (a) immunoglobulin light chain variable domains derived from a rearrangement of the human $V_L$ gene segments and the $J_L$ gene segments, wherein at least one of the human $V_L$ gene segments encodes one or more histidine codons that are not encoded by the corresponding human germline $V_L$ gene segment, and (b) immunoglobulin heavy chains comprising human heavy chain variable domains encoded by the rearranged human immunoglobulin heavy chain variable region nucleotide sequence.

Various embodiments encompass light chain constant region sequences. In some embodiments, for example, a first nucleotide sequence that encodes the rearranged heavy chain variable domain (i.e., where the first nucleotide sequence is a rearranged human immunoglobulin heavy chain variable region nucleotide sequence) is operably linked to a heavy chain constant region gene sequence, and a second nucleotide sequence that encodes the human light chain variable domain (i.e., where the second nucleotide sequence is an unrearranged human immunoglobulin light chain variable nucleotide sequence) is operably linked to a light chain constant region gene sequence. In some embodiments, a first nucleotide sequence that encodes the rearranged heavy chain variable domain (i.e., where the first nucleotide sequence is a rearranged human immunoglobulin heavy chain variable region nucleotide sequence) is operably linked to a light chain constant region gene sequence, and a second nucleotide sequence that encodes the human light chain variable domain (i.e., where the second nucleotide sequence is an unrearranged human immunoglobulin light chain variable nucleotide sequence) is operably linked to a heavy chain constant region gene sequence. In various embodiments, the light chain constant region sequence operably linked to the rearranged human immunoglobulin heavy chain variable region nucleotide sequence is a human κ light chain constant region sequence. In some embodiments, the light chain constant region sequence operably linked to the rearranged heavy chain variable domain is a mouse κ light chain constant region sequence. In some embodiments, the light chain constant region sequence operably linked to the rearranged heavy chain variable domain is a rat κ light chain constant region sequence. In some embodiments, the light chain constant region sequence operably linked to the rearranged heavy chain variable domain is a human λ light chain constant region sequence. In some embodiments, the light chain constant region sequence operably linked to the rearranged heavy chain variable domain is a mouse λ light chain constant region sequence. In some embodiments, the light chain constant region sequence operably linked to the rearranged heavy chain variable domain is a rat λ light chain constant region sequence.

In various aspects, non-human animals are provided comprising a genetically modified immunoglobulin locus that encodes a rearranged heavy chain variable domain (i.e., where an immunoglobulin locus comprises a rearranged human immunoglobulin heavy chain variable region nucleotide sequence), wherein the rearranged heavy chain variable domain comprises a heavy chain variable ($V_H$) sequence that is operably linked, via a spacer, to a heavy chain J segment ($J_H$) sequence, wherein the spacer comprises at least one amino acid residue. In some embodiments, the rearranged human immunoglobulin heavy chain variable region nucleotide sequence is operably linked to a non-human heavy chain constant region gene sequence. In some embodiments, the non-human heavy chain constant region gene sequence is a mouse or a rat constant region gene sequence. In some embodiments, the rearranged human immunoglobulin heavy chain variable region nucleotide sequence is operably linked to a human heavy chain constant region gene sequence. In some embodiments, the heavy chain constant region comprises a sequence selected from a $C_H1$, a hinge, a $C_H2$, a $C_H3$, and a combination thereof. In some embodiments, the rearranged human immunoglobulin heavy chain variable region nucleotide sequence is operably linked to a non-human light chain constant region gene sequence. In some embodiments, the non-human light chain constant region gene sequence is a mouse or a rat constant region gene sequence. In some embodiments, the rearranged human immunoglobulin heavy chain variable region nucleotide sequence is operably linked to a human light chain constant region gene sequence. In some embodiments, the spacer is a single amino acid residue. In some embodiments, the spacers are two amino acid residues. In some embodiments, the spacers are three amino acid residues. In some embodiments, the spacers are four amino acid residues. In some embodiments, the spacers are five amino acid residues. In some embodiments, the spacers are six amino acid residues.

In another aspect, genetically modified non-human animals and methods for making said animals are provided in which the animals comprise a functional universal light chain ("ULC") immunoglobulin locus. In some embodiments, such animals further comprise a rearranged heavy chain variable domain locus (i.e., a heavy chain variable domain immunoglobulin locus comprising a rearranged human immunoglobulin heavy chain variable region nucleotide sequence). A ULC is a common light chain that can be used in a bispecific format that contains a function, e.g., a modification that affects FcRn binding to improve a half-life, e.g., a bispecific that comprises a heavy chain that binds an antigen and a light chain that binds FcRn. For example, the genetically modified mice as described herein are immunized with FcRN, to obtain antibodies that bind FcRN solely through the light chains. These light chains produced by the genetically modified non-human animal are used as ULCs that assist the bispecific antibody to associate with an FcRn, thereby helping to increase half-life. The remainder of the antibody (e.g., either a second, different light chain, or a heavy chain that binds an antigen different than FcRn) is selected to perform a second function. A ULC as used in the embodiments described herein can also be used to generate antibody variable chain sequences whose diversity results primarily from the processes of somatic mutation (e.g., hypermutation), thereby elucidating antibody variable chain sequences whose antigen-binding capacity benefits from post-genomic events.

Various aspects include genetically modified non-human animals comprising in their genomes a rearranged human heavy chain variable region nucleic acid sequence, and further comprising in their genomes a nucleic acid encoding a light chain variable domain as described herein cloned onto a constant region nucleic acid sequence selected from a kappa constant region, a lambda constant region, a heavy chain constant region (e.g., selected from the group consisting of a CH1, a hinge, a CH2, a CH3, and a combination thereof). In some embodiments, the light chain variable region nucleic acid sequence is cloned onto a first human heavy chain constant region nucleic acid sequence, and a second light chain variable domain is cloned onto a second human heavy chain constant region nucleic acid sequence; wherein the first and the second human heavy chain constant region nucleic acid sequence are the same, the first light chain variable domain specifically binds a first antigen, and the second light chain variable domain specifically binds a second antigen. In these embodiments, a dimer of two polypeptides is formed, wherein each of the light chain variable domains fused to the heavy chain constant region exhibit distinct antigen-binding specificity.

In another aspect, a genetically modified non-human animal (e.g., mouse) is provided that is capable of producing a light chain that binds a receptor or other moiety that traverses the blood-brain barrier, e.g., the transferrin receptor. Previous studies have shown that low affinity antibodies directed against the transferrin receptor will traverse the blood-brain barrier and be released due to low affinity. Thus, in some embodiments, the genetically modified animals (e.g., mice) described herein are used to make a low affinity antibody to a moiety that is capable of traversing the blood-brain barrier (e.g., a transferrin receptor), wherein the low affinity antibody is bispecific and comprises a second binding specificity to a desired target (i.e., the antibody binds the traversing moiety, and also binds a different target than the traversing moiety).

Methods of making and using the genetically modified non-human animals described herein are provided. Methods are provided for placing a rearranged human heavy chain variable region nucleic acid sequence in operable linkage with an immunoglobulin heavy or light chain constant region nucleic acid sequence in the genome of a non-human animal. In various embodiments, the constant region nucleic acid sequence is human or non-human, and the non-human animal is a rodent. In various embodiments, the methods comprise making a non-human animal that further comprises an immunoglobulin light chain locus comprising one or more but less than the wild type number of human light chain variable region gene segments, e.g., two human $V_\kappa$ gene segments and one or more human $J_\kappa$ gene segments, operably linked to a human or non-human light chain constant region nucleic acid sequence. In various aspects, the methods comprise placing the aforementioned sequences in the germline of a non-human animal, e.g., a rodent, employing, e.g., transgenic technology including, e.g., employing modified pluripotent or totipotent donor cells (e.g., ES cells or iPS cells) with host embryos, germ cells (e.g., oocytes), etc. Thus, embodiments include a non-human immunoglobulin heavy chain locus in a genome of a non-human germ cell comprising a rearranged human immunoglobulin heavy chain variable region nucleotide sequence operably linked to a heavy chain constant region gene sequence, wherein the constant region gene sequence comprises a non-human sequence, a human sequence, or a combination thereof. In some embodiments, the rearranged human immunoglobulin heavy chain variable region nucleotide sequence is operably linked to an endogenous non-human immunoglobulin constant region gene sequence. In some embodiments, the endogenous non-human immunoglobulin constant region gene sequence is a mouse or a rat heavy chain constant region gene sequence.

In various aspects, a method of making a non-human animal that comprises a genetically modified immunoglobulin locus is provided, wherein the method comprises: (a) modifying a genome of a non-human animal to delete or render non-functional endogenous functional immunoglobulin heavy chain V, D, and J gene segments; and (b) placing in the genome a rearranged human immunoglobulin heavy chain variable region nucleotide sequence. In one such aspect, a method is provided for making a non-human animal that expresses a single immunoglobulin heavy chain from a rearranged heavy chain gene sequence in the germline of the non-human animal, the method comprising a step of genetically modifying a non-human animal such that its entire antibody-expressing mature B cell population expresses a heavy chain derived from (i) a single $V_H$ gene segment; (ii) an amino acid spacer of one, two, three, four, five, or six amino acids; and (iii) a single $J_H$ gene segment. In some aspects, the method comprises inactivating or replacing an endogenous heavy chain immunoglobulin variable locus with a single rearranged heavy chain gene as described herein.

In another aspect, methods of making a non-human animal that comprises a genetically modified immunoglobulin heavy chain locus are provided, such methods comprising: (a) modifying a genome of a non-human animal to delete or render non-functional endogenous functional immunoglobulin heavy chain V, D, and J gene segments; and (b) placing in the genome a rearranged human immunoglobulin heavy chain variable region nucleotide sequence. In some embodiments, substantially all endogenous functional $V_H$, D, and $J_H$ gene segments are deleted from the immunoglobulin heavy chain locus of the non-human animal or rendered non-functional (e.g., via insertion of a nucleotide sequence (e.g., an exogenous nucleotide sequence in the immunoglobulin locus or via non-functional rearrangement, or inversion of, endogenous $V_H$, D, $J_H$ segments). In some embodiments, the method comprises inserting a rearranged human immunoglobulin heavy chain variable region nucleotide sequence (i.e., a nucleotide sequence that encodes the rearranged heavy chain variable domain) into an endogenous location (i.e., targeted to where the nucleotide sequence is located in a wild type non-human animal). In some embodiments, the rearranged human immunoglobulin heavy chain variable region nucleotide sequence is present ectopically (e.g., at a locus different from the endogenous immunoglobulin chain locus in its genome, or within its endogenous locus, e.g., within an immunoglobulin variable locus, wherein the endogenous locus is placed or moved to a different location in the genome). In some embodiments, e.g., about 80% or more, about 85% or more, about 90% or more, about 95% or more, about 96% or more, about 97% or more, about 98% or more, or about 99% or more of all endogenous functional V, D, or J gene segments are deleted or rendered non-functional. In some embodiments, e.g., at least 95%, 96%, 97%, 98%, or 99% of endogenous functional heavy chain V, D, or J gene segments are deleted or rendered non-functional.

In another aspect, methods are provided for making a non-human animal that comprises a genetically modified immunoglobulin locus, comprising: (a) modifying a genome of a non-human animal to delete or render non-functional endogenous functional immunoglobulin light chain V and J gene segments; and (b) placing in an endogenous immunoglobulin light chain locus a rearranged human immunoglobulin heavy chain variable region nucleotide sequence (i.e., a nucleotide sequence that encodes a rearranged heavy chain variable domain), wherein the nucleotide sequence is operably linked to a light chain constant region gene sequence. In some embodiments, the genetically engineered immunoglobulin locus is present in the germline genome of the non-human animal. In some embodiments, the rearranged human immunoglobulin heavy chain variable region nucleotide sequence is operably linked to a κ light chain constant region gene sequence. In some embodiments, the rearranged human immunoglobulin heavy chain variable region nucleotide sequence is operably linked to a mouse or rat κ light chain constant region gene sequence. In some embodiments, the rearranged human immunoglobulin heavy chain variable region nucleotide sequence is operably linked to a human κ light chain constant region gene sequence. In some embodiments, the rearranged human immunoglobulin heavy chain variable region nucleotide sequence is operably linked to a λ light chain constant region gene sequence. In some embodiments, rearranged human immunoglobulin heavy chain variable region nucleotide sequence is operably linked to a mouse or rat λ light chain constant region gene sequence. In some embodiments, the rearranged human immunoglobulin heavy chain variable region nucleotide sequence is operably linked to a human λ light chain constant region gene sequence.

In another aspect, methods are provided for making a non-human animal that comprises a genetically modified immunoglobulin locus, comprising: (a) modifying a genome of a non-human animal to delete or render non-functional: (i) endogenous functional immunoglobulin heavy chain V, D, and J gene segments, and (ii) endogenous functional immunoglobulin light chain V and J gene segments; and (b) placing in the genome: (i) a first nucleotide sequence that encodes a rearranged heavy chain variable domain (i.e., where the first nucleotide sequence is a rearranged human immunoglobulin heavy chain variable region nucleotide sequence), wherein the first nucleotide sequence is operably linked to a light chain constant region gene sequence, and (ii) a second nucleotide sequence that encodes a human immunoglobulin light chain variable domain (i.e., where the second nucleotide sequence is an unrearranged human immunoglobulin light chain variable region nucleotide sequence), wherein the second nucleotide sequence is operably linked to a heavy chain constant region gene sequence. In some embodiments, the genetically engineered immunoglobulin locus is present in the germline genome of the non-human animal. In some embodiments, the first nucleotide sequence that encodes the rearranged heavy chain variable domain is operably linked to a K light chain constant region gene sequence. In some embodiments, the first nucleotide sequence that encodes the rearranged heavy chain variable domain is operably linked to a mouse or rat κ light chain constant region gene sequence. In some embodiments, the first nucleotide sequence that encodes the rearranged heavy chain variable domain is operably linked to a human κ light chain constant region gene sequence. In some embodiments, the first nucleotide sequence that encodes the rearranged heavy chain variable domain is operably linked to a λ light chain constant region gene sequence. In some embodiments, the first nucleotide sequence that encodes the rearranged heavy chain variable domain is operably linked to a mouse or rat λ light chain constant region gene sequence. In some embodiments, the first nucleotide sequence that encodes the rearranged heavy chain variable domain is operably linked to a human λ light chain constant region gene sequence. In some embodiments, the human immunoglobulin light chain variable domain is a κ light chain variable domain. Thus, in some embodiments, the second nucleotide sequence is a human kappa light chain variable region nucleotide sequence. In some embodiments, the human immunoglobulin light chain variable domain is a λ light chain variable domain. Thus, in some embodiments, the second nucleotide sequence is a human lambda light chain variable region nucleotide sequence. In some embodiments, the heavy chain constant region gene sequence is a non-human immunoglobulin heavy chain constant region gene sequence. In some embodiments, the non-human immunoglobulin heavy chain constant region gene sequence is a mouse or a rat heavy chain constant region gene sequence.

In another aspect, methods are provided for making a non-human animal that comprises a genetically modified immunoglobulin locus, comprising: (a) modifying a genome of a non-human animal to delete or render non-functional: (i) endogenous functional immunoglobulin heavy chain V, D, and J gene segments, and (ii) endogenous functional immunoglobulin light chain V and J gene segments; and (b) placing in the genome: (i) a first nucleotide sequence that encodes a rearranged heavy chain variable domain (i.e., where the first nucleotide sequence is a rearranged human immunoglobulin heavy chain variable region nucleotide sequence), wherein the first nucleotide sequence is operably linked to a heavy chain constant region gene sequence, and (ii) a second nucleotide sequence that encodes a human immunoglobulin light chain variable domain (i.e., where the second nucleotide sequence is an unrearranged human immunoglobulin light chain variable region nucleotide sequence), wherein the second nucleotide sequence is operably linked to a light chain constant region gene sequence. In some embodiments, the light chain constant region gene sequence is a κ light chain constant region gene sequence. In some embodiments, the light chain constant region gene sequence is a mouse or rat κ light chain constant region gene sequence. In some embodiments, the light chain constant region gene sequence is a human κ light chain constant region gene sequence. In some embodiments, the light chain constant region gene sequence is a λ light chain constant region gene sequence. In some embodiments, the light chain constant region gene sequence is a mouse or rat λ light chain constant region gene sequence. In some embodiments, the light chain constant region gene sequence is a human λ light chain constant region gene sequence. In some embodiments, the human immunoglobulin light chain variable domain is a κ light chain variable domain. In some embodiments, the human immunoglobulin light chain variable domain is a λ light chain variable domain. In some embodiments, the heavy chain constant region gene sequence is a non-human immunoglobulin heavy chain constant region gene sequence. In some embodiments, the non-human immunoglobulin heavy chain constant region gene sequence is a mouse or a rat heavy chain constant region gene sequence.

In another aspect, a method of making a non-human animal that comprises a genetically modified immunoglobulin heavy chain locus is provided comprising: (a) modifying a genome of a non-human animal to delete or render non-functional endogenous functional immunoglobulin heavy chain V, D, and J gene segments; and (b) placing in the genome a rearranged human immunoglobulin heavy chain variable region nucleotide sequence, wherein the rearranged human immunoglobulin heavy chain variable region nucleotide sequence comprises a heavy chain V gene segment ($V_H$) sequence that is operably linked, via spacer, to a heavy chain J gene segment ($J_H$) sequence, wherein the spacer comprises at least one amino acid residue. In some embodiments, the rearranged human immunoglobulin heavy chain variable region nucleotide sequence is operably linked to a non-human immunoglobulin heavy chain constant region gene sequence. In some embodiments, the non-human immunoglobulin heavy chain constant region gene sequence is a mouse or rat immunoglobulin heavy chain constant region gene sequence. In some embodiments, the rearranged human immunoglobulin heavy chain variable region nucleotide sequence is operably linked to a non-human immunoglobulin light chain constant region gene sequence. In some embodiments, the non-human immunoglobulin light chain constant region gene sequence is a mouse or rat immunoglobulin light chain constant region gene sequence. In some embodiments, the rearranged human immunoglobulin heavy chain variable region nucleotide sequence is present at an endogenous location (i.e., where the nucleotide sequence is located in a wild-type non-human animal). In some embodiments the rearranged human immunoglobulin heavy chain variable region nucleotide sequence is present ectopically (e.g., at a locus different from the endogenous immunoglobulin chain locus in its genome, or within its endogenous locus, e.g., within an immunoglobulin variable locus, wherein the endogenous locus is placed or moved to a different location in the genome). In some embodiments, the spacers are a single amino acid residue. In some embodiments, the spacers are two amino acid residues. In some embodiments, the spacers are three amino acid residues. In some embodiments, the spacers are four amino acid residues. In some embodiments, the spacers are five amino acid residues. In some embodiments, the spacers are six amino acid residues. In some embodiments, the nucleotide sequences encodes two copies, three copies, four copies, or more of the rearranged human immunoglobulin heavy chain variable region nucleotide sequence operably linked to a heavy chain constant domain gene sequence. In some embodiments, the nucleotide sequence encodes a plurality of copies of the rearranged human immunoglobulin heavy chain variable region nucleotide sequence operably linked to a heavy chain constant domain gene sequence.

Methods are provided for making a non-human animal, comprising: (a) modifying a genome of a non-human animal to delete or render non-functional (i) endogenous functional immunoglobulin heavy chain $V_H$, D, and and/or $J_H$ gene segments, and (ii) endogenous functional immunoglobulin light chain V and J gene segments; and (b) placing (i) a rearranged heavy chain variable region nucleic acid sequence at a heavy chain locus, wherein the rearranged heavy chain variable region nucleic acid sequence comprises a heavy chain V gene segment ($V_H$) sequence that is operably linked, via spacer, to a heavy chain J gene segment ($J_H$) sequence, wherein the spacer comprises at least one amino acid residue; and (ii) one or more but less than the wild type number of human immunoglobulin light chain variable region gene segments (e.g., two human $V_\kappa$ gene segments and at least one human $J_\kappa$ gene segments) operably linked to a human or non-human light chain constant region nucleic acid sequence. In some embodiments, at least one of the light chain variable region gene segments encodes one or more histidine codons that are not encoded by a corresponding human germline light chain variable gene segment.

In some aspects, a method for making a non-human animal comprising a genetically modified immunoglobulin locus is provided, comprising:

(a) modifying a genome of a non-human animal to delete or render non-functional endogenous functional immunoglobulin light chain V and J gene segments; and (b) placing in the genome of the non-human animal a rearranged human heavy chain variable region nucleotide sequence in operable linkage to a light chain constant region nucleotide sequence.

In various embodiments, the non-human animal is a rodent, e.g., a mouse, a rat, or a hamster. In some embodiments, the rodent is a mouse. In some embodiments, the light chain constant region is a rat or a mouse constant region, e.g., a rat or a mouse Cκ constant region.

In another aspect, a method for making a non-human animal comprising a genetically modified immunoglobulin locus is provided, comprising:

(a) modifying a genome of a non-human animal to delete or render non-functional:

(i) endogenous functional immunoglobulin heavy chain V, D, and/or J gene segments, and (ii) endogenous functional immunoglobulin light chain V and J gene segments; and (b) placing in the genome of the non-human animal:

(i) a first nucleotide sequence that encodes a rearranged heavy chain variable domain (i.e., where the first nucleotide sequence is a rearranged human immunoglobulin heavy chain variable region nucleotide sequence), wherein the first nucleotide sequence is operably linked to a light chain constant region gene sequence, and (ii) a second nucleotide sequence that encodes a human or non-human light chain variable domain (i.e., where the second nucleotide sequence is an unrearranged human immunoglobulin light chain variable region nucleotide sequence), wherein the second nucleotide sequence is operably linked to a heavy chain constant region gene sequence.

In various embodiments, the non-human animal is a rodent, e.g., a mouse, a rat, or a hamster. In some embodiments, the rodent is a mouse. In some embodiments, the light chain constant region is a rat or a mouse constant region, e.g., a rat or a mouse Cκ constant region. In some embodiments, the second nucleotide sequence is operably linked to a mouse or rat heavy chain constant region gene sequence selected from a $C_H1$, a hinge, a $C_H2$, a $C_H3$, and a combination thereof. In some embodiments, the second nucleotide sequence is operably linked to a human heavy chain constant region gene sequence selected from a $C_H1$, a hinge, a $C_H2$, a $C_H3$, and a combination thereof.

In another aspect, a method is provided for making a non-human animal that comprises a genetically modified immunoglobulin locus, comprising:

(a) modifying a genome of a non-human animal to delete or render non-functional:
  (i) endogenous functional immunoglobulin heavy chain V, D, and/or J gene segments, and
  (ii) endogenous functional immunoglobulin light chain V and J gene segments; and
(b) placing in the genome of the non-human animal:
  (i) a first nucleotide sequence that encodes a rearranged heavy chain variable domain (i.e., where the first nucleotide sequence is a rearranged human immunoglobulin heavy chain variable region nucleotide sequence), wherein the first nucleotide sequence is operably linked to a heavy chain constant region gene sequence; and
  (ii) a second nucleotide sequence that encodes a light chain variable domain (i.e., where the second nucleotide sequence is an unrearranged human immunoglobulin light chain variable region nucleotide sequence), wherein the second nucleotide sequence is operably linked to a light chain constant region gene sequence.

In another aspect, a method is provided for making a non-human animal that comprises a genetically modified immunoglobulin locus, comprising:
(a) modifying a genome of a non-human animal to delete or render non-functional:
  (i) endogenous functional immunoglobulin heavy chain V, D, and/or J gene segments, and
  (ii) endogenous functional immunoglobulin light chain V and J gene segments; and
(b) placing in the genome of the non-human animal:
  (i) a first allele comprising:
    (1) a first nucleotide sequence that encodes a rearranged heavy chain variable domain (i.e., where the first nucleotide sequence is a rearranged human immunoglobulin heavy chain variable region nucleotide sequence) operably linked to a heavy chain constant region gene sequence, and
    (2) a second nucleotide sequence that encodes a light chain variable domain (i.e., where the second nucleotide sequence is an unrearranged human immunoglobulin light chain variable region nucleotide sequence) operably linked to a light chain constant region gene sequence; and
  (ii) a second allele comprising:
    (1) a third nucleotide sequence that encodes a light chain variable domain (i.e., where the third nucleotide sequence is an unrearranged human immunoglobulin light chain variable region nucleotide sequence) operably linked to a heavy chain constant region gene sequence, and
    (2) a fourth nucleotide sequence that encodes the rearranged heavy chain variable domain (i.e., where the fourth nucleotide sequence is a rearranged human immunoglobulin heavy chain variable region nucleotide sequence) operably linked to a light chain constant region gene sequence.

In another aspect, a method of making a non-human animal that comprises a genetically modified immunoglobulin heavy chain locus is provided comprising: (a) modifying a genome of a non-human animal to delete or render non-functional endogenous functional immunoglobulin heavy chain V, D, and and/or J gene segments; and (b) placing in the genome rearranged human immunoglobulin heavy chain variable region nucleotide sequence, wherein the rearranged human immunoglobulin heavy chain variable region nucleotide sequence comprises a heavy chain V gene segment ($V_H$) sequence that is operably linked, via spacer, to a heavy chain J gene segment ($J_H$) sequence, wherein the spacer comprises at least one amino acid residue.

In another aspect, a method for making a non-human animal comprising a genetically modified immunoglobulin locus is provided, comprising:
(a) modifying a genome of a non-human animal to delete or render non-functional:
  (i) endogenous functional immunoglobulin heavy chain V, D, and/or J gene segments, and
  (ii) endogenous functional immunoglobulin light chain V and J gene segments; and
(b) placing in the genome of the non-human animal:
  (i) a rearranged human immunoglobulin heavy chain variable region nucleotide sequence in operable linkage to a heavy chain constant region nucleotide sequence; and
  (ii) one or more but less than the wild type number of human immunoglobulin light chain variable region gene segments in operable linkage to a light chain constant region nucleic acid sequence.

In various embodiments, the non-human animal is a rodent, e.g., a mouse, a rat, or a hamster. In some embodiments, the rodent is a mouse. In some embodiments, the light chain constant region is a rat or a mouse constant region, e.g., a rat or a mouse Cκ constant region. In some embodiments, the rearranged human heavy chain variable region nucleic acid sequence is operably linked to a mouse or rat heavy chain constant region gene sequence selected from a $C_H1$, a hinge, a $C_H2$, a $C_H3$, and a combination thereof. In some embodiments, the rearranged heavy chain variable region nucleic acid sequence is operably linked to a human heavy chain constant region gene sequence selected from a $C_H1$, a hinge, a $C_H2$, a $C_H3$, and a combination thereof.

In another aspect, a method for making a non-human animal comprising a genetically modified immunoglobulin locus is provided, comprising:
(a) modifying a genome of a non-human animal to delete or render non-functional:
  (i) endogenous functional immunoglobulin heavy chain V, D, and/or J gene segments, and
  (ii) endogenous functional immunoglobulin light chain V and J gene segments; and
(b) placing in the genome of the non-human animal:
  (i) a rearranged human immunoglobulin heavy chain variable region nucleotide sequence in operable linkage to a light chain constant region nucleotide sequence; and
  (ii) one or more but less than the wild type number of human immunoglobulin light chain variable $V_L$ and $J_L$ gene segments in operable linkage to a heavy chain constant region nucleic acid sequence.

In various embodiments, the non-human animal is a rodent, e.g., a mouse, a rat, or a hamster. In some embodiments, the rodent is a mouse. In some embodiments, the light chain constant region is a rat or a mouse constant region, e.g., a rat or a mouse Cκ constant region.

In another aspect, nucleic acid sequences encoding a rearranged heavy chain variable domain (i.e., nucleotide sequences that are rearranged human immunoglobulin heavy chain variable region nucleotide sequences; i.e., a pre-rearranged variable heavy chain VDJ nucleotide sequence) are provided. In some embodiments, the nucleic acid sequence is derived from a human V, D, and J gene sequence or segment. In some embodiments, the nucleic acid sequence is derived from a human germline V segment, a human germline D segment, and a human germline J segment. In some embodiments, the human $V_H$ segment corresponds to observed variants in the human population. In various embodiments, the nucleic acid sequence comprises a human V gene selected from the group consisting of $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H3$-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, $V_H7$-81, and a polymorphic variant thereof. In some embodiments, the human V segment is $V_H3$-23 or polymorphic variant thereof. In various embodiments, the nucleic acid sequence comprises a human D gene segment selected from the group consisting of D1-1, D1-7, D1-14, D1-20, D1-26, D2-2, D2-8, D2-15, D2-21, D3-3, D3-9, D3-10, D3-16, D3- 22, D4-4, D4-11, D4-17, D4-23, D5-12, D5-5, D5-18, D5-24, D6-6, D6-13, D6-19, D6-25, D7-27, and a polymorphic variant thereof. In some embodiments, the nucleic acid sequence comprises a human D segment that is not autoreactive (non-immunogenic) in the animal. In some embodiments, the nucleic acid sequence comprises a human D segment that is capable of being expressed in a heavy chain variable sequence of a mature B cell of a mouse. In some embodiments, the nucleic acid sequence further comprises a human or non-human animal heavy chain constant region gene sequence selected from a $C_H1$, a hinge, a $C_H2$, a $C_H3$, and a combination thereof. In specific embodiments, the nucleic acid comprises a constant region gene sequence comprising a $C_H1$, a hinge, a $C_H2$, and a $C_H3$. In various embodiments, the nucleic acid sequence comprises a human J gene segment is selected from the group consisting of $J_H1$, $J_H2$, $J_H3$, 44, $J_HS$, $J_H6$, and a polymorphic variant thereof. In some embodiments, the rearranged human immunoglobulin heavy chain variable region nucleotide sequence encodes the sequence of human $V_H3$-23/GY/$J_H4$-4 (SEQ ID NO: 137). In some embodiments, the nucleic acid sequence encodes a rearranged heavy chain variable domain comprising the sequence of human $V_H3$-23/$X_1X_2$/J (wherein X1 is any amino acid, and X2 is any amino acid). In some embodiments, $X_1$ is Gly and $X_2$ is Tyr. In some embodiments, the nucleic acid sequence encodes a rearranged heavy chain variable domain comprising the sequence of human $V_H3$-23/$X_1X_2$/$J_H4$-4 (wherein X1 is any amino acid, and $X_2$ is any amino acid). In some embodiments, $X_2$ is an amino acid comprising a phenyl group. In specific embodiments, $X_2$ is selected from Tyr and Phe. In some embodiments, the nucleic acid sequence further comprises a human or non-human animal light chain constant region gene sequence.

In another aspect, a nucleic acid construct is provided comprising a rearranged human immunoglobulin heavy chain variable region nucleotide sequence (i.e., a pre-rearranged heavy chain VDJ sequence) as described herein. In some embodiments, the nucleic acid construct is designed in such a way that the rearranged human immunoglobulin heavy chain variable region nucleotide sequence is operably linked to a human or non-human animal heavy chain constant region gene sequence. In some embodiments, the nucleic acid construct contains two copies, three copies, four copies, or more of the rearranged human immunoglobulin heavy chain variable region nucleotide sequence operably linked to a heavy chain constant region gene sequence. In some embodiments, the nucleic acid construct is a targeting vector. In some embodiments, the targeting vector comprises an Adam6a gene, an Adam6b gene, or both, in order to prevent fertility problems associated with the deletion of the Adam6a/6b genes (see, for example, US 2012-0322108A1, incorporated by reference in its entirety). In some embodiments, the Adam6a and the Adam6b genes are placed at 5' upstream of the transcriptional unit of the universal heavy chain sequence. In some embodiments, the targeting vector comprises a selection cassette flanked by recombination sites. In some embodiments, the targeting vector comprises one or more site-specific recombination sites (e.g., a loxP or a FRT site).

In another aspect, methods are provided for obtaining a light chain variable region ($V_L$) amino acid sequence capable of binding an antigen independently from a heavy chain variable region amino acid sequence, comprising: (a) immunizing a genetically modified non-human animal as described herein (e.g., a genetically modified animal comprising a rearranged human heavy chain variable region nucleic acid sequence in operable linkage to a heavy or light chain constant region nucleic acid sequence) with an antigen of interest, wherein the non-human animal mounts an immune response to the antigen; and (b) obtaining a rearranged light chain (VJ) nucleic acid sequence of a light chain variable domain that specifically binds the antigen from a cell (e.g., mature B cell) of the genetically modified non-human animal. In various embodiments, the light chain variable regions produced by such methods are provided.

In some aspects, methods for obtaining a nucleic acid sequence that encodes an immunoglobulin light chain variable region ($V_L$) domain capable of binding an antigen independently from a heavy chain variable region are provided, comprising: (a) immunizing a non-human animal with an antigen of interest or an immunogen thereof, wherein the non-human animal comprises in its genome (i) a rearranged human immunoglobulin heavy chain variable region nucleic acid sequence operably linked to a heavy chain constant region nucleic acid sequence, (b) allowing the non-human animal to mount an immune response, (c) isolating from the immunized non-human animal a cell comprising a nucleic acid sequence that encodes a light chain variable domain that can bind the antigen, and (d) obtaining from the cell a nucleic acid sequence that encodes the light chain variable domain ($V_L$ domain) that can bind the antigen. In some embodiments, the heavy chain constant region gene sequence is a mouse or rat heavy chain constant region gene sequence. In some embodiments, the heavy chain constant region gene sequence is a human heavy chain constant region gene sequence. In some embodiments, the rearranged heavy chain variable domain expressed by the genetically modified locus is not autoreactive, i.e., non-immunogenic to the non-human animal. In some embodiments, the non-human animal further comprises in its genome two or more but less than the wild type number of human immunoglobulin light chain variable region gene segments ($V_L$ and $J_L$). In some embodiments, the human immunoglobulin light chain variable region gene segments ($V_L$ and $J_L$) are operably linked to a light chain constant region nucleic acid sequence. In some embodiments, the isolating step (c) is carried out via fluorescence-activated cell sorting (FACS) or flow cytometry. In some embodiments, the cell comprising the nucleic acid sequence that encodes the light chain variable domain that bind the antigen is a lymphocyte. In some embodiments, the lymphocyte comprises natural killer cells, T cells, or B cells. In some embodiments, the method further comprises a step of (c)' fusing the lymphocyte with a cancer cell. In certain embodiments, the cancer cell is a myeloma cell.

Thus, in various aspects, methods are provided for obtaining a nucleic acid sequence that encodes an immunoglobulin light chain variable domain ($V_L$) capable of binding an antigen independently from a heavy chain variable domain, comprising:

(a) immunizing a non-human animal with an antigen of interest or an immunogen thereof, wherein the non-human animal comprises in its genome (i) a rearranged human immunoglobulin heavy chain variable region nucleic acid sequence operably linked to a heavy chain constant region nucleic acid sequence; and (ii) unrearranged human immunoglobulin light chain variable region gene segments ($V_L$ and $J_L$) operably linked to a light chain constant region nucleic acid sequence;

(b) allowing the non-human animal to mount an immune response;

(c) isolating from the immunized non-human animal a cell comprising a nucleic acid sequence that encodes a light chain variable domain that can bind the antigen; and (d) obtaining from the cell a nucleic acid sequence that encodes the light chain variable domain ($V_L$ domain) that can bind the antigen.

In some embodiments, the isolating step (c) is carried out via fluorescence-activated cell sorting (FACS) or flow cytometry. In some embodiments, the cell comprising the nucleic acid sequence that encodes the light chain variable domain that bind the antigen is a lymphocyte. In particular embodiments, the lymphocyte comprises natural killer cells, T cells, or B cells. In some embodiments, the methods further comprise a step of (c)' fusing the lymphocyte with a cancer cell. In particular embodiments, the cancer cell is a myeloma cell. In some embodiments, the nucleic acid sequence of (d) is fused with a nucleic acid sequence encoding an immunoglobulin constant region nucleic acid sequence. In some embodiments, the light chain constant region nucleic acid sequence is a human kappa sequence or a human lambda sequence. In some embodiments, the light chain constant region nucleic acid sequence is a mouse kappa sequence or a mouse lambda sequence. In some embodiments, the light chain constant region nucleic acid sequence is a rat kappa sequence or a rat lambda sequence. In some embodiments, the heavy chain constant region nucleic acid sequence is a human sequence selected from a CH1, a hinge, a CH2, a CH3, and a combination thereof. In some embodiments, the heavy chain constant region nucleic acid sequence is a mouse or rat selected from a CH1, a hinge, a CH2, a CH3, and a combination thereof. In some embodiments, the nucleic acid sequence of (d) comprises one or more histidine codon substitutions or insertions that are derived from the unrearranged $V_L$ gene segment in the genome of the animal.

In various aspects, methods are provided for obtaining a nucleic acid sequence that encodes an immunoglobulin light chain variable domain ($V_L$) capable of binding an antigen independently from a heavy chain variable domain, comprising:

(a) immunizing a non-human animal with an antigen of interest or an immunogen thereof, wherein the non-human animal comprises in its genome (i) a rearranged human immunoglobulin heavy chain variable region nucleic acid sequence operably linked to a light chain constant region nucleic acid sequence; and (ii) unrearranged human immunoglobulin light chain variable region gene segments ($V_L$ and $J_L$) operably linked to a heavy chain constant region nucleic acid sequence;

(b) allowing the non-human animal to mount an immune response;

(c) isolating from the immunized non-human animal a cell comprising a nucleic acid sequence that encodes a light chain variable domain that can bind the antigen; and (d) obtaining from the cell a nucleic acid sequence that encodes the light chain variable domain ($V_L$ domain) that can bind the antigen.

In some embodiments, the isolating step (c) is carried out via fluorescence-activated cell sorting (FACS) or flow cytometry. In some embodiments, the cell comprising the nucleic acid sequence that encodes the light chain variable domain that bind the antigen is a lymphocyte. In particular embodiments, the lymphocyte comprises natural killer cells, T cells, or B cells. In some embodiments, the methods further comprise a step of (c)' fusing the lymphocyte with a cancer cell. In particular embodiments, the cancer cell is a myeloma cell. In some embodiments, the nucleic acid sequence of (d) is fused with a nucleic acid sequence encoding an immunoglobulin constant region nucleic acid sequence. In some embodiments, the light chain constant region nucleic acid sequence is a human kappa sequence or a human lambda sequence. In some embodiments, the light chain constant region nucleic acid sequence is a mouse kappa sequence or a mouse lambda sequence. In some embodiments, the light chain constant region nucleic acid sequence is a rat kappa sequence or a rat lambda sequence. In some embodiments, the heavy chain constant region nucleic acid sequence is a human sequence selected from a CH1, a hinge, a CH2, a CH3, and a combination thereof. In some embodiments, the heavy chain constant region nucleic acid sequence is a mouse or rat selected from a CH1, a hinge, a CH2, a CH3, and a combination thereof. In some embodiments, the nucleic acid sequence of (d) comprises one or more histidine codon substitutions or insertions that are derived from the unrearranged $V_L$ gene segment in the genome of the animal.

In some aspects, methods are provided for obtaining a nucleic acid sequence that encodes an immunoglobulin light chain variable domain ($V_L$) capable of binding an antigen independently from a heavy chain variable domain, comprising:

(a) immunizing a non-human animal with an antigen of interest or an immunogen thereof, wherein the non-human animal comprises in its genome (i) a rearranged human immunoglobulin heavy chain variable region nucleic acid sequence operably linked to a heavy chain constant region nucleic acid sequence; and (ii) two or more but less than the wild type number of human immunoglobulin light chain variable region gene segments ($V_L$ and $J_L$) operably linked to a light chain constant region nucleic acid sequence;

(b) allowing the non-human animal to mount an immune response;

(c) isolating from the immunized non-human animal a cell comprising a nucleic acid sequence that encodes a light chain variable domain that can bind the antigen; and (d) obtaining from the cell a nucleic acid sequence that encodes the light chain variable domain ($V_L$ domain) that can bind the antigen.

In some embodiments, the isolating step (c) is carried out via fluorescence-activated cell sorting (FACS) or flow cytometry. In some embodiments, the cell comprising the nucleic acid sequence that encodes the light chain variable domain that bind the antigen is a lymphocyte. In particular embodiments, the lymphocyte comprises natural killer cells, T cells, or B cells. In some embodiments, the methods further comprise a step of (c)' fusing the lymphocyte with a cancer cell. In particular embodiments, the cancer cell is a myeloma cell. In some embodiments, the nucleic acid sequence of (d) is fused with a nucleic acid sequence encoding an immunoglobulin constant region nucleic acid sequence. In some embodiments, the light chain constant region nucleic acid sequence is a human kappa sequence or a human lambda sequence. In some embodiments, the light chain constant region nucleic acid sequence is a mouse kappa sequence or a mouse lambda sequence. In some embodiments, the light chain constant region nucleic acid sequence is a rat kappa sequence or a rat lambda sequence. In some embodiments, the heavy chain constant region nucleic acid sequence is a human sequence selected from a CH1, a hinge, a CH2, a CH3, and a combination thereof. In some embodiments, the heavy chain constant region nucleic acid sequence is a mouse or rat selected from a CH1, a hinge, a CH2, a CH3, and a combination thereof. In some embodiments, the nucleic acid sequence of (d) comprises one or more histidine codon substitutions or insertions that are derived from the unrearranged $V_L$ gene segment in the genome of the animal.

In some aspects, methods are provided for obtaining a nucleic acid sequence that encodes an immunoglobulin light chain variable domain ($V_L$) capable of binding an antigen independently from a heavy chain variable domain, comprising:
- (a) immunizing a non-human animal containing a genetically modified immunoglobulin locus as described herein with an antigen of interest, wherein the non-human animal comprises in its genome a rearranged human immunoglobulin heavy chain variable region nucleic acid sequence operably linked to a heavy chain constant region nucleic acid sequence;
- (b) allowing the non-human animal to mount an immune response;
- (c) harvesting a lymphocyte (e.g., a B cell) from the immunized non-human animal;
- (d) fusing the lymphocyte with a myeloma cell to form a hybridoma cell; and
- e) obtaining from the hybridoma cell a nucleic acid sequence that encodes a light chain variable domain ($V_L$ domain) that can bind the antigen.

In another aspect, methods are provided for obtaining a nucleic acid sequence that encodes an immunoglobulin light chain variable domain ($V_L$) nucleic acid sequence of an immunoglobulin light chain capable of binding an antigen independently from a heavy chain variable region, comprising:
- (a) immunizing a non-human animal containing a genetically modified immunoglobulin locus as described herein with an antigen of interest, wherein the non-human animal comprises in its genome a rearranged human immunoglobulin heavy chain variable region nucleic acid sequence operably linked to a heavy chain constant region nucleic acid sequence;
- (b) allowing the non-human animal to mount an immune response;
- (c) identifying a lymphocyte (e.g., a B cell) from the immunized non-human animal that expresses a $V_L$ amino acid sequence that binds the antigen independently from a heavy chain variable region; and,
- (d) cloning a nucleic acid sequence encoding the $V_L$ amino acid sequence of (c) from the lymphocyte of (c).

In another aspect, methods are provided for obtaining an immunoglobulin light chain variable region ($V_L$) amino acid sequence capable of binding an antigen independently from a heavy chain variable region, comprising:
- (a) immunizing a non-human animal containing a genetically modified immunoglobulin locus as described herein with an antigen of interest, wherein the non-human animal comprises in its genome (i) a first nucleotide sequence that encodes a rearranged heavy chain variable domain (i.e., where the first nucleotide sequence is a rearranged human immunoglobulin heavy chain variable region nucleotide sequence), wherein the first nucleotide sequence is operably linked to a light chain constant region gene sequence; and (ii) a second nucleotide sequence that encodes a human or non-human light chain variable domain (i.e., where the second nucleotide sequence is an unrearranged human immunoglobulin light chain variable nucleotide sequence), wherein the second nucleotide sequence is operably linked to a heavy chain constant region gene sequence;
- (b) allowing the non-human animal to mount an immune response;
- (c) harvesting a lymphocyte (e.g., a B cell) from the immunized non-human animal;
- (d) fusing the lymphocyte with a myeloma cell to form a hybridoma cell; and
- e) obtaining from the hybridoma cell a nucleic acid sequence that encodes a light chain variable domain ($V_L$ domain) that can bind the antigen.

In another aspect, methods are provided for obtaining a nucleic acid sequence that encodes an immunoglobulin light chain variable domain ($V_L$) capable of binding an antigen independently from a heavy chain variable domain, comprising:
- (a) immunizing a non-human animal containing a genetically modified immunoglobulin locus as described herein with an antigen of interest, wherein the non-human animal comprises in its genome (i) a first nucleotide sequence that encodes a rearranged heavy chain variable domain (i.e., where the first nucleotide sequence is a rearranged human immunoglobulin heavy chain variable region nucleotide sequence), wherein the first nucleotide sequence is operably linked to a light chain constant region gene sequence; and (ii) a second nucleotide sequence that encodes a human or non-human light chain variable domain (i.e., where the second nucleotide sequence is an unrearranged human immunoglobulin light chain variable nucleotide sequence), wherein the second nucleotide sequence is operably linked to a heavy chain constant region gene sequence;
- (b) allowing the non-human animal to mount an immune response;
- (c) identifying a lymphocyte (e.g., a B cell) from the immunized non-human animal that expresses a $V_L$ amino acid sequence that binds the antigen independently from a heavy chain variable region; and,
- (d) cloning a nucleic acid sequence encoding the VL amino acid sequence of (c) from the lymphocyte of (c).

In another aspect, methods are provided for obtaining an immunoglobulin light chain variable region ($V_L$) amino acid sequence capable of binding an antigen independently from a heavy chain variable region, comprising:
- (a) immunizing a non-human animal containing a genetically modified immunoglobulin locus as described herein with an antigen of interest, wherein the non-human animal comprises in its genome (i) a rearranged human immunoglobulin heavy chain variable region nucleic acid sequence operably linked to a heavy chain constant region nucleic acid sequence; and (ii) two or more but less than the wild type number of human immunoglobulin light chain variable region gene segments ($V_L$ and $J_L$);
- (b) allowing the non-human animal to mount an immune response;
- (c) harvesting a lymphocyte (e.g., a B cell) from the immunized non-human animal;
- (d) fusing the lymphocyte with a myeloma cell to form a hybridoma cell; and e) obtaining from the hybridoma cell a nucleic acid sequence that encodes a light chain variable domain ($V_L$ domain) that can bind the antigen.

In another aspect, methods are provided for obtaining an immunoglobulin light chain variable region ($V_L$) nucleic acid sequence of an immunoglobulin light chain capable of binding an antigen independently from a heavy chain variable region, comprising:

(a) immunizing a non-human animal containing a genetically modified immunoglobulin locus as described herein with an antigen of interest, wherein the non-human animal comprises in its genome (i) a rearranged human immunoglobulin heavy chain variable region nucleic acid sequence operably linked to a heavy chain constant region nucleic acid sequence; and (ii) two or more but less than the wild type number of human immunoglobulin light chain variable region gene segments ($V_L$ and $J_L$);

(b) allowing the non-human animal to mount an immune response;

(c) identifying a lymphocyte (e.g., a B cell) from the immunized non-human animal that expresses a $V_L$ amino acid sequence that binds the antigen independently from a heavy chain variable region; and, (d) cloning a nucleic acid sequence encoding the VL amino acid sequence of (c) from the lymphocyte of (c).

In various embodiments, the light chain variable domain described herein is an effector light chain variable domain. In some embodiments, the effector light chain variable domain specifically binds FcRn in order to improve a half-life of multispecific antibodies. For example, a bispecific antibody comprises a heavy chain variable domain that binds an antigen and a light chain variable domain that binds FcRn. In some embodiments, the genetically modified mice as described herein are immunized with FcRN, to obtain antibodies that bind FcRN solely through the light chains. These light chains produced by the genetically modified non-human animal are used as universal or common light chains that assist the bispecific antibody to associate with an FcRn, thereby helping to increase half-life. The remainder of the antibody (e.g., either a second, different light chain, or a heavy chain that binds an antigen different than FcRn) is selected to perform a second function.

In additional aspects, a genetically modified immunoglobulin locus obtainable by any of the methods as described herein is provided. In various embodiments, the light chain variable regions produced by the methods as described herein and the nucleic acid sequence encoding such light chain variable regions are also provided.

In some aspects, an immunoglobulin locus in a germline genome of a non-human animal is provided comprising (1) a rearranged human immunoglobulin heavy chain variable region nucleotide sequence that is operably linked to a heavy chain constant region gene sequence, and (2) an unrearranged human immunoglobulin light chain variable region nucleotide sequence that is operably linked to a light chain constant region gene sequence. In some aspects, an immunoglobulin locus in a germline genome of a non-human animal is provided comprising (1) a rearranged human immunoglobulin heavy chain variable region nucleotide sequence that is operably linked to a light chain constant region gene sequence, and (2) an unrearranged human immunoglobulin light chain variable region nucleotide sequence that is operably linked to a heavy chain constant region gene sequence. In some aspects, an immunoglobulin locus in a germline genome of a non-human animal is provided comprising (1) a rearranged human immunoglobulin heavy chain variable region nucle- otide sequence that is operably linked to a heavy chain constant region gene sequence, and (2) a nucleotide sequence that encodes two or more but less than the wild type number of human immunoglobulin light chain variable region gene segments ($V_L$ and JO. In some embodiments, the light chain constant region gene sequence is a κ light chain constant region gene sequence. In some embodiments, the light chain constant region gene sequence is a λ light chain constant region gene sequence. In some embodiments, the light chain constant region gene sequence is a mouse or rat light chain constant region gene sequence. In some embodiments, the light chain variable region nucleotide sequence is a κ light chain variable region gene sequence. In some embodiments, the light chain variable region nucleotide sequence is a λ light chain variable region gene sequence. In some embodiments, the light chain variable region nucleotide sequence is a mouse or rat light chain variable region gene sequence.

Additional aspects include antigen-binding proteins (e.g. antibodies) made by the genetically modified non-human animals described herein. Likewise, antigen-binding proteins (e.g., recombinant antibodies) with light chain variable region ($V_L$) sequences derived from or produced by (i.e., expressed from the unrearranged human immunoglobulin light chain variable region gene segments) the genetically modified non-human animals described herein are also provided. In some embodiments, the antigen-binding proteins produced by the methods as described herein comprise a heavy chain and a light chain, wherein the heavy chain does not interfere with the binding of the light chain to the antigen, and/or the heavy chain does not bind the antigen in the absence of the light chain. In some embodiments, the light chain variable domain binds an antigen of interest with a $K_D$ that is no more than one order of magnitude higher in the absence of heavy chain than in the presence of heavy chain (e.g., $K_D \sim 10^{-10}$ in the presence of heavy chain or $K_D \sim 10^{-9}$ in the absence of heavy chain). In some embodiments, the antigen-binding proteins as described herein include an immunoglobulin light chain that can specifically bind an antigen of interest with an affinity ($K_D$) lower than $10^{-6}, 10^{-7}, 10^{-8}, 10^{-9}$ or $10^{-10}$. In some embodiments, the immunoglobulin light chain produced by the methods are capable of specifically binding an antigen of interest in the absence of a heavy chain variable region with an affinity ($K_D$) lower than $10^{-6}, 10^{-7}, 10^{-8}, 10^{-9}$, or $10^{-19}$.

In various embodiments, the light chain variable domains generated as described herein specifically bind a target molecule ("T"). A target molecule is any protein, polypeptide, or other macromolecule whose activity or extracellular concentration is desired to be attenuated, reduced or eliminated. In many instances, the target molecule to which a light chain variable region binds is a protein or polypeptide (i.e., a "target protein"); however, also provided are embodiments wherein the target molecule ("T") is a carbohydrate, glycoprotein, lipid, lipoprotein, lipopolysaccharide, or other non-protein polymer or molecule to which a light chain variable region binds. In various embodiments, T can be a cell surface-expressed target protein or a soluble target protein. Target binding by the antigen-binding molecule may take place in an extracellular or cell surface context. In certain embodiments, however, the antigen-binding molecule binds a target molecule inside the cell, for example within an intracellular component such as the endoplasmic reticulum, Golgi, endosome, lysosome, etc. Examples of cell surface-expressed target molecules include cell surface-expressed receptors, membrane-bound ligands, ion channels, and any other monomeric or multimeric polypeptide component with an extracellular portion that is attached to or associated with a cell membrane.

Non-limiting, exemplary cell surface-expressed target molecules that may be targeted by the multispecific antigen-binding molecules provided herein include, e.g., cytokine receptors (e.g., receptors for IL-1, IL-4, IL-6, IL-13, IL-22, IL-25, IL-33, etc.), as well as cell surface targets including other type 1 transmembrane receptors such as PRLR, G-protein coupled receptors such as GCGR, ion channels such as Nav1.7, ASIC1 or ASIC2, non-receptor surface proteins such as MHC-I (e.g., HLA-B*27), etc. In embodiments in which T is a cell surface-expressed target protein, the D1 component of the multispecific antigen-binding molecule can be, e.g., an antibody or antigen-binding fragment of an antibody that specifically binds T, or a ligand or portion of a ligand that specifically interacts with the cell surface-expressed target protein. For example, if T is IL-4R, the D1 component can comprise or consist of IL-4 or a receptor-binding portion thereof. Examples of soluble target molecules include cytokines, growth factors, and other ligands and signaling proteins. Non-limiting exemplary soluble target protein that may be targeted by the multispecific antigen-binding molecules provided herein include, e.g., IL-1, IL-4, IL-6, IL-13, IL-22, IL-25, IL-33, SOST, DKK1, etc. Soluble targets molecules also include, e.g., non-human target molecules such as allergens (e.g., Fel D1, Betv1, CryJ1), pathogens (e.g., *Candida albicans, S. aureus*, etc.), and pathogenic molecules (e.g., lipopolysaccharide (LPS), lipotechoic acid (LTA), Protein A., toxins, etc.). In embodiments in which T is a soluble target molecule, the D1 component of the multispecific antigen-binding molecule can be, e.g., an antibody or antigen-binding fragment of an antibody that specifically binds T, or a receptor or portion of a receptor that specifically interacts with the soluble target molecule. For example, if T is IL-4, the D1 component can comprise or consist of IL-4R or a ligand-binding portion thereof. Target molecules also include tumor-associated antigens.

In another aspect, antigen-binding proteins (e.g., bispecific or trispecific antibodies) can be prepared utilizing antigen-specific light chain variable domains derived from (i.e., with human light chain variable region ($V_L$) sequences generated by) a non-human animal comprising an immunoglobulin locus with a rearranged human heavy chain variable region nucleic acid sequence (i.e., an animal comprising a predesigned, rearranged heavy chain VDJ sequence). Such antigen-specific, reverse chimeric (e.g., human variable/mouse constant) light chains can be used to derive antigen-specific light chain variable region sequences that can be cloned in-frame into an expression vector with a suitable human light chain constant region sequence. An antigen-specific human heavy chain variable region(s) (specific for a different epitope on the same or different antigen than the antigen-specific light chain) from an animal comprising an immunoglobulin locus with a rearranged human heavy chain variable region nucleic acid sequence (i.e., a mouse comprising a predesigned, rearranged heavy chain VDJ sequence), can be cloned in-frame into an expression vector comprising human heavy chain constant region sequence, and the antigen-specific human light and heavy chains can be co-expressed in a suitable cell to obtain an antigen-binding protein (e.g., bispecific or trispecific human antibody). Alternatively, a previously selected antigen-specific heavy chain, e.g., a heavy chain from an antibody that comprises a light chain derived from the same variable region gene segment as the one used in the rearranged human heavy chain variable region nucleic acid sequence may be cloned in-frame into an expression vector comprising human heavy chain constant region sequence, and the antigen-specific human light and heavy chains can be co-expressed in a suitable cell to obtain an antigen-binding protein (e.g., bispecific or trispecific human antibody). In some embodiments, the rearranged human immunoglobulin heavy chain variable region nucleotide sequence is operably linked to a non-human heavy chain constant region gene sequence (e.g., mouse or rat, kappa or lambda). In some embodiments, the rearranged human immunoglobulin heavy chain variable region nucleotide sequence is operably linked to a non-human light chain constant region gene sequence (e.g., mouse or rat, kappa or lambda). In some embodiments, the human light chain variable region ($V_L$) sequences are kappa gene sequences.

In another aspect, a method for making a multispecific antigen-binding protein is provided comprising:
(a) immunizing a first non-human animal containing a first genetically modified immunoglobulin locus as described herein with an antigen of interest, wherein the first non-human animal comprises in its genome (i) a rearranged human immunoglobulin heavy chain variable region nucleotide sequence operably linked to a heavy chain constant region nucleic acid sequence;
(b) allowing the first non-human animal to mount an immune response;
(c) harvesting a first lymphocyte (e.g., a B cell) from the immunized first non-human animal, wherein the first lymphocyte expresses affinity matured antibodies, wherein the affinity matured antibodies comprise a human variable domain fused to a non-human constant domain;
(d) identifying a nucleic acid sequence that encodes the human light chain variable domain of the affinity matured antibodies;
(e) cloning the nucleic acid sequence of (d) in a first expression construct in frame with a suitable human constant region nucleic acid sequence (e.g., a human lambda or kappa sequence) to form a first polypeptide gene;
(f) immunizing a second non-human animal containing a genetically modified immunoglobulin locus as described herein with a second antigen of interest, wherein the second non-human animal comprises in its genome (i) unrearranged human V, D, and J gene segments linked to a non-human heavy chain constant region nucleic acid sequence; and (ii) a single rearranged human light chain variable region sequence;
(g) allowing the second non-human animal to mount an immune response;
(h) harvesting a second lymphocyte from the immunized second non-human animal, wherein the second lymphocyte expresses affinity matured antibodies, wherein the affinity matured antibodies comprise a human heavy chain variable domain fused to a non-human constant domain;
(i) identifying a nucleic acid sequence that encodes a human heavy chain variable domain of the affinity matured antibodies that specifically binds the second antigen;
(j) cloning the nucleic acid sequence of (i) in a second expression construct in frame with a suitable human constant region nucleic acid sequence (e.g., a human IgG1 constant sequence) to form a second polypeptide gene; and
(k) introducing the first expression construct and the second expression construct into a cell suitable for expressing the first polypeptide gene and the second polypeptide gene so as to form an antigen-binding protein comprising a dimer of the second polypeptide, wherein each monomer of the second polypeptide is associated with a monomer of the first polypeptide.

In various embodiments, the first expression construct and the second expression construct are on separate vectors. In various embodiments, the first expression construct and the second expression construct are on the same vector. In various embodiments, the first antigen and the second antigen are different. In one embodiment, the first antigen and the second antigen are the same. In various embodiments, the first antigen is a cell surface receptor, and the second antigen is selected from a soluble antigen and an antigen bound to a cell surface. In specific embodiments, the first antigen is an Fc receptor (e.g., an FcRN), the second antigen is a soluble protein, and the antigen-binding protein comprises one or more histidine substitutions and insertions derived from the $V_L$ gene segment in the genome of the non-human animal.

In another aspect, a method for making a multispecific antigen-binding protein is provided comprising:

(a) immunizing a first non-human animal containing a first genetically modified immunoglobulin locus as described herein with an antigen of interest, wherein the first non-human animal comprises in its genome (i) a first nucleotide sequence that encodes a rearranged heavy chain variable domain (i.e., where the first nucleotide sequence is a rearranged human immunoglobulin heavy chain variable region nucleotide sequence), wherein the first nucleotide sequence is operably linked to a light chain constant region gene sequence; and (ii) a second nucleotide sequence that encodes a human or non-human light chain variable domain (i.e., where the second nucleotide sequence is an unrearranged human immunoglobulin light chain variable nucleotide sequence), wherein the second nucleotide sequence is operably linked to a heavy chain constant region gene sequence;

(b) allowing the first non-human animal to mount an immune response;

(c) harvesting a first lymphocyte (e.g., a B cell) from the immunized first non-human animal, wherein the first lymphocyte expresses affinity matured antibodies, wherein the affinity matured antibodies comprise a human variable domain fused to a non-human constant domain;

(d) identifying a nucleic acid sequence that encodes the human light chain variable domain of the affinity matured antibodies;

(e) cloning the nucleic acid sequence of (d) in a first expression construct in frame with a suitable human constant region nucleic acid sequence (e.g., a human lambda or kappa sequence) to form a first polypeptide gene;

(f) immunizing a second non-human animal containing a genetically modified immunoglobulin locus as described herein with a second antigen of interest, wherein the second non-human animal comprises in its genome (i) unrearranged human V, D, and J gene segments linked to a non-human heavy chain constant region nucleic acid sequence; and (ii) a single rearranged human light chain variable region sequence;

(g) allowing the second non-human animal to mount an immune response;

(h) harvesting a second lymphocyte from the immunized second non-human animal, wherein the second lymphocyte expresses affinity matured antibodies, wherein the affinity matured antibodies comprise a human heavy chain variable domain fused to a non-human constant domain;

(i) identifying a nucleic acid sequence that encodes a human heavy chain variable domain of the affinity matured antibodies that specifically binds the second antigen;

(j) cloning the nucleic acid sequence of (i) in a second expression construct in frame with a suitable human constant region nucleic acid sequence (e.g., a human IgG1 constant sequence) to form a second polypeptide gene; and (k) introducing the first expression construct and the second expression construct into a cell suitable for expressing the first polypeptide gene and the second polypeptide gene so as to form an antigen-binding protein comprising a dimer of the second polypeptide, wherein each monomer of the second polypeptide is associated with a monomer of the first polypeptide.

In various embodiments, the first expression construct and the second expression construct are on separate vectors. In various embodiments, the first expression construct and the second expression construct are on the same vector. In some embodiments, the first antigen and the second antigen are different. In some embodiments, the first antigen and the second antigen are the same. In various embodiments, the first antigen is a cell surface receptor, and the second antigen is selected from a soluble antigen and an antigen bound to a cell surface. In specific embodiments, the first antigen is an Fc receptor (e.g., an FcRN), the second antigen is a soluble protein, and the antigen-binding protein comprises one or more histidine substitutions and insertions derived from the $V_L$ gene segment in the genome of the non-human animal.

In another aspect, a method for making a multispecific antigen-binding protein is provided comprising:

(a) immunizing a first non-human animal containing a first genetically modified immunoglobulin locus as described herein with an antigen of interest, wherein the first non-human animal comprises in its genome (i) a rearranged human immunoglobulin heavy chain variable region nucleotide sequence operably linked to a heavy chain constant region nucleic acid sequence; and (ii) two or more but less than the wild type number of human immunoglobulin light chain variable region gene segments ($V_L$ and $J_L$);

(b) allowing the first non-human animal to mount an immune response;

(c) harvesting a first lymphocyte (e.g., a B cell) from the immunized first non-human animal, wherein the first lymphocyte expresses affinity matured antibodies, wherein the affinity matured antibodies comprise a human variable domain fused to a non-human constant domain;

(d) identifying a nucleic acid sequence that encodes the human light chain variable domain of the affinity matured antibodies;

(e) cloning the nucleic acid sequence of (d) in a first expression construct in frame with a suitable human constant region nucleic acid sequence (e.g., a human lambda or kappa sequence) to form a first polypeptide gene;

(f) immunizing a second non-human animal containing a genetically modified immunoglobulin locus as described herein with a second antigen of interest, wherein the second non-human animal comprises in its genome (i) unrearranged human V, D, and J gene segments linked to a non-human heavy chain constant region nucleic acid sequence; and (ii) a single rearranged human light chain variable region sequence, wherein the single rearranged human light chain variable region sequence is derived from the same VL gene segment as the V_L gene segment encoding the light chain variable domain of step (c);

(g) allowing the second non-human animal to mount an immune response;

(h) harvesting a second lymphocyte from the immunized second non-human animal, wherein the second lymphocyte expresses affinity matured antibodies, wherein the affinity matured antibodies comprise a human heavy chain variable domain fused to a non-human constant domain;

(i) identifying a nucleic acid sequence that encodes a human heavy chain variable domain of the affinity matured antibodies that specifically binds the second antigen;

(j) cloning the nucleic acid sequence of (i) in a second expression construct in frame with a suitable human constant region nucleic acid sequence (e.g., a human IgG1 constant sequence) to form a second polypeptide gene; and (k) introducing the first expression construct and the second expression construct into a cell suitable for expressing the first polypeptide gene and the second polypeptide gene so as to form an antigen-binding protein comprising a dimer of the second polypeptide, wherein each monomer of the second polypeptide is associated with a monomer of the first polypeptide.

In various embodiments, the first expression construct and the second expression construct are on separate vectors. In various embodiments, the first expression construct and the second expression construct are on the same vector. In various embodiments, the first antigen and the second antigen are different. In various embodiments, the first antigen and the second antigen are the same. In various embodiments, the first antigen is a cell surface receptor, and the second antigen is selected from a soluble antigen and an antigen bound to a cell surface. In various embodiments, the first antigen is an Fc receptor (e.g., an FcRN), the second antigen is a soluble protein, and the antigen-binding protein comprises one or more histidine substitutions and insertions derived from the $V_L$ gene segment in the genome of the non-human animal.

In another aspect, a method for making a multispecific antigen-binding protein is provided comprising:

(a) immunizing a non-human animal containing a genetically modified immunoglobulin locus as described herein with a first antigen, wherein the non-human animal comprises in its genome: (i) rearranged human immunoglobulin heavy chain variable region nucleotide sequence operably linked to a heavy chain constant region nucleic acid sequence; and (ii) one or more human immunoglobulin $V_L$ and $J_L$ gene segments;

(b) allowing the non-human animal to mount an immune response;

(c) harvesting a lymphocyte (e.g., a B cell) from the immunized non-human animal, wherein the lymphocyte expresses affinity matured antibodies comprising a human immunoglobulin light chain variable domain fused to a mouse immunoglobulin constant domain;

(d) identifying a first nucleic acid sequence that encodes the human light chain variable domain of the affinity matured antibodies;

(e) cloning the first nucleic acid sequence of (d) into a first expression vector in frame with a human light chain constant region nucleic acid sequence;

(f) introducing into a host cell: (i) the first expression vector comprising the first nucleic acid sequence in frame with the human light chain constant region nucleic acid sequence; and (ii) a second expression vector comprising a second nucleic acid sequence that encodes a first antigen-specific heavy chain variable domain fused to a human heavy chain constant region;

(g) culturing the host cell to allow expression of multispecific antibodies; and (h) isolating the multispecific antibodies, wherein the multispecific antibodies comprise the first antigen-specific heavy chain and the light chain variable domain, wherein the heavy chain variable domain of the multispecific antibodies exhibit an antigen binding specificity distinct from the light chain variable domain.

In various embodiments, the multispecific antibodies are bispecific antibodies. In some embodiments, the multispecific antibodies are trispecific antibodies, and step (f) further comprises introducing a third expression vector comprising a third nucleic acid sequence that encodes a second antigen-specific heavy chain variable domain fused with the human heavy chain constant region sequence.

In another aspect, a method for making a multispecific antigen-binding protein is provided comprising:

(a) immunizing a non-human animal containing a genetically modified immunoglobulin locus as described herein with a first antigen, wherein the non-human animal comprises in its genome: (i) a rearranged heavy chain variable domain operably linked to a heavy chain constant region nucleic acid sequence; and (ii) one or more but less than the wild type number of human immunoglobulin $V_L$ and $J_L$ gene segments;

(b) allowing the non-human animal to mount an immune response;

(c) harvesting a lymphocyte (e.g., a B cell) from the immunized non-human animal, wherein the lymphocyte expresses affinity matured antibodies comprising a human immunoglobulin light chain variable domain fused to a mouse immunoglobulin constant domain;

(d) identifying a first nucleic acid sequence that encodes the human light chain variable domain of the affinity matured antibodies;

(e) cloning the first nucleic acid sequence of (d) into a first expression vector in frame with a human light chain constant region nucleic acid sequence;

(f) introducing into a host cell: (i) the first expression vector comprising the first nucleic acid sequence in frame with the human light chain constant region nucleic acid sequence; and (ii) a second expression vector comprising a second nucleic acid sequence that encodes a first antigen-specific heavy chain variable domain fused to a human heavy chain constant region;

(g) culturing the host cell to allow expression of multispecific antibodies; and (h) isolating the multispecific antibodies, wherein the multispecific antibodies comprise the first antigen-specific heavy chain and the light chain variable domain, wherein the heavy chain variable domain of the multispecific antibodies exhibit an antigen binding specificity distinct from the light chain variable domain.

In various embodiments, the multispecific antibodies are bispecific antibodies. In some embodiments, the multispecific antibodies are trispecific antibodies, and step (f) further comprises introducing a third expression vector comprising a third nucleic acid sequence that encodes a second antigen-specific heavy chain variable domain fused with the human heavy chain constant region sequence.

In another aspect, methods are provided for making an antigen-binding protein that comprises an immunoglobulin light chain variable domain that can bind an antigen independently from a heavy chain variable domain. Such methods comprise
- (a) immunizing a genetically modified non-human animal with a first antigen that comprises a first epitope or immunogenic portion thereof, wherein the non-human animal comprises in its genome:
  - (i) a rearranged human heavy chain variable region nucleic acid sequence operably linked to a heavy chain constant region nucleic acid sequence; and
  - (ii) unrearranged human immunoglobulin light chain variable region gene segments ($V_L$ and $J_L$) operably linked to an immunoglobulin light chain constant region nucleic acid sequence;
- (b) allowing the non-human animal to mount an immune response to the first epitope or immunogenic portion thereof;
- (c) isolating from the non-human animal a cell comprising a nucleic acid sequence that encodes a light chain variable domain that specifically binds the first epitope or immunogenic portion thereof;
- (d) obtaining from the cell of (c) the nucleic acid sequence that encodes the light chain variable domain that specifically binds the first epitope or immunogenic portion thereof;
- (e) employing the nucleic acid sequence of (d) in an expression construct, fused to a human immunoglobulin constant region nucleic acid sequence; and
- (f) expressing the nucleic acid sequence of (d) in a production cell line that expresses a human immunoglobulin heavy chain that specifically binds a second antigen or epitope to form an antigen-binding protein whose light chain is encoded by the nucleic acid of (d) and that binds the first epitope or immunogenic portion thereof independently from the heavy chain, and whose heavy chain specifically binds the second antigen or epitope.

In some embodiments at least one of the unrearranged human light chain $V_L$ or $J_L$ gene segments encode one or more histidine codons that are not encoded by a corresponding human germline light chain variable gene segment. In some embodiments, the first epitope is derived from a cell surface receptor. In some embodiments, the cell surface receptor is an Fc receptor. In particular embodiments, the Fc receptor is FcRn. In some embodiments, the second antigen or epitope is derived from a soluble antigen. In some embodiments, the second antigen or epitope is derived from a cell surface receptor. In some embodiments, the first antigen is an Fc receptor, the second antigen is a soluble protein, and the antigen-binding protein comprises one or more histidine substitutions and insertions derived from the $V_L$ gene segment in the genome of the non-human animal.

In another aspect, methods are provided for making an antigen-binding protein that comprises an immunoglobulin light chain variable domain that can bind an antigen independently from a heavy chain variable domain. Such methods comprise
- (a) immunizing a genetically modified non-human animal with a first antigen that comprises a first epitope or immunogenic portion thereof, wherein the non-human animal comprises in its genome:
  - (i) a rearranged human heavy chain variable region nucleic acid sequence operably linked to a light chain constant region nucleic acid sequence; and
  - (ii) unrearranged human immunoglobulin light chain variable region gene segments ($V_L$ and $J_L$) operably linked to an immunoglobulin heavy chain constant region nucleic acid sequence;
- (b) allowing the non-human animal to mount an immune response to the first epitope or immunogenic portion thereof;
- (c) isolating from the non-human animal a cell comprising a nucleic acid sequence that encodes a light chain variable domain that specifically binds the first epitope or immunogenic portion thereof;
- (d) obtaining from the cell of (c) the nucleic acid sequence that encodes the light chain variable domain that specifically binds the first epitope or immunogenic portion thereof;
- (e) employing the nucleic acid sequence of (d) in an expression construct, fused to a human immunoglobulin constant region nucleic acid sequence; and
- (f) expressing the nucleic acid sequence of (d) in a production cell line that expresses a human immunoglobulin heavy chain that specifically binds a second antigen or epitope to form an antigen-binding protein whose light chain is encoded by the nucleic acid of (d) and that binds the first epitope or immunogenic portion thereof independently from the heavy chain, and whose heavy chain specifically binds the second antigen or epitope.

In some embodiments at least one of the unrearranged human light chain $V_L$ or $J_L$ gene segments encode one or more histidine codons that are not encoded by a corresponding human germline light chain variable gene segment. In some embodiments, the first epitope is derived from a cell surface receptor. In some embodiments, the cell surface receptor is an Fc receptor. In particular embodiments, the Fc receptor is FcRn. In some embodiments, the second antigen or epitope is derived from a soluble antigen. In some embodiments, the second antigen or epitope is derived from a cell surface receptor. In some embodiments, the first antigen is an Fc receptor, the second antigen is a soluble protein, and the antigen-binding protein comprises one or more histidine substitutions and insertions derived from the $V_L$ gene segment in the genome of the non-human animal.

In another aspect, methods are provided for making an antigen-binding protein that comprises an immunoglobulin light chain variable domain that can bind an antigen independently from a heavy chain variable domain. Such methods comprise
- (a) immunizing a genetically modified non-human animal with a first antigen that comprises a first epitope or immunogenic portion thereof, wherein the non-human animal comprises in its genome:
  - (i) a rearranged human heavy chain variable region nucleic acid sequence operably linked to a heavy chain constant region nucleic acid sequence; and
  - (ii) two or more but less than the wild type number of human immunoglobulin light chain variable region gene segments ($V_L$ and $J_L$) operably linked to an immunoglobulin light chain constant region nucleic acid sequence;
- (b) allowing the non-human animal to mount an immune response to the first epitope or immunogenic portion thereof;
- (c) isolating from the non-human animal a cell comprising a nucleic acid sequence that encodes a light chain variable domain that specifically binds the first epitope or immunogenic portion thereof;
- (d) obtaining from the cell of (c) the nucleic acid sequence that encodes the light chain variable domain that specifically binds the first epitope or immunogenic portion thereof;

(e) employing the nucleic acid sequence of (d) in an expression construct, fused to a human immunoglobulin constant region nucleic acid sequence; and (f) expressing the nucleic acid sequence of (d) in a production cell line that expresses a human immunoglobulin heavy chain that specifically binds a second antigen or epitope to form an antigen-binding protein whose light chain is encoded by the nucleic acid of (d) and that binds the first epitope or immunogenic portion thereof independently from the heavy chain, and whose heavy chain specifically binds the second antigen or epitope.

In some embodiments at least one of the human light chain $V_L$ or $J_L$ gene segments encode one or more histidine codons that are not encoded by a corresponding human germline light chain variable gene segment. In some embodiments, the first epitope is derived from a cell surface receptor. In some embodiments, the cell surface receptor is an Fc receptor. In particular embodiments, the Fc receptor is FcRn. In some embodiments, the second antigen or epitope is derived from a soluble antigen. In some embodiments, the second antigen or epitope is derived from a cell surface receptor. In some embodiments, the first antigen is an Fc receptor, the second antigen is a soluble protein, and the antigen-binding protein comprises one or more histidine substitutions and insertions derived from the $V_L$ gene segment in the genome of the non-human animal.

In another aspect, to allow for a facile separation of the antigen-binding proteins described herein, one of the heavy chains is modified to omit a Protein A-binding determinant, resulting in a differential Protein A-binding affinity of a homodimeric binding protein from a heterodimeric binding protein. Compositions and methods that address this issue are described in U.S. Pat. No. 8,586,713, granted 19 Nov. 2013, entitled "Readily Isolated Bispecific Antibodies with Native Immunoglobulin Format," hereby incorporated by reference. Once the specie comprising heterodimeric heavy chain with an identical light chain is selected, this bispecific antigen binding protein can be screened to confirm the retention of its pH-dependent antigen binding property.

In various aspects, a pluripotent cell, induced pluripotent, or totipotent stem cells derived from a non-human animal comprising the various genomic modifications herein are provided. In some embodiments, the pluripotent or totipotent cell is derived from a non-human animal. In some embodiments, the non-human animal is a rodent, e.g., a mouse, a rat, or a hamster. In some embodiments, the rodent is a mouse. In specific embodiments, the pluripotent cell is an embryonic stem (ES) cell. In some embodiments, the pluripotent cell comprises in its genome: (i) an immunoglobulin heavy chain locus that comprises a rearranged human heavy chain variable region nucleic acid sequence operably linked to a heavy chain constant region nucleic acid sequence; and (ii) an immunoglobulin light chain locus comprising one or more but less than the wild type number of human immunoglobulin light chain variable $V_L$ and $J_L$ gene segments, operably linked to a light chain constant region nucleic acid sequence. In specific embodiments, the pluripotent, induced pluripotent, or totipotent stem cells are mouse or rat embryonic stem (ES) cells. In some embodiments, the pluripotent, induced pluripotent, or totipotent stem cells have an XX karyotype or an XY karyotype.

Cells that comprise a nucleus containing a genetic modification as described herein are also provided, e.g., a modification introduced into a cell by pronuclear injection. In another aspect, a hybridoma or quadroma is provided, derived from a cell of the non-human animal as described herein. In some embodiments, the non-human animal is a rodent, such as a mouse, a rat, or a hamster.

In another aspect, a lymphocyte isolated from a genetically modified non-human animal as described herein is provided. In some embodiments, the lymphocyte is a B cell, wherein the B cell comprises an immunoglobulin genomic locus comprising a rearranged human immunoglobulin heavy chain variable region nucleotide sequence operably linked to a human or a non-human animal (e.g., mouse or rat) heavy chain or light chain constant region gene sequence. In some embodiments, the B cell is capable of producing antibodies wherein the rearranged heavy chain variable domain as described herein is operably linked to a heavy chain or light chain constant domain.

In another aspect, a non-human animal embryo comprising a cell whose genome comprises: (i) an immunoglobulin heavy chain locus comprising a rearranged human heavy chain variable region nucleic acid sequence operably linked to a constant region nucleic acid sequence; and (ii) an immunoglobulin light chain locus comprising two or more but less than the wild type number of human immunoglobulin light chain variable region gene segments, operably linked to a light chain constant region nucleic acid sequence.

In various embodiments, the genetically modified non-human animals express an antibody repertoire (e.g., an IgG repertoire) that is derived from the nucleotide sequence that encodes the rearranged heavy chain variable domain, and a plurality of light chain V segments (and a plurality of light chain J segments). In some embodiments, the genetically modified locus produces an antibody population that comprises an immunoglobulin light chain that is capable of specifically binding an antigen of interest with an affinity ($K_D$) lower than $10^{-6}$, $10^{-7}$, $10^{-8}$, $10^{-9}$ or $10^{-10}$. In some embodiments, the immunoglobulin light chain expressed by the genetically modified locus is capable of specifically binding an antigen of interest in the absence of a heavy chain variable region with an affinity ($K_D$) lower than $10^{-6}$, $10^{-7}$, $10^{-8}$, $10^{-9}$, or $10^{-10}$.

In various embodiments, the genetic modifications described herein do not affect fertility of the non-human animal (see, for example, US 2012-0322108A1, incorporated by reference in its entirety). In some embodiments, the heavy chain locus comprises an endogenous Adam6a gene, Adam6b gene, or both, and the genetic modification does not affect the expression and/or function of the endogenous Adam6a gene, Adam6b gene, or both. In some embodiments, the genome of the genetically modified non-human animal comprises an ectopically located Adam6a gene, Adam6b gene, or both. In some embodiments, an Adam6a and/or Adam6b gene is placed 5' upstream of the transcriptional unit of the rearranged heavy chain variable region nucleic acid sequence. In some embodiments, the Adam6a and/or the Adam6b gene is placed 3' downstream of the transcriptional unit of the rearranged heavy chain variable region nucleic acid sequence.

In some embodiments, the genetically modified heavy chain locus does not comprise an Intergenic Control Region 1 (IGCR1) nucleic acid sequence. In some embodiments, the genetically modified heavy chain locus comprises an IGCR1 sequence downstream of the rearranged heavy chain variable region nucleic acid sequence. In some embodiments, the IGCR1 nucleic acid sequence is present between the rearranged heavy chain variable region nucleic acid sequence and the most V-proximal $D_H$ gene segment.

In some aspects, as noted earlier, the immunoglobulin light chain locus of the non-human animals described herein comprises a limited repertoire of light chain variable gene segments, e.g., (i) one, two or more but less than the wild type number of human $V_L$ gene segments. In some embodiments, the non-human animal is a mouse; and the immunoglobulin light chain variable domain is generated from a rearrangement of one of two human Vκ gene segments and one of 1, 2, 3, 4, or 5 human Jκ gene segments. In some embodiments, the mouse exhibits a ratio of (a) B cells in the bone marrow that express an immunoglobulin having a λ light chain to (b) B cells in the bone marrow that express an immunoglobulin having a κ light chain, of about 1 to about 15. In some embodiments, the rearrangement includes a human Vκ1-39 gene segment. In some embodiments, the rearrangement includes a human Vκ3-20 gene segment. In some embodiments, the two human Vκ gene segments is at an endogenous immunoglobulin Vκ locus, and, in some embodiments, the two human Vκ gene segments replace all or substantially all mouse immunoglobulin Vκ gene segments. In some embodiments, the two human Vκ gene segments are at an endogenous immunoglobulin Vκ locus, and, in some embodiments, the two human Vκ gene segments replace all or substantially all mouse immunoglobulin Vκ and Jκ gene segments. In some embodiments, the two human Vκ gene segments are operably linked to two or more (e.g., 2, 3, 4, 5) human Jκ gene segments. In some other embodiments, the light chain variable domain of the mouse is generated through a rearrangement of a human Vκ1-39 gene segment or a human Vκ3-20 gene segment and one of two or more (e.g., 2, 3, 4, or 5) human Jκ gene segments. In some such embodiments, the ratio of immature B cells in the bone marrow that express an immunoglobulin having a λ light chain to immature B cells that express an immunoglobulin having a κ light chain is about 1 to about 13. In some other embodiments, the light chain variable domain of the mouse is generated through a rearrangement of a human Vκ1-39 gene segment or a human Vκ3-20 gene segment and one of two or more (e.g., 2, 3, 4, or 5) human Jκ gene segments, and the ratio of mature B cells in the bone marrow that express an immunoglobulin having a λ light chain to immature B cells that express an immunoglobulin having a κ light chain is about 1 to about 7.

In particular embodiments, the light chain variable domain of a genetically modified mouse as described herein is generated through a rearrangement of a human Vκ1-39 gene segment or a human Vκ3-20 gene segment and one of two or more (e.g., 2, 3, 4, or 5) human Jκ gene segments, and has a pro B cell population in the bone marrow within the range of about $2.5 \times 10^4$ to about $1.5 \times 10^5$ cells, inclusive, for example about $2.5 \times 10^4$, $3.0 \times 10^4$, $3.5 \times 10^4$, $4.0 \times 10^4$, $4.5 \times 10^4$, $5.0 \times 10^4$, $5.5 \times 10^4$, $6.0 \times 10^4$, $6.5 \times 10^4$, $7.0 \times 10^4$, $7.5 \times 10^4$, $8.0 \times 10^4$, $8.5 \times 10^4$, $9.0 \times 10^4$, $9.5 \times 10^4$, $1.0 \times 10^5$, or $1.5 \times 10^5$ cells; in some embodiments, a modified rodent (e.g., a mouse) described herein comprises a pro B cell population in the bone marrow of about $2.88 \times 10^4$ cells; in some embodiments, a modified rodent (e.g., a mouse) described herein comprises a pro B cell population in the bone marrow of about $6.42 \times 10^4$ cells; in some embodiments, a modified rodent (e.g., a mouse) described herein comprises a pro B cell population in the bone marrow of about $9.16 \times 10^4$ cells; in some embodiments, a modified rodent (e.g., a mouse) described herein comprises a pro B cell population in the bone marrow of about $1.19 \times 10^5$ cells. Exemplary pro B cells in the bone marrow of genetically modified rodents (e.g., mice) as described herein are characterized by expression of CD19, CD43, c-kit and/or a combination thereof (e.g., CD19$^+$, CD43$^+$, c-kit$^+$). In some embodiments, a rodent (e.g., mouse) as described herein expresses a light chain generated through a rearrangement of a human Vκ1-39 gene segment or a human Vκ3-20 gene segment and one of two or more (e.g., 2, 3, 4, or 5) human Jκ gene segments, and has a pre B cell population in the bone marrow within in the range of about $1 \times 10^6$ to about $2 \times 10^6$ cells, inclusive, for example, about $1.0 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, or $2.0 \times 10^6$ cells; in some embodiments, a modified rodent (e.g., a mouse) described herein comprises a pre B cell population in the bone marrow of about $1.25 \times 10^6$ cells; in some embodiments, a modified rodent (e.g., a mouse) described herein comprises a pre B cell population in the bone marrow of about $1.46 \times 10^6$ cells; in some embodiments, a modified rodent (e.g., a mouse) described herein comprises a pre B cell population in the bone marrow of about $1.64 \times 10^6$ cells; in some embodiments, a modified rodent (e.g., a mouse) described herein comprises a pre B cell population in the bone marrow of about $2.03 \times 10^6$ cells. Exemplary pre B cells in the bone marrow of genetically modified rodents (e.g., mice) as described herein are characterized by expression of CD19, CD43, c-kit and/or a combination thereof (e.g., CD19$^+$, CD43$^-$, c-kit$^-$).

In various embodiments, a genetically modified mouse as described herein expresses a light chain generated through a rearrangement of a human Vκ1-39 gene segment or a human Vκ3-20 gene segment and one of two or more (e.g., 2, 3, 4, or 5) human Jκ gene segments, and has an immature B cell population in the bone marrow within the range of about $5 \times 10^5$ to about $7 \times 10^5$ cells, inclusive, for example, about $5.0 \times 10^5$, $5.1 \times 10^5$, $5.2 \times 10^5$, $5.3 \times 10^5$, $5.4 \times 10^5$, $5.5 \times 10^5$, $5.6 \times 10^5$, $5.7 \times 10^5$, $5.8 \times 10^5$, $5.9 \times 10^5$, $6.0 \times 10^5$, $6.1 \times 10^5$, $6.2 \times 10^5$, $6.3 \times 10^5$, $6.4 \times 10^5$, $6.5 \times 10^5$, $6.6 \times 10^5$, $6.7 \times 10^5$, $6.8 \times 10^5$, $6.9 \times 10^5$, or $7.0 \times 10^5$ cells; in some embodiments, a modified rodent (e.g., a mouse) described herein comprises an immature B cell population in the bone marrow of about $5.33 \times 10^5$ cells; in some embodiments, a modified rodent (e.g., a mouse) described herein comprises an immature B cell population in the bone marrow of about $5.80 \times 10^5$ cells; in some embodiments, a modified rodent (e.g., a mouse) described herein comprises an immature B cell population in the bone marrow of about $5.92 \times 10^5$ cells; in some embodiments, the rodent (e.g., mouse) comprises an immature B cell population in the bone marrow of about $6.67 \times 10^5$ cells. Exemplary immature B cells in the bone marrow of genetically modified rodents (e.g., mice) as described herein are characterized by expression of IgM, B220 and/or a combination thereof (e.g., IgM$^+$, B220$^{int}$).

In various embodiments, a genetically modified mouse as described herein expresses a light chain generated through a rearrangement of a human Vκ1-39 gene segment or a human Vκ3-20 gene segment and one of two or more (e.g., 2, 3, 4, or 5) human Jκ gene segments, and has a mature B cell population in the bone marrow within the range of about $3 \times 10^4$ to about $1.5 \times 10^5$ cells, inclusive, for example about $3.0 \times 10^4$, $3.5 \times 10^4$, $4.0 \times 10^4$, $4.5 \times 10^4$, $5.0 \times 10^4$, $5.5 \times 10^4$, $6.0 \times 10^4$, $6.5 \times 10^4$, $7.0 \times 10^4$, $7.5 \times 10^4$, $8.0 \times 10^4$, $8.5 \times 10^4$, $9.0 \times 10^4$, $9.5 \times 10^4$, $1.0 \times 10^5$, or $1.5 \times 10^5$ cells; in some embodiments, a modified rodent (e.g., a mouse) described herein comprises a mature B cell population in the bone marrow of about $3.11 \times 10^4$ cells; in some embodiments, a modified rodent (e.g., a mouse) described herein comprise a mature B cell population in the bone marrow of about $1.09 \times 10^5$ cells; in some embodiments, a modified rodent (e.g., a mouse) described herein comprises a mature B cell population in the bone marrow of about $1.16 \times 10^5$ cells; in some embodiments, a modified rodent (e.g., a mouse) described herein comprises a mature B cell population in the bone marrow of about $1.44 \times 10^5$ cells. Exemplary mature B cells in the bone marrow of genetically modified rodents (e.g., mice) as described herein are characterized by expression of IgM, B220 and/or a combination thereof (e.g., IgM$^+$, B220$^{hi}$.

In various embodiments, a genetically modified rodent (e.g., mouse) as described herein expresses a light chain generated through a rearrangement of a human Vκ1-39 gene segment or a human Vκ3-20 gene segment and one of two or more (e.g., 2, 3, 4, or 5) human Jκ gene segments, and has a total B cell population in the bone marrow within the range of about $1\times10^6$ to about $3\times10^6$ cells, inclusive, for example about $1.0\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2.0\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$ or $2.0\times10^6$ cells; in some embodiments, a modified rodent (e.g., a mouse) described herein comprises a total B cell population in the bone marrow of about $1.59\times10^6$ cells; in some embodiments, a modified rodent (e.g., a mouse) described herein comprises a total B cell population in the bone marrow of about $1.75\times10^6$ cells; in some embodiments, a modified rodent (e.g., a mouse) described herein comprises a total B cell population in the bone marrow of about $2.13\times10^6$ cells; in some embodiments, a modified rodent (e.g., a mouse) described herein comprises a total B cell population in the bone marrow of about $2.55\times10^6$ cells. An exemplary total B cells in the bone marrow of genetically modified rodents (e.g., mice) as described herein are characterized by expression CD19, CD20 and/or a combination thereof (e.g., CD19$^+$).

In various embodiments, a genetically modified rodent (e.g., a mouse) as described herein comprises an immunoglobulin κ light chain locus that comprises two unrearranged human immunoglobulin Vκ gene segments and two or more (e.g., 2, 3, 4, or 5) unrearranged human Jκ gene segments, wherein the rodent (e.g., mouse) comprises a peripheral splenic B cell population comprising transitional (e.g., T1, T2 and T3) B cell populations that are about the same as a rodent (e.g., a mouse) that comprises a wild type complement of immunoglobulin κ light chain V and J gene segments. Exemplary transitional B cell populations (e.g., T1, T2 and T3) in the spleen of a genetically modified rodent (e.g., a mouse) as described herein are characterized by expression of IgM, CD23, CD93, B220 and/or a combination thereof.

In various embodiments, a genetically modified rodent (e.g., a mouse) as described herein comprises a T1 B cell population in the spleen (e.g., CD93$^+$, B220$^+$, IgM$^{hi}$, CD23$^-$) within the range of about $2\times10^6$ to about $7\times10^6$ cells, inclusive, for example about $2.0\times10^6$, $2.5\times10^6$, $3.0\times10^6$, $3.5\times10^6$, $4.0\times10^6$, $4.5\times10^6$, $5.0\times10^6$, $5.5\times10^6$, $6.0\times10^6$, $6.5\times10^6$, or $7.0\times10^6$ cells; in some embodiments, a modified rodent (e.g., a mouse) as described herein comprises a T1 B cell population in the spleen of about $2.16\times10^6$ cells; in some embodiments, a rodent (e.g., a mouse) as described herein comprises a T1 B cell population in the spleen of about $3.63\times10^6$ cells; in some embodiments, a modified rodent (e.g., a mouse) described herein comprises a T1 B cell population in the spleen of about $3.91\times10^6$; in some embodiments, a modified rodent (e.g., a mouse) described herein comprises a T1 B cell population in the spleen of about $6.83\times10^6$ cells.

In various embodiments, a genetically modified rodent (e.g., a mouse) as described herein comprises a T2 B cell population in the spleen (e.g., CD93$^+$, B220$^+$, IgM$^{hi}$, CD23$^+$) within the range of about $1\times10^6$ to about $7\times10^6$ cells, inclusive, for example about $1.0\times10^6$, $1.5\times10^6$, $2.0\times10^6$, $2.5\times10^6$, $3.0\times10^6$, $3.5\times10^6$, $4.0\times10^6$, $4.5\times10^6$, $5.0\times10^6$, $5.5\times10^6$, $6.0\times10^6$, $6.5\times10^6$, or $7.0\times10^6$ cells; in some embodiments, a modified rodent (e.g., a mouse) described herein comprises a T2 B cell population in the spleen of about $1.30\times10^6$ cells; in some embodiments, a modified rodent (e.g., a mouse) described herein comprises a T2 B cell population in the spleen of about $2.46\times10^6$ cells; in some embodiments, a modified rodent (e.g., a mouse) described herein comprises a T2 B cell population in the spleen of about $3.24\times10^6$; in some embodiments, a modified rodent (e.g., a mouse) described herein comprises a T2 B cell population in the spleen of about $6.52\times10^6$ cells.

In various embodiments, a genetically modified rodent (e.g., a mouse) as described herein a T3 B cell population in the spleen (e.g., CD93$^+$, B220$^+$, IgM$^{lo}$, CD23$^+$) within the range of about $1\times10^6$ to about $4\times10^6$ cells, inclusive, for example about $1.0\times10^6$, $1.5\times10^6$, $2.0\times10^6$, $2.5\times10^6$, $3.0\times10^6$, $3.5\times10^6$, or $4.0\times10^6$ cells; in some embodiments, a modified rodent (e.g., a mouse) described herein comprises a T3 B cell population in the spleen of about $1.08\times10^6$ cells; in some embodiments, a modified rodent (e.g., a mouse) described herein comprises a T3 B cell population in the spleen of about $1.35\times10^6$ cells; in some embodiments, a modified rodent (e.g., a mouse) described herein comprises a T3 B cell population in the spleen of about $3.37\times10^6$; in some embodiments, a modified rodent (e.g., a mouse) described herein comprises a T1 B cell population in the spleen of about $3.63\times10^6$ cells.

Marginal zone B cells are noncirculating mature B cells that segregate anatomically into the marginal zone (MZ) of the spleen. In rodents, MZ B cells are sessile and reside in the outer white pulp of the spleen between the marginal sinus and the red pulp. This region contains multiple subtypes of macrophages, dendritic cells, and the MZ B cells; it is not fully formed until 2 to 3 weeks after birth in rodents and 1 to 2 years in humans. The MZ B cells within this region typically express high levels of sIgM, CD21, CD1, CD9 with low to negligible levels of sIgD, CD23, CD5, and CD11 b that help to distinguish them phenotypically from follicular (FO) B cells and B1 B cells. Similar to B1 B cells, MZ B cells can be rapidly recruited into the early adaptive immune responses in a T cell independent manner. The MZ B cells are especially well positioned as a first line of defense against systemic blood-borne antigens that enter the circulation and become trapped in the spleen. It is believed they are especially reactive to bacterial cell wall components and are an important source of lipid-specific antibodies. MZ B cells also display a lower activation threshold than their FO B cell counterparts with heightened propensity for plasma cell differentiation that contributes further to the accelerated primary antibody response.

In various embodiments, a genetically modified rodent (e.g., a mouse) as described herein comprising a rearranged human immunoglobulin heavy chain variable region nucleotide sequence (e.g., $V_H3$-23/D/$J_H4$) has increased levels of marginal zone B cells relative to wild type rodents (e.g., wild type mice). In some embodiments, marginal zone B cells in a genetically modified rodent (e.g., mouse) comprising a rearranged human immunoglobulin heavy chain variable region nucleotide sequence are increased by 10%, 20%, 30%, 40%, 50% or more relative to wild type rodents (e.g., wild type mice).

In various embodiments, a genetically modified rodent (e.g., mouse) as described herein comprises an immunoglobulin κ light chain locus that comprises two unrearranged human immunoglobulin Vκ gene segments and 1, 2, 3, 4, or 5 unrearranged human immunoglobulin Jκ gene segments, and wherein the rodent (e.g., mouse) comprises a peripheral splenic B cell population comprising marginal zone and marginal zone precursor B cell populations that are about the same as a rodent (e.g., mouse) that comprises a wild type complement of immunoglobulin Vκ and Jκ gene segments. Exemplary marginal zone B cell populations in the spleen of a genetically modified rodent (e.g., mouse) as described herein are characterized by expression of IgM, CD21/35, CD23, CD93, B220 and/or a combination thereof.

In various embodiments, a genetically modified rodent (e.g., mouse) as described herein comprises marginal zone B cell population in the spleen (e.g., CD93⁻, B220⁺, IgM$^{hi}$, CD21/35$^{hi}$, CD23⁻) within the range of about 1×10⁶ to about 3×10⁶ cells, inclusive, for example, about 1.0×10⁶, 1.5×10⁶, 2.0×10⁶, 2.5×10⁶, or 3.0×10⁶ cells; in some embodiments, a modified rodent (e.g., a mouse) described herein comprises a marginal zone B cell population in the spleen of about 1.47× 10⁶ cells; in some embodiments, a modified rodent (e.g., a mouse) described herein comprises a marginal zone B cell population in the spleen of about 1.49×10⁶ cells; in some embodiments, a modified rodent (e.g., a mouse) described herein comprises a marginal zone B cell population in the spleen of about 2.26×10⁶ cells; in some embodiments, a modified rodent (e.g., a mouse) described herein comprises a marginal zone B cell population in the spleen of about 2.33× 10⁶ cells.

In various embodiments, a genetically modified rodent (e.g., mouse) is provided, wherein the rodent (e.g., mouse) comprises an immunoglobulin κ light chain locus that comprises two unrearranged human immunoglobulin Vκ gene segments and 1, 2, 3, 4, or 5 unrearranged human immunoglobulin Jκ gene segments, and wherein the rodent (e.g., mouse) comprises a peripheral splenic B cell population comprising follicular (e.g., FO-I and FO-II) B cell population(s) that are about the same as a rodent (e.g., mouse) that comprises a wild type complement of immunoglobulin Vκ and Jκ gene segments. Exemplary follicular B cell populations (e.g., FO-I and FO-II) in the spleen of a genetically modified rodent (e.g., mouse) as described herein are characterized by expression of IgM, IgD, CD21/35, CD93, B220 and/or a combination thereof.

In various embodiments, a genetically modified rodent (e.g., mouse) as described herein comprises a follicular type 1 B cell population in the spleen (e.g., CD93⁻, B220⁺, CD21/ 35$^{int}$, IgM$^{lo}$, IgD$^{hi}$) within the range of about 3×10⁶ to about 1.5×10⁷ cells, inclusive, for example about 3.0×10⁶, 3.5×10⁶, 4.0×10⁶, 4.5×10⁶, 5.0×10⁶, 5.5×10⁶, 6.0×10⁶, 6.5×10⁶, 7.0× 10⁶, 7.5×10⁶, 8.0×10⁶, 8.5×10⁶, 9.0×10⁶, 9.5×10⁶, 1.0×10⁷, or 1.5×10⁷ cells; in some embodiments, a modified rodent (e.g., a mouse) as described herein comprises a follicular type 1 B cell population in the spleen of about 3.57×10⁶ cells; in some embodiments, a modified rodent (e.g., a mouse) described herein comprises a follicular type 1 B cell population in the spleen of about 6.31×10⁶ cells; in some embodiments, a modified rodent (e.g., a mouse) described herein comprises a follicular type 1 B cell population in the spleen of about 9.42×10⁶ cells; in some embodiments, a modified rodent (e.g., a mouse) described herein comprise a follicular type 1 B cell population in the spleen of about 1.14×10⁷ cells.

In various embodiments, a genetically modified rodent (e.g., mouse) as described herein comprises a follicular type 2 B cell population in the spleen (e.g., CD93⁻, B220⁺, CD21/ 35$^{int}$, IgM$^{lo}$, IgD$^{hi}$) within the range of about 1×10⁶ to about 2×10⁶ cells, inclusive, for example, 1.0×10⁶, 1.25×10⁶, 1.5× 10⁶, 1.75×10⁶, or 2.0×10⁶ cells; in some embodiments, a modified rodent (e.g., a mouse) described herein comprises a follicular type 2 B cell population in the spleen of about 1.14×10⁶ cells; in some embodiments, a modified rodent (e.g., a mouse) described herein comprises a follicular type 2 B cell population in the spleen of about 1.45×10⁶ cells; in some embodiments, a modified rodent (e.g., a mouse) described herein comprises a follicular type 2 B cell population in the spleen of about 1.80×10⁶; in some embodiments, a modified rodent (e.g., a mouse) described herein comprises a follicular type 2 B cell population in the spleen of about 2.06×10⁶ cells.

The capabilities of the genetically modified non-human animals described herein to apply selective pressure to genes or polynucleotides encoding light chain variable regions or domains (e.g., light chain CDR3s) can be applied to a variety of variable light chain gene sequences. In other words, the rearranged heavy chain variable domain gene sequences disclosed herein can be paired with one or more genetic modifications of a light chain locus and/or the insertion of nucleotide sequences encoding light chain variable domains into a heavy chain locus. This can be accomplished by, for example, mating (i.e., cross-breeding or intercrossing of animals with single modification) the non-human animals described herein (restricted to a common or universal heavy chain variable domain) with non-human animals comprising genetic modifications within one or more light chain-encoding loci. Genetically modified non-human animals comprising immunoglobulin loci with both a rearranged heavy chain variable domain and one or more light chain modifications can also be generated by targeted gene replacement of multiple loci, either simultaneously or sequentially (e.g., by sequential recombination in embryonic stem cells). Neither the type nor method of modification at the light chain loci limits embodiments described herein unless specifically noted. Rather, the selective pressure facilitated by embodiments described herein can be applied to virtually any polynucleotide sequence capable of being expressed and functioning as a light chain antigen-binding sequence, thereby driving the evolution of fitter antibody variable regions.

For example, as described herein, genetically modified non-human animals comprising an immunoglobulin locus with a rearranged heavy chain variable domain gene sequence may further comprise (e.g., via cross-breeding or multiple gene targeting strategies) one or more modifications as described in WO 2011/072204, WO 2011/163311, WO 2011/ 163314, WO 2012/018764, WO 2012/141798, U.S. 2013/ 0185821, WO 2013/022782, WO 2013/096142, WO2013/ 116609; these publications are incorporated herein by reference in their entirety. In particular embodiments, a genetically modified mouse comprising a rearranged heavy chain variable region nucleic acid sequence in a light chain locus (i.e, a rearranged heavy chain variable domain gene sequence operably linked to a human or non-human κ light chain constant region gene sequence) is crossed to a genetically modified mouse comprising an immunoglobulin heavy chain locus comprising human light chain variable region gene segments (e.g., 40 human Vκ genes and all human Jκ genes inserted into a mouse heavy chain locus; see, e.g., U.S. pre-grant publication 2012/0096572, incorporated herein by reference). In specific embodiments, a genetically modified mouse comprising a rearranged heavy chain variable region nucleic acid sequence in a light chain locus (i.e, a rearranged heavy chain variable domain gene sequence operably linked to a human or non-human κ light chain constant region gene sequence) is crossed to a genetically modified mouse comprising an immunoglobulin heavy chain locus comprising one or more (e.g., two) but less than the wild type number of human light chain variable region gene segments. The resulting mice are able to produce kappa+ B cells with variable heavy chains derived from genomic light chain variable sequence, thus facilitating the identification of kappa VJ sequences that bind to specific targets, which can then be reformatted back to a light chain and paired with a variety of heavy chains to produce bi or tri specific antibodies.

EXAMPLES

The following examples are put forth so as to provide those of ordinary skill in the art with a complete disclosure and description of how to make and use non-human animals described herein, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Cloning and Expression Analysis of Candidate Universal Heavy Chain Sequences

Previous studies have shown that $hV_H3$-23 is a thermostable human variable heavy chain gene segment and is also one of the most commonly used variable segments in the human repertoire. Thus, codon-optimized human $V_H3$-23, D4-4 (reading frame 2 or 3), and $J_H4$ (or $J_H6$) gene segments were selected for designing a rearranged heavy chain variable sequence (hereinafter "Universal Heavy Chain" or "UHC").

Briefly, the following four candidate rearranged VDJ sequences were synthesized de novo (by IDT) and cloned into CMV expression vectors (e.g., pRG1301 or pRG1368): (1) $hV_H3$-23(D4-4_RF2)$J_H4$ (SEQ ID NO: 148); (2) $hV_H3$-23 (D4-4_RF2)$J_H6$ (SEQ ID NO: 146); (3) $hV_H3$-23(D4-4_RF3)$J_H4$ (SEQ ID NO: 147); (4) $hV_H3$-23(D4-4_RF3)$J_H6$ (SEQ ID NO: 145). All these constructs were designed in a way that the synthesized UHC genes can be ligated into pRG1301 (hIgG1) or pRG1368 (mIgG1) vectors following digestion with Xho I/Sap I. For expression analysis, the four UHC genes (1-4) in pIDTSMART were subcloned into Xho I/Sap I sites of pRG1301 (hIgG1) or pRG1368 (mIgG1), and each expression construct was transfected separately into CHO cells. Upon transfection, all four candidate VDJ sequences were expressed at a sufficient level, and the expressed peptides were capable of pairing with different κ and λ light chains.

In order to avoid potential autoreactive antibodies that might lead to B cell depletion in the genetically modified mice, the ASAP antibody database of Regeneron Pharmaceuticals, which was generated from the antibodies produced by VELOCIMMUNE® humanized mice, was searched for antibodies containing an amino acid sequence that is similar to $hV_H3$-23(D4-4)$J_H4$ (FIG. 5). More specifically, the criteria that were used to identify non-autoreactive antibodies included the amino acid sequence of DYSNY (SEQ ID NO: 144) or sequences similar to DYSNY (SEQ ID NO: 144). Expression studies in CHO cells, however, revealed that UHC sequences containing DYSNY (SEQ ID NO: 144) did not express well in mammalian cells. Therefore, another sequence that lacks the D but has the sequence YSNY (i.e., antibody H1H2002B; AKGYYFDY (SEQ ID NO: 143); wherein AK is from 3-23; GY is from a D or an N addition or N and P additions; and YFDY is $J_H4$) was selected instead and tested for its expression in CHO cells. The modified UHC sequence was expressed at a sufficient level in CHO cells. These results suggested that some amino acid residues (i.e., a spacer) are required between the sequence encoded by a heavy chain V gene segment and the sequence encoded by a heavy chain J gene segment for proper expression of the rearranged VDJ sequence in mammalian cells.

In addition, the expression levels of the peptide AKGYYFDY derived from the rearranged VDJ sequence ($V_H3$-23/GY/$J_H4$; HIH2002B) in CHO cells were compared with the peptide derived from of $V_H3$-23/D4-4 (reading frame 2)/$J_H4$ (SEQ ID NO: 148), with respect to expression with five human κ chains, three human λ chains, and other rearranged VDJ sequences (i.e., $V_H3$-20 and $V_H1$-39). The selected rearranged VDJ sequence ($V_H3$-23/GY/$J_H4$) showed expression levels equivalent to those of the controls.

Based on these data, $V_H3$-23/GY/$J_H4$ (SEQ ID NO: 137; HIH2002B) was selected as a rearranged heavy chain variable domain sequence for creating a genetically modified mouse. Detailed targeting strategies for generating a mouse containing a genetically modified immunoglobulin locus that encodes a rearranged heavy chain variable domain (i.e., a mouse that comprises an immunoglobulin locus comprising a rearranged human immunoglobulin heavy chain variable region) are illustrated in FIGS. 1-9 and as described below.

Example 2

Construction of Immunoglobulin Heavy Chain Loci Containing a Rearranged VDJ Sequence Construction of immunoglobulin heavy chain loci containing a rearranged human VDJ sequence was carried out by series of homologous recombination reactions in bacterial cells (BHR) using Bacterial Artificial Chromosome (BAC) DNA. Several targeting constructs for creation of a genetically engineered mouse that expresses the rearranged heavy chain variable domain were generated using VELOCIGENE® genetic engineering technology (see, e.g., U.S. Pat. No. 6,586,251 and Valenzuela, D. M. et al. (2003), High-throughput engineering of the mouse genome coupled with high-resolution expression analysis, Nature Biotechnology 21(6):652-659, incorporated herein by reference in their entireties).

Briefly, targeting vectors were designed to introduce a rearranged human immunoglobulin heavy chain variable region nucleotide sequence (i.e., $hV_H3$-23(D)$J_H4$; SEQ ID NO: 136) into a genetically modified mouse in which all or substantially all endogenous functional immunoglobulin heavy chain V, D, J gene segments have been deleted. In addition, the targeting vectors included a genomic region comprising Adam6a and Adam6b genes in order to prevent fertility problems associated with the deletion of the genomic region comprising Adam6a/6b genes in mice (see, for example, US 2012-0322108A1, incorporated by reference herein in its entirety).

Initially, a BHR donor for modifying a mouse BAC clone comprising a leader sequence (which guides the heavy chain through the endoplasmic reticulum), a rearranged heavy chain variable region nucleotide sequence ($V_H3$-23(D)$J_H4$; SEQ ID NO: 136) and an intron of $hJ_H4$ (SEQ ID NO: 140) that are operably linked to a 2239-bp $V_H3$-23 promoter (SEQ ID NO: 139), was constructed. Additionally, the genomic locus was flanked 5' and 3' by mouse IgH homology boxes for homologous recombination with the MAID1115 BAC clone (FIG. 1).

In addition, the following five modifications have been carried out to create a targeting construct containing a rearranged human immunoglobulin heavy chain variable region nucleotide sequence.

First, a spectinomycin selection cassette was introduced into the upstream of the $V_H3$-23 promoter (between the I-CeuI and SpeI sites) to generate pJSh0038 (UHC minilocus; SEQ ID NO: 142) (FIG. 1, 1. I-CeuI/SpeI Ligation (Amp+Spec)). The UHC mini-locus contains: (1) a spectinomycin (Spec) cassette with I-CeuI/AscI sites for ligation; (2)

2239-bp hV$_H$3-23 promoter (SEQ ID NO: 139); (3) a rearranged hV$_H$3-23(D)J$_H$4 nucleotide sequence (SEQ ID NO: 136); (4) an hJ$_H$4 intron (SEQ ID NO: 140); and (5) mouse homology boxes for BHR (MAID 1115).

Second, a hygromycin selection cassette (EM7-HYG) was targeted into the 5' end of the genomic region of the MAID 1115 BAC clone, which contains a loxP-flanked neomycin cassette (Pgk-Neo) in the upstream of the IgM genomic region. Insertion of the hygromycin cassette deleted the loxP site located at the 5' end of the MAID 1115 clone. The bacterial cells containing the genetically modified BAC clone (VI432) were selected via hygromycin/kanamycin selection (FIG. 2, 2. BHR (Hyg+Kan)).

Third, the UHC mini-locus, which was constructed in Step 1, was targeted into the upstream of the IgM locus of the VI432 BAC clone. The introduction of the UHC mini-locus replaced the floxed neomycin selection cassette with a new spectinomycin cassette (VI443). Bacterial cells containing the genetically modified BAC clones (VI443) were selected via spectinomycin and hygromycin selection (FIG. 2; 3. BHR (Spec+Hyg)).

Fourth, the VI421 BAC clone, which comprises, from 5' to 3', (1) an Adam6a gene (present in a 3' to 5' direction); (2) a neomycin cassette (present in a 3' to 5' direction) flanked by FRT sites; (3) an Adam6b gene (present in a 3' to 5' direction); (4) Intergenic Control Region 1 (IGCR1; i.e., a key V(D)J recombination regulatory region); and (5) a spectinomycin cassette (present in a 5' to 3' direction), were targeted with the pDBa0049 construct, which contains a chloramphenicol (Cm) cassette; an AscI restriction site upstream of the chloramphenicol gene; and 5' and 3' homology arms. The targeting of the pDBa0049 construct removed IGCR1 and the spectinomycin cassette from the V1421 clone; and introduced a new AscI restriction site and a chloramphenicol cassette to the downstream of the Adam6b gene. Bacterial cells containing the successfully targeted clone (V1444) were selected via chloramphenicol and kanamycin selection (FIG. 3; 4. BHR (Cm+Kan)).

Figure 3:
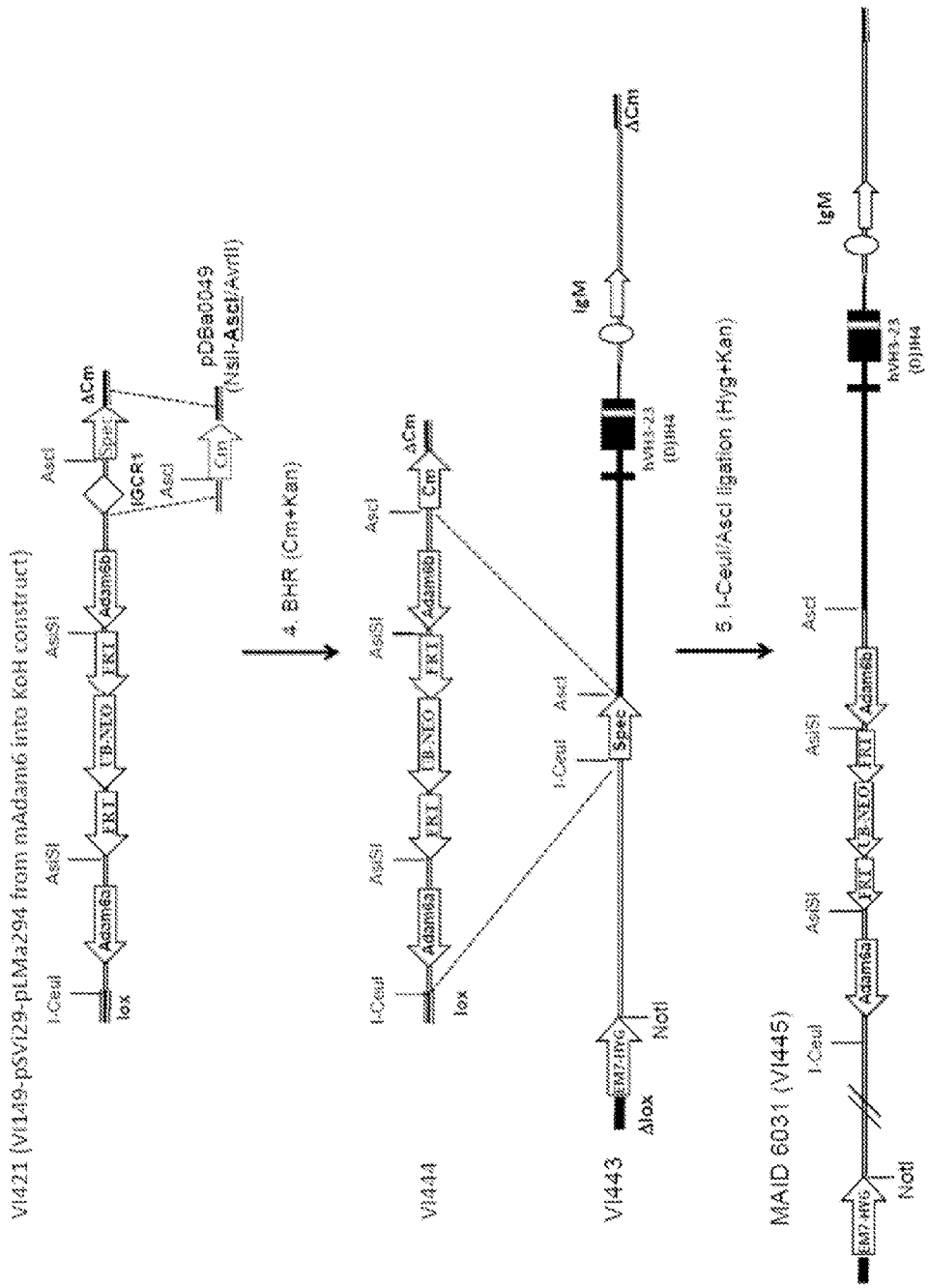
FIG. 3 illustrates schemes for (A) targeting the pDBa0049 construct comprising a chloramphenicol cassette into the 3' end of the VI421 clone, which comprises, from 5' to 3', an Adam6a gene (present in a 3' to 5' direction); a neomycin cassette (present in a 3' to 5' direction) flanked by FRT sites; an Adam6b gene (present in a 3' to 5' direction); Intergenic Control Region 1 (IGCR1; a key V(D)J recombination regulatory region); and a spectinomycin cassette (present in a 5' to 3' direction) (4. BHR (Cm+Kan)); and (B) targeting the genomic locus of the VI444 BAC clone containing the Adam6a and 6b genes into the upstream of the universal heavy chain (UHC) genomic locus of the VI443 BAC clone between the I-CeuI and the AscI sites via restriction digestion and ligation (5. I-CeuI/AscI ligation (Hyg+Kan)).
Figure 4:
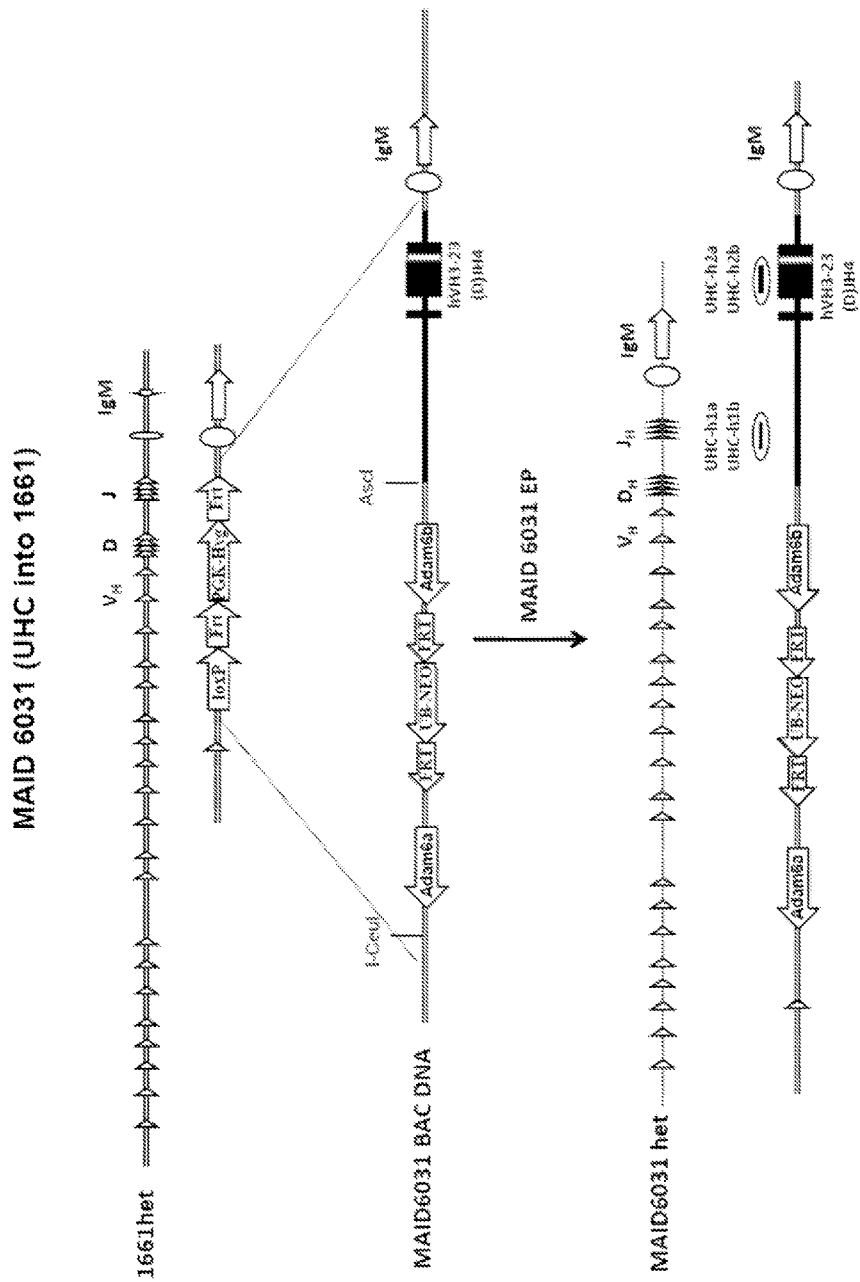
FIG. 4 illustrates schemes for (A) targeting the final construct (MAID6031 BAC DNA) into ES cells isolated from the 1661 heterozygous mouse; and shows (B) the genomic location of the probes and primers used in the screening assays.
Figure 6:
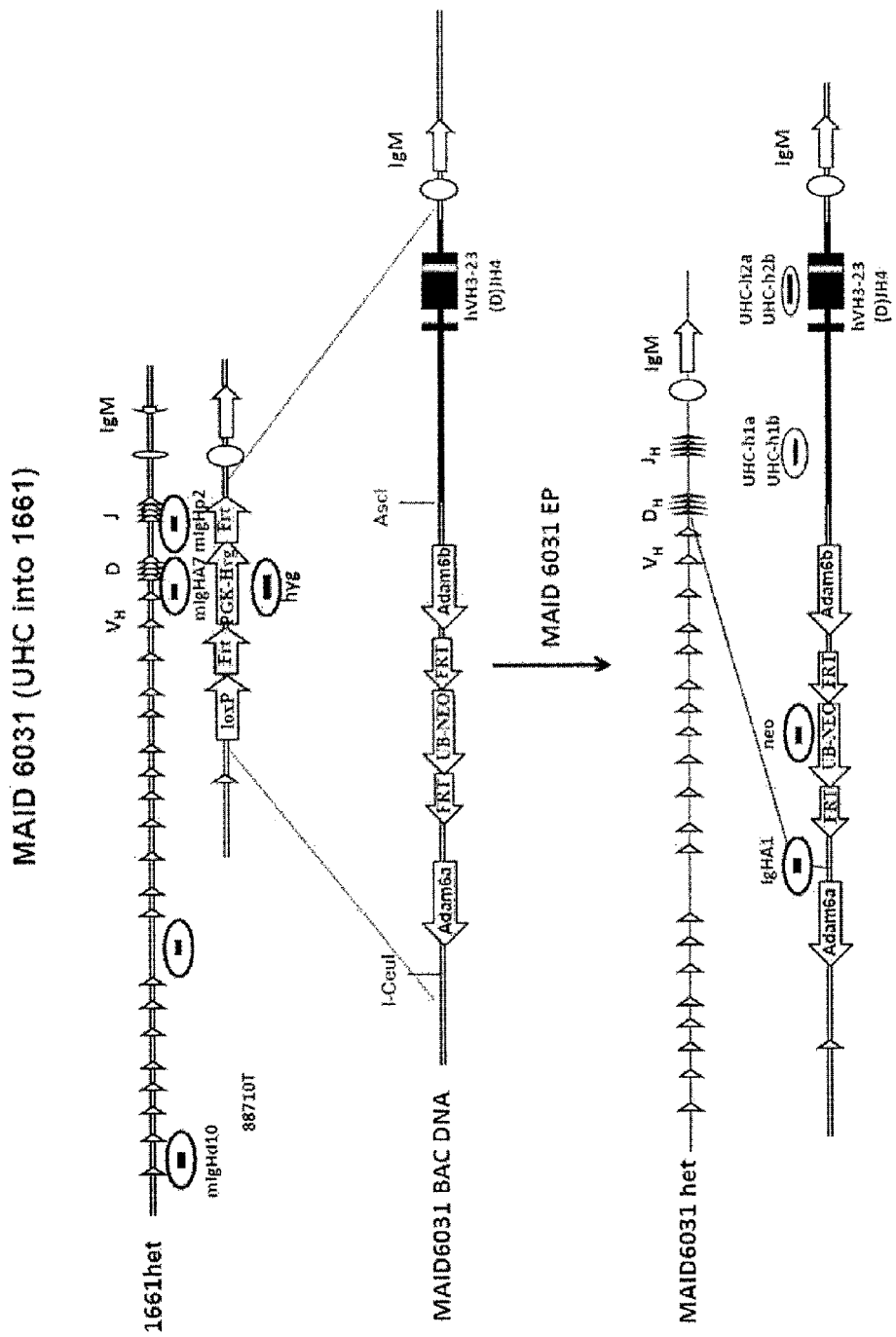
FIG. 6 illustrates the genomic organization of the 6031 bacterial artificial chromosome (BAC) DNA and 6031 heterozygous ES cells, and the genomic location of the primers and probes used in the screening assays.
Figure 9:
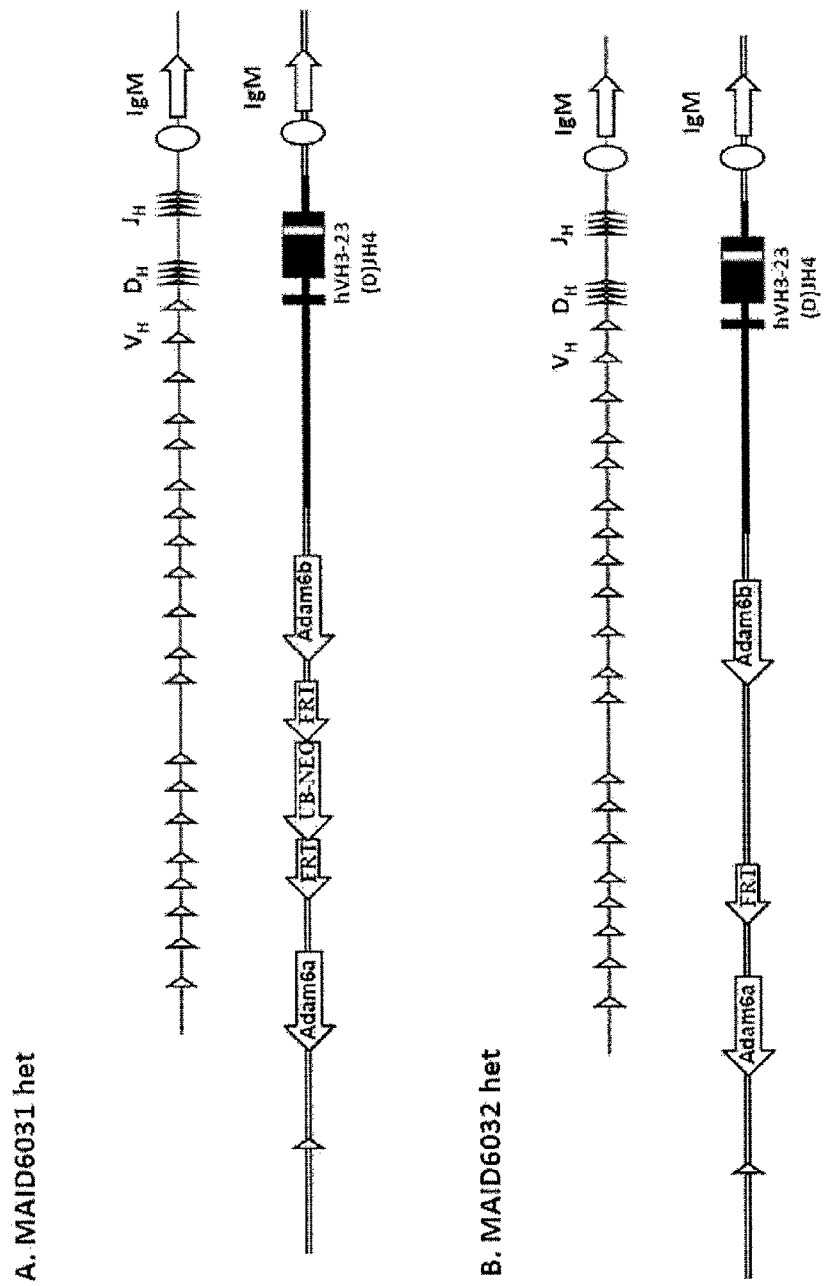
FIG. 9 illustrates the genomic structure of the immunoglobulin heavy chain locus of genetically modified F0 mice, which contains one copy of the targeted allele (including the Adam6a/6b genes and the rearranged human immunoglobulin heavy chain variable region nucleotide sequence ($hV_H3$-23(D)$J_H4$;). (A) MAID 6031 het: a heterozygous F0 mouse comprising a genetically modified immunoglobulin heavy chain locus with a selection cassette; (B) MAID 6032 het: a heterozygous F0 mouse comprising a genetically modified immunoglobulin heavy chain locus without a selection cassette.
Figure 10:
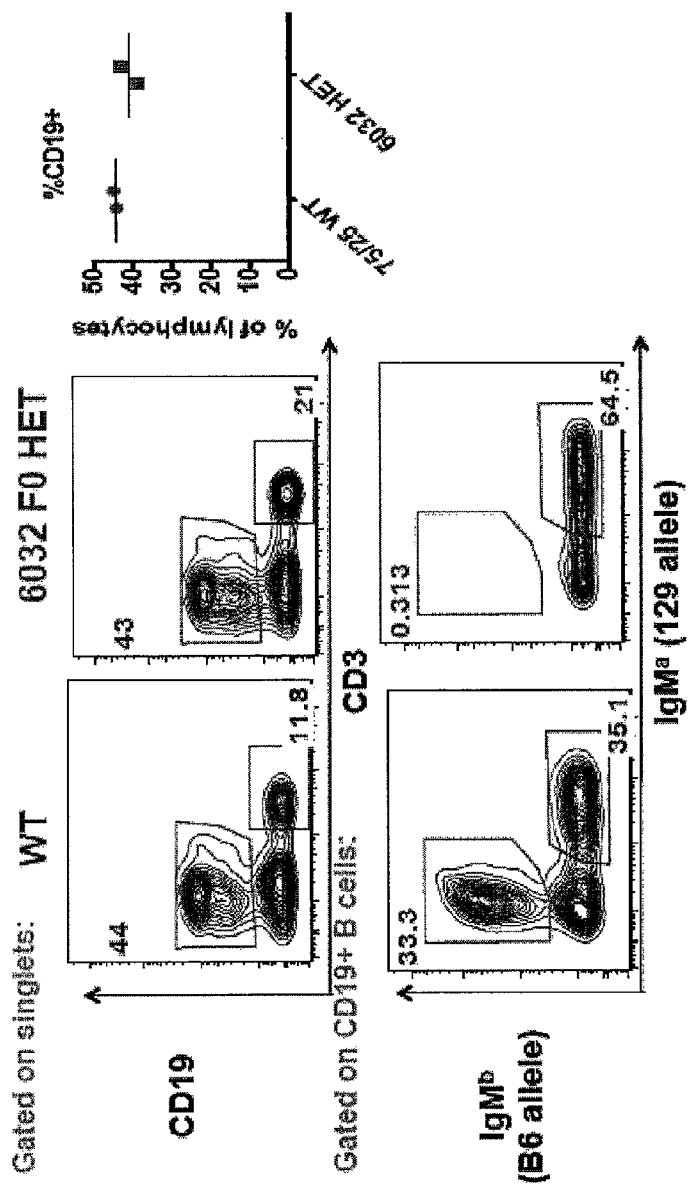
FIG. 10 shows the result of fluorescence-activated cell sorting (FACS) analysis of the bone marrow cells isolated from a wild type or 6032 heterozygous mouse. Upper Panel: Bone marrow cells isolated from a wild type or an F0 6032 heterozygous mouse were gated on singlets and sorted based on CD19 expression (a B cell marker) and CD3 expression (a T cell marker). Lower Panel: CD19+-gated B cells were sorted based on the presence of $IgM^b$ antibodies (antibodies produced from a wild type allele; B6 allele) or $IgM^a$ antibodies (antibodies produced from the genetically modified allele (129 allele) encoding a rearranged heavy chain variable domain ($hV_H3$-23(D)$J_H4$).

Fifth, the genomic region of the V1444 BAC clone containing the Adam6a and/or 6b genes were introduced into the upstream of the universal heavy chain genomic locus in the VI443 BAC clone between the I-CeuI and the AscI sites via restriction digestion and ligation (FIG. 3). This modification introduces Adam6a and/or 6b genes into the clone and replaces the spectinomycin cassette with a neomycin cassette, yielding a final targeting construct (MAID6031; V1445). The bacterial cells (BHR) containing the final targeting construct (MAID 6031; VI445) were selected based on hygromycin and kanamycin selection (FIG. 3, 5. I-CeuI/AscI ligation (Hyg+Kan)).

The final targeting construct (MAID6031) for the creation of a genomic locus containing a rearranged human heavy chain variable domain sequence contains, from 5' to 3', (1) a 5' homology arm containing about 20000 bp of a mouse genomic sequence upstream of the endogenous Ig heavy chain locus; (2) an Adam6a gene; (3) a 5' FRT site; (4) a neomycin cassette; (5) a 3' FRT site, (6) an Adam6b gene; (7) 2239 by of hVH3-23 promoter (SEQ ID NO: 139); (8) a rearranged human immunoglobulin heavy chain nucleotide sequence (hVH3-23(D)J$_H$4; SEQ ID NO: 136); (9) an hJ$_H$4 intron (SEQ ID NO: 140); and (10) a 3' homology arm containing about 7400 by of a mouse genomic sequence downstream of the mouse J$_H$ gene segments.

The final targeting construct, MAID6031 BAC DNA, was linearized and electroporated into ES cells isolated from the 1661 heterozygous mouse (FIG. 4.), which contain a wild-type Ig heavy chain VDJ genomic loci and a mutated VDJ genomic loci in which all V$_H$, D, J$_H$ genes have been deleted. Successfully targeted mouse ES cells were screened using the primers and probes set forth in FIGS. 6-8. The successfully targeted mouse ES cells were introduced into host mouse embryos using VELOCIMOUSE® technology to produce a genetically modified heterozygous F0 mouse. In order to generate mice (MAID 6032 het) without the selection cassette (i.e., FRT-Ub-Neo-FRT), the successfully targeted ES cells were electroporated with a plasmid that expresses Flp recombinase prior to introducing into host embryos. Alternatively, MAID6031 heterozygous male mice harboring the selection cassette were bred to female mice that express Flp recombinase in order to remove the cassette. Heterozygous mice bearing the modification were bred to each other to generate homozygotes (MAID 6032 HO) that are capable of making immunoglobulin heavy chains only from the genetically modified locus.

Example 3

Characterization of Genetically Modified Mice Expressing a Rearranged Heavy Chain Variable Domain All mice were housed and bred in specific pathogen-free conditions at Regeneron Pharmaceuticals. Three wild type (WT) littermate control mice (16 weeks old, male, n=2; Background: 75% C57/BL6 and 25% 129) and two to four MAID 6032 HET F0 mice (FIG. 9; 9 weeks old, male, n=2; Background: 50% C57/BL6 and 50% 129) were sacrificed, and blood, spleens and bone marrow were harvested from the animals. Additionally, four wild type (WT) littermate control mice (10 weeks old; 2 male and 2 female) and four MAID 6032 homozygous ("HO") F2 mice (10 weeks old; 3 male; 1 female) were sacrificed, and blood, spleens and bone marrow were harvested from the animals. Blood was collected into BD microtainer tubes with EDTA (Cat #365973). Bone marrow was collected from femurs by flushing with complete RPMI medium (RPMI medium supplemented with fetal calf serum, sodium pyruvate, Hepes, 2-mercaptoethanol, non-essential amino acids, and gentamycin). Red blood cells from peripheral blood, spleen and bone marrow preparations were lysed with ACK lysis buffer and washed with complete RPMI medium.

Flow Cytometry

In order to examine the ability of the genetically modified heterozygous F0 mice (MAID 6032 HET) described herein to produce antibodies derived from the genetically modified allele (i.e., from the allele that contains a single copy of the rearranged V$_H$3-23/D/J$_H$4), fluorescence-activated cell sorting (FACS) analysis was performed using blood, spleen, bone marrow cells isolated from a wild-type or a 6032 heterozygous mouse.

Figure 11:
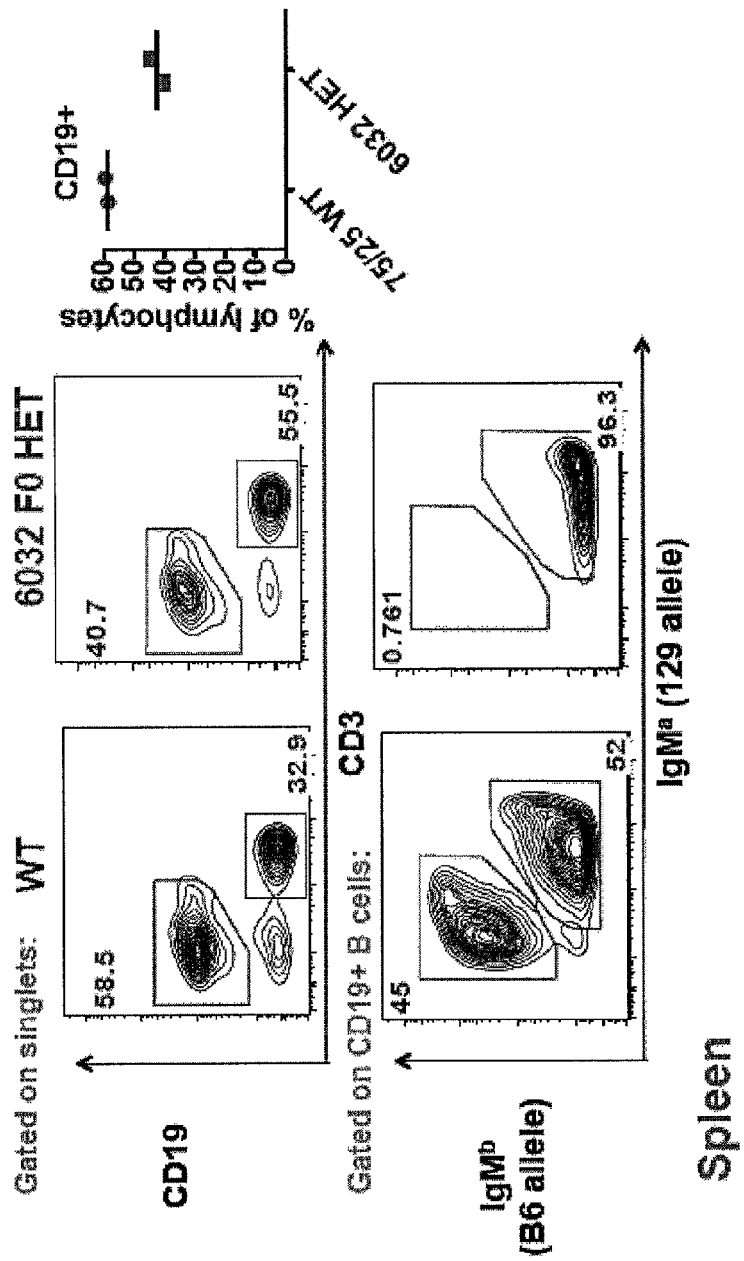
FIG. 11 shows the result of FACS analysis of the spleen cells isolated from a wild type or 6032 heterozygous mouse. Upper Panel: Spleen cells isolated from a wild type or F0 6032 heterozygous mouse were gated on singlets and sorted based on CD19 expression (a B cell marker) and CD3 expression (a T cell marker). Lower Panel: CD19+-gated B cells were sorted based on the presence of $IgM^b$ antibodies (antibodies produced from a wild type allele; B6 allele) or $IgM^a$ antibodies (antibodies produced from the genetically modified allele (129 allele) encoding a rearranged heavy chain variable domain ($hV_H3$-23(D)$J_H4$).
Figure 12:
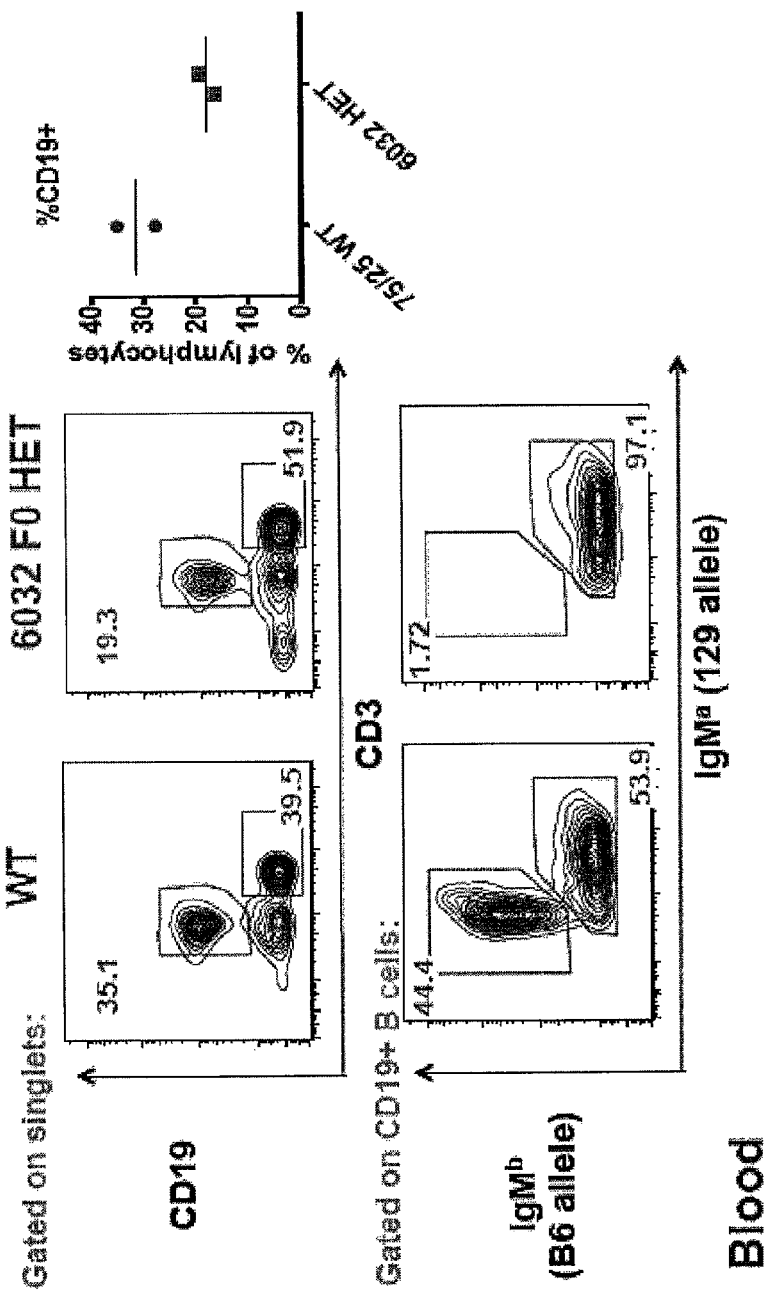
FIG. 12 shows the result of FACS analysis of the blood cells isolated from a wild type or 6032 heterozygous mouse. Upper Panel: Blood cells isolated from a wild type or F0 6032 heterozygous mouse were gated on singlets and sorted based on CD19 expression (a B cell marker) and CD3 expression (a T cell marker). Lower Panel: CD19+-gated B cells were sorted based on the presence of $IgM^b$ antibodies (antibodies produced from a wild type allele; B6 allele) or $IgM^a$ antibodies (antibodies produced from the genetically modified allele (129 allele) encoding a rearranged heavy chain variable domain (hV$_H$3-23(D)J$_H$4).

Briefly, 1×10$^6$ cells were incubated with mouse anti-CD16/CD32 antibodies (2.4G2, BD) on ice for 10 minutes, followed by labeling with the following antibody cocktail for 30 min on ice: anti-mouse FITC-IgM$^a$ (DS-1, BD Biosciences), Pacific blue-CD3 (17A2, BioLegend), APC-H7-CD19 (1 D3, BD Biosciences) and PE-IgM$^b$ (AF6-78, BioLegend). Stained cells were washed and fixed in 2% formaldehyde. Data acquisition was performed on the BD LSRFortessa flow cytometer and analyzed with FlowJo. Bone marrow cells, spleen cells, and blood cells isolated from a wild type or F0 6032 heterozygous mouse were gated on singlets and sorted based on CD19 expression (a B cell marker) or CD3 expression (a T cell marker). In addition, CD19+-gated B cells were sorted based on the presence of IgM$^b$ antibodies (IgM antibodies produced from a wild type allele (B6 allele)) or IgM$^a$ antibodies (antibodies produced from the genetically modified allele (129 allele) comprising a rearranged heavy chain variable region nucleotide sequence (hV$_H$3-23(D)J$_H$4;). The FACS analysis (FIGS. 11-12) suggested that the mice heterozygous with respect to the targeted allele (i.e., containing one copy of the rearranged heavy chain variable sequence; MAID 6032 het) were able to produce IgM antibodies mostly derived from the genetically modified 129 (IgM$^a$) allele.

In order to examine the ability of the genetically modified homozygous F2 mice (MAID 6032 HO) described herein to produce antibodies derived from the genetically modified allele (i.e., from the allele that contains a single copy of the rearranged V$_H$3-23/D/J$_H$4), fluorescence-activated cell sorting (FACS) analysis was performed as described above using spleen and bone marrow cells isolated from a wild-type or a 6032 homozygous mouse.

Only mature B lymphocytes can enter the lymphoid follicles of spleen and lymph nodes and thus efficiently participate in the immune response. Mature, long-lived B lymphocytes derive from short-lived precursors generated in the bone marrow. Selection into the mature pool is an active process and takes place in the spleen. Two populations of splenic B cells have been identified as precursors for mature B cells. Transitional B cells of type 1 (T1) are recent immigrants from the bone marrow. They develop into the transitional B cells of type 2 (T2), which are cycling and found exclusively in the primary follicles of the spleen. Mature B cells can be generated from T1 or T2 B cells. Loder, F. et al., J. Exp. Med., 190(1): 75-89, 1999.

Figure 13A:
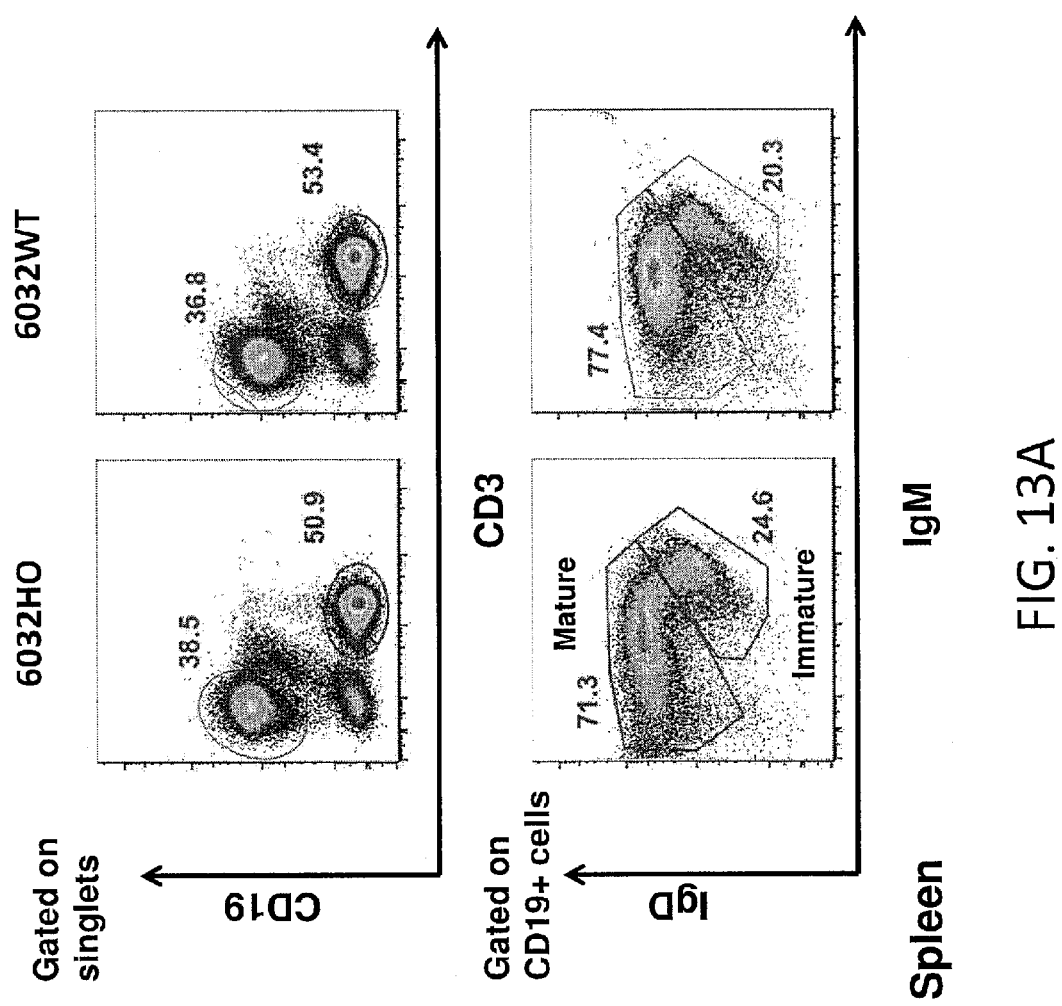
FIG. 13A shows the results of FACS analysis for the total number of CD19+ B cells immature B cells (CD19+IgD$^{int}$IgMhi) and mature B cells (CD19+IgM$^{lo}$IgD$^{hi}$) in harvested spleens from wild type mice (WT) and mice homozygous (6032HO) for a rearranged human immunoglobulin variable region nucleotide sequence (V$_H$3-23/D/J$_H$4). Upper Panel: Spleen cells isolated from a wild type or F2 6032 homozygous mouse were gated on singlets and sorted based on CD19 expression (a B cell marker) and CD3 expression (a T cell marker). The bottom panel shows representative contour plots of splenocytes gated on CD19+ and stained for immunoglobulin D (IgD) and immunoglobulin M (IgM) from a wild type mouse (WT) and a mouse homozygous for a rearranged heavy chain human immunoglobulin variable region nucleotide sequence (V$_H$3-23/D/J$_H$4). Percentage of cells within each gated region is shown.
Figure 13B:
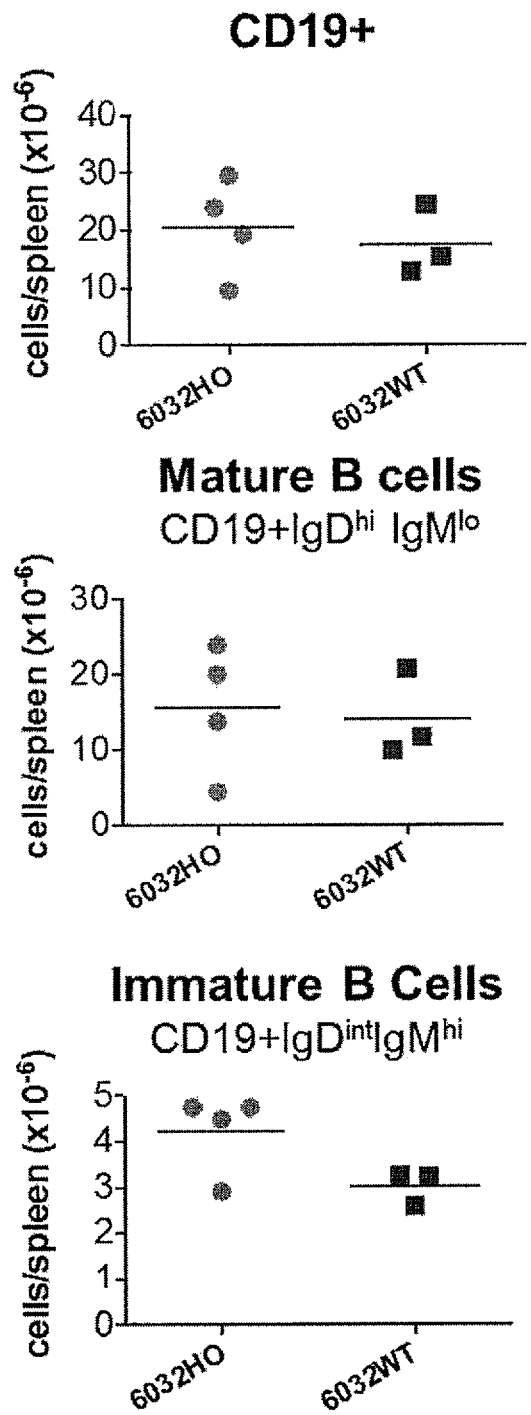
FIG. 13B shows the total number of B cells (CD19+), mature B cells (CD19+IgD$^{hi}$ IgM$^{lo}$) and immature B cells (CD19+IgD$^{int}$IgM$^{hi}$) in harvested spleens from wild type (WT) and mice homozygous for a rearranged human immunoglobulin heavy chain variable region nucleotide sequence (V$_H$3-23/D/J$_H$4).
Figure 13C:
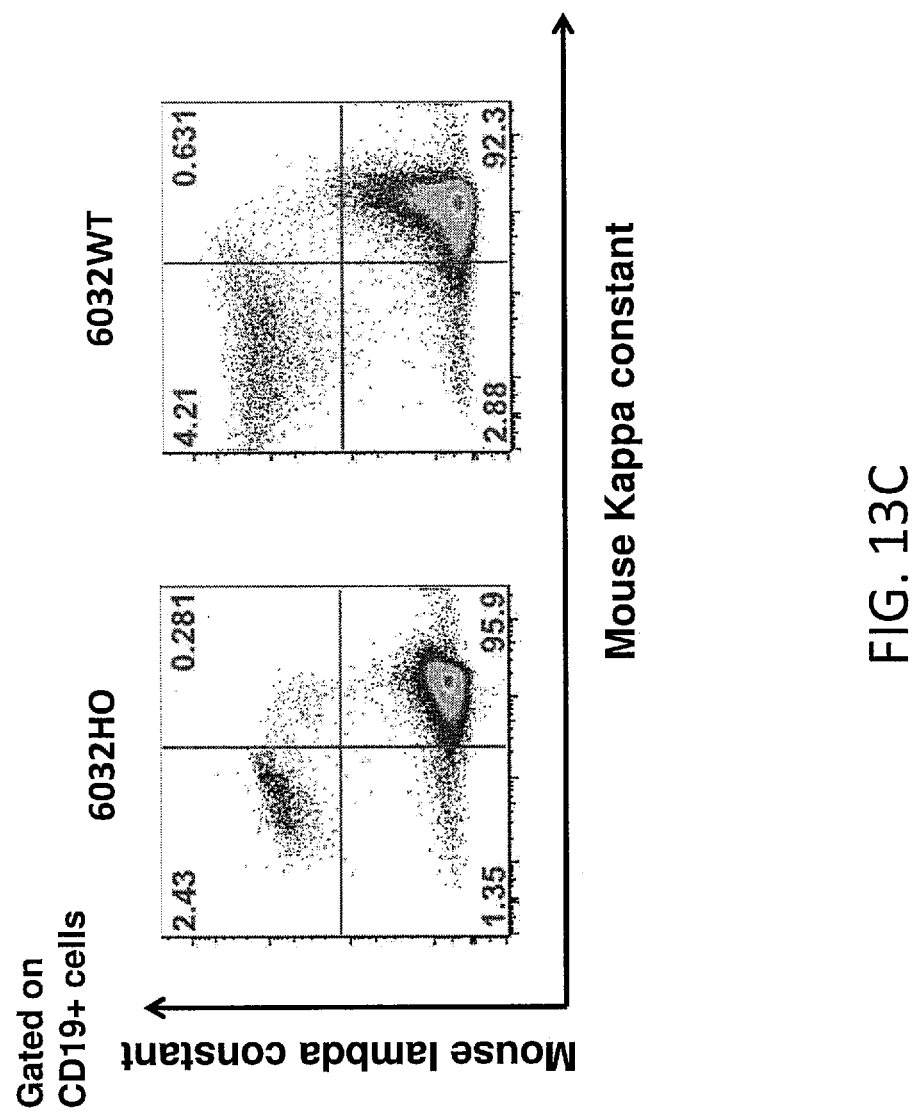
FIG. 13C shows representative contour plots of Igλ+ and Igκ+ splenocytes gated on CD19+ from a wild type mouse (WT) and a mouse (6032HO) homozygous for a rearranged human immunoglobulin heavy chain variable region nucleotide sequence (V$_H$3-23/D/J$_H$4).
Figure 13D:
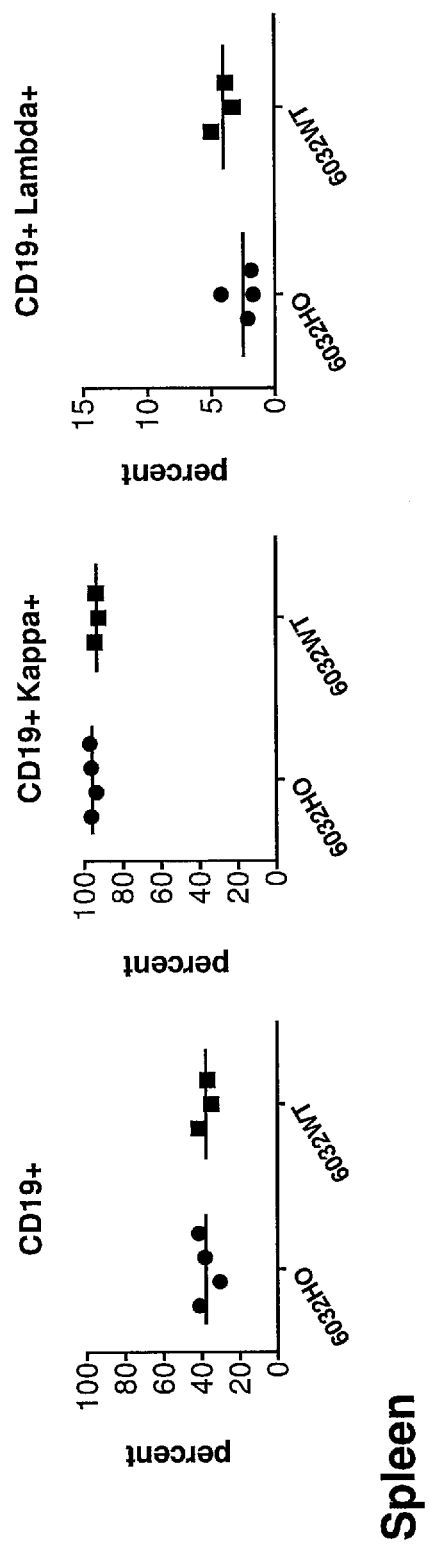
FIG. 13D shows the total number of B cells (CD19+), Igκ+ B cells (CD19+Igkappa+) and Igλ+ B cells (CD19+Iglambda+) in harvested spleens from wild type (WT) and mice homozygous for a rearranged human immunoglobulin heavy chain variable region nucleotide sequence (V$_H$3-23/D/J$_H$4).
Figure 13E:
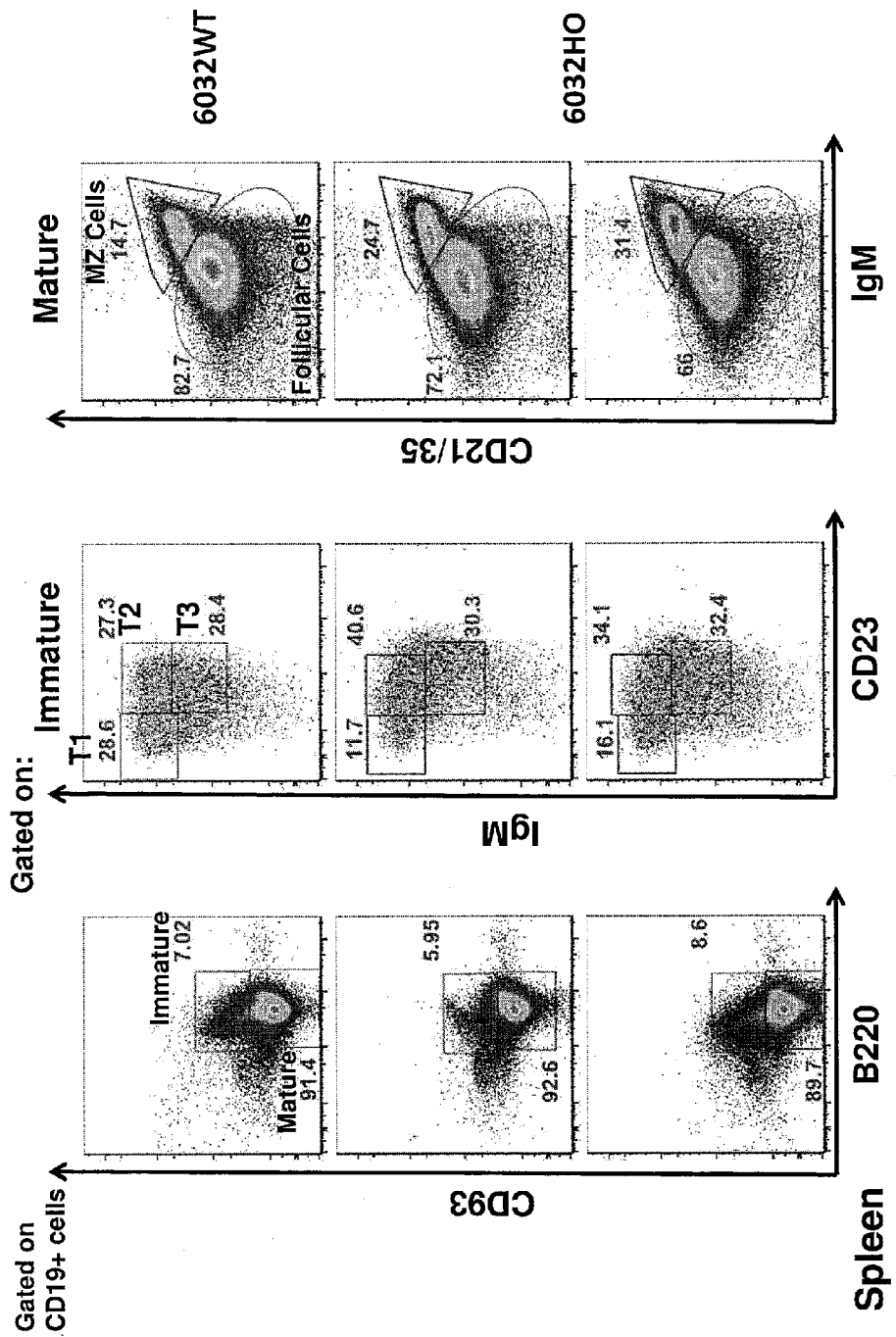
FIG. 13E shows the peripheral B cell development in a wild type mouse and mice homozygous for a rearranged human immunoglobulin heavy chain variable region nucleotide sequence (V$_H$3-23/D/J$_H$4). The first column (left) of contour plots show CD93+ and B220+ splenocytes gated on CD19+ indicating immature and mature B cells. The second column (middle) of contour plot shows IgM+ and CD23+ expression in immature B cells indicating T1 (IgD–IgM+ CD21$^{lo}$CD23–), T2 (IgD$^{hi}$IgM$^{hi}$CD21$^{mid}$CD23+) and T3 B cell populations. The third column (right) of contour plots shows CD21+(CD35+) and IgM+ expression of mature B cells indicating a smaller first population that give rise to marginal zone B cells and a second population that gives rise to follicular (FO) B cells. Percentage of cells within each gated region is shown.

The FACS analysis (FIGS. 13A and 13B) suggested that the mice homozygous with the respect to the targeted allele (i.e., containing two copies of the rearranged heavy chain variable sequence: MAID 6032 HO) were able to produce normal splenic mature and immature B cell populations, albeit with a slight decrease in the lambda sequences relative to wild type (FIGS. 13C and 13D). Also in the spleen, the MAID 6032HO mice demonstrated a slight decrease in T1 population B cells and an increase in marginal zone B cells (FIG. 13E).

Figure 14A:
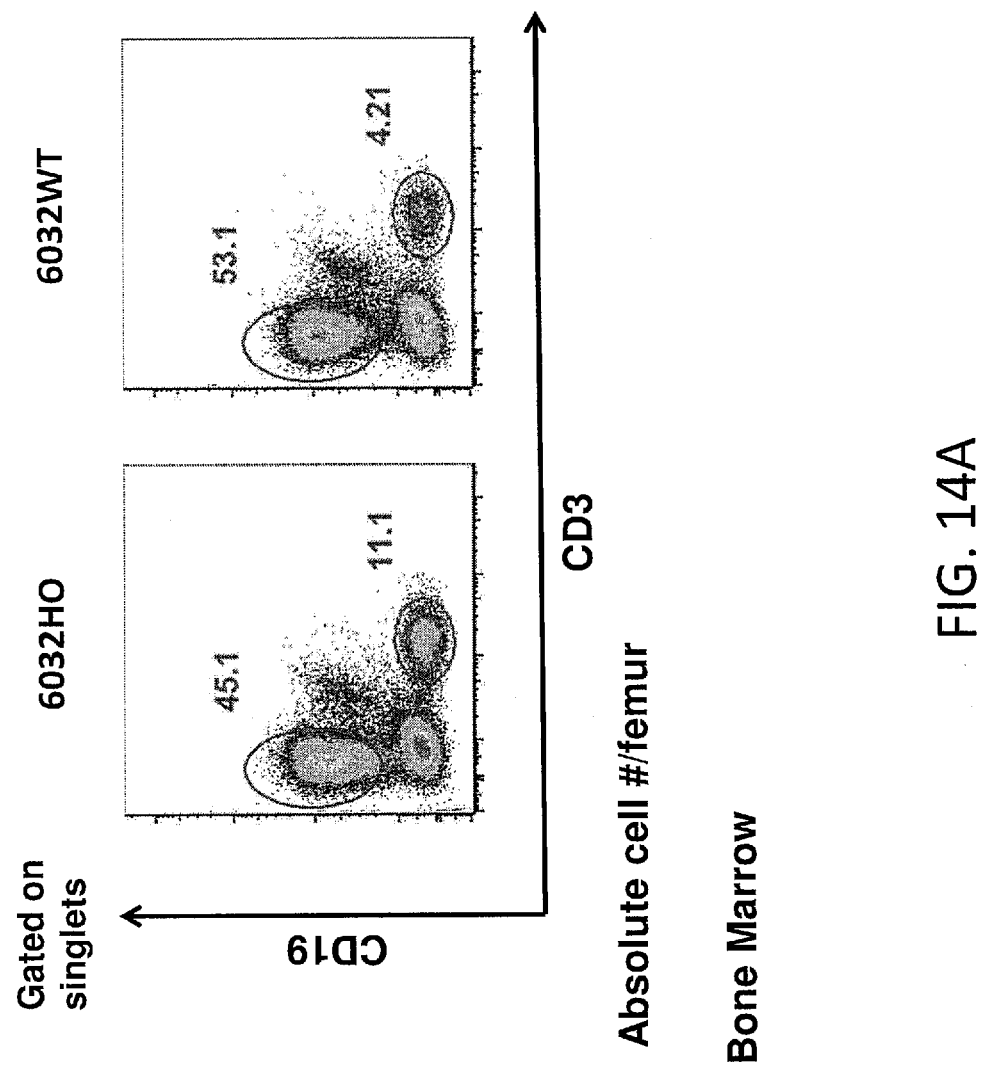
FIG. 14A shows representative contour plots of bone marrow stained for B and T cells (CD19+ and CD3+, respectively) from a wild type mouse (WT) and a mouse homozygous for a rearranged human immunoglobulin heavy chain variable region nucleotide sequence (V$_H$3-23/D/J$_H$4).
Figure 14B:
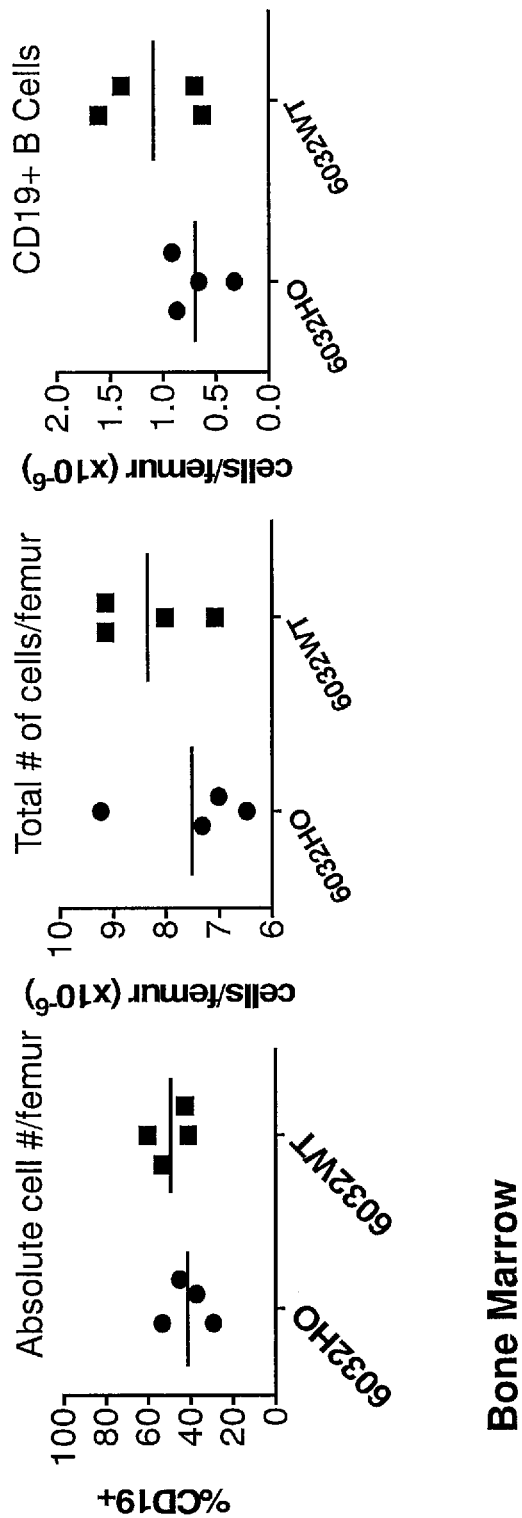
FIG. 14B shows the absolute number of cells (left), the total number of cells (middle) and the total number of B (CD19+) cells (right) in bone marrow isolated from the femurs of wild type mice (WT) and mice homozygous for rearranged human immunoglobulin heavy chain variable region nucleotide sequence (V$_H$3-23/D/J$_H$4).
Figure 14C:
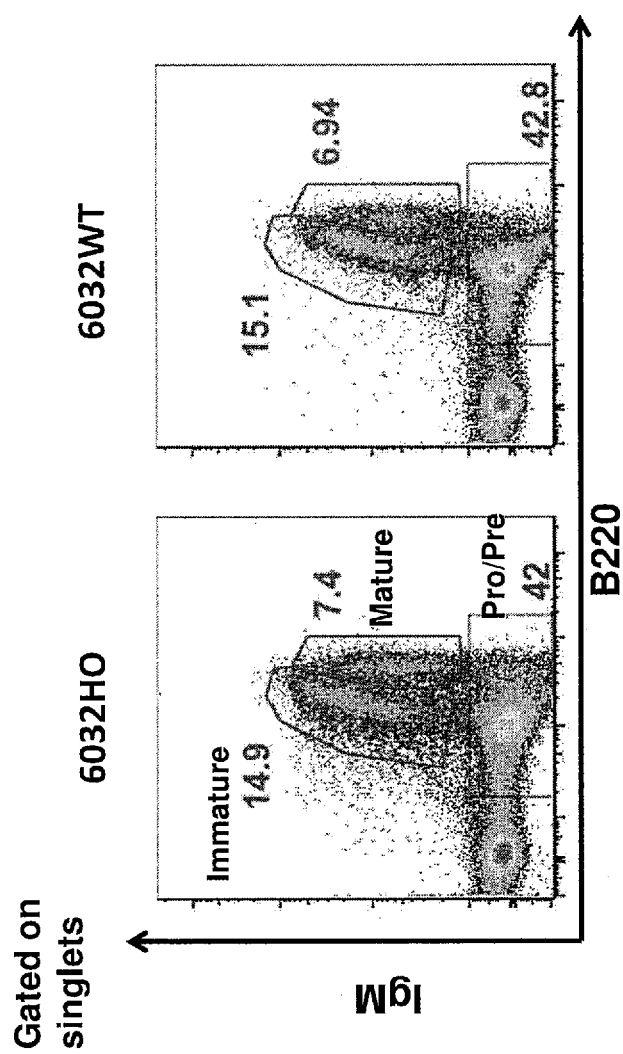
FIG. 14C shows representative contour plots of bone marrow gated on singlets stained for immunoglobulin M (IgM) and B220 from a wild type mouse (WT) and a mouse homozygous for a rearranged human immunoglobulin heavy chain variable region nucleotide sequence (V$_H$3-23/D/J$_H$4). Immature, mature and pro/pre B cells are noted on each of the contour plots.
Figure 14D:
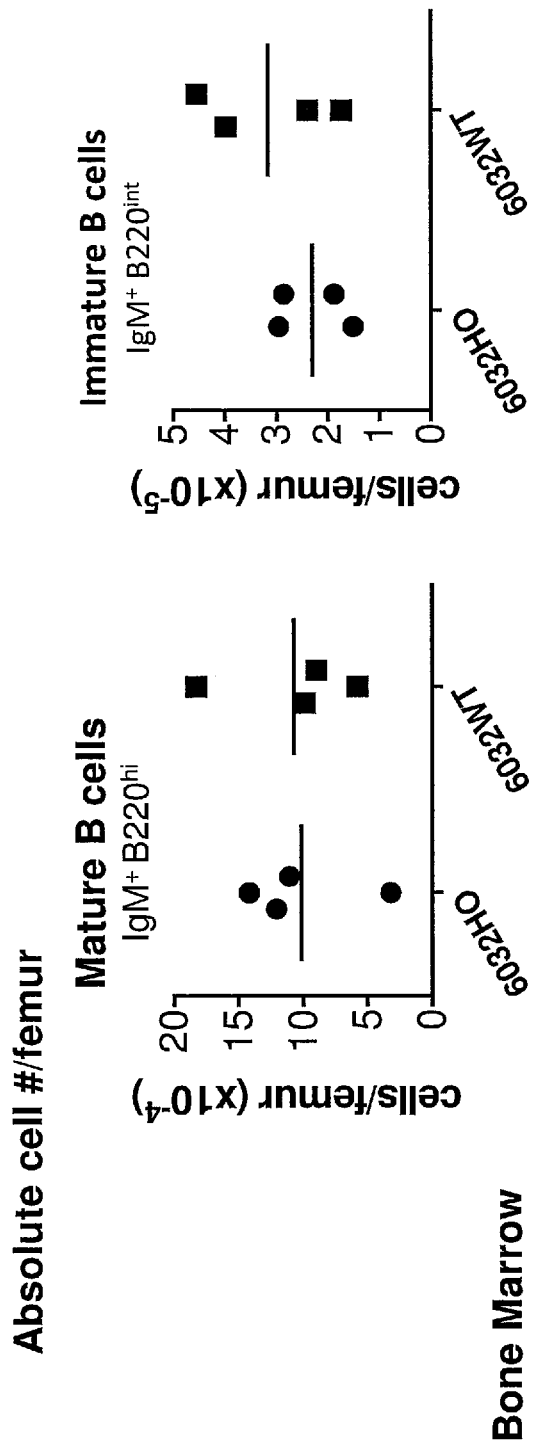
FIG. 14D shows the total number and mature B (B220$^{hi}$IgM+) and immature B (B220$^{int}$IgM+) cells in bone marrow isolated from the femurs of wild type mice (WT) and mice homozygous for a rearranged human immunoglobulin heavy chain variable region nucleotide sequence (V$_H$3-23/D/J$_H$4).
Figure 14E:
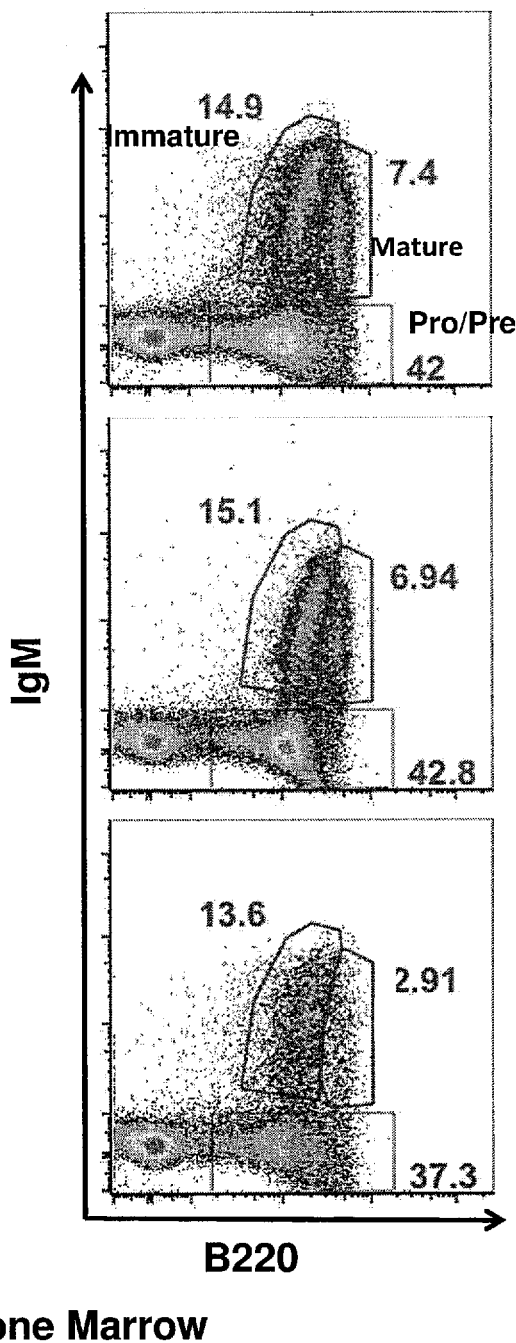
FIG. 14E shows representative contour plots of bone marrow gated on singlets stained for immunoglobulin M (IgM) and B220 from a wild type mouse (WT) and mice homozygous for a rearranged human immunoglobulin heavy chain variable region nucleotide sequence (V$_H$3-23/D/J$_H$4). Immature, mature and pro/pre B cells are noted on each of the contour plots.
Figure 14F:
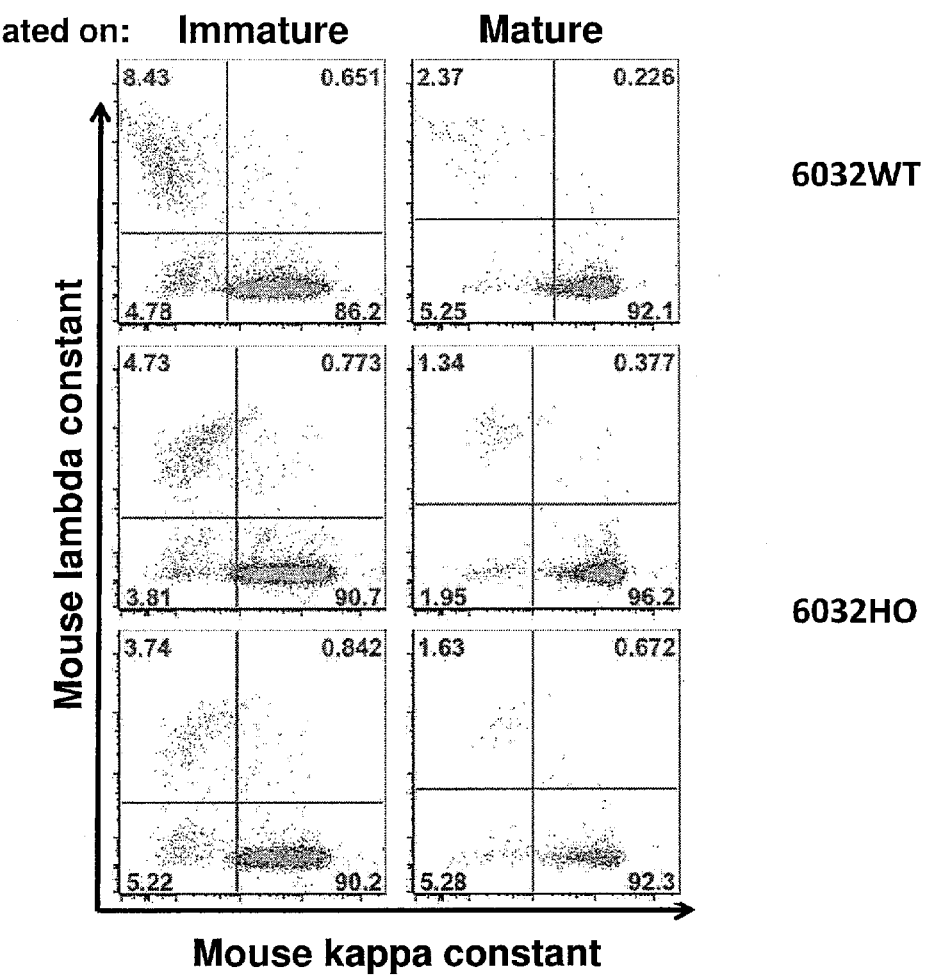
FIG. 14F shows representative contour plots of bone marrow gated on immature (B220$^{int}$IgM+) and mature (B220$^{hi}$IgM+) B cells stained for Igκ and Igλ expression isolated from the femurs of a wild type mouse (WT) and mice homozygous for a rearranged human immunoglobulin heavy chain variable region nucleotide sequence (V$_H$3-23/D/J$_H$4).

In the bone marrow, the MAID6032 HO mice produced near normal B cell populations (FIGS. 14A-14E) with a usage of lambda sequences that was half of wild type (FIG. 14F).

Immunization Studies

Five WT (75% C57BL6/25% 129 background) and three to four MAID 6032 HET mice were immunized in the footpad with 0.025 ml of a mixture containing 2.35 µg of an antigen X, 10 µg CpG oligonucleotide (ODN 1826, InvivoGen, cat# tlrl-1826), and 25 µg Aluminum Phosphate Gel Adjuvant (Brenntag cat#7784-30-7). Mice were boosted six times with the same dosage. On days 15 and 24 post primary immunization, blood was collected from anaesthetized mice using a retro-orbital bleed into BD serum separator tubes (BD, cat #365956), and serum was collected as per manufacturer's directions.

To measure the levels of antigen-specific IgG antibodies and to counterscreen the mmh (myc-myc-his) tag, ELISA plates (Nunc) were coated with either 1 µg/ml of an antigen X incubated overnight at 4 deg C. Excess antigen was washed off before blocking with PBS+1% BSA for 1 hr at RT. Serial dilutions of serum were applied and plates were incubated for 1 hr at RT before washing. Plates were incubated with horseradish peroxidase (HRP)-conjugated anti-IgG (cat #1030-05, Southern Biotech) antibody for 1 hr at RT. Following washing, plates were developed with TMB substrate (cat#555214, BD). Reactions were stopped with 1N sulfuric acid, and O.D. was read at 450 nm, using a Vκ tor X5 Perkin Elmer Reader. Data was analyzed with Graph Pad Prism to calculate the dilution of serum that falls two times above background. All animal experiments were approved by IACUC and Regeneron Pharmaceuticals.

Figure 15:
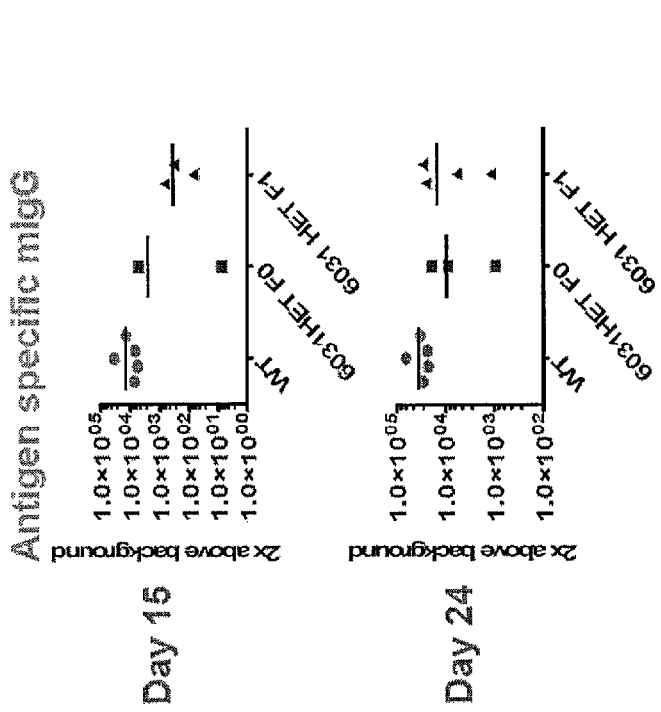
FIG. 15 shows the levels of antigen-specific mIgGs in the mouse sera (Wild type or 6031 HET F0 and F1) at Day 15 and Day 24 following footpad immunization.

As shown in FIG. 15, the genetically modified FO and F1 mice (MAID 6032 het), which are heterozygous with respect to the targeted allele (i.e., containing one copy of the rearranged V$_H$3-23/D/J$_H$4 nucleotide sequence), were able to produce antigen-specific IgG antibodies at levels comparable to those produced by wild type mice at both Days 15 and 24 post primary immunization.

Example 3

Generation and Analysis of Mice Comprising Two Human Light Chain V Segments

Figure 20:
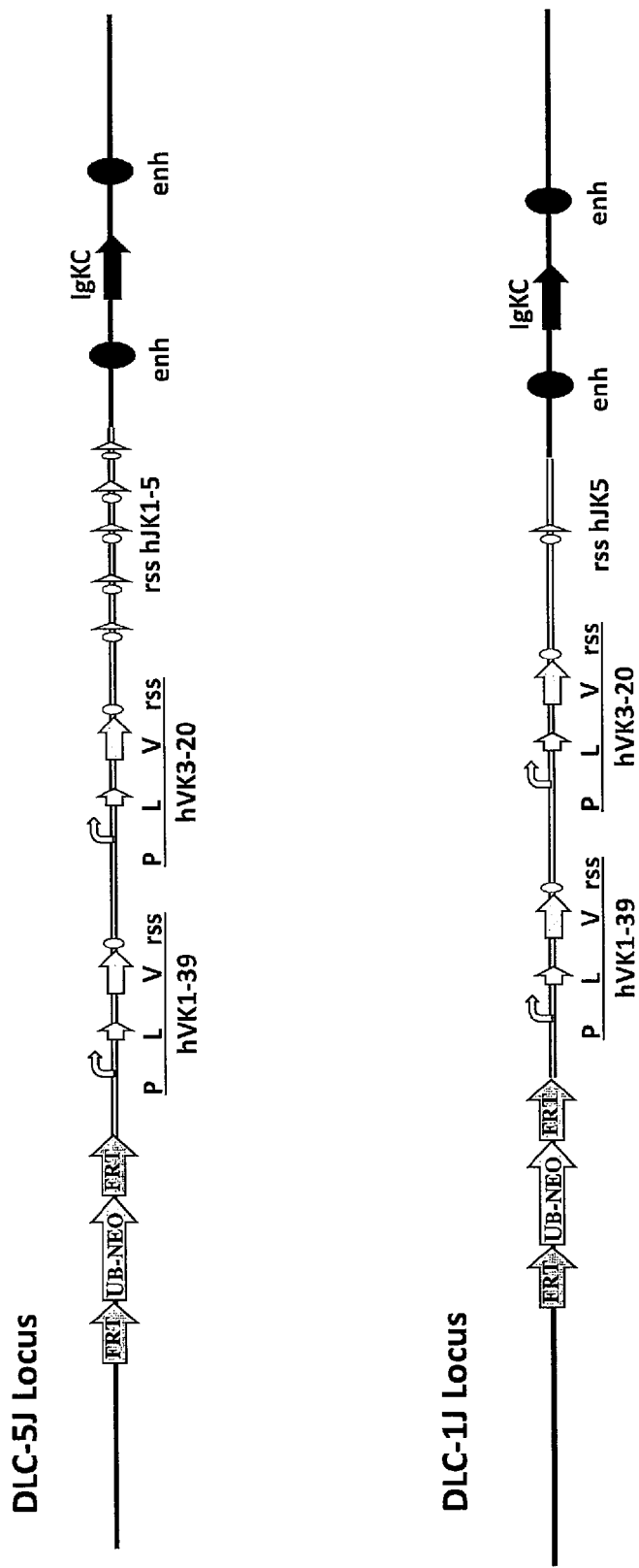
FIG. 20 shows examples of two genetically modified dual light chain (DLC) loci. The locus on the top (DLC-5J) contains an engineered human DNA fragment containing two human Vκ gene segments and five human Jκ gene segments. The locus on the bottom (DLC-1J) contains an engineered human DNA fragment containing two human Vκ gene segments and one human Jκ gene segment. Each locus is capable of rearranging to form a human Vκ region operably linked to an endogenous light chain constant region (e.g., a Cκ). Immunoglobulin promoters (P, open arrow above locus), leader exons (L, short open arrows), and the two human Vκ gene segments (long open arrows), all flanked upstream (5') by a neomycin cassette containing Frt recombination sites are shown. Recombination signal sequences engineered with each of the human gene segments (Vκ and Jκ) are indicated by open ovals juxtaposed with each gene segment. In most embodiments, unless indicated otherwise, filled shapes and solid lines represent mouse sequences, and open shapes and double lines represent human sequences. The diagrams are not presented to scale.

Example 3.1: Construction of Targeting Vector for Generation of Mice that Comprise Two Human Light Chain V Segments Two engineered light chain loci containing two human Vκ gene segments (e.g., a human Vκ1-39 and human Vκ3-20 gene segment; i.e., a dual light chain ("DLC")) were constructed (FIG. 20). One engineered light chain locus contained two human Vκ gene segments and five human Jκ gene segments in unrearranged configuration (DLC-5J). The second engineered light chain locus contained two human Vκ gene segments and one human Jκ gene segment in unrearranged configuration (DLC-1J). For each of the two additional engineered light chain loci, the human gene segments were flanked 3' with recombination signal sequences to allow for in vivo rearrangement of the human gene segments in B cells.

Engineering and Generation of DLC-1J Mice.

Engineering steps that result in generation of a light chain locus comprising two human Vκ gene segments (Vκ1-39 and Vκ3-20) and one human Jκ gene segment (Jκ5), otherwise termed as DLC-1J, are depicted in FIG. 21. Specifically, human Vκ1-39 and Vκ3-20 sequences were amplified by PCR from BAC templates (Invitrogen), and together with an amplified sequence containing recombination signal sequence (rss) and human Jκ5 segment, cloned via a four-way ligation into a plasmid containing a UB-hygromycin selection cassette (FIG. 21A). 5' and 3' arms were attached as depicted in FIGS. 21B and 21C.

Figure 21A:
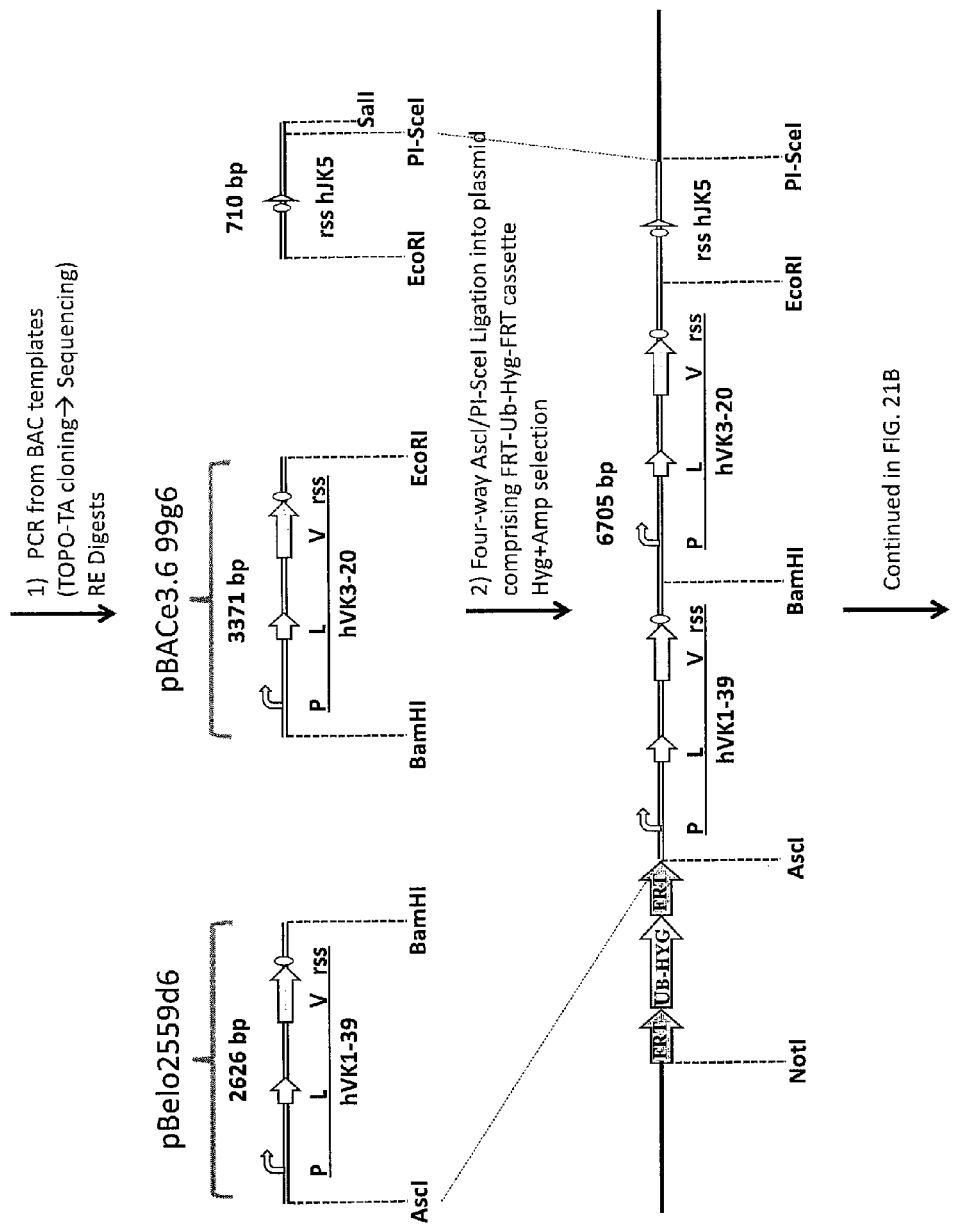
Figure 21C:
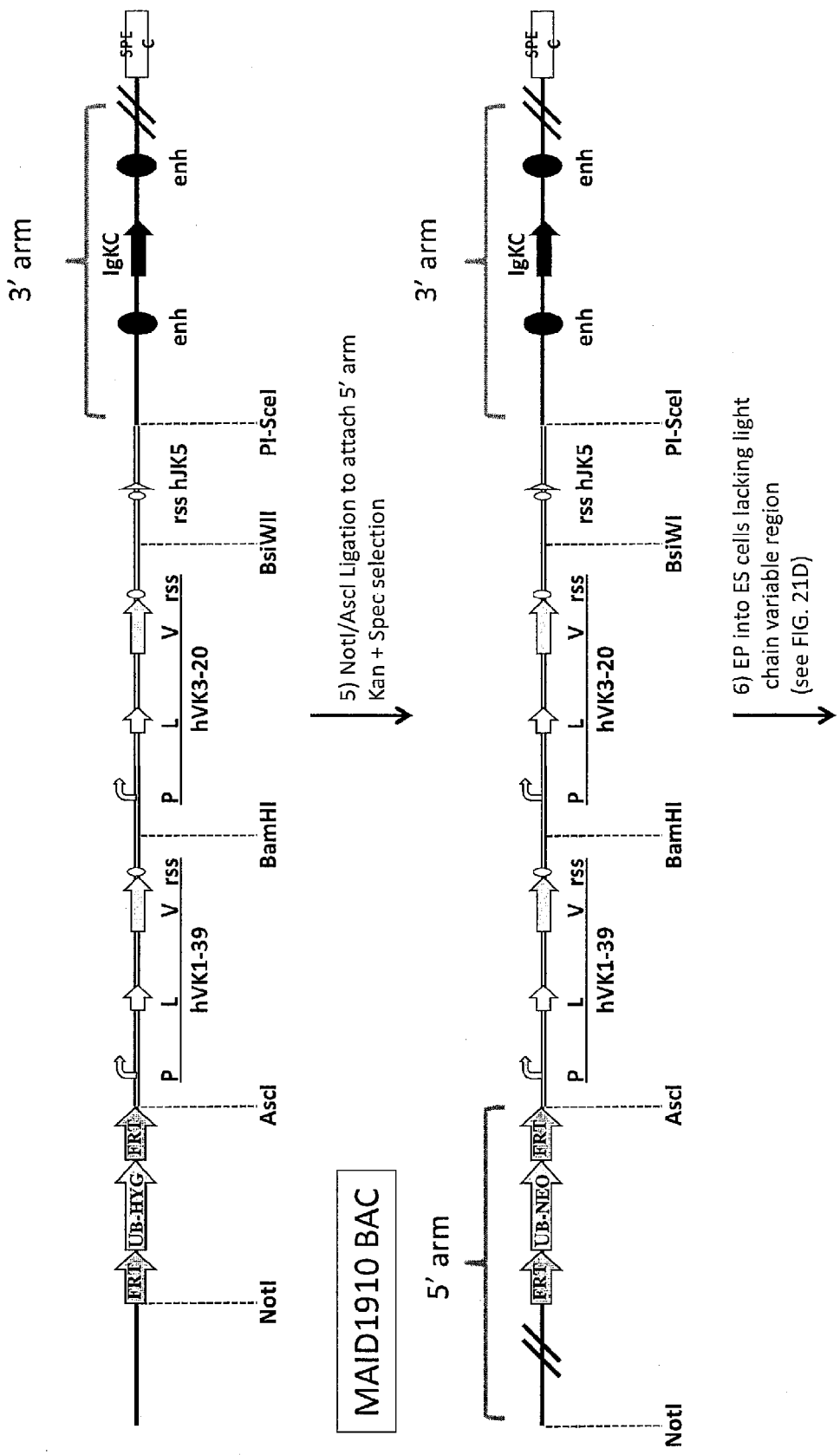

The resultant targeting construct is depicted in FIG. 21C (bottom diagram; DLC-1J), with recombination signal sequences (RSS) in clear ovals. Modified BAC DNA clone of the engineered DLC-1J light chain locus operably linked to mouse sequences (i.e., upstream and downstream sequences of the endogenous immunoglobulin κ light chain locus) was confirmed by PCR using primers located at sequences within the engineered light chain locus containing the two human Vκ gene segments, followed by electroporation into ES cells comprising deletion of the mouse Igκ variable locus (comprising κ variable and joining gene segments) (FIG. 21D) to create a mouse that expresses either of the two human Vκ gene segments. Positive ES cell clones that contained the engineered DLC-1J light chain locus was confirmed by Taqman™ screening and karyotyping using probes specific for the engineered DLC-1J light chain locus. Sequences of primers and probes used for ES cell screening of DLC-1J ES cells are depicted in Table 8 below and are included in Sequence Listing.

TABLE 8

Primers and Probes Used for ES Cell Screening

| Probe Name | Assay/type of probe | Location detected | Probe Sequence | Forward Primer | Reverse Primer |
|---|---|---|---|---|---|
| 1633h2 | GOA/ TAQMAN™ | Vκ1-39 | ATCAGCAGAAACCA GGGAAAGCCCCT (SEQ ID NO: 44) | GGGCAAGTCAG AGCATTAGCA (SEQ ID NO: 45) | TGCAAACTGGATG CAGCATAG (SEQ ID NO: 46) |
| 1635h2 | GOA/ TAQMAN™ | Vκ3-20 | AAAGAGCCACCCTC TCCTGCAGGG (SEQ ID NO: 65) | TCCAGGCACCCTG TCTTTG (SEQ ID NO: 66) | AAGTAGCTGCTGC TAACACTCTGACT (SEQ ID NO: 67) |
| Neo | GOA | neo | TGGGCACAACAGAC AATCGGCTG (SEQ ID NO: 38) | GGTGGAGAGGC TATTCGGC (SEQ ID NO: 39) | GAACACGGCGGCA TCAG (SEQ ID NO: 40) |
| Jxn 1-39/ 3-20 | GOA/BHQ1 | 1-39/3-20 BamHI junction | TCTTTTGCCCCGGA TCCGATCAG (SEQ ID NO: 84; restriction site bolded) | GGGAGGCTCCTC TGAACTCTAAG (SEQ ID NO: 85) | GTCCAGTCACTCG GTTGCTAT (SEQ ID NO: 86) |

Confirmed ES cell clones were then used to implant female mice to give rise to a litter of pups comprising DLC-1J light chain locus and expressing a human light chain variable domain fused with a mouse Cκ domain. Sequences of primers and probes used for genotyping of the pups are listed in Table 8 above. The sequence through the engineered DLC-1J locus, including 100 nucleotides of mouse sequence upstream and downstream of the inserted engineered sequence is presented in FIGS. 22A-22D and set forth in SEQ ID NO:82.

Figure 21D:
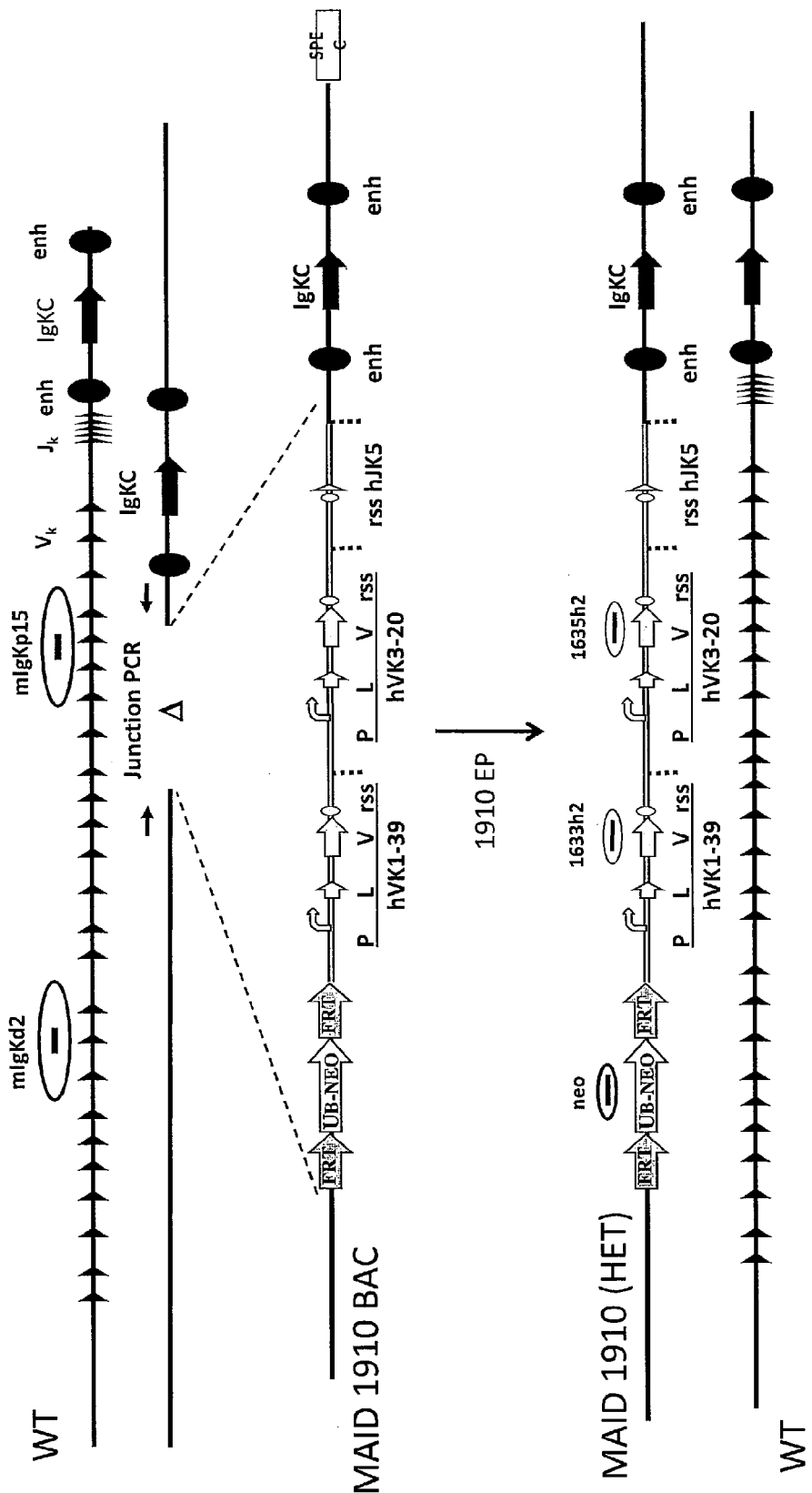
Figure 21E:
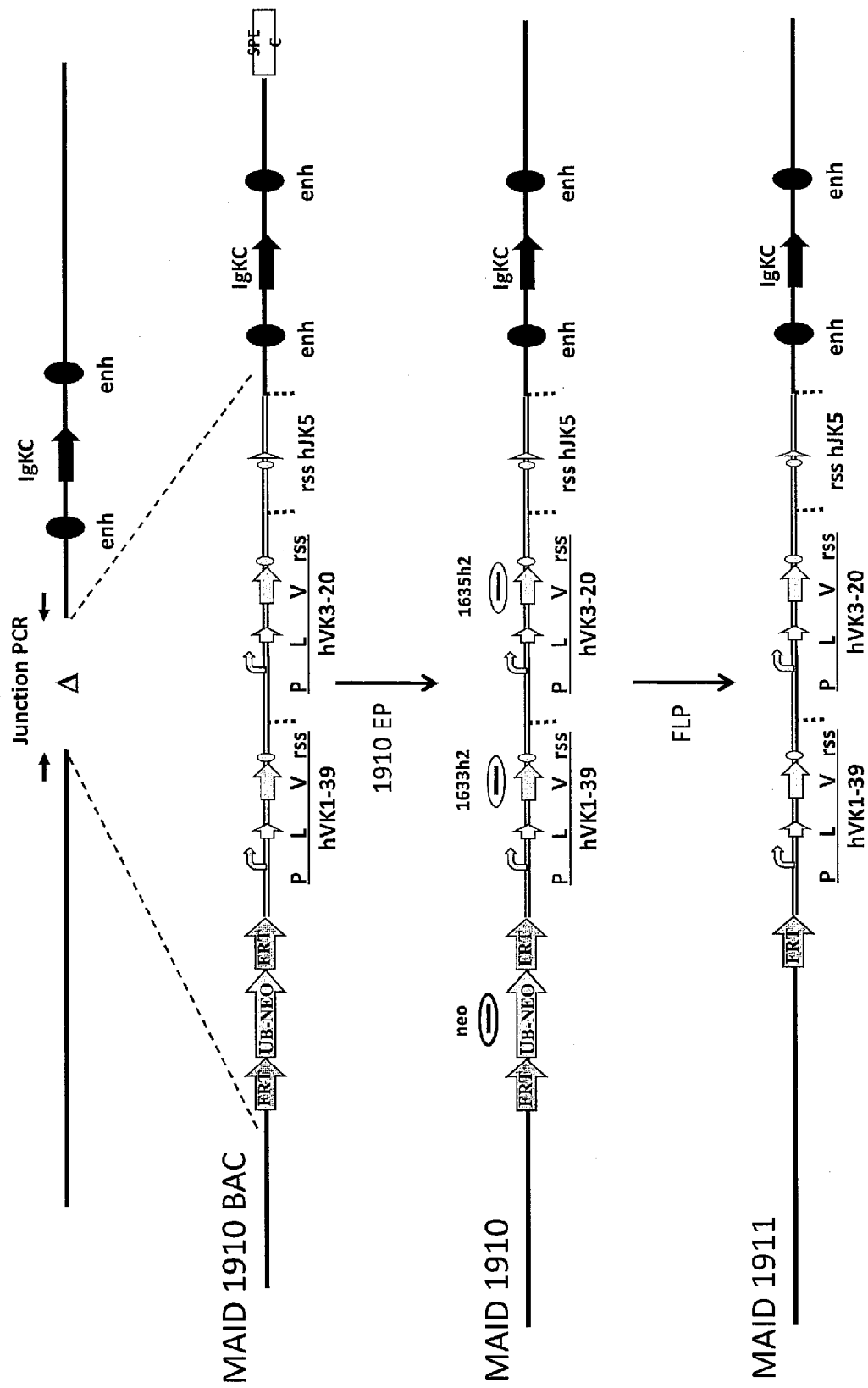
FIG. 21E shows deletion of the selection cassette in ES cells using FLP enzyme. In most embodiments, unless indicated otherwise, filled shapes and solid lines represent mouse sequences, and open shapes and double lines represent human sequences. The diagrams are not presented to scale.

ES cells bearing the engineered light chain locus may be transfected with a construct that expresses FLP in order to remove the FRTed neomycin cassette introduced by the targeting construct (see FIG. 21E). Optionally, the neomycin cassette is removed by breeding to mice that express FLP recombinase (e.g., U.S. Pat. No. 6,774,279). Optionally, the neomycin cassette is retained in the mice.

Figure 23A:
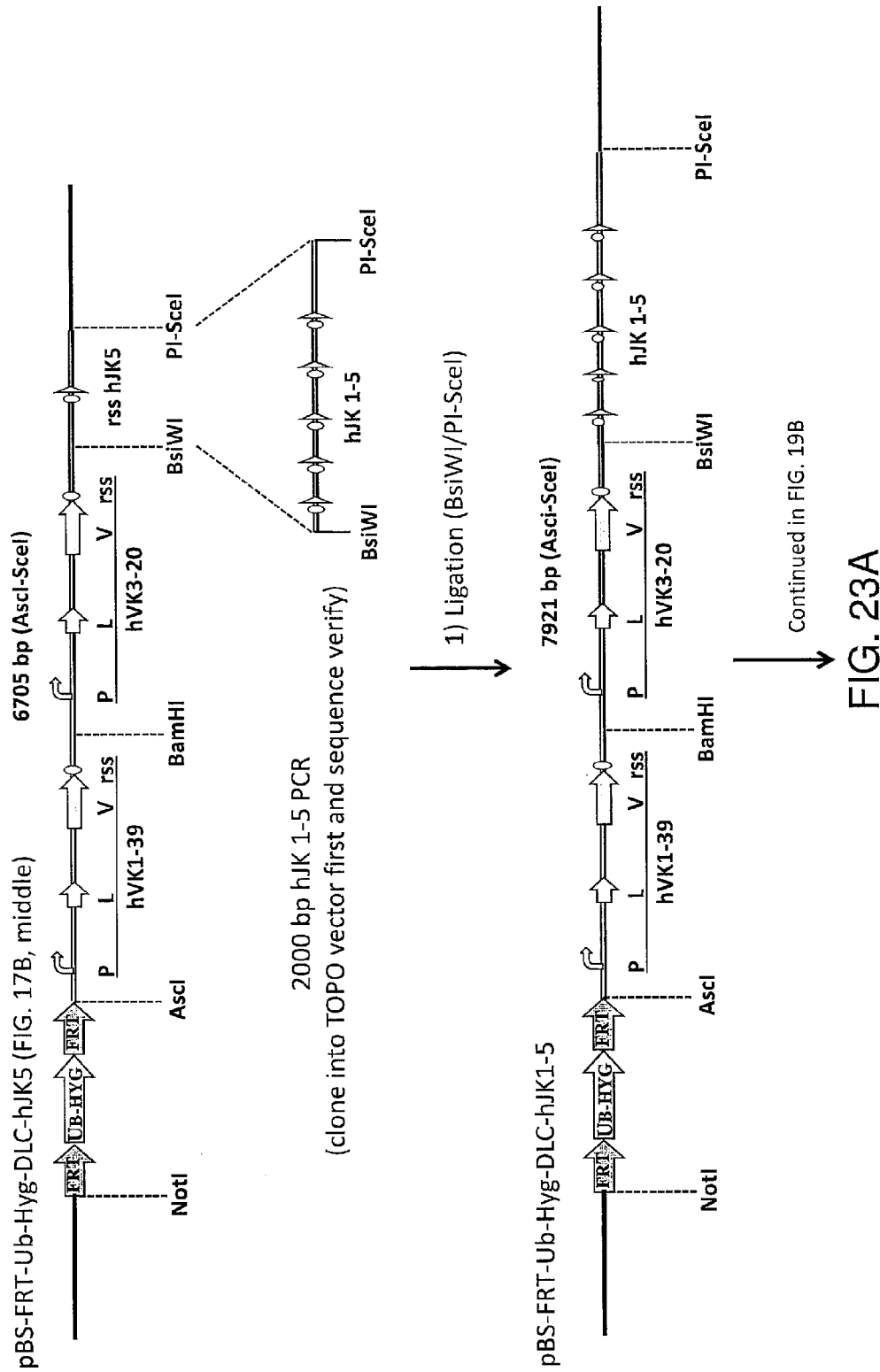
FIGS. 23A-23B show a general strategy for construction of a targeting vector for the engineering of an immunoglobulin kappa locus comprising two human Vκ segments (hVκ1-39 and hVκ3-20) and five human Jκ segments, as well as mouse enhancers and IgκC arm.

Engineering and Generation of DLC-5J Mice. To generate a light chain locus comprising two human Vκ gene segments (Vκ1-39 and Vκ3-20) and five human Jκ gene segments (Jκ1, Jκ2, Jκ3, Jκ4, and Jκ5), otherwise termed as DLC-5J, a 2000 base pair amplified sequence comprising all 5 human Jκ's was ligated into a vector comprising two human Vκ gene segments and one human Jκ, depicted in FIG. 21B (middle) (see FIG. 23A). Subsequent engineering steps involved attachment of 3' and 5' arms as depicted in FIG. 23B.

Figure 23B:
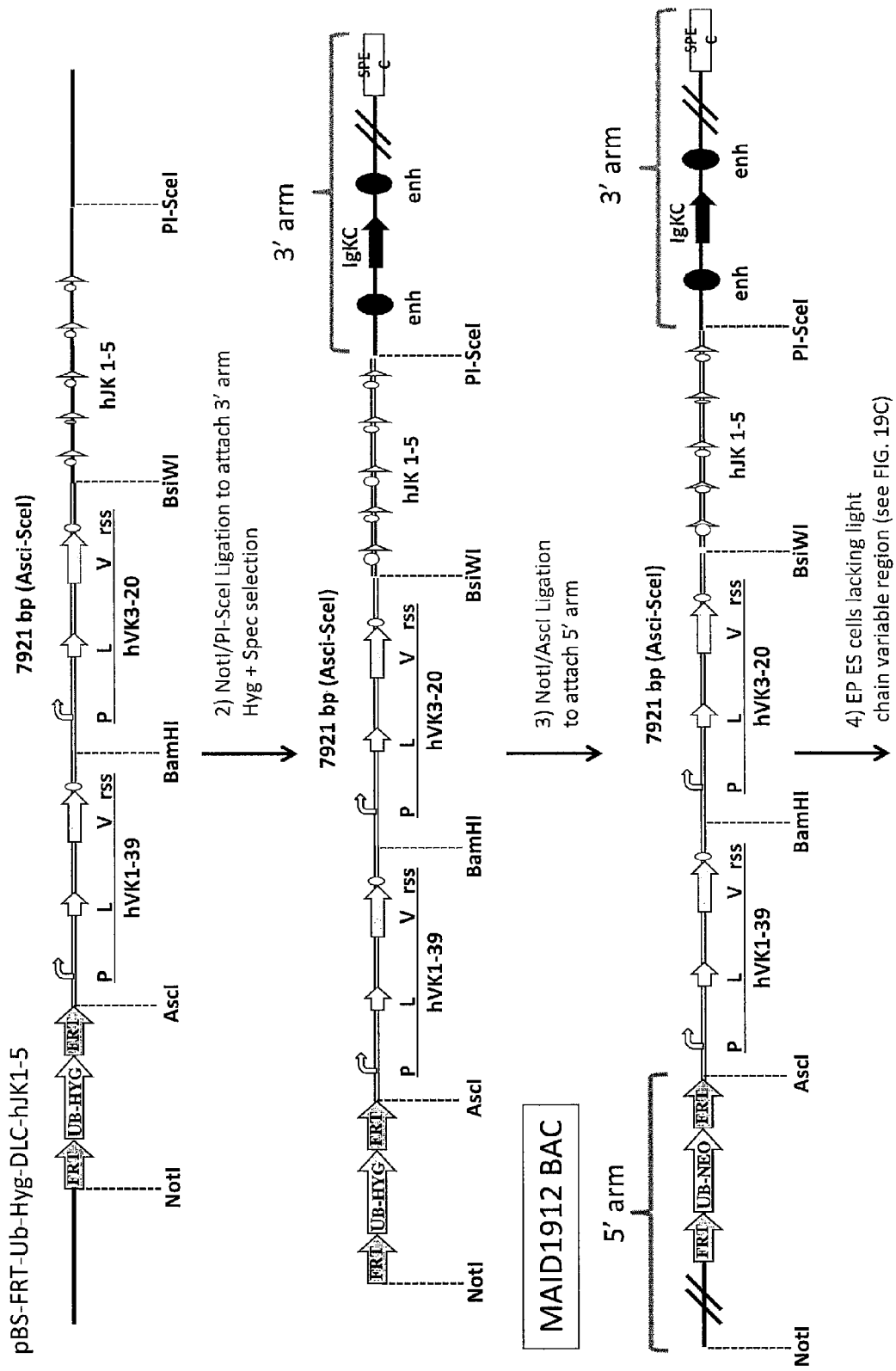
Figure 23C:
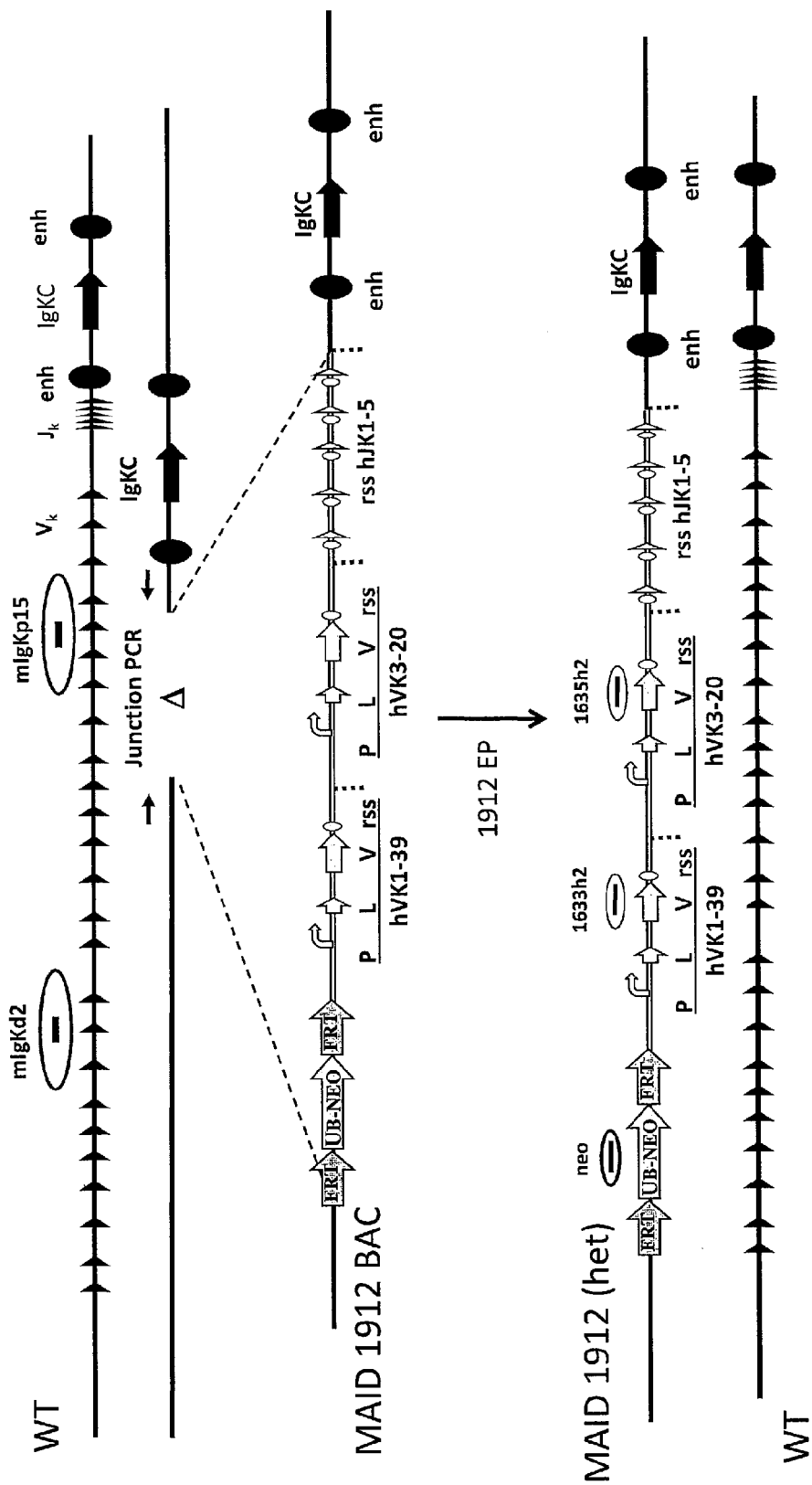

The resultant targeting construct is depicted in FIG. 23B (bottom diagram; DLC-5J), with recombination signal sequences (RSS) in clear ovals. Modified BAC DNA clone the engineered DLC-5J light chain locus operably linked to mouse sequences (i.e., upstream and downstream sequences of the endogenous immunoglobulin κ light chain locus) was confirmed by PCR using primers located at sequences within the engineered light chain locus containing the two human Vκ gene segments, followed by electroporation into ES cells comprising deletion of the mouse Igκ variable locus (comprising κ variable and joining gene segments) (FIG. 23C) to create a mouse that expresses either of the two human Vκ gene segments. Positive ES cell clones that contained the engineered DLC-5J light chain locus was confirmed by Taqman™ screening and karyotyping using probes specific for the engineered DLC-5J light chain locus. Sequences of primers and probes used for ES cell screening of DLC-5J ES cells are depicted in Table 9 below and are included in Sequence Listing.

TABLE 9

Primers and Probes Used for ES Cell Screening

| Probe Name | Assay/type of probe | Location detected | Probe Sequence | Forward Primer | Reverse Primer |
|---|---|---|---|---|---|
| 1633h2 | GOA/ TAQMAN™ | Vκ1-39 | ATCAGCAGAAACC AGGGAAAGCCCCT (SEQ ID NO: 44) | GGGCAAGTCAG AGCATTAGCA (SEQ ID NO: 45) | TGCAAACTGGATG CAGCATAG (SEQ ID NO: 46) |
| 1635h2 | GOA/ TAQMAN™ | Vκ3-20 | AAAGAGCCACCCT CTCCTGCAGGG (SEQ ID NO: 65) | TCCAGGCACCCTG TCTTTG (SEQ ID NO: 66) | AAGTAGCTGCTGC TAACACTCTGACT (SEQ ID NO: 67) |
| Neo | GOA | neo | TGGGCACAACAGA CAATCGGCTG (SEQ ID NO: 38) | GGTGGAGAGGC TATTCGGC (SEQ ID NO: 39) | GAACACGGCGGC ATCAG (SEQ ID NO: 40) |
| Jxn 1-39/ 3-20 | GOA/BHQ1 | 1-39/3-20 BamHI junction | TCTTTTGCCCCGG ATCCGATCAG (SEQ ID NO: 84; restriction site bolded) | GGGAGGCTCCTC TGAACTCTAAG (SEQ ID NO: 85) | GTCCAGTCACTC GGTTGCTAT (SEQ ID NO: 86) |

TABLE 9-continued

Primers and Probes Used for ES Cell Screening

| Probe Name | Assay/type of probe | Location detected | Probe Sequence | Forward Primer | Reverse Primer |
|---|---|---|---|---|---|
| Jxn 3-20/ Jk1-5 | GOA/BHQ1 | 3-20/Jk1-5 BsiWI junction | CTTCAACTGTGGC GTACGCACC (SEQ ID NO: 87, restriction site bolded) | ACGCAGATGTA GCCAAACCCT (SEQ ID NO: 88) | CAGCTGCTGAAG CTCAACTC (SEQ ID NO: 89) |

Confirmed ES cell clones were then used to implant female mice to give rise to a litter of pups comprising DLC-5J light chain locus and expressing a human light chain variable domain fused with a mouse Cκ domain. Sequences of primers and probes used for genotyping of the pups are listed in Table 9 above. The sequence through the engineered DLC-5J locus, including 100 nucleotides of mouse sequence upstream and downstream of the inserted engineered sequence is presented in FIGS. 24A-24D and set forth in SEQ ID NO:83.

Figure 23D:
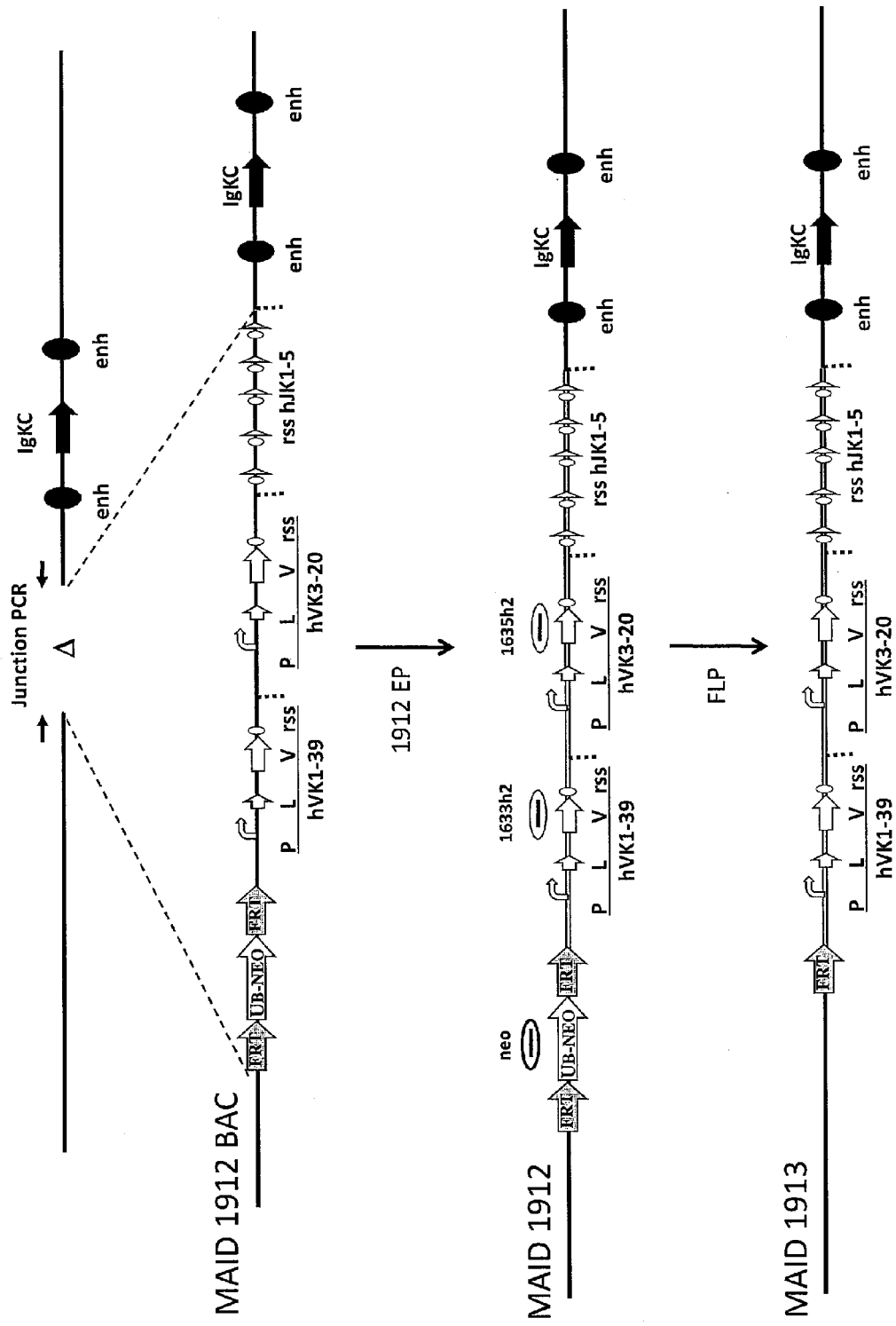
FIG. 23D shows deletion of the selection cassette in ES cells using FLP enzyme. In most embodiments, unless indicated otherwise, filled shapes and solid lines represent mouse sequences, and open shapes and double lines represent human sequences. The diagrams are not presented to scale.
Figure 25A:
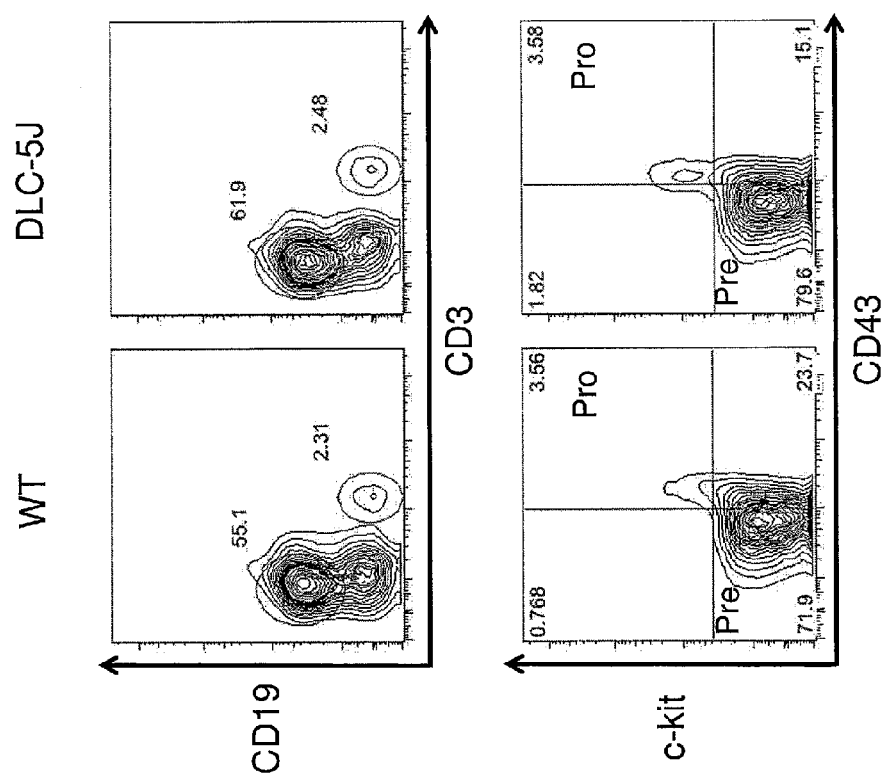
FIG. 25A, in the top panel, shows representative contour plots of bone marrow stained for B and T cells (CD19+ and CD3+, respectively) from a wild type mouse (WT) and a mouse homozygous for two human Vκ and five human Jκ gene segments (DLC-5J). The bottom panel shows representative contour plots of bone marrow gated on CD19+ and stained for ckit+ and CD43+ from a wild type mouse (WT) and a mouse homozygous for two human Vκ and five human Jκ gene segments (DLC-5J). Pro and Pre B cells are noted on the contour plots of the bottom panel.
Figure 25B:
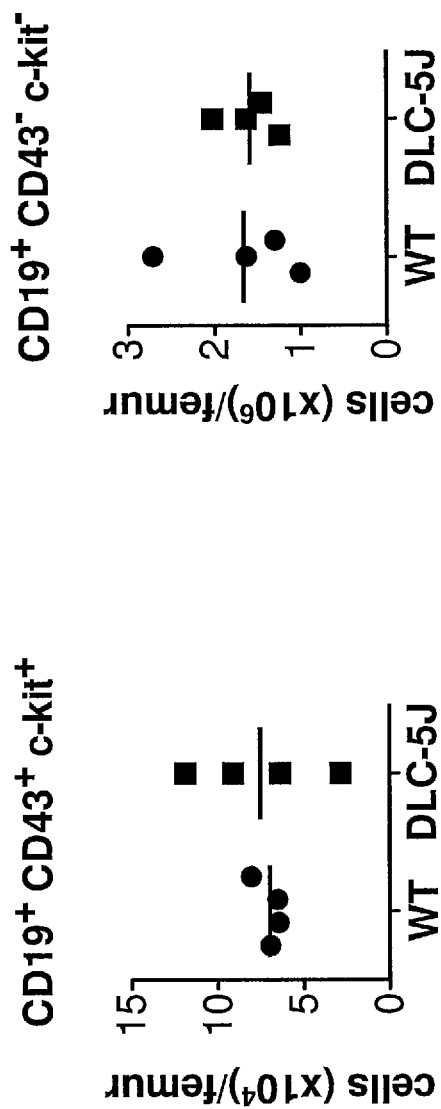
FIG. 25B shows the number of Pro (CD19+CD43+ckit+) and Pre (CD19+CD43−ckit−) B cells in bone marrow harvested from the femurs of wild type mice (WT) and mice homozygous for two human Vκ and five human Jκ gene segments (DLC-5J).
Figure 26A:
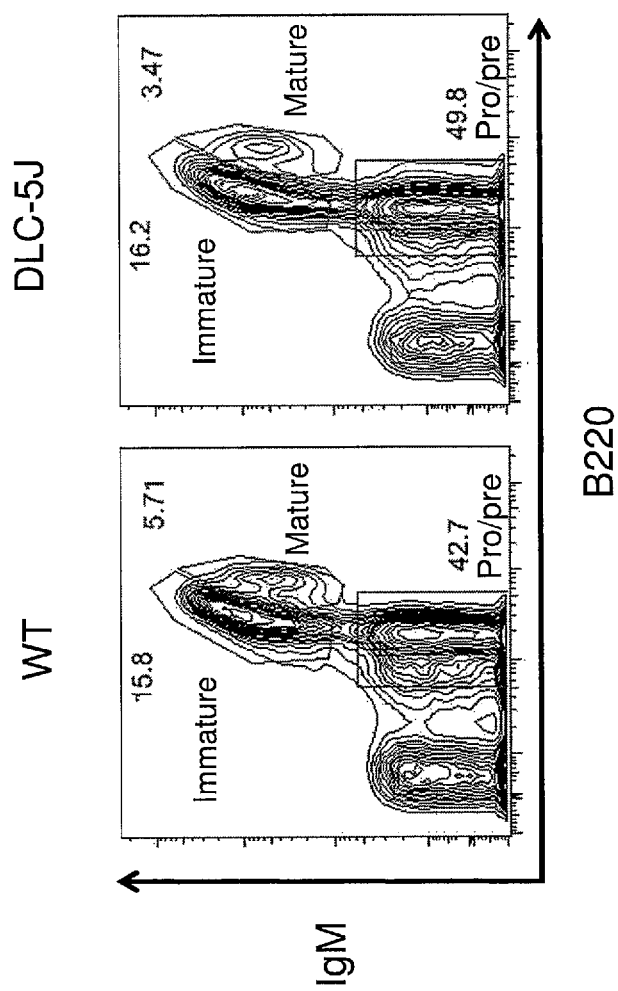
FIG. 26A shows representative contour plots of bone marrow gated on singlets stained for immunoglobulin M (IgM) and B220 from a wild type mouse (WT) and a mouse homozygous for two human Vκ and five human Jκ gene segments (DLC-5J). Immature, mature and pro/pre B cells are noted on each of the contour plots.
Figure 26B:
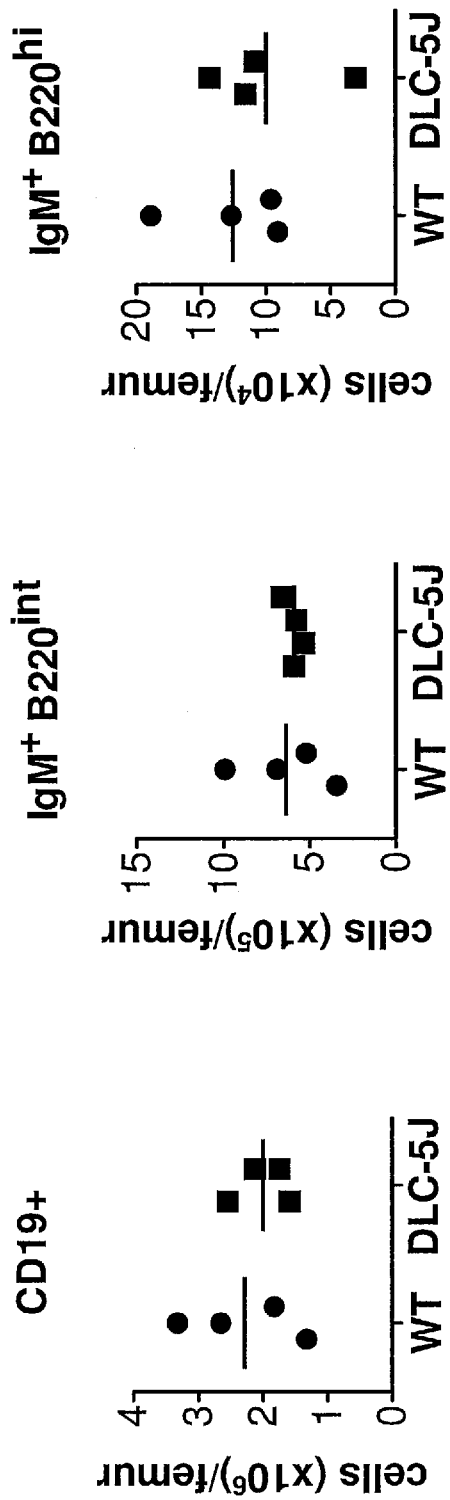
FIG. 26B shows the total number of B (CD19+), immature B (B220$^{int}$IgM+) and mature B (B220$^{hi}$IgM+) cells in bone marrow isolated from the femurs of wild type mice (WT) and mice homozygous for two human Vκ and five human Jκ gene segments (DLC-5J).
Figure 27A:
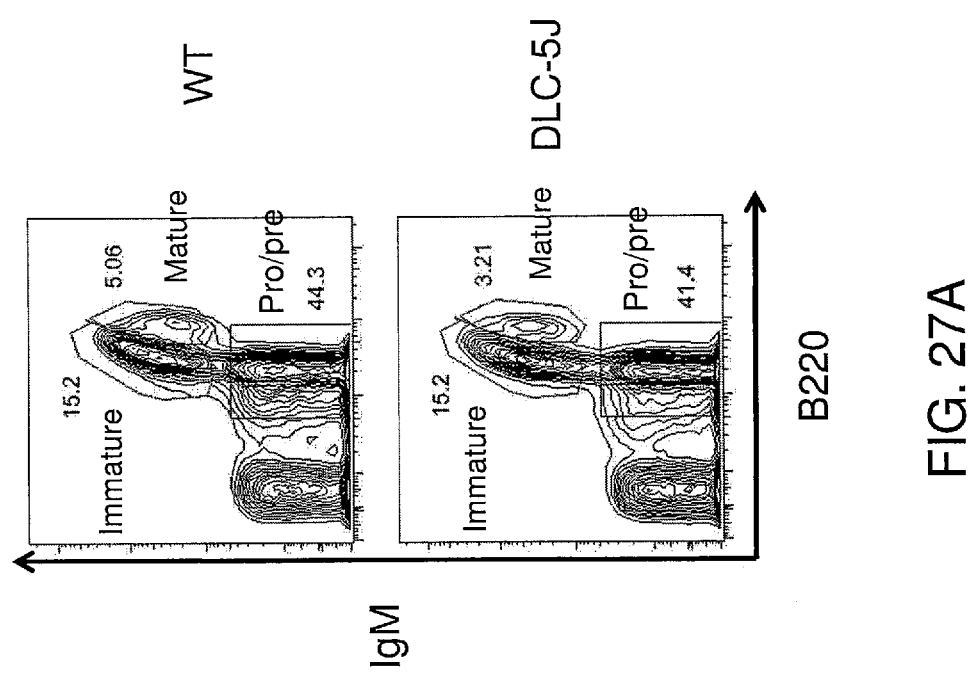
FIG. 27A shows representative contour plots of bone marrow gated on singlets stained for immunoglobulin M (IgM) and B220 from a wild type mouse (WT) and a mouse homozygous for two human Vκ and five human Jκ gene segments (DLC-5J). Immature, mature and pro/pre B cells are noted on each of the contour plots.
Figure 27B:
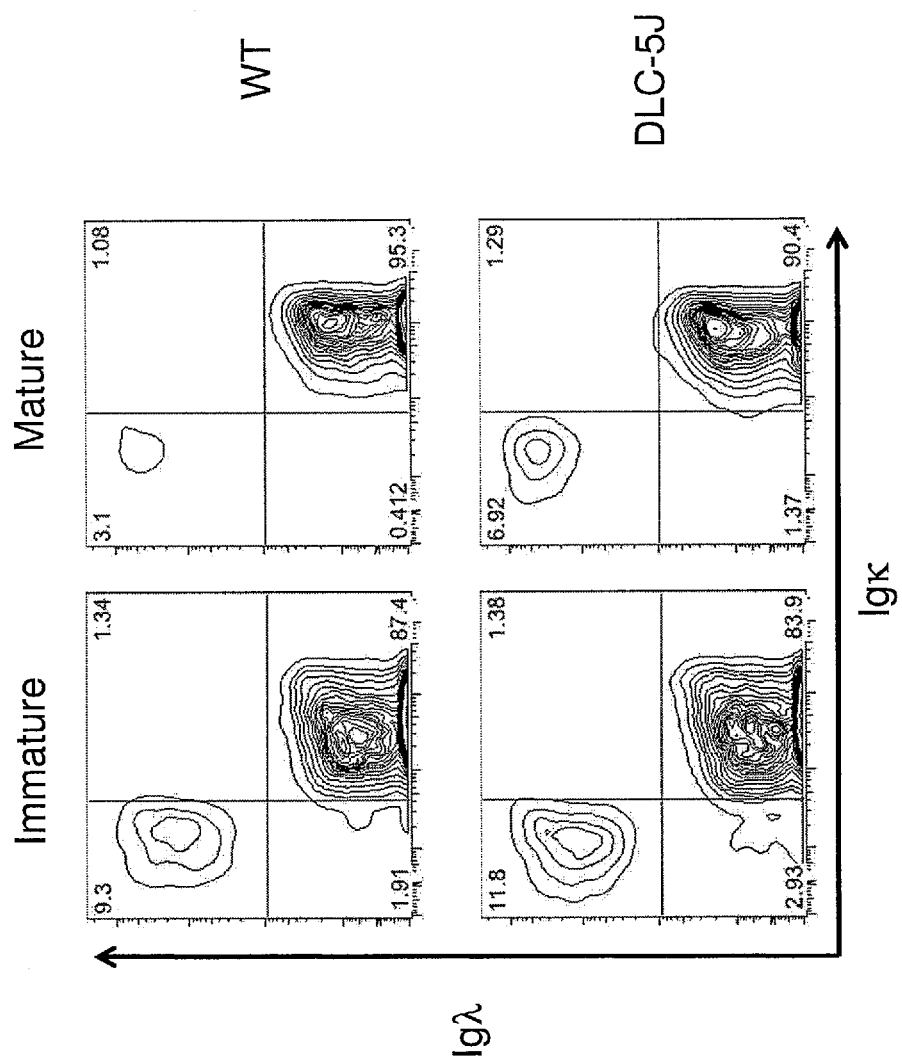
FIG. 27B shows representative contour plots of bone marrow gated on immature (B220$^{int}$IgM+) and mature (B220$^{hi}$IgM+) B cells stained for Igκ and Igλ expression isolated from the femurs of a wild type mouse (WT) and a mouse homozygous for two human Vκ and five human Jκ gene segments (DLC-5J).
Figure 28A:
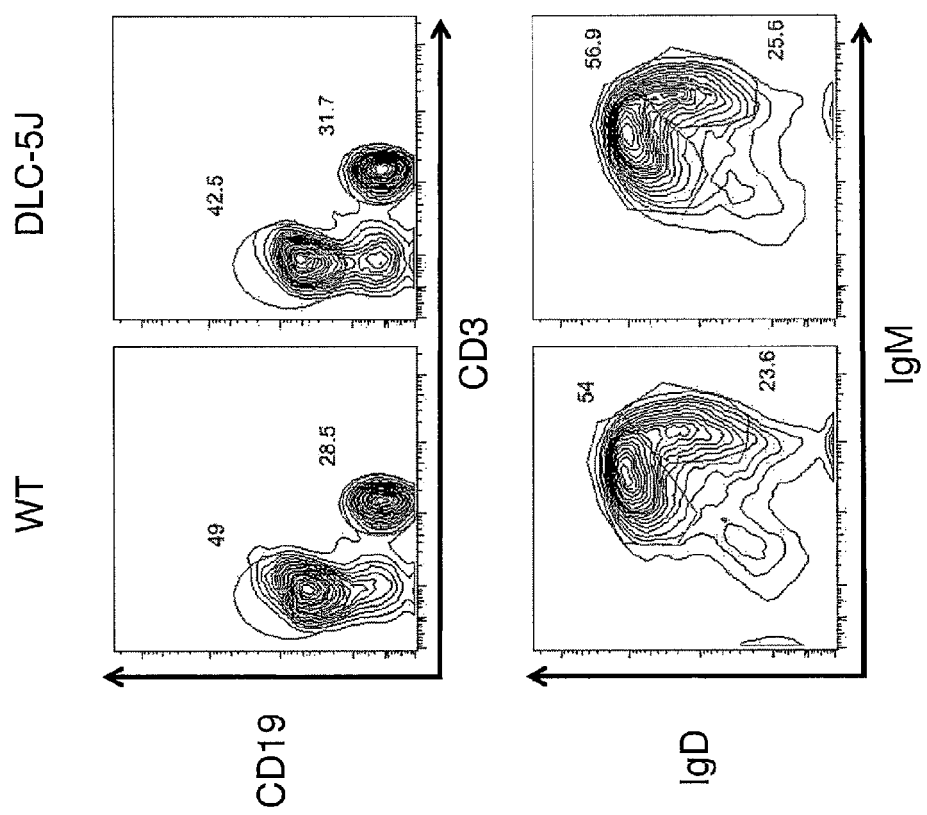
FIG. 28A, in the top panel, shows representative contour plots of splenocytes gated on singlets and stained for B and T cells (CD19+ and CD3+, respectively) from a wild type mouse (WT) and a mouse homozygous for two human Vκ and five human Jκ gene segments (DLC-5J). The bottom panel shows representative contour plots of splenocytes gated on CD19+ and stained for immunoglobulin D (IgD) and immunoglobulin M (IgM) from a wild type mouse (WT) and a mouse homozygous for two human Vκ and five human Jκ gene segments (DLC-5J). Mature (54 for WT, 56.9 for DLC-5J) and transitional (23.6 for WT, 25.6 for DLC-5J) B cells are noted on each of the contour plots.
Figure 28B:
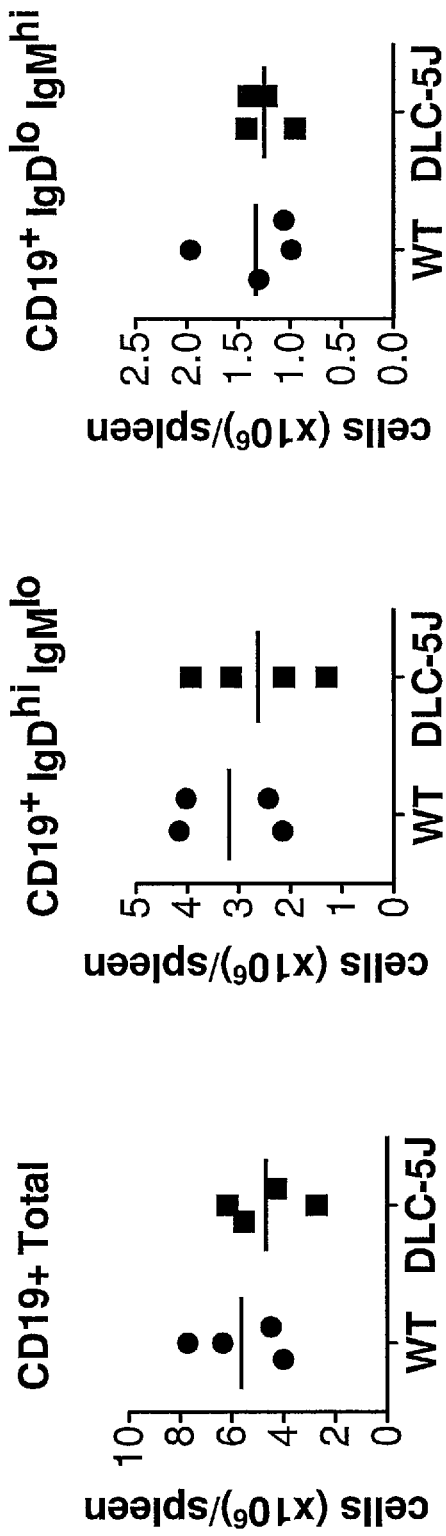
FIG. 28B shows the total number of CD19+ B cells, transitional B cells (CD19+IgM$^{hi}$IgDlo) and mature B cells (CD19+IgM$^{lo}$IgDhi) in harvested spleens from wild type mice (WT) and mice homozygous for two human Vκ and five human Jκ gene segments (DLC-5J).
Figure 29A:
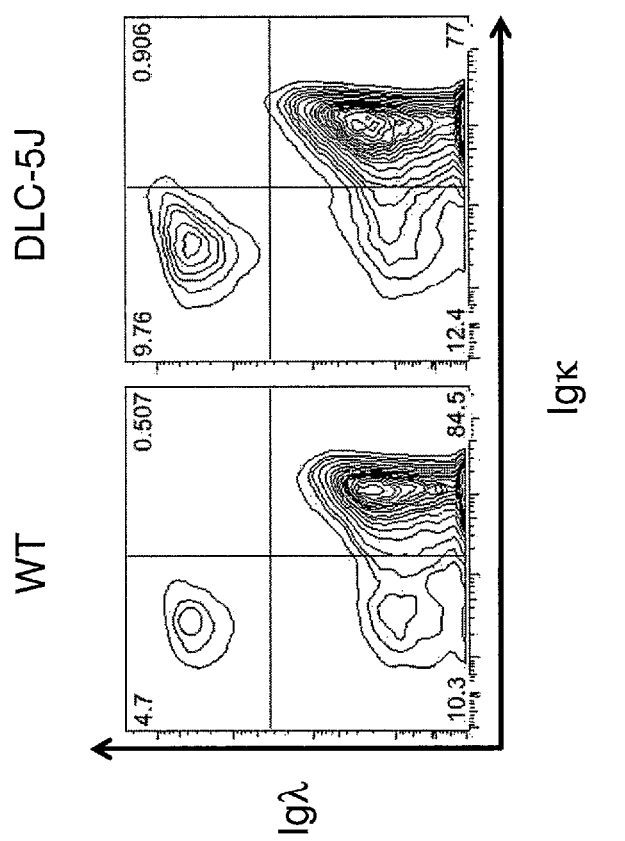
FIG. 29A shows representative contour plots of Igλ+ and Igκ+ splenocytes gated on CD19+ from a wild type mouse (WT) and a mouse homozygous for two human Vκ and five human Jκ gene segments (DLC-5J).
Figure 29B:
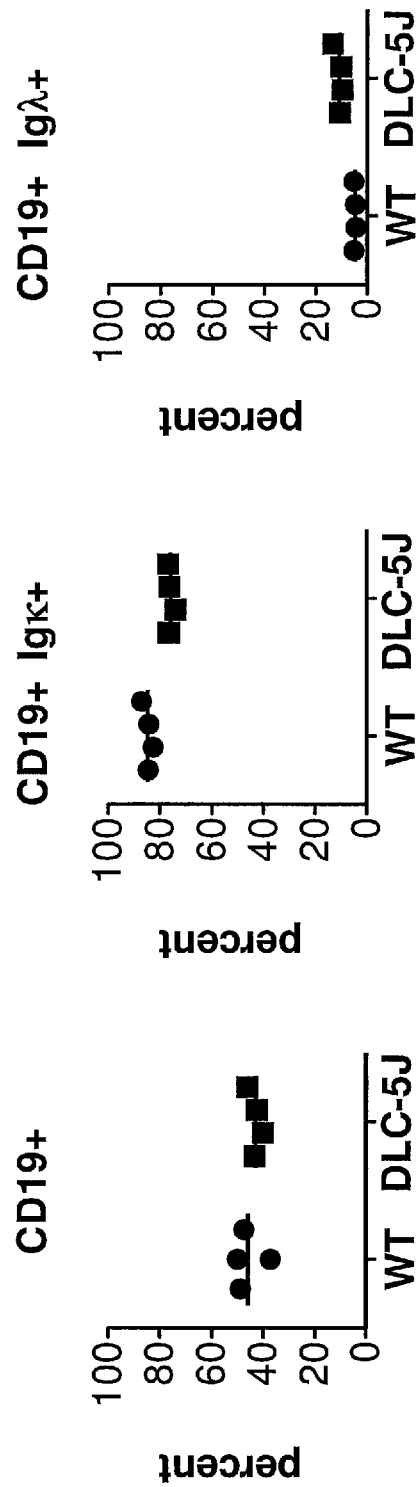
FIG. 29B shows the total number of B cells (CD19+), Igκ+ B cells (CD19+IgK+) and Igλ+ B cells (CD19+Igλ+) in harvested spleens from wild type (WT) and mice homozygous for two human Vκ and five human Jκ gene segments (DLC-5J).

ES cells bearing the engineered light chain locus may be transfected with a construct that expresses FLP in order to remove the FRTed neomycin cassette introduced by the targeting construct (see FIG. 23D). Optionally, the neomycin cassette is removed by breeding to mice that express FLP recombinase (e.g., U.S. Pat. No. 6,774,279). Optionally, the neomycin cassette is retained in the mice.

Example 3.2: Characterization of Mice that Comprise Two Human V Segments

Flow Cytometry. B cell populations and B cell development in DLC mice were validated by flow cytometry analysis of splenocyte and bone marrow preparations. Cell suspensions from mice homozygous for two human Vκ gene segments and five human Jκ gene segments (n=4), mice homozygous for two human Vκ gene segments and one human Jκ gene segment (n=4), and wild type mice (n=4) were made using standard methods and stained with fluorescently labeled antibodies.

Briefly, $1 \times 10^6$ cells were incubated with anti-mouse CD16/CD32 (clone 2.4G2, BD Pharmigen) on ice for 10 minutes, followed by labeling with the following antibody cocktail for 30 minutes on ice: APC-H7 conjugated anti-mouse CD19 (clone 1D3, BD Pharmigen), Pacific Blue conjugated anti-mouse CD3 (clone 17A2, BioLegend), FITC conjugated anti-mouse Igκ (clone 187.1, BD Pharmigen) or anti-mouse CD43 (clone 1 B11, BioLegend), PE conjugated anti-mouse Ig λ (clone RML-42, BioLegend) or anti-mouse c-kit (clone 2B8, BioLegend), PerCP-Cy5.5 conjugated anti-mouse IgD (BioLegend), PE-Cy7 conjugated anti-mouse IgM (clone II/41, eBioscience), APC conjugated anti-mouse B220 (clone RA3-6B2, eBioscience). Following staining, cells were washed and fixed in 2% formaldehyde. Data acquisition was performed on an LSRII flow cytometer and analyzed with FlowJo (Tree Star, Inc.). Gating: total B cells (CD19+CD3−), Igκ+ B cells (Igκ+Ig$_\lambda$−CD19+CD3−), Ig$_\lambda$+ B cells (Igκ−Ig$_\lambda$+CD19+CD3−). Results for the bone marrow compartment are shown in FIG. 25A-27B. Results for the splenic compartment are shown in FIG. 28A-FIG. 31.

Figure 30A:
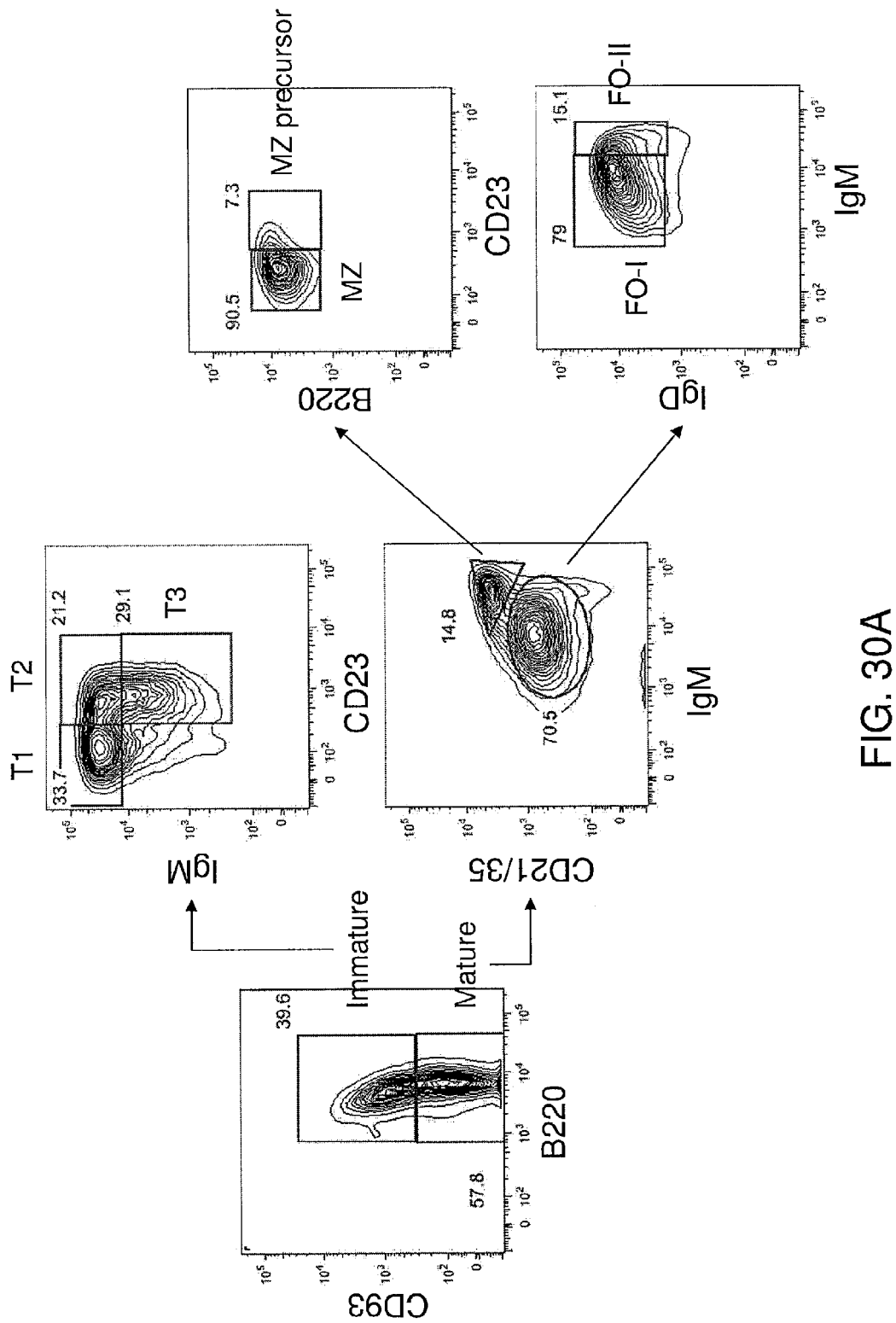
FIG. 30A shows the peripheral B cell development in mice homozygous for two human Vκ and five human Jκ gene segments. The first (far left) contour plot shows CD93+ and B220+ splenocytes gated on CD19+ indicating immature (39.6) and mature (57.8) B cells. The second (top middle) contour plot shows IgM+ and CD23+ expression in immature B cells indicating T1 (33.7; IgD−IgM+CD21$^{lo}$CD23−), T2 (21.2; IgD$^{hi}$IgM$^{hi}$CD21$^{mid}$CD23+) and T3 (29.1) B cell populations. The third (bottom middle) contour plot shows CD21+(CD35+) and IgM+ expression of mature B cells indicating a small population (14.8) which give rise to marginal zone B cells and a second population (70.5) which gives rise to follicular (FO) B cells. The fourth (top right) contour plot shows B220+ and CD23+ expression in mature B cells indicating marginal zone (90.5; MZ) and marginal zone precursor (7.3; IgM$^{hi}$IgD$^{hi}$CD21$^{hi}$CD23+) B cell populations. The fifth (bottom right) contour plot shows IgD+ and IgM+ expression in mature B cells indicating FO-I (79.0; IgD$^{hi}$IgM$^{lo}$CD21$^{mid}$CD23+) and FO-II (15.1; IgD$^{hi}$IgM$^{hi}$CD21$^{mid}$CD23+) B cell populations. Percentage of cells within each gated region is shown.
Figure 30B:
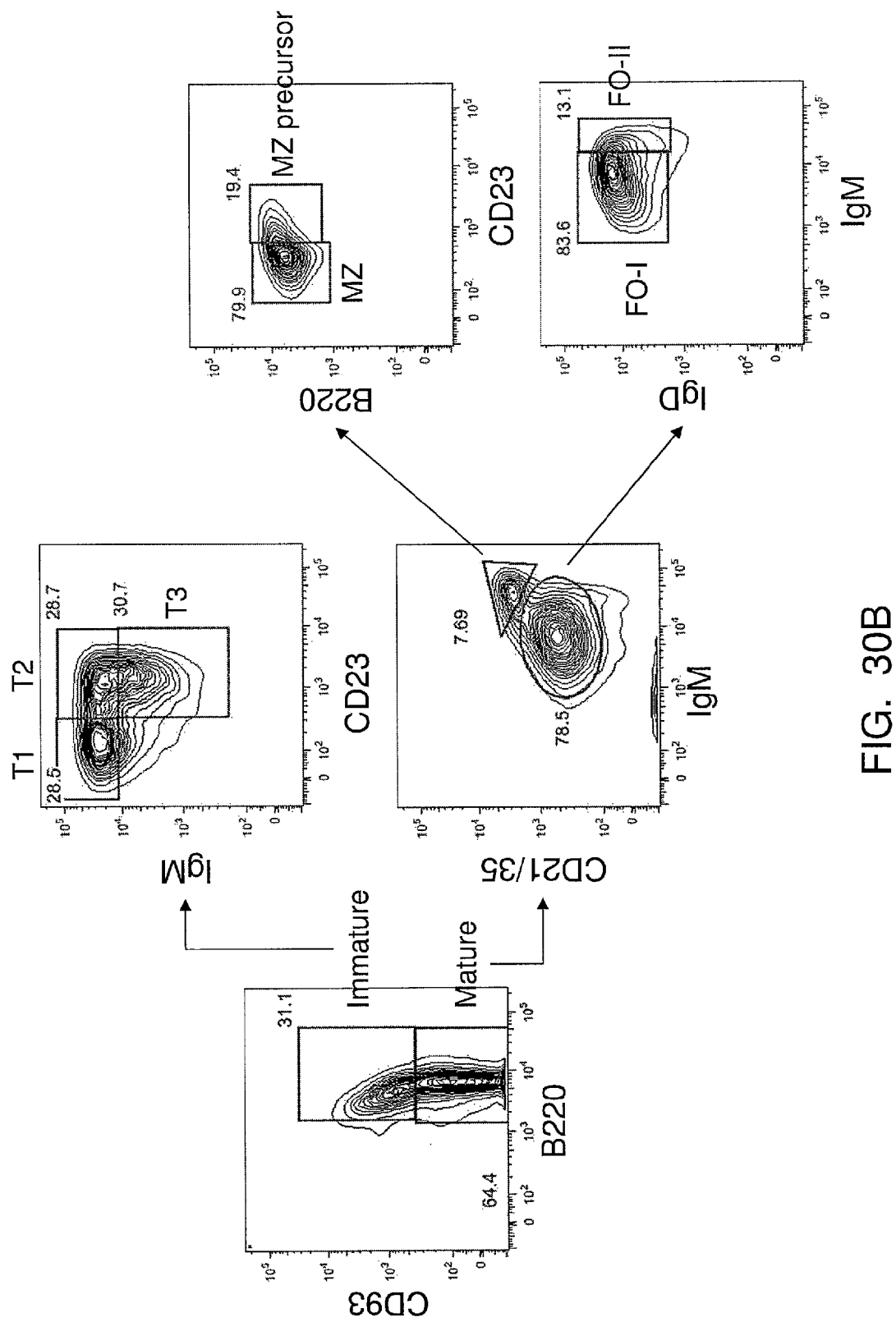
FIG. 30B shows the peripheral B cell development in wild type mice. The first (far left) contour plot shows CD93+ and B220+ splenocytes gated on CD19+ indicating immature (31.1) and mature (64.4) B cells. The second (top middle) contour plot shows IgM+ and CD23+ expression in immature B cells indicating T1 (28.5; IgD−IgM+CD21$^{lo}$CD23−), T2 (28.7; IgD$^{hi}$IgM$^{hi}$CD21$^{mid}$CD23+) and T3 (30.7) B cell populations. The third (bottom middle) contour plot shows CD21+(CD35+) and IgM+ expression of mature B cells indicating a small population (7.69) which give rise to marginal zone B cells and a second population (78.5) which gives rise to follicular (FO) B cells. The fourth (top right) contour plot shows B220+ and CD23+ expression in mature B cells indicating marginal zone (79.9; MZ) and marginal zone precursor (19.4; IgM$^{hi}$IgD$^{hi}$CD21$^{hi}$CD23+) B cell populations. The fifth (bottom right) contour plot shows IgD+ and IgM+ expression in mature B cells indicating FO-I (83.6; IgD$^{hi}$IgM$^{lo}$CD21$^{mid}$CD23+) and FO-II (13.1; IgD$^{hi}$IgM$^{hi}$CD21$^{mid}$CD23+) B cell populations. Percentage of cells within each gated region is shown.
Figure 31:
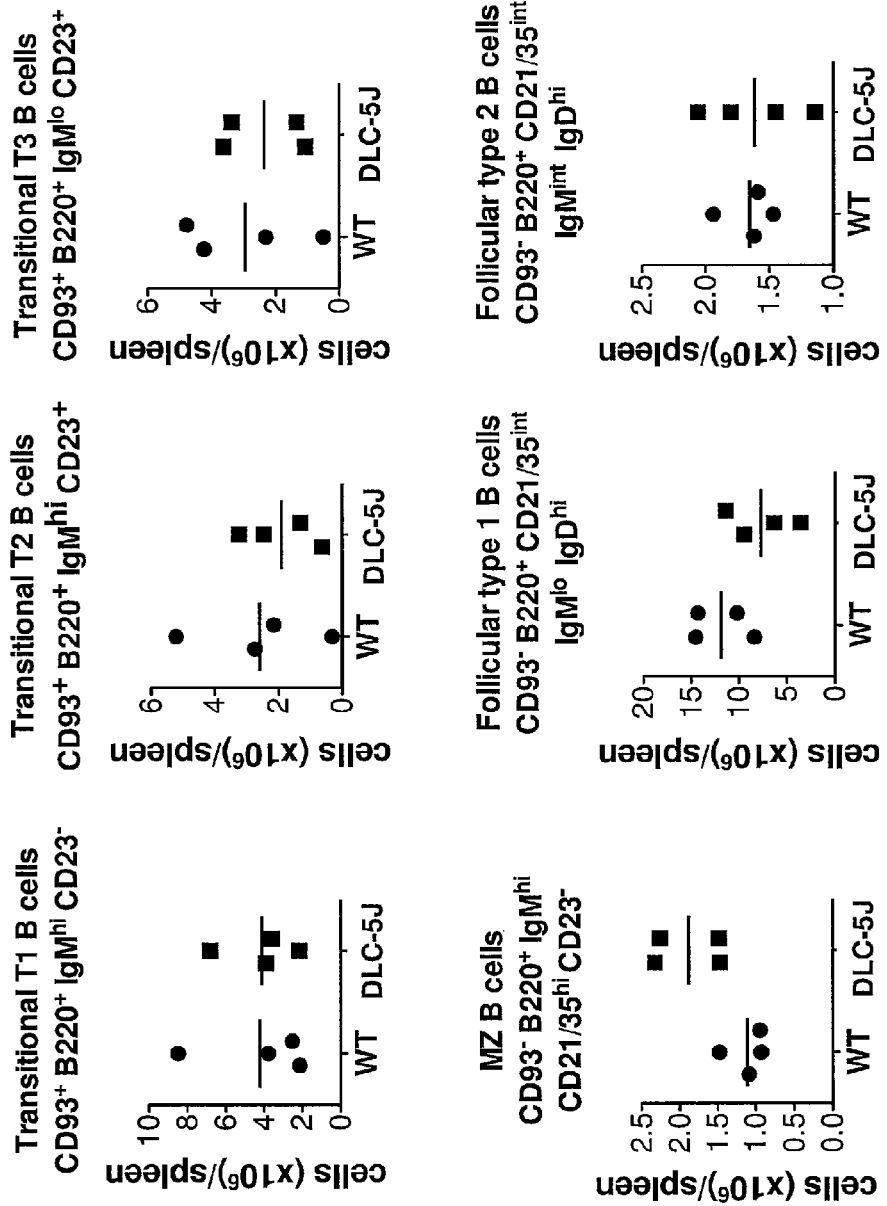
FIG. 31 shows the total number of transitional, marginal zone and follicular B cell populations in harvested spleens of wild-type (WT) and mice homozygous for two human Vκ and five human Jκ gene segments (DLC-5J).

As shown in this Example, DLC-5J mice demonstrate normal B cell populations within the splenic and bone marrow compartments (FIG. 25A-31). DLC-5J mice demonstrated immature, mature and pre/pro B cell populations within the bone marrow compartment that are substantially the same as observed in wild-type littermates. In fact, the DLC-5J locus was capable of competing with the endogenous lambda light chain locus to yield a kappa:lambda ratio that is substantially the same as that observed in wild-type mice (FIG. 27B). Also, DLC-5J mice demonstrate a normal peripheral B cell development as progression of B cells through various stages in the splenic compartment (e.g., immature, mature, T1, T2 T3, marginal zone precursor, marginal zone, follicular-I, follicular-II, etc.) occurs in a manner substantially the same as observed in wild type mice (FIG. 30A-31). In contrast, DLC-1J mice demonstrated a lower overall number of B cells and an increased lambda light chain usage as compared to the engineered kappa light chain (data not shown).

Dual Light Chain Expression. Expression of both human Vκ gene segments was analyzed in homozygous mice using a quantitative PCR assay. Briefly, CD19+ B cells were purified from bone marrow and whole spleens of wild type mice, mice homozygous for a replacement of the mouse heavy chain and κ light chain variable loci with corresponding human heavy chain and κ light chain variable region loci (Hκ), as well as mice homozygous for an engineered κ light chain loci containing two human Vκ gene segments and either five human Jκ gene segments (DLC-5J) or one human Jκ gene segment (DLC-1J). Relative expression was normalized to expression of mouse Cκ region (n=3 to 5 mice per group). Results are shown in FIG. 32 and FIG. 33.

Figure 32:
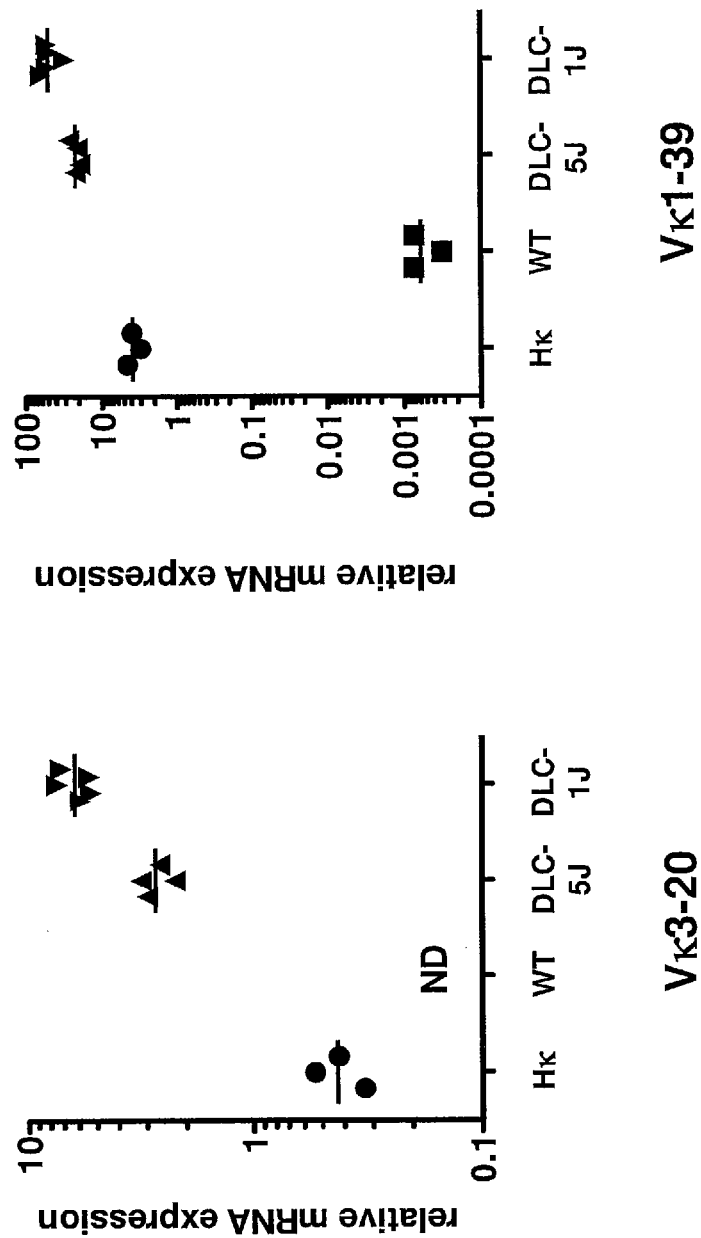
FIG. 32 shows the relative mRNA expression in bone marrow (y-axis) of Vκ3-20-derived and Vκ1-39-derived light chains in a quantitative PCR assay using probes specific for Vκ3-20 or Vκ1-39 gene segments in mice homozygous for a replacement of the endogenous Vκ and Jκ gene segments with human Vκ and Jκ gene segments (Hκ) (human light chain of a VELOCIMMUNE® mouse), wild type mice (WT), mice homozygous for two human Vκ gene segments and five human Jκ gene segments (DLC-5J) and mice homozygous for two human Vκ gene segments and one human Jκ gene segment (DLC-1J). Signals are normalized to expression of mouse Cκ. ND: not detected.
Figure 33:
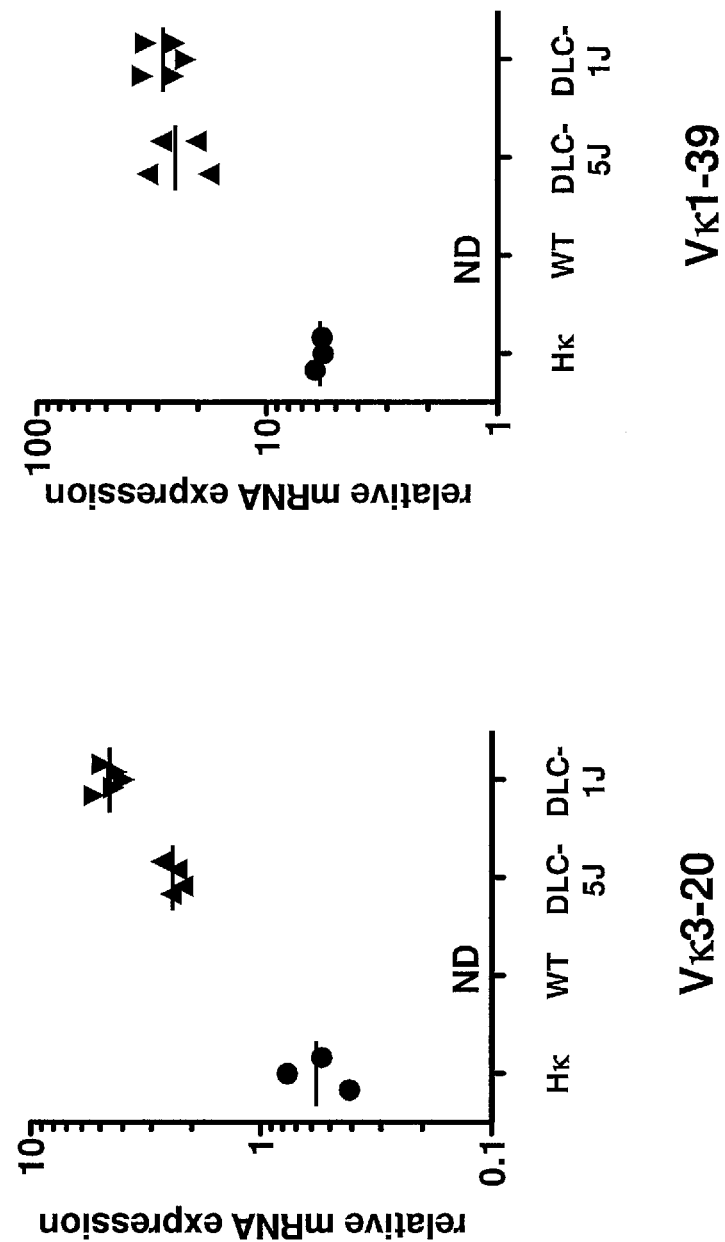
FIG. 33 shows the relative mRNA expression in whole spleens (y-axis) of Vκ3-20-derived and Vκ1-39-derived light chains in a quantitative PCR assay using probes specific for Vκ3-20 or Vκ1-39 gene segments in mice homozygous for a replacement of the endogenous Vκ and Jκ gene segments with human Vκ and Jκ gene segments (Hκ) (human light chain of a VELOCIMMUNE® mouse), wild type mice (WT), mice homozygous for two human Vκ gene segments and five human Jκ gene segments (DLC-5J) and mice homozygous for two human Vκ gene segments and one human Jκ gene segment (DLC-1J). Signals are normalized to expression of mouse Cκ. ND: not detected.

Expression of light chains containing a rearranged human Vκ3-20 or human Vκ1-39 gene segment were detected in both the bone marrow and spleen of DLC-5J and DLC-1J mice (FIG. 32 and FIG. 33). In the bone marrow compartment, expression of both human Vκ3-20-derived and human Vκ1-39-derived light chains in both strains of DLC mice was significantly higher as compared to mice comprising a replacement of mouse Vκ and Jκ gene segment with corresponding human Vκ and Jκ gene segments (Hκ; FIG. 32). Human Vκ3-20-derived light chain expression was observed at about six-fold (DLC-5J) to fifteen-fold (DLC-1J) higher than in Hκ mice. DLC-1J mice demonstrated about two-fold higher expression of human Vκ3-20-derived light chains over DLC-5J mice in the bone marrow compartment. Human Vκ1-39-derived light chain expression was observed at about six-fold (DLC-5J) to thirteen-fold (DLC-1J) higher than in Hκ mice. DLC-1J mice demonstrated about two-fold higher expression of human Vκ1-39-derived light chains over DLC-5J mice in the bone marrow compartment.

In the splenic compartment, expression of both human Vκ3-20-derived and human Vκ1-39-derived light chains in both strains of DLC mice was significantly higher as compared to Hκ mice (FIG. 33). Human Vκ3-20-derived light chain expression was observed at about four-fold (DLC-5J) and eight-fold (DLC-1J) higher than in Hκ mice. DLC-1J mice demonstrated about two-fold higher expression of human Vκ3-20-derived light chains over DLC-5J mice in the splenic compartment. Human Vκ1-39-derived light chain expression was observed at about four-fold (DLC-5J) to five-fold (DLC-1J) higher than in Hκ mice. DLC-1J mice demonstrated similar expression of human Vκ1-39-derived light chains as compared to DLC-5J mice in the splenic compartment.

Human Vκ/Jκ Usage in DLC-5J Mice. Mice homozygous for two unrearranged human Vκ gene segments and five unrearranged human Jκ gene segments (DLC-5J) were analyzed for human Vκ/Jκ gene segment usage in splenic B cells by reverse-transcriptase polymerase chain reaction (RT-PCR).

Briefly, spleens from homozygous DLC-5J (n=3) and wild type (n=2) mice were harvested and meshed in 10 mL of RPMI 1640 (Sigma) containing 10% heat-inactivated fetal bovine serum using frosted glass slides to create single cell suspensions. Splenocytes were pelleted with a centrifuge (1200 rpm for five minutes) and red blood cells were lysed in 5 mL of ACK lysing buffer (GIBCO) for three minutes. Splenocytes were diluted with PBS (Irvine Scientific), filtered with a 0.7 μm cell strainer and centrifuged again to pellet cells, which was followed by resuspension in 1 mL of PBS.

RNA was isolated from pelleted splenocytes using AllPrep DNA/RNA mini kit (Qiagen) according to manufacturer's specifications. RT-PCR was performed on splenocyte RNA using 5' RACE (Rapid Amplification of cDNA ends) System with primers specific for the mouse Cκ gene according to manufacturer's specifications (Invitrogen). The primers specific for the mouse Cκ gene were 3' mIgκC RACE1 (AAGAAGCACA CGACTGAGGC AC; SEQ ID NO: 90) and mIgκC3'-1 (CTCACTGGAT GGTGGGAAGA TGGA; SEQ ID NO: 91). PCR products were gel-purified and cloned into pCR®2.1-TOPO® vector (TOPO® TA Cloning® Kit, Invitrogen) and sequenced with M13 Forward (GTAAAACGAC GGCCAG; SEQ ID NO: 92) and M13 Reverse (CAGGAAACAG CTATGAC; SEQ ID NO: 93) primers located within the vector at locations flanking the cloning site. Ten clones from each spleen sample were sequenced. Sequences were compared to the mouse and human immunoglobulin sets from the IMGT/V-QUEST reference directory sets to determine Vκ/Jκ usage. Table 10 sets forth the Vκ/Jκ combinations for selected clones observed in RT-PCR clones from each splenocyte sample. Table 11 sets forth the amino acid sequence of the human Vκ/human Jκ and human Jκ/mouse Cκ junctions of selected RT-PCR clones from DLC-5J homozygous mice. Lower case letters indicate mutations in the amino acid sequence of the variable region or non-template additions resulting from N and/or P additions during recombination.

As shown in this example, mice homozygous for two unrearranged human Vκ gene segments and five unrearranged human Jκ gene segments (DLC-5J) operably linked to the mouse Cκ gene are able to productively recombine both human Vκ gene segments to multiple human Jκ gene segments to produce a limited immunoglobulin light chain repertoire. Among the rearrangements in DLC-5J homozygous mice shown in Table 10, unique human Vκ/Jκ rearrangements were observed for Vκ1-39/Jκ2 (1), Vκ1-39/Jκ3 (1), Vκ3-20/Jκ1 (7), Vκ3-20/Jκ2 (4) and Vκ3-20/Jκ3 (1). Further, such unique rearrangements demonstrated junctional diversity through the presence of unique amino acids within the CDR3 region of the light chain (Table 11) resulting from either mutation and/or the recombination of the human Vκ and Jκ gene segments during development. All the rearrangements showed functional read through into mouse Cκ (Table 11).

Taken together, these data demonstrate that mice engineered to present a choice of no more than two human Vκ gene segments, both of which are capable of rearranging (e.g., with one or more and, in some embodiments, up to five human Jκ gene segments) and encoding a human $V_L$ domain of an immunoglobulin light chain have B cell numbers and development that is nearly wild-type in all aspects. Such mice produce a collection of antibodies having immunoglobulin light chains that have one of two possible human $V_L$ gene segments present in the collection. The mouse produces this collection of antibodies in response to antigen challenge and, and the collection of antibodies is associated with a diversity of reverse chimeric (human variable/mouse constant) heavy chains.

TABLE 10

Vκ/Jκ Combinations Observed in Splenocyte Samples

| Mouse ID No. | Genotype | Clone | Vκ/Jκ Combination |
|---|---|---|---|
| 1089451 | DLC-5J | 1-2 | 1-39/3 |
|  |  | 1-4 | 3-20/2 |
|  |  | 1-7 | 3-20/1 |
|  |  | 1-8 | 3-20/2 |
| 1089452 | DLC-5J | 2-2 | 3-20/1 |
|  |  | 2-3 | 3-20/1 |
|  |  | 2-6 | 3-20/2 |
|  |  | 2-8 | 3-20/2 |
|  |  | 2-9 | 3-20/1 |
|  |  | 2-10 | 1-39/2 |
| 1092594 | DLC-5J | 3-1 | 3-20/1 |
|  |  | 3-2 | 3-20/1 |
|  |  | 3-4 | 3-20/1 |
|  |  | 3-6 | 3-20/3 |
|  |  | 3-9 | 3-20/2 |
| 1092587 | WT | 1-1 | 19-93/1 |
|  |  | 1-2 | 6-25/1 |
|  |  | 1-3 | 4-91/5 |
|  |  | 1-5 | 3-10/4 |
|  |  | 1-6 | 4-86/4 |
|  |  | 1-8 | 19-93/1 |
|  |  | 1-10 | 19-93/2 |
| 1092591 | WT | 2-1 | 19-93/1 |
|  |  | 2-3 | 6-20/5 |
|  |  | 2-4 | 6-25/5 |
|  |  | 2-5 | 1-117/1 |
|  |  | 2-6 | 8-30/1 |
|  |  | 2-7 | 8-19/2 |
|  |  | 2-8 | 8-30/1 |
|  |  | 2-10 | 1-117/1 |

TABLE 11

Amino Acid Sequences of the Human Vκ/Human Jκ and Human Jκ/Mouse Cκ Junctions from DLC-5J Homozygous Mice

| Clone | Vκ/Jκ | Sequence of hVκ/hJκ/mCκ Junction (CDR3 underlined, mIgκC italics) | SEQ ID NO: |
|---|---|---|---|
| 2-10 | 1-39/2 | QPEDFATYY<u>CQQSYSTPYT</u>FGQGTKLEIK*RADAAPTVSI* | 94 |
| 1-2 | 1-39/3 | QPEDFATYY<u>CQQSYSTPFT</u>FGPGTKVDIK*RADAAPTVSI* | 95 |
| 1-7 | 3-20/1 | EPEDFAVYY<u>CQQYGSSPrT</u>FGQGTKVEIK*RADAAPTVSI* | 96 |
| 2-2 | 3-20/1 | EPEDFAVYY<u>CQQYGSSrT</u>FGQGTKVEIK*RADAAPTVSI* | 97 |
| 2-3 | 3-20/1 | EPEDFAVYY<u>CQQYGSSPWT</u>FGQGTKVEIK*RADAAPTVSI* | 98 |
| 2-9 | 3-20/1 | dPEDFAVYY<u>CQQYGSSPrT</u>FGQGTKVEIK*RADAAPTVSI* | 99 |

TABLE 11-continued

Amino Acid Sequences of the Human Vκ/Human Jκ and Human Jκ/Mouse Cκ Junctions from DLC-5J Homozygous Mice

| Clone | Vκ/Jκ | Sequence of hVκ/hJκ/mCκ Junction (CDR3 underlined, mIgκC italics) | SEQ ID NO: |
|---|---|---|---|
| 3-1 | 3-20/1 | EPEDFAVYY<u>CQQYGSSPrTF</u>GQGTKVEIK*RADAAPTVSI* | 100 |
| 3-2 | 3-20/1 | EPEDFAVYY<u>CQQYGSSPWTF</u>GQGTKVEIK*RADAAPTVSI* | 101 |
| 3-4 | 3-20/1 | EPEDFAVYY<u>CQQYGSSPPTF</u>GQGTKVEIK*RADAAPTVSI* | 102 |
| 3-9 | 3-20/2 | EPEDFAVYY<u>CQQYGSSPYTF</u>GQGTKLEIK*RADAAPTVSI* | 103 |
| 3-6 | 3-20/3 | EPEDFAVYY<u>CQQYGSSiFTF</u>GPGTKVDIK*RADAAPTVSI* | 104 |

Figure 35A:
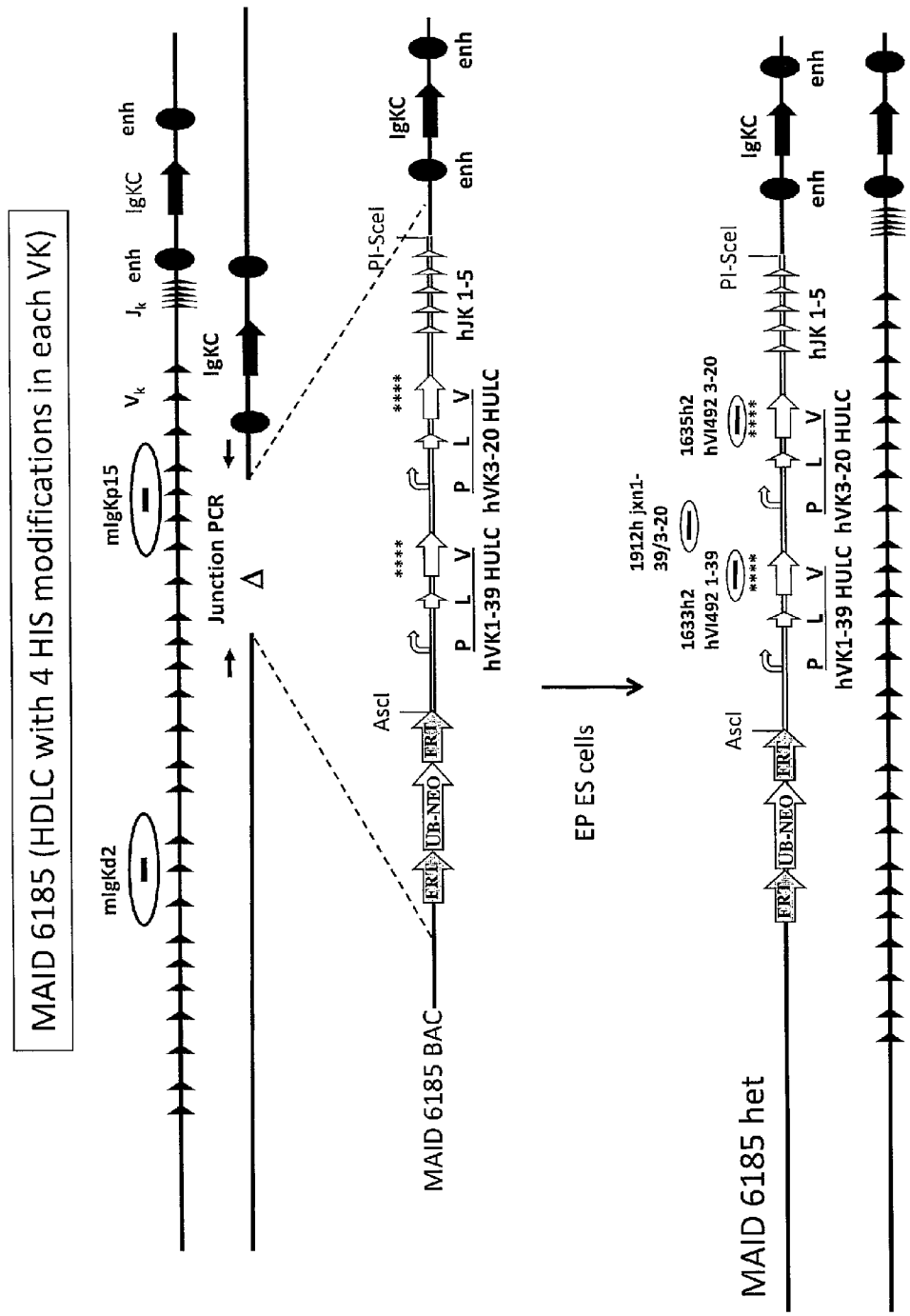

Example 4
Generation and Characterization of Mice Comprising Two Histidine-Substituted Human Light Chains Example 4.1: Engineering and Generation of Mice Comprising Two V Kappa Segments Each Containing Four Histidine Substitutions Histidine substitutions were introduced into the dual light chain locus as described above for Vκ1-39 and Vκ3-20 ULC mice. Briefly, the DLC sequence depicted in FIG. 23A (bottom) was subjected to site-directed mutagenesis, first modifying the W1-39 sequence, and subsequently modifying the Vκ3-20 sequence, using primers depicted in FIG. 34. The resultant dual light chain sequence contained Vκ1-39 segment with histidines introduced into the germline sequence at positions 105, 106, 108, and 111, Vκ3-20 segment with histidines introduced into the germline sequence at positions 105, 106, 107, and 109, as well as all five Jκ segments (Jκ1, Jκ2, Jκ3, Jκ4, and Jκ5). A subsequent engineering step involved attachment of a 5' arm carrying an FRT-UB-NEO-FRT cassette, and a 3' arm carrying a mouse Igκ enhancers and constant region. This targeting vector was electroporated into ES cells comprising deletion of the mouse Igκ variable locus (comprising κ variable and joining gene segments), as depicted in FIG. 35A (recombination signal sequences, RSS, are omitted in this figure). Targeted ES cells were screened by a modification of allele assay as described above, using primers and probes that detected the regions described above in Tables 1, 5, 8, and 9 (specifically, 1633h2, 1635h2, neo, Jxn 1-39/3-20, mIgKd2, and mIgKp15), as well as two additional sets of primers and probes listed in Table 12 below. The sequences of these two additional sets of primers and probes are included in the Sequence Listing.

A confirmed ES cell clone is then used to implant female mice to give rise to a litter of pups comprising DLC-5J light chain locus with four histidine modifications at each of the two present $V_L$ segment sequences, and expressing a human light chain variable domain fused with a mouse Cκ domain. Some of the same sequences as used for ES cell screening are also used for genotyping of pups.

Figure 35B:
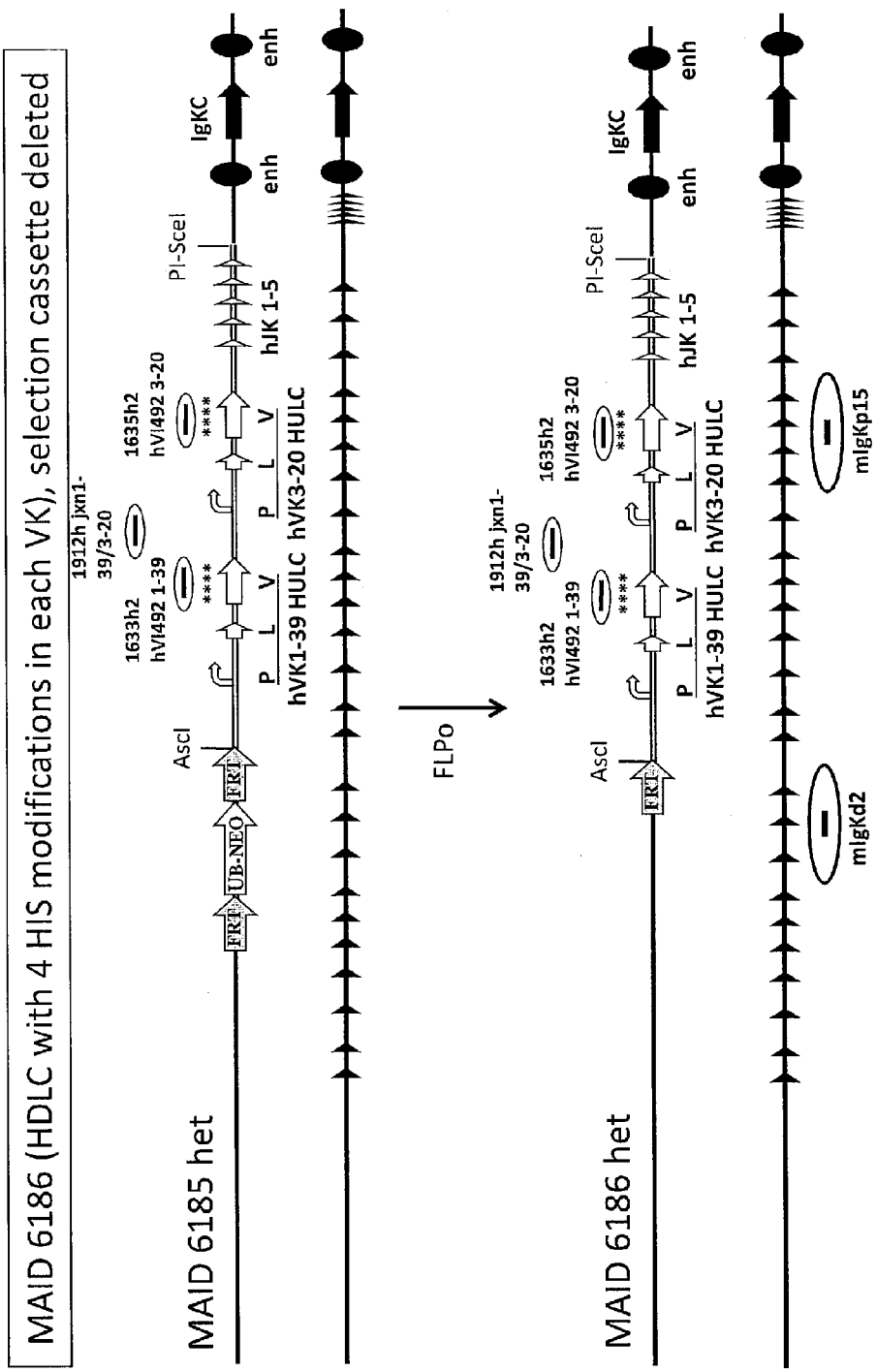
FIG. 35B shows deletion of the selection cassette in ES cells using FLPo enzyme. In most embodiments, unless indicated otherwise, filled shapes and solid lines represent mouse sequences, and open shapes and double lines represent human sequences. The diagrams are not presented to scale.

ES cells bearing the engineered light chain locus may be transfected with a construct that expresses FLP (e.g., FLPo) in order to remove the FRTed neomycin cassette introduced by the targeting construct (see FIG. 35B, RSS are omitted in this figure). Optionally, the neomycin cassette is removed by breeding to mice that express FLP recombinase (e.g., U.S. Pat. No. 6,774,279). Optionally, the neomycin cassette is retained in the mice.

Example 4.2: Engineering and Generation of Mice Comprising Two V Kappa Segments Each Containing Three Histidine Substitutions Three histidine substitutions were introduced into each Vκ1-39 and Vκ3-20 of the dual light chain mice. Briefly, the DLC sequence depicted in FIG. 23A (bottom) was subjected to site-directed mutagenesis, first modifying the W1-39 sequence, and subsequently modifying the Vκ3-20 sequence, using primers depicted in FIG. 36. The resultant dual light chain sequence contained Vκ1-39 segment with histidines introduced into the germline sequence at positions 106, 108, and 111, Vκ3-20 segment with histidines introduced into the germline sequence at positions 105, 106, and 109, as well as all five Jκ segments (Jκ1, Jκ2, Jκ3, Jκ4, and Jκ5). A subsequent engineering step involved attachment of a 5' arm carrying an FRT-UB-NEO-FRT cassette, and a 3' arm carrying a mouse Igκ enhancers and constant region. This targeting vector was electroporated into ES cells comprising deletion of

TABLE 12

Primers and Probes Used for ES Cell Screening

Figure 37A:
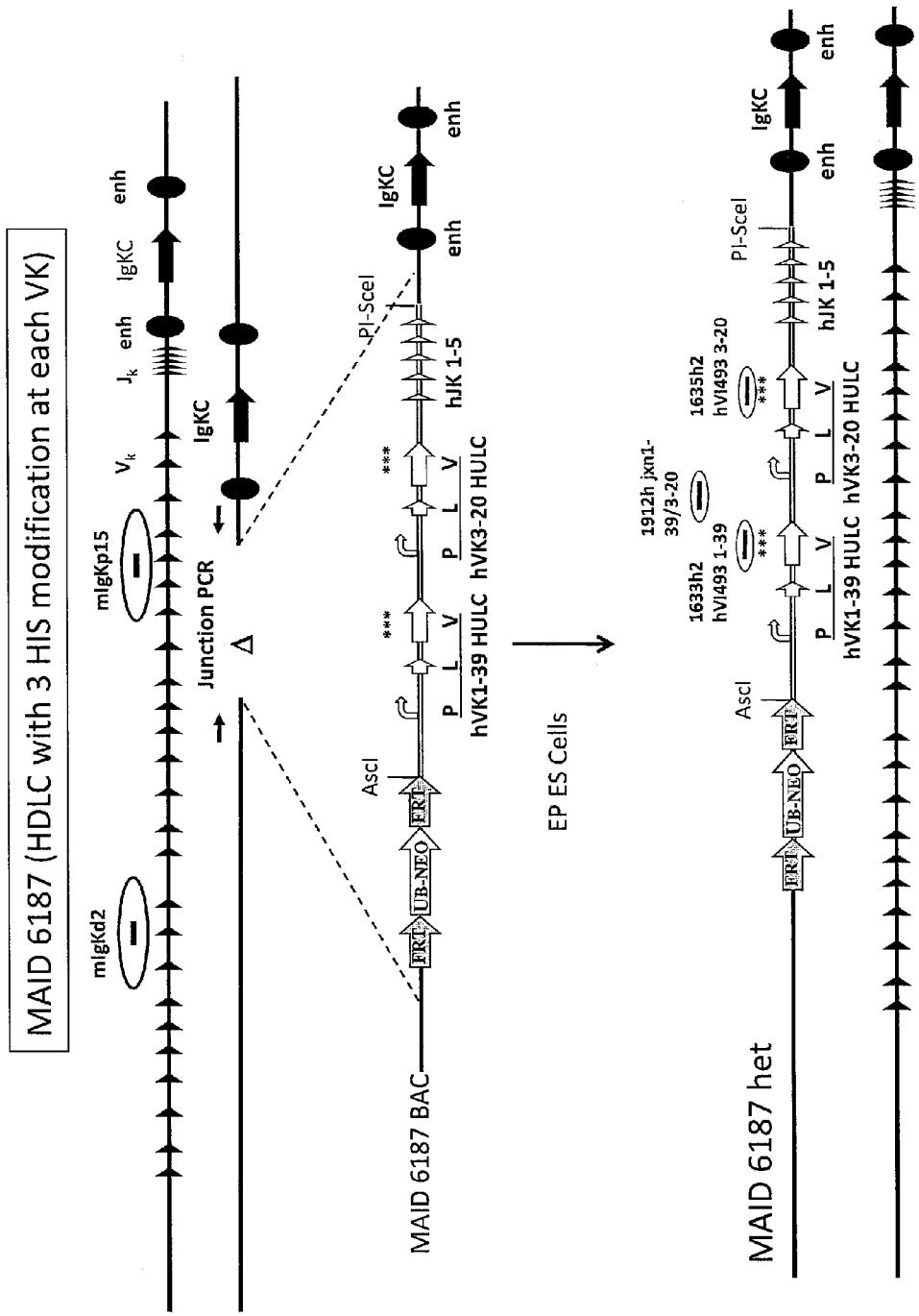

| Probe Name | Assay/type of probe | Location detected | Probe Sequence | Forward Primer | Reverse Primer |
|---|---|---|---|---|---|
| hVI492 1-39 | GOA/ FAM-BHQ+ | MAID 6185 (4 HIS-1-39 specific) | AACTTACTACTGT CACCA (SEQ ID NO: 111) | CAGCAGTCT GCAACCTGAA (SEQ ID NO: 112) | GGCTCGTCCT CACACATC (SEQ ID NO: 113) |
| hVI492 3-20 | GOA/ FAM-BHQ+ | MAID 6185 (4 HIS-3-20 specific) | TTACTGTCACCA TCATG (SEQ ID NO: 114) | GCAGACTGG AGCCTGAAGA (SEQ ID NO: 115) | AAGCTGAATC ACTGTGGGAG GTG (SEQ ID NO: 116) | the mouse Igκ variable locus (comprising κ variable and joining gene segments), as depicted in FIG. 37A (RSS are omitted in this figure). Targeted ES cells were screened by a modification of allele assay as described above, using primers and probes that detected the regions described above in Tables 1, 5, 8, and 9 (specifically, 1633h2, 1635h2, neo, Jxn 1-39/3-20, mIgKd2, and mIgKp15), as well as two additional sets of primers and probes listed in Table 13 below. The sequences of these two additional sets of primers and probes are included in the Sequence Listing.

TABLE 13

Primers and Probes Used for ES Cell Screening

| Probe Name | Assay/type of probe | Location detected | Probe Sequence | Forward Primer | Reverse Primer |
|---|---|---|---|---|---|
| hVI493 1-39 | GOA/ FAM-BHQ+ | MAID 6187 (3 HIS-1-39 specific) | CTTACTACTGT CAACATAG (SEQ ID NO: 123) | CAGCAGTCTG CAACCTGAA (SEQ ID NO: 124) | GGCTCGTCCT CACACATC (SEQ ID NO: 125) |
| hVI493 3-20 | GOA/ FAM-BHQ+ | MAID 6187 (3 HIS-3-20 specific) | TACTGTCAC CATTATGG (SEQ ID NO: 126) | GCAGACTGGA GCCTGAAGA (SEQ ID NO: 127) | AAGCTGAATCAC TGTGGGAGGTG (SEQ ID NO: 128) |

A confirmed ES cell clone is then used to implant female mice to give rise to a litter of pups comprising DLC-5J light chain locus with four histidine modifications at each of the two present $V_L$ segment sequences, and expressing a human light chain variable domain fused with a mouse Cκ domain. Some of the same sequences as used for ES cell screening are also used for genotyping of pups.

Figure 37B:
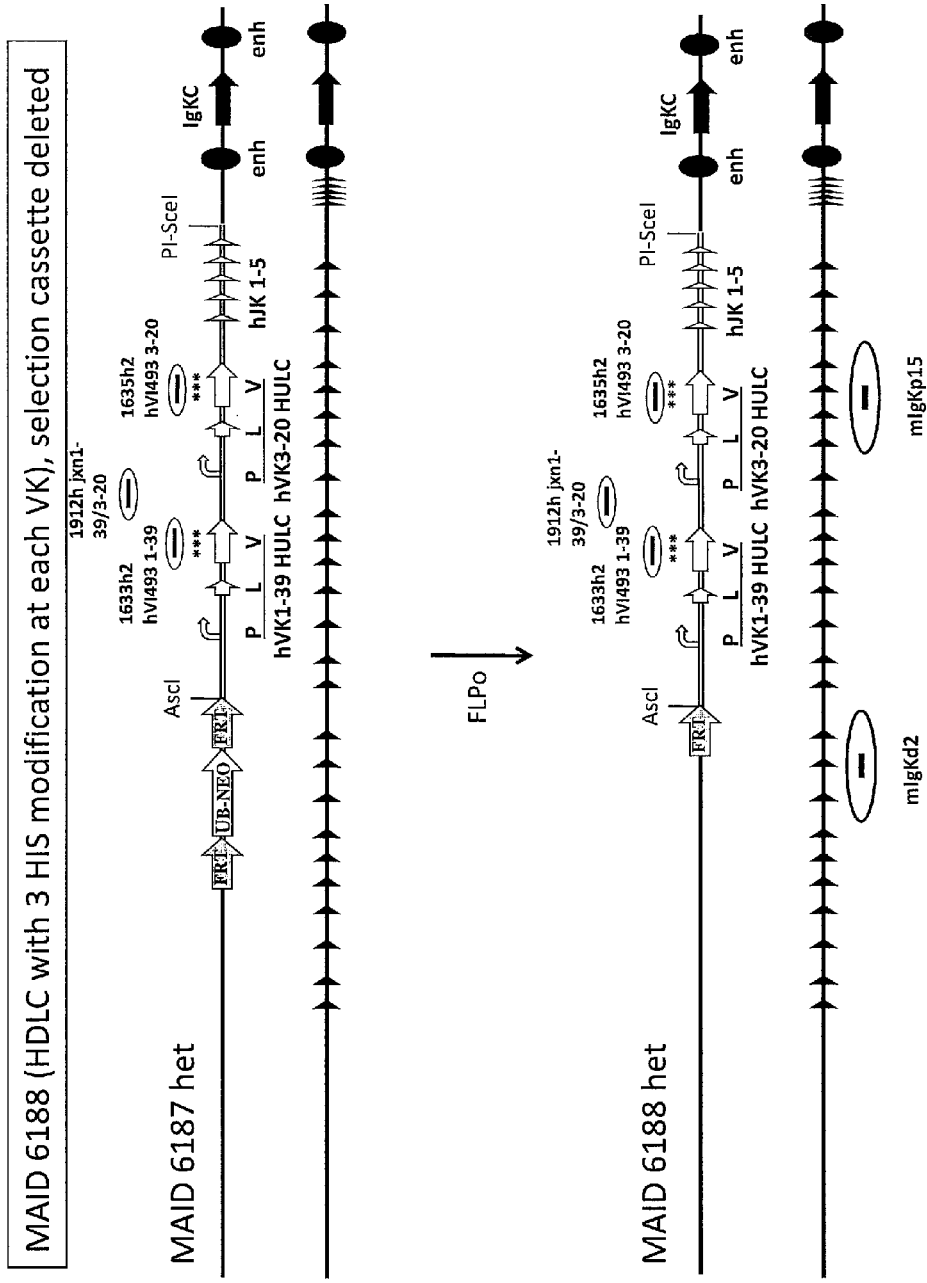
FIG. 37B shows deletion of the selection cassette in ES cells using FLPo enzyme. In most embodiments, unless indicated otherwise, filled shapes and solid lines represent mouse sequences, and open shapes and double lines represent human sequences. The diagrams are not presented to scale.

ES cells bearing the engineered light chain locus may be transfected with a construct that expresses FLP (e.g., FLPo) in order to remove the FRTed neomycin cassette introduced by the targeting construct (see FIG. 37B, RSS are omitted in this figure). Optionally, the neomycin cassette is removed by breeding to mice that express FLP recombinase (e.g., U.S. Pat. No. 6,774,279). Optionally, the neomycin cassette is retained in the mice.

Example 4.3: Breeding of Mice Comprising a Human Histidine-Substituted Dual Light Chains Mice bearing an engineered human histidine-substituted dual light chain locus are bred with mice that contain a deletion of the endogenous λ light chain locus to generate progeny that expresses, as their only light chains, the engineered histidine-substituted light chains derived from the dual light chain locus.

Mice bearing an engineered human histidine-substituted dual light chain locus are bred with mice that contain a replacement of the endogenous mouse heavy chain variable locus with human heavy chain variable locus (see U.S. Pat. No. 6,596,541 and U.S. Pat. No. 8,502,018; the VELOCIMMUNE® mouse, Regeneron Pharmaceuticals, Inc.).

Example 4.4: Detection of Histidine Modifications in Immunoglobulin Light Chains Obtained from Mice Comprising Two V Kappa Segments Each Containing Three Histidine Substitutions V kappa amplicons from splenic B cell mRNA was prepared using reverse-transcriptase PCR (RT-PCR) and high throughput screening.

Briefly, spleens from five heterozygous mice comprising two V kappa segments (Vκ1-39 and Vκ3-20) each containing three histidine substitutions (mice whose kappa locus is depicted in FIG. 35) and endogenous mouse heavy chains were harvested and homogenized in 1×PBS (Gibco) using glass slides. Cells were pelleted in a centrifuge (500 xg for 5 minutes), and red blood cells were lysed in ACK Lysis buffer (Gibco) for 3 minutes. Cells were washed with 1×PBS and filtered using a 0.7 μm cell strainer. B-cells were isolated from spleen cells using MACS magnetic positive selection for CD19 (Miltenyi Biotec). Total RNA was isolated from pelleted B-cells using the RNeasy Plus kit (Qiagen). PolyA+ mRNA was isolated from total RNA using the Oligotex Direct mRNA mini kit (Qiagen).

Double-stranded cDNA was prepared from splenic B cell mRNA by 5' RACE using the SMARTer Pico cDNA Synthesis Kit (Clontech). The Clontech reverse transcriptase and dNTPs were substituted with Superscript II and dNTPs from Invitrogen. Immunoglobulin light chain repertoires were amplified from the cDNA using primer specific for IgK constant region and the SMARTer 5' RACE primer (Table 14). PCR products were cleaned up using a QIAquick PCR Purification Kit (Qiagen). A second round of PCR was done using the same 5' RACE primer and a nested 3' primer specific for the IgK constant region (Table 15). Second round PCR products were purified using a SizeSelect E-gel system (Invitrogen). A third PCR was performed with primers that added 454 adapters and barcodes. Third round PCR products were purified using Agencourt AMPure XP Beads. Purified PCR products were quantified by SYBR-qPCR using a KAPA Library Quantification Kit (KAPA Biosystems). Pooled libraries were subjected to emulsion PCR (emPCR) using the 454 GS Junior Titanium Series Lib-A emPCR Kit (Roche Diagnostics) and bidirectional sequencing using Roche 454 GS Junior instrument according to the manufacturer's protocols.

TABLE 14

First Round PCR Primer

| NAME | SEQUENCE (SEQ ID NO) |
|---|---|
| 3' mIgK outer | AAGAAGCACACGACTGAGGCAC (SEQ ID NO: 129) |

TABLE 15

Second Round PCR Primer

| NAME | SEQUENCE (SEQ ID NO) |
|---|---|
| 3' mIgK inner | GGAAGATGGATACAGTTGGTGC (SEQ ID NO: 130) |

For bioinformatics analysis, the 454 sequence reads were sorted based on the sample barcode perfect match and trimmed for quality. Sequences were annotated based on alignment of rearranged Ig sequences to human germline V and J segments database using local installation of igblast (NCBI, v2.2.25+). A sequence was marked as ambiguous and removed from analysis when multiple best hits with identical score were detected. A set of perl scripts was developed to analyze results and store data in mysql database. CDR3 region of the kappa light chain was defined between conserved C codon and FGXG motif.

FIG. 38 represents alignments of amino acids sequence encoded by human germline IGKV3-20 (FIG. 38A) or IGKV1-39 (FIG. 38B) sequence with amino acid translations of exemplary Vκ sequences obtained from productively rearranged antibodies generated in mice comprising a histidine-modified DLC-5J (comprising a light chain variable locus comprising Vκ1-39 and Vκ3-20 gene segments, each segment with three histidine modifications as described above). The sequence reads showed that the majority of productively rearranged light chains retained at least one histidine introduced into its germline CDR3. In some instances, in the majority of all productively rearranged human light chains comprising Vκ3-20 sequence that retain at least one histidine residue, all three histidine modifications introduced into their germline CDR3 are retained (see FIG. 38A). In some instances, in productively rearranged human light chains comprising Vκ1-39 sequence that retain at least one histidine residue, about 50% of light chains retain all three histidines introduced into their germline CDR3 (see FIG. 38B top alignment), while about 50% of light chains retain two out of three histidines introduced into their germline CDR3 (see FIG. 38B bottom alignment). In some instances, histidines at the last position of the V segment sequence may be lost due to V-J rearrangement.

Example 5

Generation and Analysis of Mice Comprising a Single Rearranged Human Immunoglobulin Heavy Chain Nucleotide Sequence and Two V Kappa Gene Segments Mice comprising a rearranged heavy chain variable region nucleic acid sequence in the heavy chain locus (MAID6031; "UHC mouse") were generated as described above. Briefly, in the UHC mouse, all endogenous functional heavy chain variable gene segments were deleted and replaced with a single rearranged heavy chain variable region nucleic acid sequence that encodes $hV_H3-23/D/J_H4$, which is operably linked to an endogenous heavy chain constant region nucleic acid sequence.

Mice comprising genetically engineered light chain loci containing two human Vκ gene segments (e.g., a human Vκ1-39 and human Vκ3-20 gene segment) and either one human Jκ segment (Jκ5; DLC-1J) or five human Jκ gene segments (hJκ1-5; DLC-5J) were generated as described above. Briefly, one engineered light chain locus contains two human Vκ gene segments and five human Jκ gene segments (Jκ1-5) in unrearranged configuration and is operably linked to an endogenous mouse κ constant region sequence (MAID 1911 (DLC-5J); FIG. 19E). The other engineered light chain locus contains two human Vκ gene segments and one human Jκ (Jκ1) gene segment in unrearranged configuration and is operably linked to an endogenous mouse κ constant region sequence (MAID 1913(DLC-1J); FIG. 21D). For each of the two additional engineered light chain loci, the human gene segments were flanked 3' with recombination signal sequences to allow for in vivo rearrangement of the human gene segments in B cells.

Homozygous UHC mice (MAID6031) described above were bred to homozygous DLC-5J (MAID1911) mice to produce a mouse heterozygous for the UHC allele and the DLC-5J allele. Similarly, homozygous UHC mice (MAID6031) were bred to homozygous DLC-1J (MAID1913) mice to generate a mouse heterozygous for the UHC allele and the DLC-1J allele. F1 heterozygous mice generated from these crosses were bred each other to obtain mice homozygous for each allele. The presence of the genetically modified alleles in the immunoglobulin heavy chain and light chain loci was confirmed by TAQMAN™ screening and karyotyping using specific probes and primers described above.

Mice heterozygous for the UHC allele and the DLC-5J were bred to each other to generate homozygotes (MAID 1912HO 6032HO; "DLC×UHC") that express immunoglobulin "light" chains mostly from the genetically modified locus. The MAID 1912HO 6032HO (homozygous DLC× UHC) mice comprise an insertion of the Universal Heavy Chain described herein (e.g., $hV_H3-23/hD/hJ_H4$) into the mouse heavy chain locus in which all endogenouse variable heavy chain VDJ genes have been deleted and DLC-5J (hVκ1-39 hVκ3-20 hJκ1-5) the mouse kappa (κ) light chain locus in which all mouse Vκ and Jκ genes have been deleted.

Figure 39:
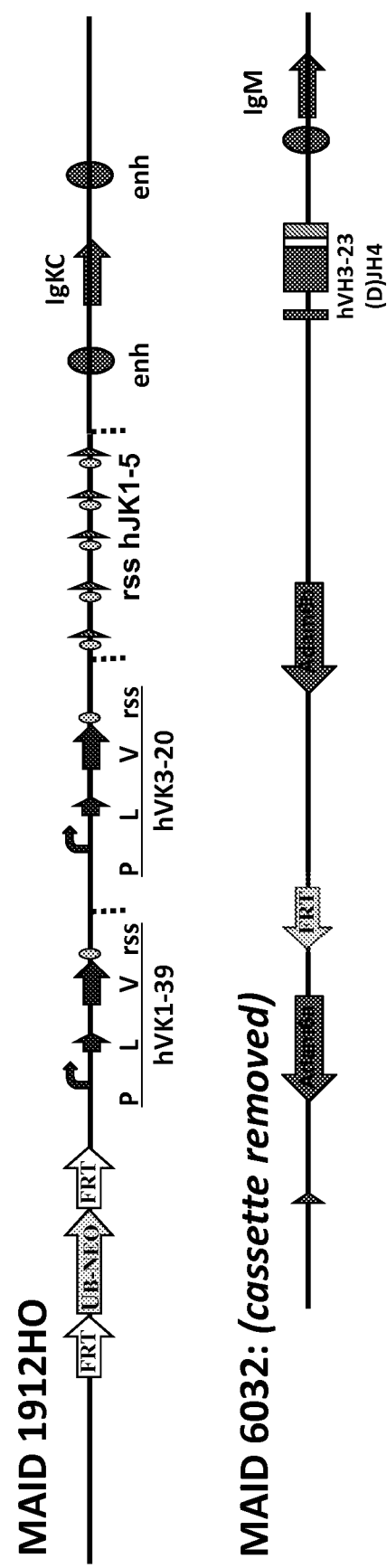
FIG. 39 illustrates the genomic structure of genetically modified F2 mice comprising rearranged heavy chain variable region nucleic acid sequence in the heavy chain loci (MAID6032; "UHC mouse") and further comprising genetically engineered light chain loci containing two human Vκ gene segments (e.g., a human Vκ1-39 and human Vκ3-20 gene segment) and five human Jκ gene segments (hJκ1-5; DLC-5J) (MAID 1912HO).

All mice were housed and bred in specific pathogen-free conditions at Regeneron Pharmaceuticals. Three F5 VELOCIMMUNE® (MAID 12930 1640HO ("VI3"); see U.S. Pat. No. 8,502,018, incorporated by reference herein) mice (14 weeks old, male; Background: 26.5% C57/BL6, 22.75% 129 and 50.75% Balb/c) and three MAID 1912HO 6032HO F2 mice (FIG. 39; 7-8 weeks old, female; Background: 18.75 C57/BL6, 18.75% 129, and 62.5% Balb/c) were sacrificed, and spleens and bone marrow were harvested from the animals. Bone marrow was collected from femurs by flushing with complete RPMI medium (RPMI medium supplemented with fetal calf serum, sodium pyruvate, Hepes, 2-mercaptoethanol, non-essential amino acids, and gentamycin). Red blood cells from spleen and bone marrow preparations were lysed with ACK lysis buffer and washed with complete RPMI medium.

Flow Cytometry

In order to examine the ability of the genetically modified homozygous "DLC×UHC" (MAID 1912HO 6032HO) mice described herein to produce antibodies derived from the genetically modified alleles (e.g., from the allele that contains a single copy of the rearranged $V_H3-23/D/J_H4$ in the heavy chain locus and the allele that contains two human Vκ five human Jκ genes in the light chain locus), fluorescence-activated cell sorting (FACS) analysis was performed as in Example 3.

Figure 40A:
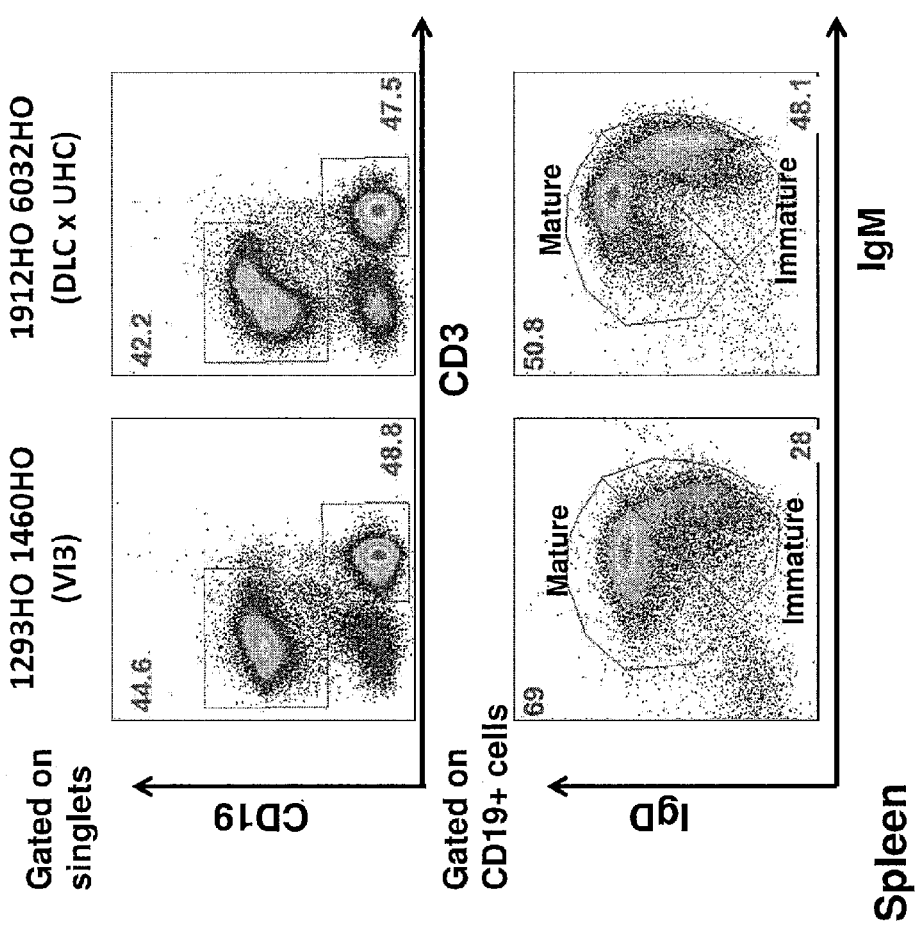
FIG. 40A, in the top panel, shows representative contour plots of splenocytes gated on singlets and stained for B and T cells (CD19$^+$ and CD3$^+$, respectively) from genetically modified control mice (VI3; 1293HO 1460HO) and mice homozygous for a rearranged heavy chain variable region nucleic acid sequence in the heavy chain loci and two human Vκ and five human Jκ gene segments in the light chain loci (MAID 1912HO 6032 HO; DLC×UHC). The bottom panel shows representative contour plots of splenocytes gated on CD19$^+$ and stained for immunoglobulin D (IgD) and immunoglobulin M (IgM) from genetically modified control mice (VI3; 1293HO 1460HO) and mice homozygous for a rearranged heavy chain variable region nucleic acid sequence in the heavy chain loci and two human Vκ and five human Jκ gene segments in the light chain loci (MAID 1912HO 6032 HO; DLC×UHC). Mature and immature B cells are noted on each of the contour plots.
Figure 40B:
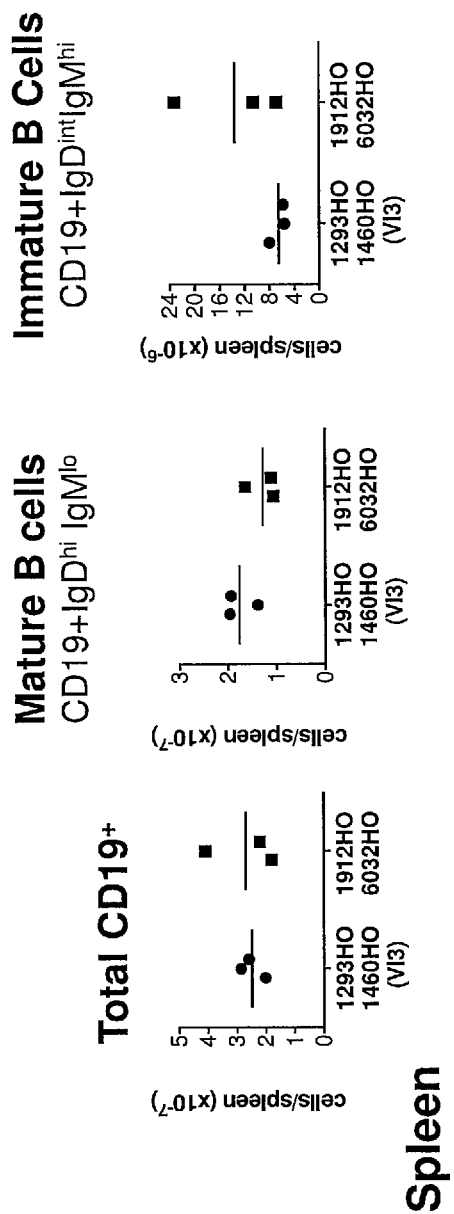
FIG. 40B shows the total number of CD19$^+$ B cells, mature B cells (CD19$^+$IgM$^{lo}$IgD$^{hi}$) and immature B cells (CD19$^+$IgM$^{hi}$IgD$^{int}$) in harvested spleens from genetically modified control mice (VI3; 1293HO 1460HO) and mice homozygous for a rearranged heavy chain variable region nucleic acid sequence in the heavy chain loci and two human Vκ and five human Jκ gene segments in the light chain loci (MAID 1912HO 6032 HO; DLC×UHC).
Figure 41A:
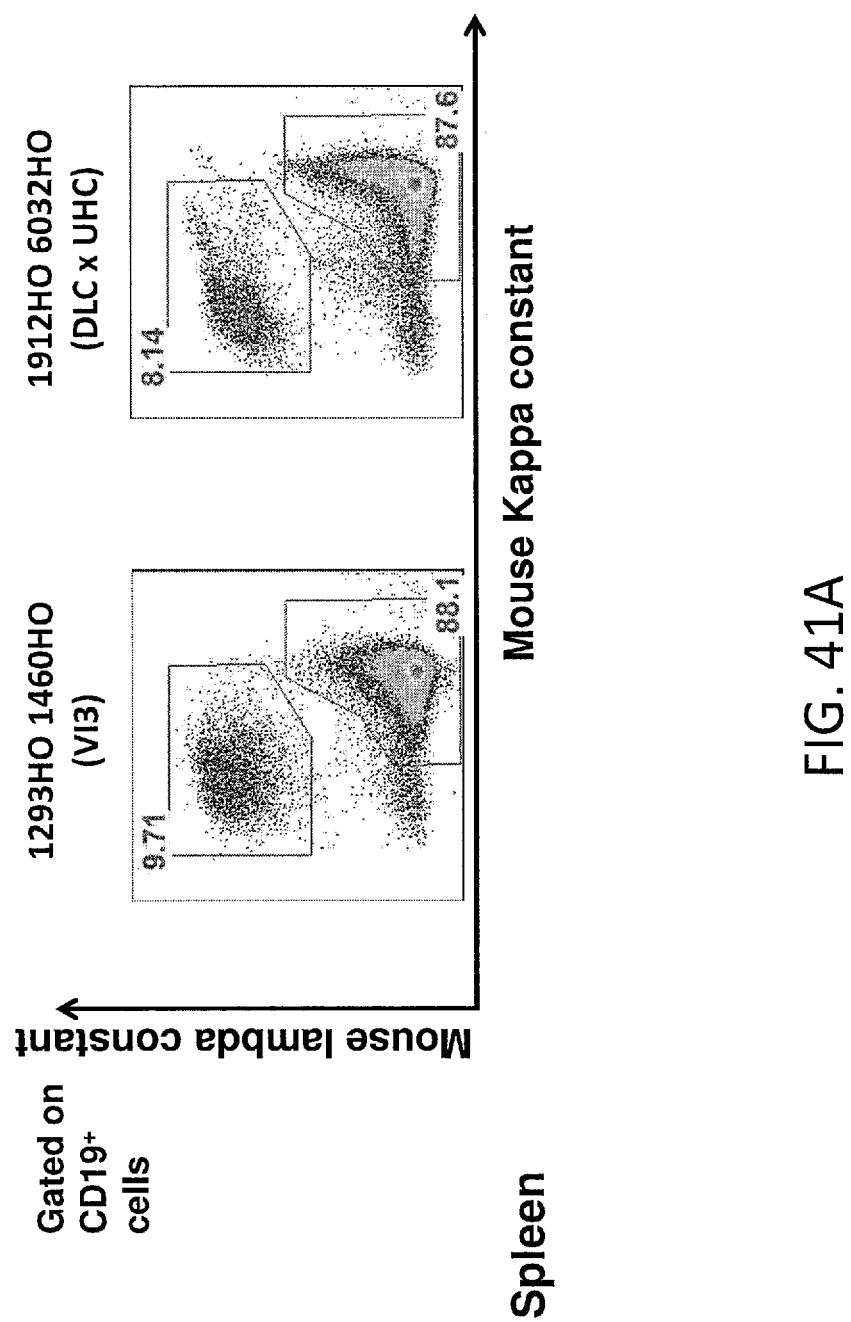
FIG. 41A shows representative contour plots of Igλ$^+$ and Igκ$^+$ splenocytes gated on CD19$^+$ from genetically modified control mice (VI3; 1293HO 1460HO) and mice homozygous for a rearranged heavy chain variable region nucleic acid sequence in the heavy chain loci and two human Vκ and five human Jκ gene segments in the light chain loci (MAID 1912HO 6032 HO; DLC×UHC).
Figure 41B:
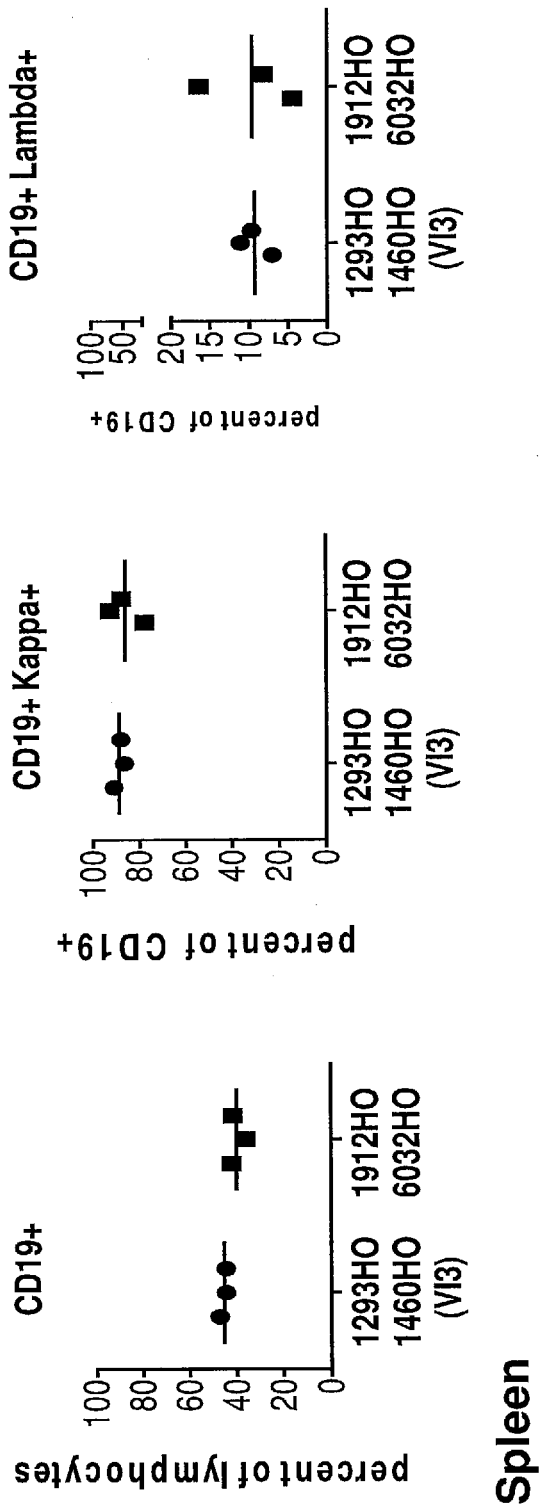
FIG. 41B shows the total number of B cells (CD19$^+$), Igκ$^+$ B cells (CD19$^+$Igλ$^+$) and Igλ$^+$ B cells (CD19$^+$Iλ$^+$) in harvested spleens from genetically modified control mice (VI3; 1293HO 1460HO) and mice homozygous for a rearranged heavy chain variable region nucleic acid sequence in the heavy chain loci and two human Vκ and five human Jκ gene segments in the light chain loci (MAID 1912HO 6032 HO; DLC×UHC).
Figure 42:
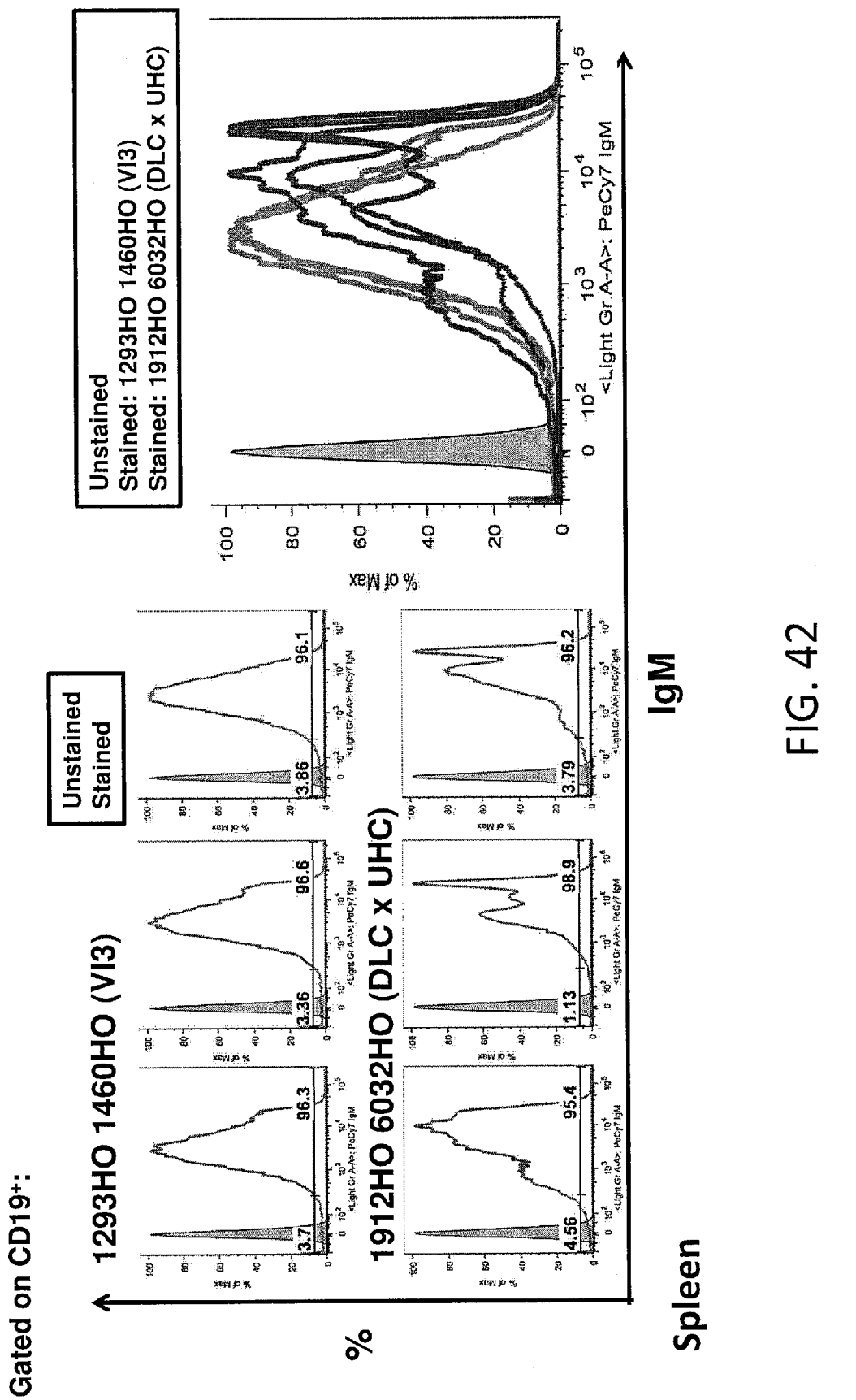
FIG. 42 shows flow cytometric analyses of IgM surface expression on B cells in harvested spleens from genetically modified control mice (VI3; 1293HO 1460HO) and mice homozygous for a rearranged heavy chain variable region nucleic acid sequence in the heavy chain loci and two human Vκ and five human Jκ gene segments in the light chain loci (MAID 1912HO 6032 HO; DLC×UHC). Cells were stained with fluorescent (PE-Cy7 conjugated) antibody against IgM.

In the splenic compartment, MAID 1912HO 6032HO mice demonstrated CD19+B cell numbers and mature B cell numbers that were substantially the same as the numbers observed in VELOCIMMUNE® (VI3) mice (FIGS. 40A-40B), which serve as a control for the specific effects observed in MAID 1912HO 6032HO mice relative to mice with other genetic modifications in their immunoglobulin loci; also, the humoral immune system of VELOCIMMUNE® mice functions like that of wild type mice (supra). The MAID 1912HO 6032HO mice demonstrated a 2-fold increase in immature B cell numbers in the spleen compared to VI3 mice (FIGS. 40A-40B). The MAID 1912HO 6032HO mice were also substantially similar to VI3 mice with respect to kappa and gamma light chain usage (FIGS. 41A-41B). MAID 1912HO 6032HO (DLC×UHC) mice also demonstrated increased surface IgM on splenic B cells (i.e., more IgM surface expression per cell) as compared to VI3 mice (FIG. 42).

Figure 43A:
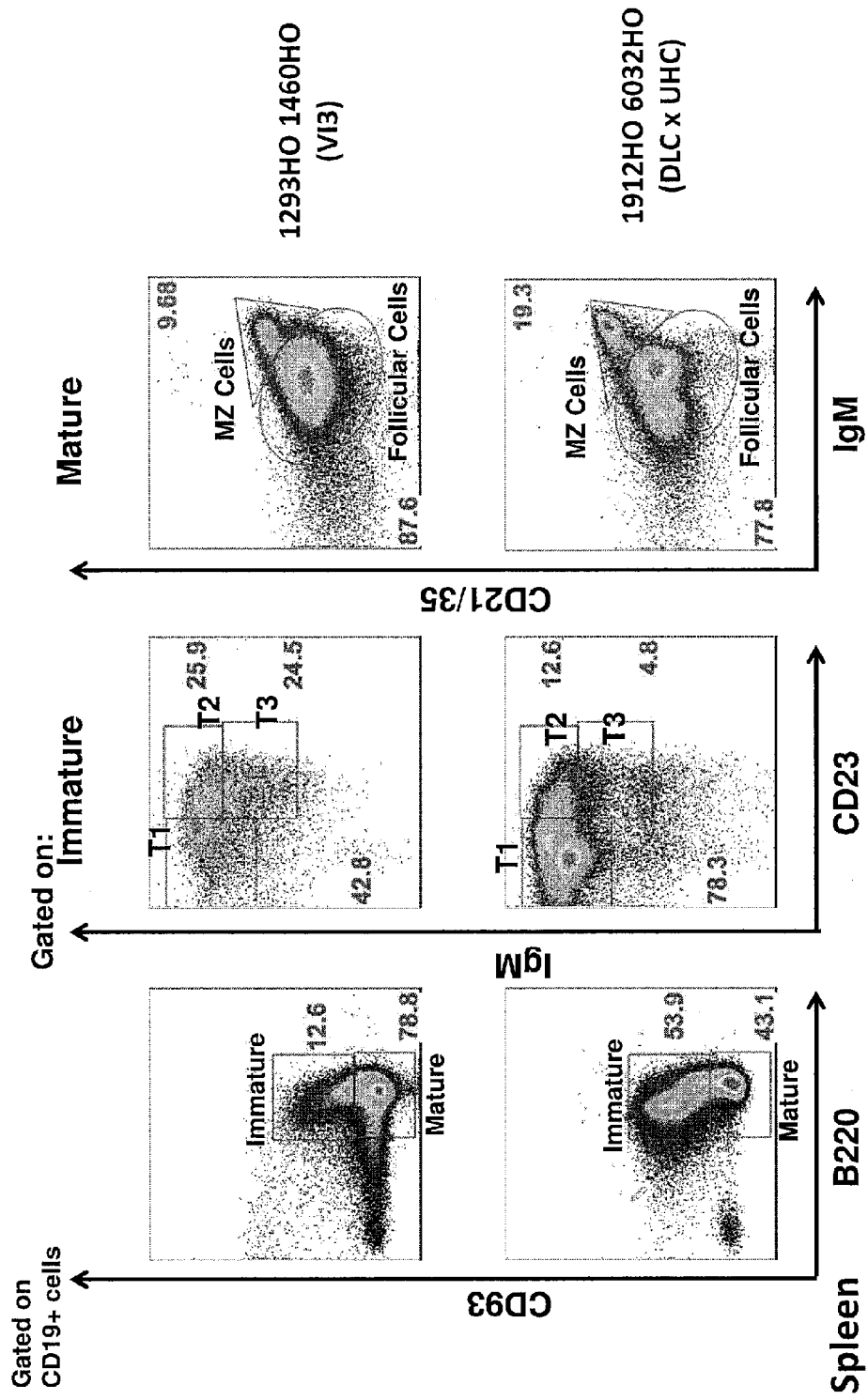
FIG. 43A shows the peripheral B cell development in genetically modified control mice (VI3; 1293HO 1460HO) and mice homozygous for a rearranged heavy chain variable region nucleic acid sequence in the heavy chain loci and two human Vκ and five human Jκ gene segments in the light chain loci (MAID 1912HO 6032 HO; DLC×UHC). The first (far left) contour plot shows CD93$^+$ and B220$^+$ splenocytes gated on CD19$^+$ indicating immature and mature B cells. The second (middle) contour plot shows IgM$^+$ and CD23$^+$ expression in immature B cells indicating T1 (IgD$^-$IgM$^+$CD21$^{lo}$CD23$^-$), T2 (IgD$^{hi}$IgM$^{hi}$CD21$^{mid}$CD23$^+$) and T3 B cell populations. The third (right) contour plot shows CD21+(CD35$^+$) and IgM$^+$ expression of mature B cells indicating first smaller populations which give rise to marginal zone B cells and second larger populations which gives rise to follicular (FO) B cells. Percentage of cells within each gated region is shown.
Figure 43B:
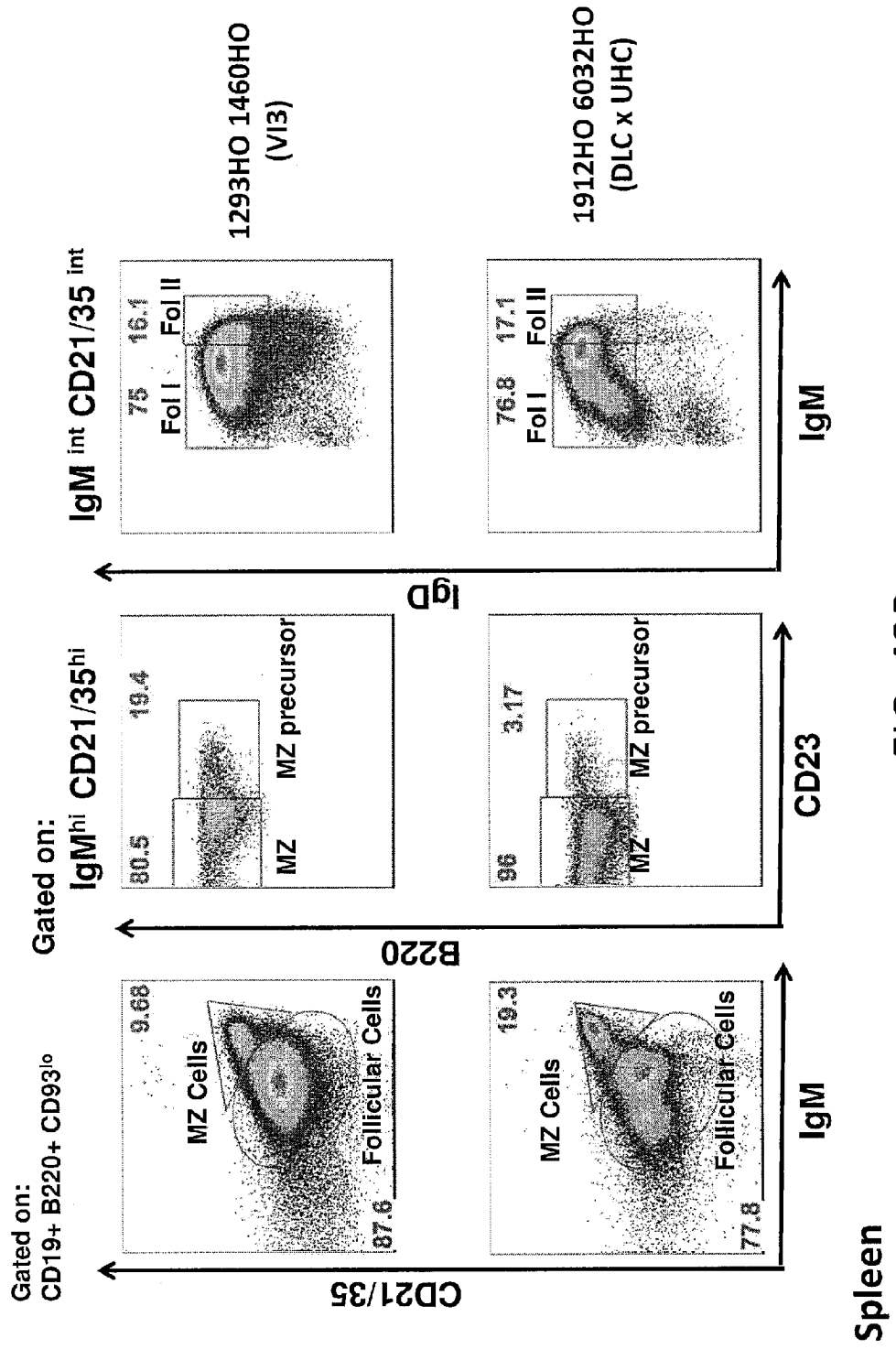
FIG. 43B shows the peripheral B cell development in genetically modified control mice (VI3; 1293HO 1460HO) and mice homozygous for a rearranged heavy chain variable region nucleic acid sequence in the heavy chain loci and two human Vκ and five human Jκ gene segments in the light chain loci (MAID 1912HO 6032 HO; DLC×UHC). The first (left) contour plot shows CD21$^+$ (CD35$^+$) and IgM$^+$ expression of mature B cells indicating a small population which give rise to marginal zone B cells and a second population which gives rise to follicular (FO) B cells. The second (middle) contour plot shows B220$^+$ and CD23$^+$ expression in mature B cells indicating marginal zone (MZ) and marginal zone precursor (IgM$^{hi}$IgD$^{hi}$CD21$^{hi}$CD23$^+$) B cell populations. The third (right) contour plot shows IgD$^+$ and IgM$^+$ expression in mature B cells indicating FO-I (IgD$^{hi}$IgM$^{int}$CD21$^{int}$CD23$^+$) and FO-II (IgD$^{hi}$IgM$^{int}$CD21$^{int}$CD23$^+$) B cell populations. Percentage of cells within each gated region is shown.

Also, the MAID 1912HO 6032HO (DLC×UHC) mice demonstrated altered peripheral B cell development as progression of B cells through various stages in the splenic compartment (e.g., immature, mature, T1, T2 T3, marginal zone precursor, marginal zone, follicular-1, follicular-11, etc.) occurred in a different manner than observed in VI3 mice (FIG. 43A). Specifically, the MAID 1912HO 6032HO (DLC×UHC) mice demonstrated more immature, T1 and marginal zone (MZ) B cells in the splenic compartment as compared to VI3 mice. The numbers of follicular-1 and follicular-11 cells in the MAID 1912HO 6032HO (DLC×UHC) mice were substantially the same as observed in VI3 mice (FIG. 43B).

Figure 44A:
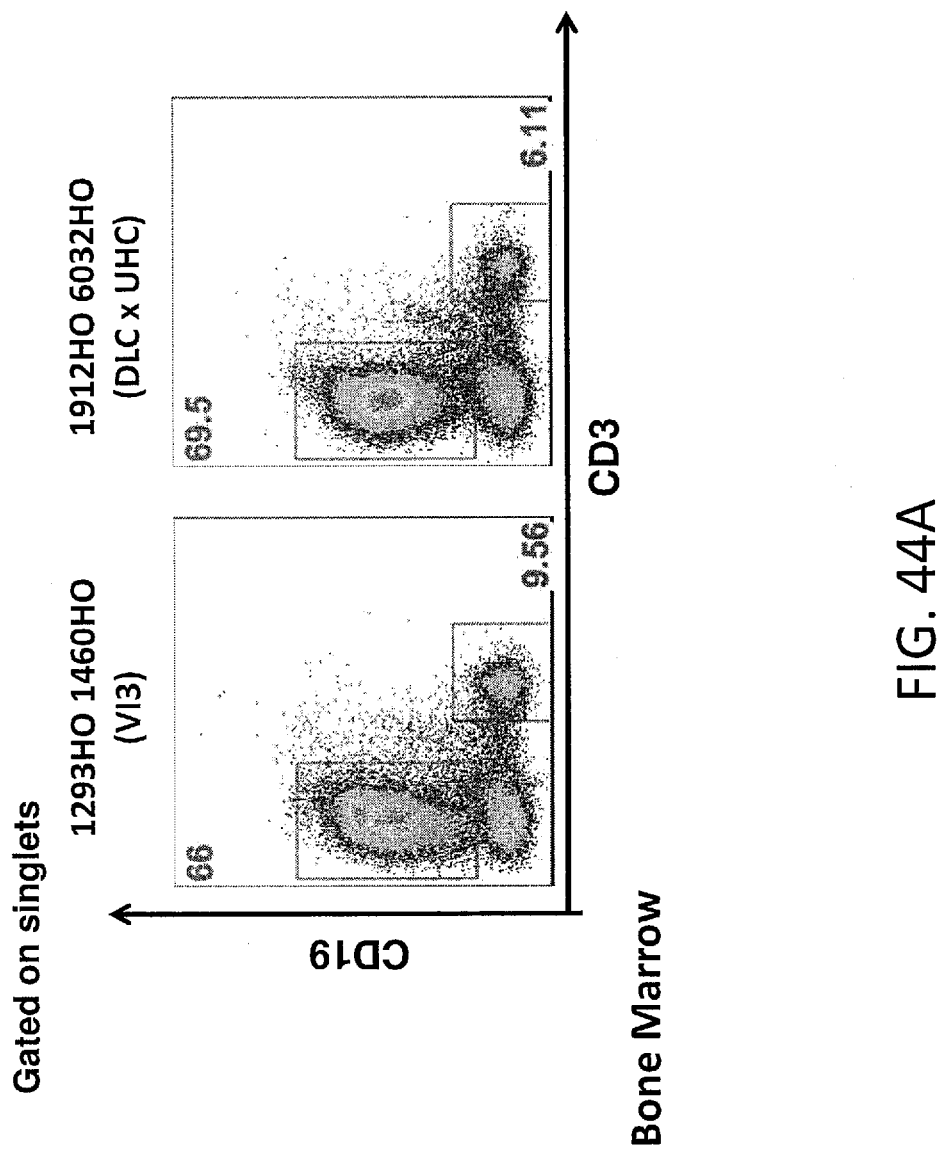
FIG. 44A shows representative contour plots of bone marrow stained for B and T cells (CD19$^+$ and CD3$^+$, respectively) from a genetically modified control mouse (VI3; 1293HO 1460HO) and a mouse homozygous for a rearranged heavy chain variable region nucleic acid sequence in the heavy chain loci and two human Vκ and five human Jκ gene segments in the light chain loci (MAID 1912HO 6032 HO; DLC×UHC).
Figure 44B:
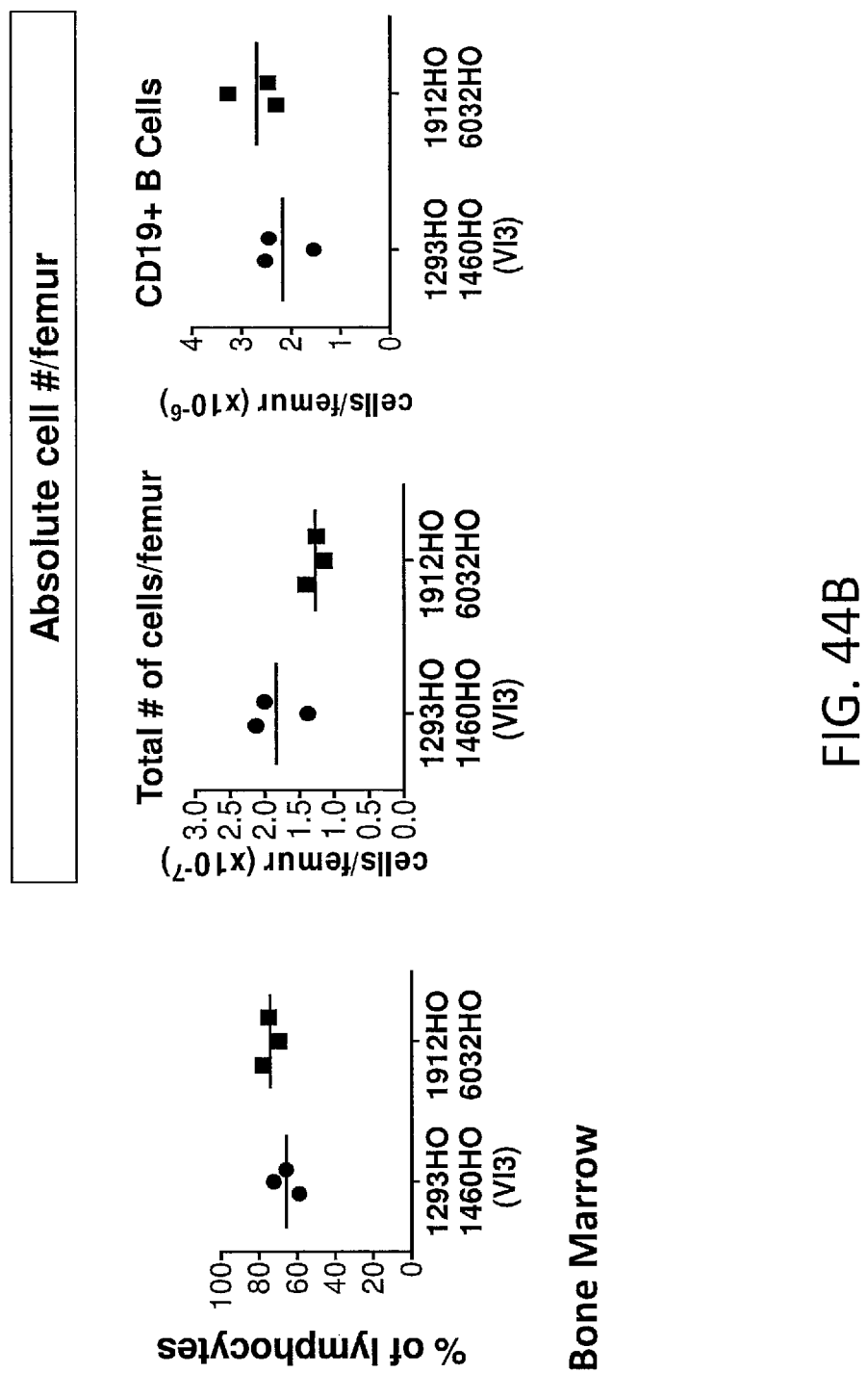
FIG. 44B shows the percentage of lymphocytes, total number of cells/femur and number of CD19+ B cells in bone marrow harvested from the femurs of genetically modified control mice (VI3; 1293HO 1460HO) and mice homozygous for a rearranged heavy chain variable region nucleic acid sequence in the heavy chain loci and two human Vκ and five human Jκ gene segments in the light chain loci (MAID 1912HO 6032 HO; DLC×UHC).
Figure 45A:
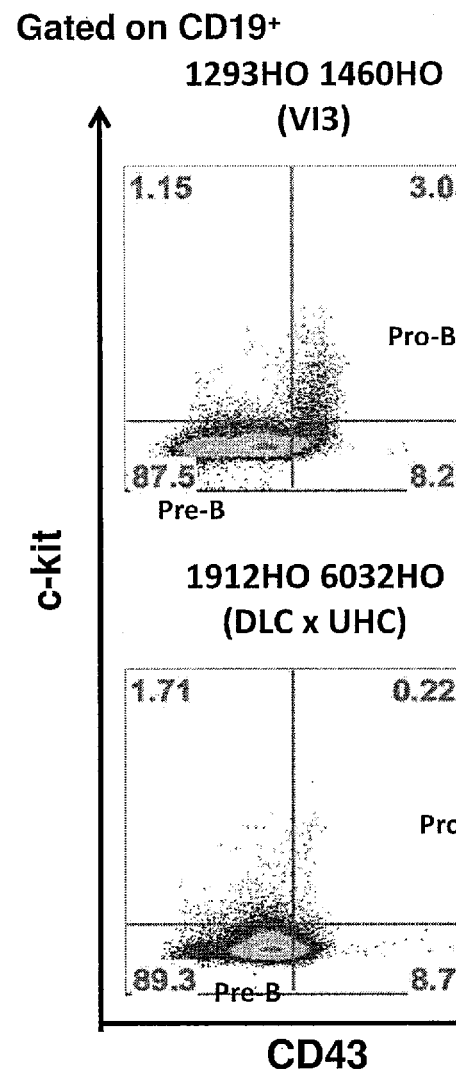
FIG. 45A shows representative contour plots of bone marrow gated on CD19$^+$ and stained for ckit$^+$ and CD43$^+$ from a genetically modified control mouse (VI3; 1293HO 1460HO) and a mouse homozygous for a rearranged heavy chain variable region nucleic acid sequence in the heavy chain loci and two human Vκ and five human Jκ gene segments in the light chain loci (MAID 1912HO 6032 HO; DLC×UHC). Pro and Pre B cells are noted on the contour plots.
Figure 45B:
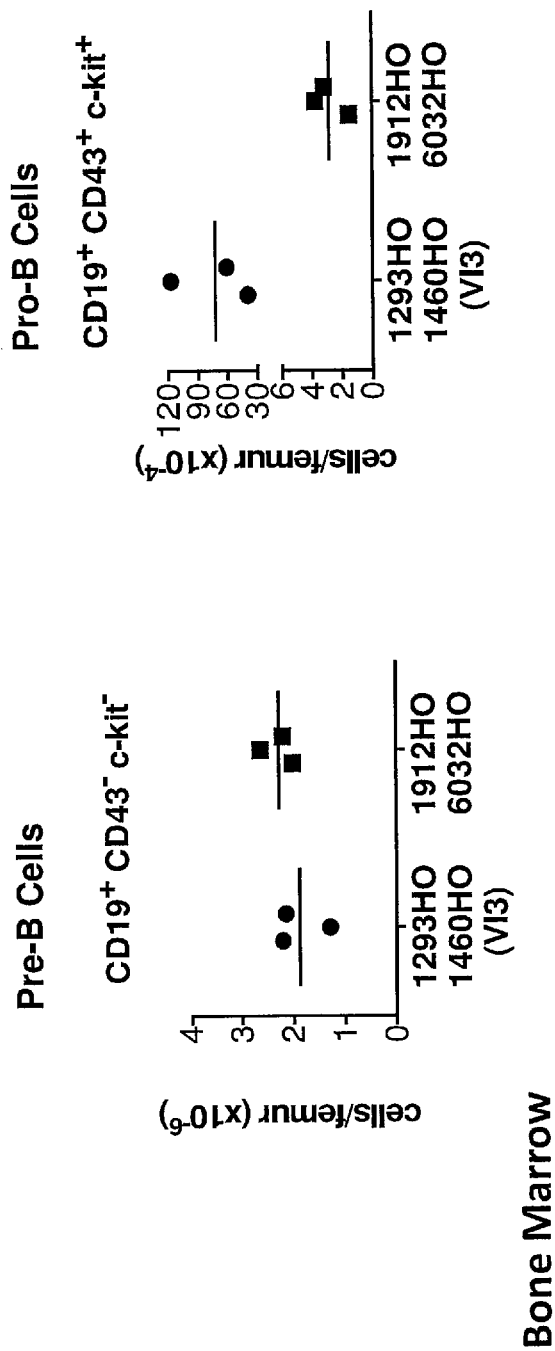
FIG. 45B shows the number of Pre (CD19$^+$CD43$^-$ckit$^-$) and Pro (CD19$^+$CD43$^+$ckit$^+$) B cells in bone marrow harvested from the femurs of genetically modified control mice (VI3; 1293HO 1460HO) and mice homozygous for a rearranged heavy chain variable region nucleic acid sequence in the heavy chain loci and two human Vκ and five human Jκ gene segments in the light chain loci (MAID 1912HO 6032HO; DLC×UHC).
Figure 46A:
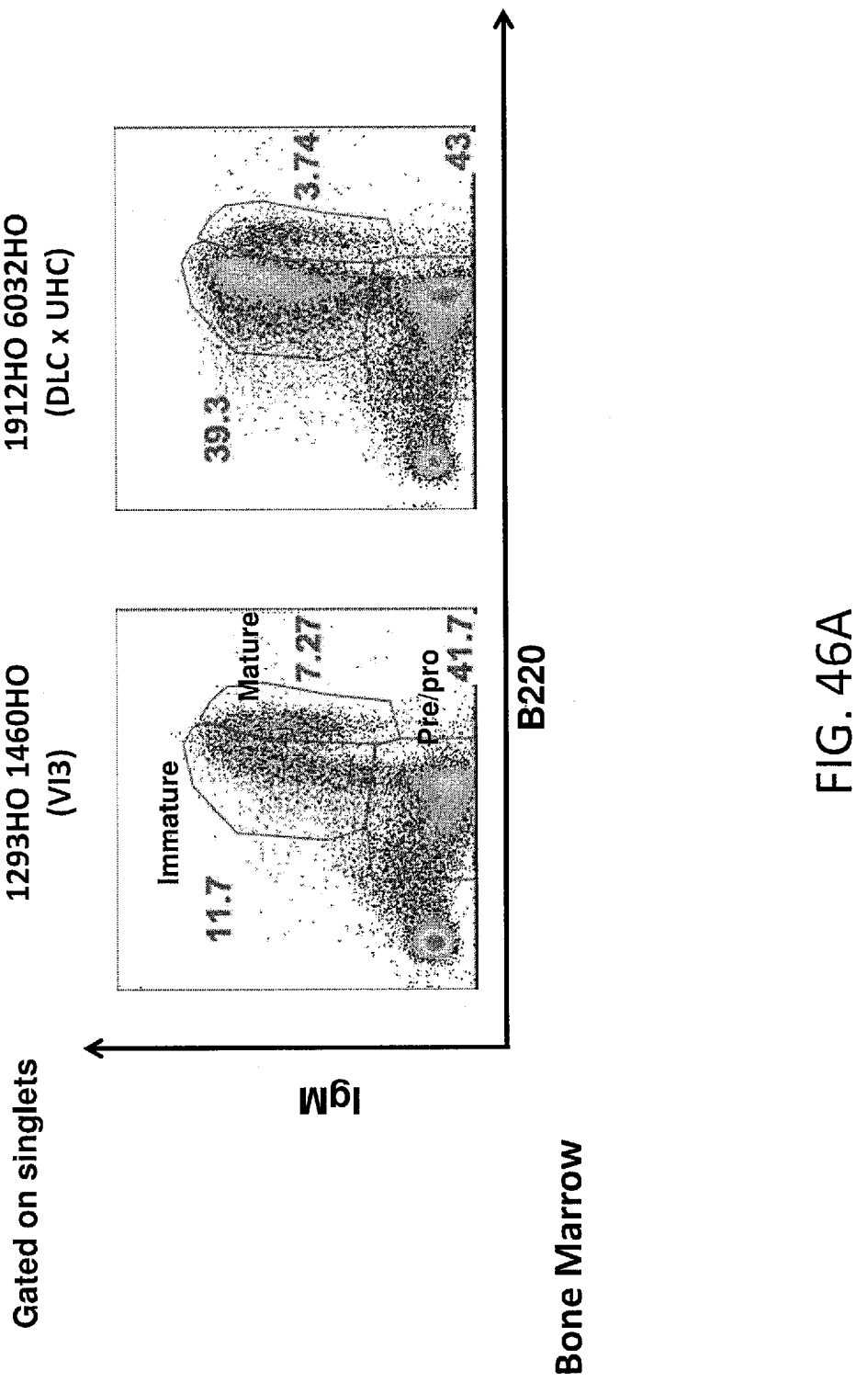
FIG. 46A shows representative contour plots of bone marrow gated on singlets stained for immunoglobulin M (IgM) and B220 from a genetically modified control mouse (VI3; 1293HO 1460HO) and a mouse homozygous for a rearranged heavy chain variable region nucleic acid sequence in the heavy chain loci and two human Vκ and five human Jκ gene segments in the light chain loci (MAID 1912HO 6032 HO; DLC×UHC). Immature, mature and pro/pre B cells are noted on each of the contour plots.
Figure 46B:
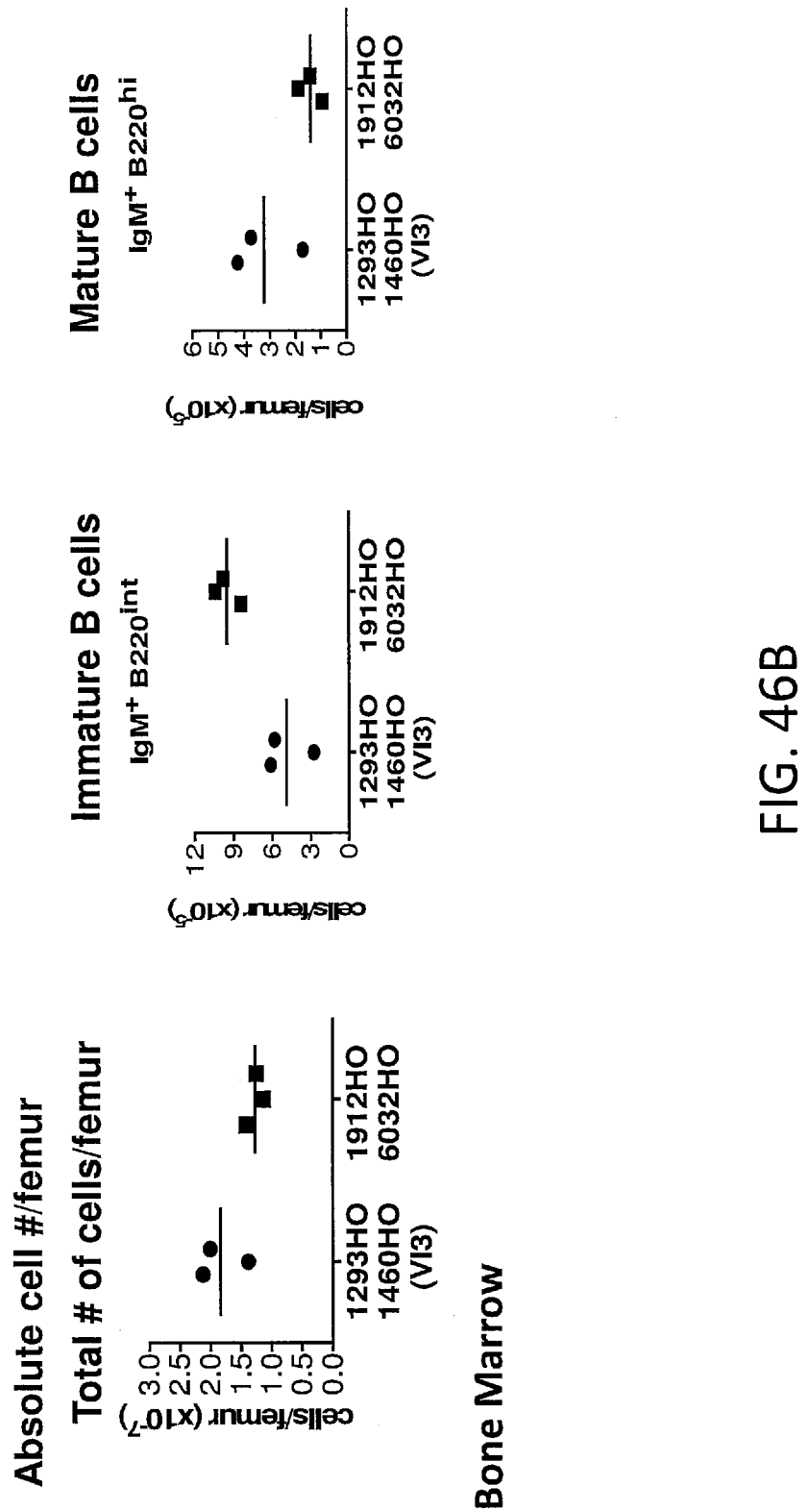
FIG. 46B shows the total number cell/femur, immature B (B220$^{int}$IgM$^+$) and mature B (B220$^{hi}$IgM$^+$) cells in bone marrow isolated from the femurs of genetically modified control mice (VI3; 1293HO 1460HO) and mice homozygous for a rearranged heavy chain variable region nucleic acid sequence in the heavy chain loci and two human Vκ and five human Jκ gene segments in the light chain loci (MAID 1912HO 6032 HO; DLC×UHC).
Figure 47:
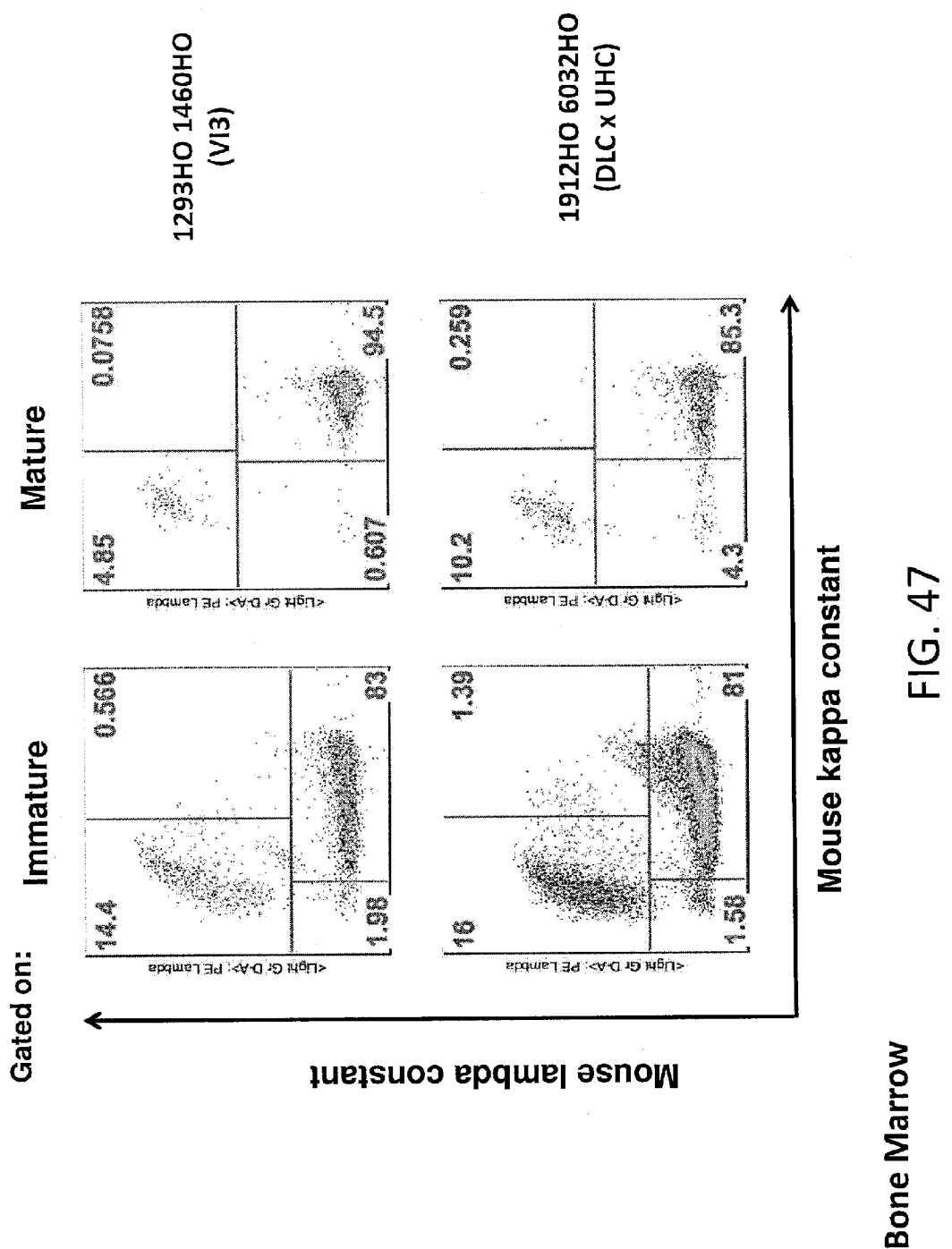
FIG. 47 shows representative contour plots of bone marrow gated on immature (B220$^{int}$IgM$^+$) and mature (B220$^{hi}$IgM$^+$) B cells stained for Igλ and Igκ expression isolated from the femurs of a genetically modified control mouse (VI3; 1293HO 1460HO) and a mouse homozygous for a rearranged heavy chain variable region nucleic acid sequence in the heavy chain loci and two human Vκ and five human Jκ gene segments in the light chain loci (MAID 1912HO 6032 HO; DLC×UHC).

In the bone marrow compartment, MAID 1912HO 6032HO (DLC×UHC) mice demonstrated similar numbers of CD19+ B cells compare to VI3 mice controls (FIGS. 44A-44B). However, the MAID 1912HO 6032HO (DLC×UHC) mice demonstrated about 25-fold fewer pro-B cells in the bone marrow as compared to VI3 mice (FIGS. 45A-45B). The MAID 1912HO 6032HO (DLC×UHC) mice also demonstrated about 2-fold less immature B cells and 2-fold less mature B cells in the bone marrow compared to VI3 mice (FIGS. 46A-46B). Also, the MAID 1912HO 6032HO (DLC×UHC) mice demonstrated a preference (2-fold increase) for lambda expression compared to VI3 mice (FIG. 47).

Immunization Studies

Five WT (75% C57BL6/25% 129 background) and seven F2 MAID1912HO 6031 HET (homozygous DLC×heterozygous UHC) mice were immunized in the footpad with 0.025 ml of a mixture containing 2.35 µg of an antigen X, 10 µg CpG oligonucleotide (ODN 1826, InvivoGen, cat# tlrl-1826), and 25 µg Aluminum Phosphate Gel Adjuvant (Brenntag cat#7784-30-7). Mice were boosted six times with the same dosage. On days 0, 15 and 23 post primary immunization, blood was collected from anaesthetized mice using a retroorbital bleed into BD serum separator tubes (BD, cat #365956), and serum was collected as per manufacturer's directions. A second round of immunization was performed as above five weeks after the first round of immunization.

Figure 48:
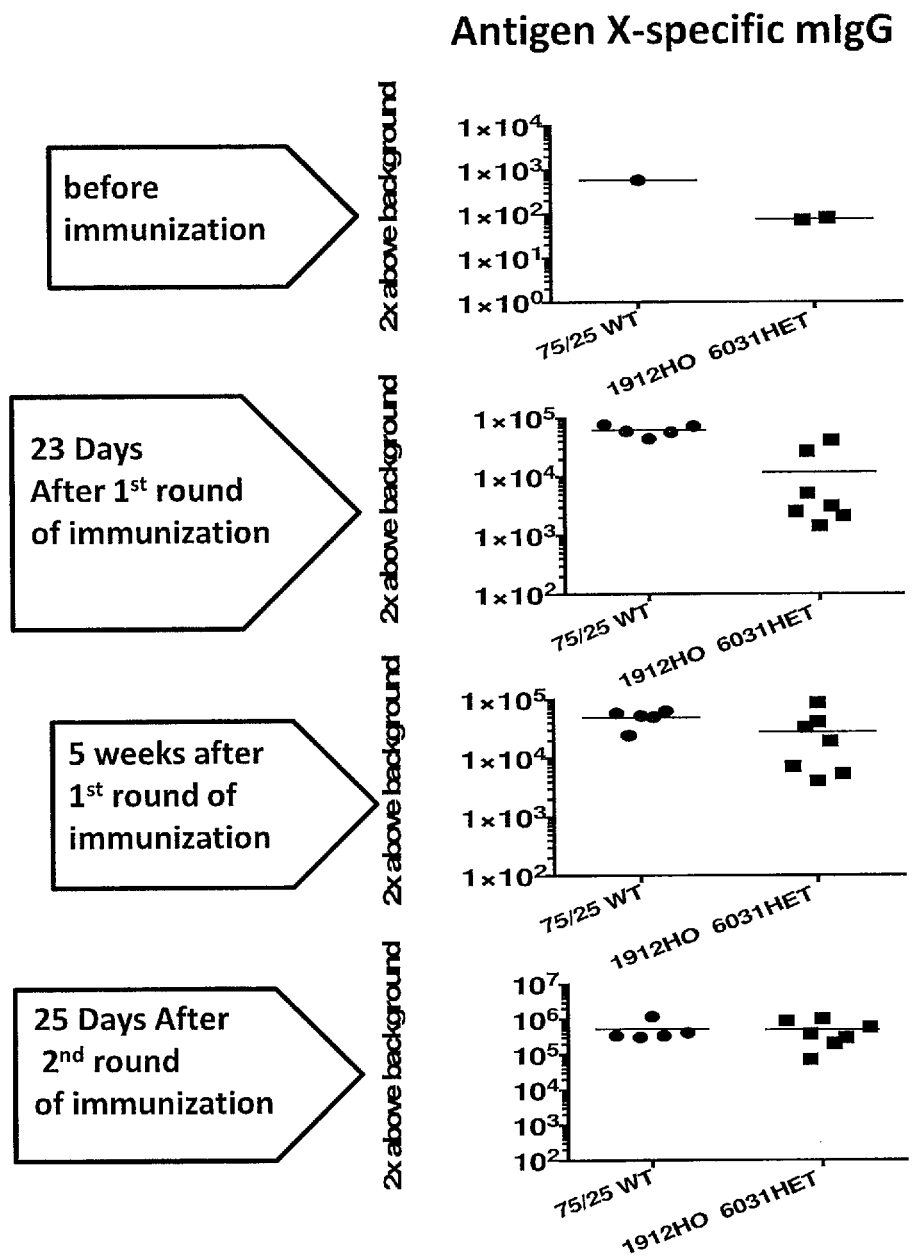
FIG. 48 shows the levels of antigen-specific mIgGs in the mouse sera (Wild type or 1912HO 6031 HET (homozygous DLC×heterozygous UHC)) before footpad immunization, 23 days following a 1$^{st}$ round of footpad immunization, 5 weeks following the 1$^{st}$ round of footpad immunization, and after a 2$^{nd}$ round of footpad immunization.

To measure the levels of antigen-specific IgG antibodies, ELISAs were performed as in Example 3. As shown in FIG. 48, the genetically modified mice, which are heterozygous with respect to the targeted allele containing the rearranged $V_H3$-23/D/$J_H4$ nucleotide sequence and homozygous with respect to the targeted allele containing DLC-5J, were able to produce antigen-specific IgG antibodies at levels comparable to those produced by wild type mice at both 23 days and 5 weeks after the primary immunization. The MAID1912HO 6031HET (homozygous DLC×heterozygous UHC) mice were also able to produce antigen-specific IgG antibodies at levels comparable to those produced by wild type mice after the $2^{nd}$ round of immunization.

Thus, these mice produce antibodies comprising a reverse chimeric light chain (human light chain variable domain and mouse Cκ) derived from a rearrangement of one of the two human $V_L$ gene segments (Vκ1-39 or Vκ3-20 gene segments) and human Jκ segments and a reverse chimeric heavy chain (human heavy chain variable domain and mouse $C_H$) derived from a single rearranged human heavy chain variable gene segment. Reverse chimeric antibodies (i.e., antibodies comprised of these reverse chimeric chains) are obtained upon immunization with an antigen of interest.

Example 6

Generation and Analysis of Mice Comprising a Single Rearranged Human Immunoglobulin Heavy Chain Nucleotide Sequence and Two V Kappa Gene Segments Containing Three Histidine Substitutions Similarly, mice bearing an engineered human light chain locus comprising a histidine-modified dual light chain (e.g., mice comprising two human $V_L$ gene segments with histidine modifications described herein above) are bred with mice that contain a replacement of the endogenous mouse heavy chain variable locus with universal human heavy chain locus (locus comprising a single rearranged human heavy chain variable domain as described herein above). Thus, these mice produce antibodies comprising a reverse chimeric light chain (human light chain variable domain and mouse CO derived from a rearrangement of one of the two histidine-modified human $V_L$ gene segments (Vκ1-39 or Vκ3-20 gene segments) and human Jκ segments and a reverse chimeric heavy chain (human heavy chain variable domain and mouse CH) derived from a single rearranged human heavy chain variable domain. Reverse chimeric antibodies are obtained upon immunization with an antigen of interest. pH-dependent human antibodies generated in such mice are identified using antibody isolation and screening methods known in the art or described above.

Variable light and heavy chain region nucleotide sequences of B cells expressing the antibodies are identified, and fully human light and heavy chains are made by fusion of the variable light and heavy chain region nucleotide sequences to human $C_L$ and $C_H$ nucleotide sequences, respectively. Light chains of interest, e.g., light chains that bind to the antigen of interest (e.g., light chains from antibodies that also demonstrate pH-dependent antigen properties using a variety of assays known in the art, e.g., BIACORE™ assay) are co-expressed in a suitable expression system with heavy chains derived from other antibodies, e.g., heavy chains derived from antibodies that comprise light chains derived from the same $V_L$ gene segment as that in the light chain of interest (e.g., Vκ1-39 or Vκ3-20), and the reconstituted antibody is tested for its ability to retain antigen-binding and pH-dependent antigen-binding properties.

Example 7

Construction of Mice Comprising an Immunoglobulin Light Chain Locus Containing a Rearranged Heavy Chain VDJ Sequence Mice comprising a rearranged heavy chain variable region nucleic acid sequence in the kappa light chain locus (MAID6079; "UHC on kappa mouse") were generated by similar methods to those described above for targeting the heavy chain locus. Briefly, in the UHC on kappa mouse, all endogenous functional light chain kappa variable Vκ and Jκ gene segments were deleted and replaced with a single rearranged heavy chain variable region nucleic acid sequence that encodes $hV_H3$-23/D/$J_H4$, which is operably linked to an endogenous light chain constant region nucleic acid sequence. The final targeting construct for the creation of a genomic locus containing a rearranged human heavy chain variable domain sequence contains, from 5' to 3', (1) a 5' homology arm containing about 22500 by of a mouse genomic sequence upstream of the endogenous Ig light chain locus; (2) a 5' FRT site; (3) a neomycin cassette; (4) a 3' FRT site, (5) 2239 by of $hV_H3$-23 promoter (SEQ ID NO: 139); (6) a rearranged human immunoglobulin heavy chain nucleotide sequence (hV$_H$3-23/D/J$_H$4; SEQ ID NO: 136); (7) an hJ$_H$4 intron (SEQ ID NO: 140); and (8) a 3' homology arm containing about 75000 by of a mouse genomic sequence downstream of the mouse JL gene segments. Heterozygous mice bearing the modification were bred to each other to generate homozygotes (MAID 6079HO) that are capable of making immunoglobulin "light" chains only from the genetically modified locus. The MAID 6079HO (homozygous UHC on kappa) mice comprise an insertion of the Universal Heavy Chain described herein (e.g., hV$_H$3-23/hD/hJ$_H$4) into the mouse kappa (K) light chain locus in which all mouse Vκ and Jκ genes have been deleted.

Figure 49:
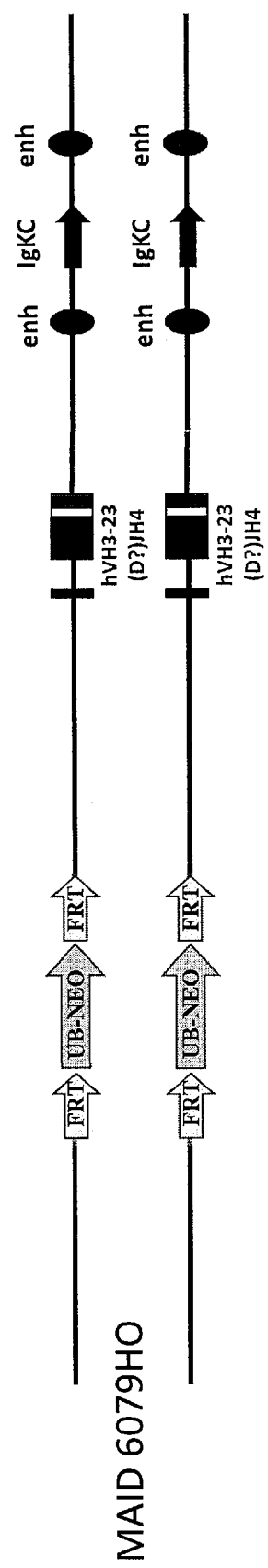
FIG. 49 illustrates the genomic structure of genetically modified F1 mice containing a rearranged heavy chain variable region nucleic acid sequences in the kappa light chain loci (i.e., a rearranged heavy chain VDJ sequence operably linked to a kappa light chain constant nucleic acid sequence).

All mice were housed and bred in specific pathogen-free conditions at Regeneron Pharmaceuticals. Four MAID 6079HO F1 mice (FIG. 49; 7-12.5 weeks old, male and female) and four MAID 6079 F1 wild type littermate control mice (7-12.5 weeks old, male and female) were sacrificed, and spleens and bone marrow were harvested from the animals. Bone marrow was collected from femurs by flushing with complete RPMI medium (RPMI medium supplemented with fetal calf serum, sodium pyruvate, Hepes, 2-mercaptoethanol, non-essential amino acids, and gentamycin). Red blood cells from spleen and bone marrow preparations were lysed with ACK lysis buffer and washed with complete RPMI medium.

Flow Cytometry

In order to examine the ability of the genetically modified homozygous "UHC on kappa mouse" (MAID 6079HO) mice described herein to produce antibodies derived from the genetically modified allele (e.g., from the allele that contains a single copy of the rearranged V$_H$3-23/D/J$_H$4 in a kappa light chain locus), fluorescence-activated cell sorting (FACS) analysis was performed as in Example 3.

Figure 50A:
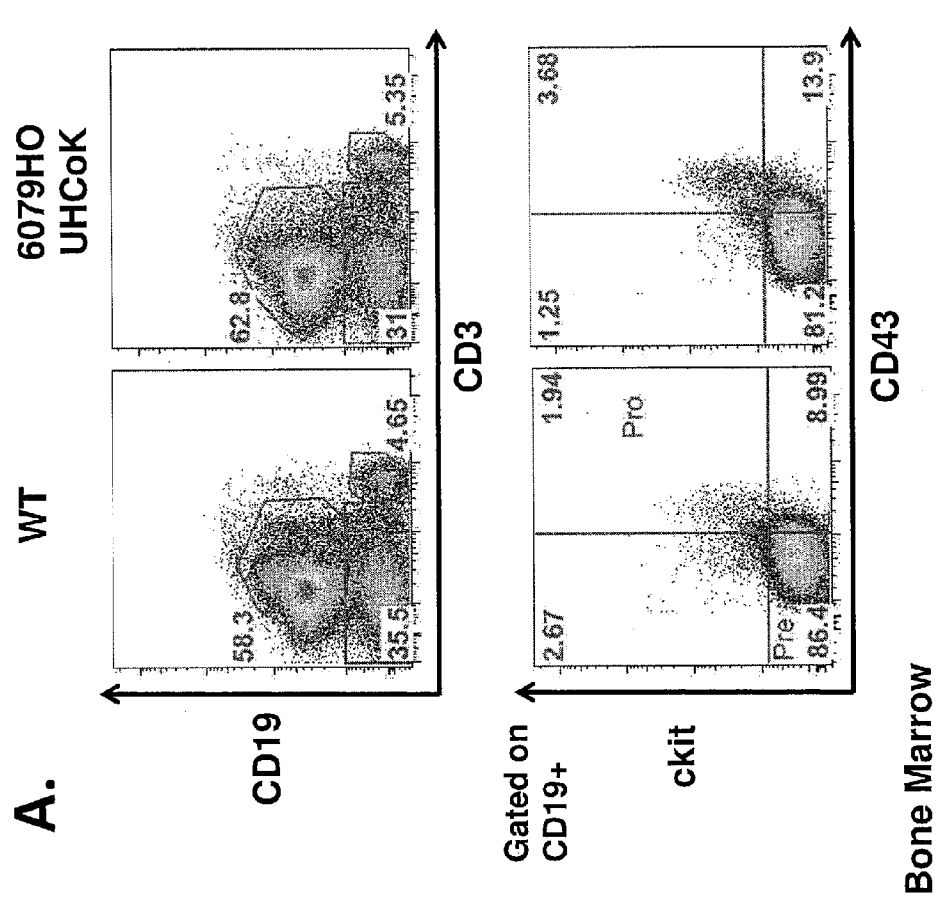
FIG. 50A in the top panel, shows representative contour plots of bone marrow stained for B and T cells (CD19$^+$ and CD3$^+$, respectively) from a wild type mouse (WT) and a mouse homozygous for a rearranged heavy chain variable region nucleic acid sequence (hV$_H$3-23/D/J$_H$4) in the kappa light chain locus. The bottom panel shows representative contour plots of bone marrow gated on CD19$^+$ and stained for ckit$^+$ and CD43$^+$ from a wild type mouse (WT) and a mouse homozygous for a rearranged heavy chain variable region nucleic acid sequence (hV$_H$3-23/D/J$_H$4) in the kappa light chain locus. Pro and Pre B cells are noted on the contour plots of the bottom panel.
Figure 50B:
FIG. 50B shows the number of Pro (CD19$^+$CD43$^+$ckit$^+$) and Pre (CD19$^+$CD43$^-$ckit$^-$) B cells in bone marrow harvested from the femurs of wild type mice (WT) and mice homozygous for a rearranged heavy chain variable region nucleic acid sequence (hV$_H$3-23/D/J$_H$4) in the kappa light chain locus.
Figure 51A:
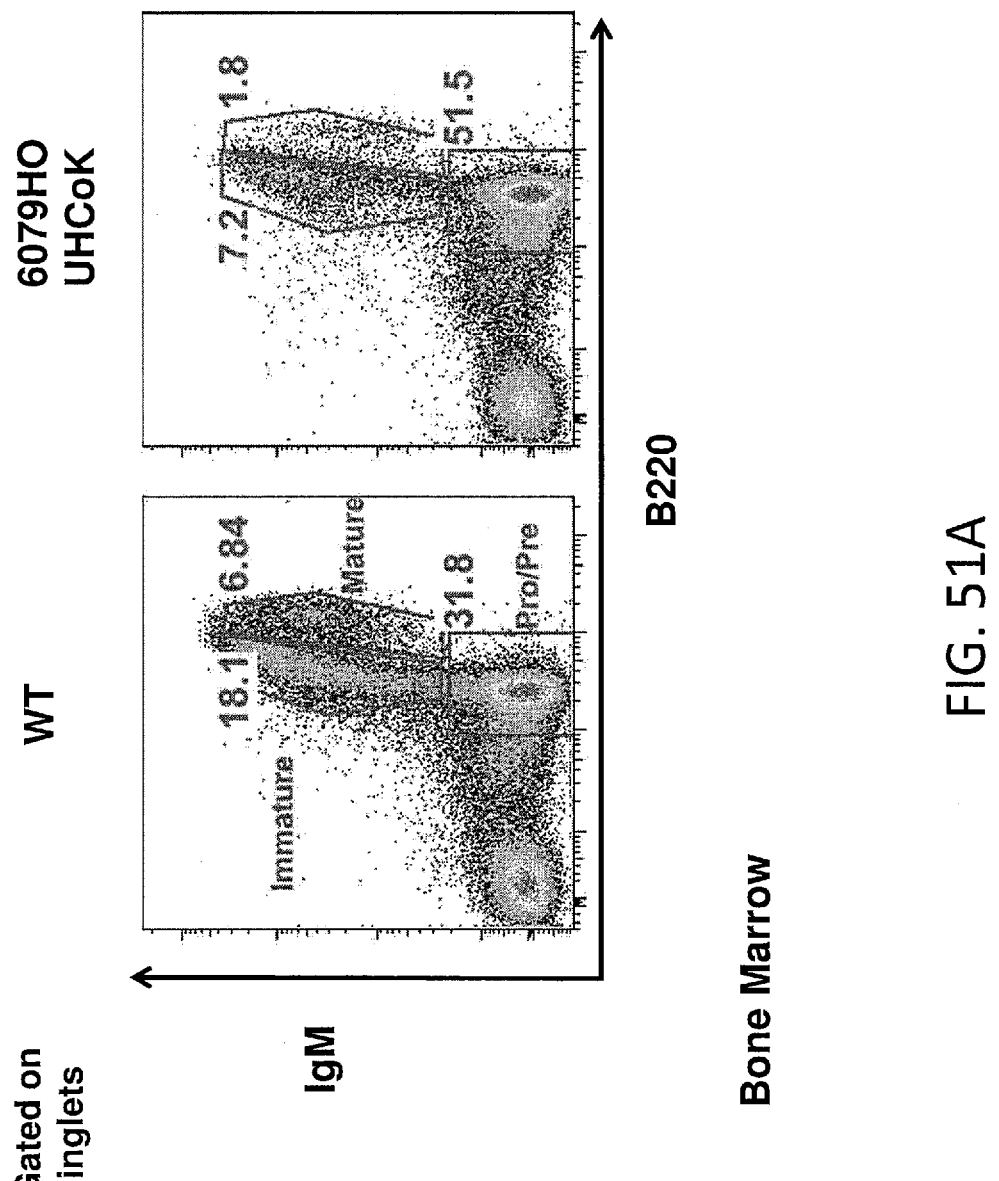
FIG. 51A shows representative contour plots of bone marrow gated on singlets stained for immunoglobulin M (IgM) and B220 from a wild type mouse (WT) and a mouse homozygous for a rearranged heavy chain variable region nucleic acid sequence (hV$_H$3-23/D/J$_H$4) in the kappa light chain locus. Immature, mature and pro/pre B cells are noted on each of the contour plots.
Figure 51B:
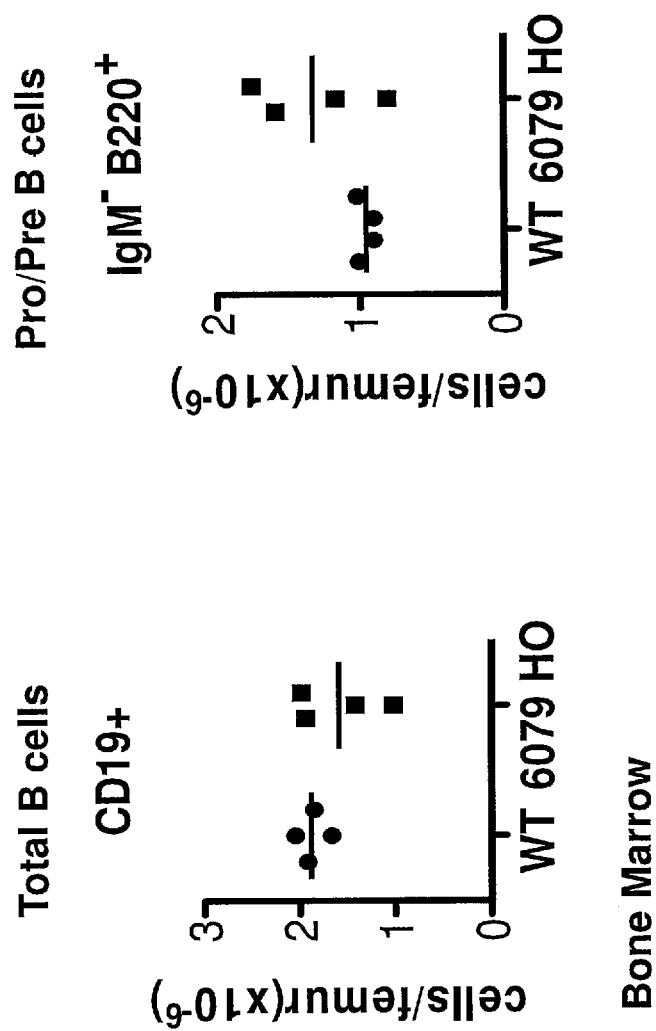
FIG. 51B shows the total number of B (CD19$^+$) and pro/pre B (IgM$^-$B220$^+$) cells in bone marrow isolated from the femurs of wild type mice (WT) and mice homozygous for a rearranged heavy chain variable region nucleic acid sequence (hV$_H$3-23/D/J$_H$4) in the kappa light chain locus.
Figure 51C:
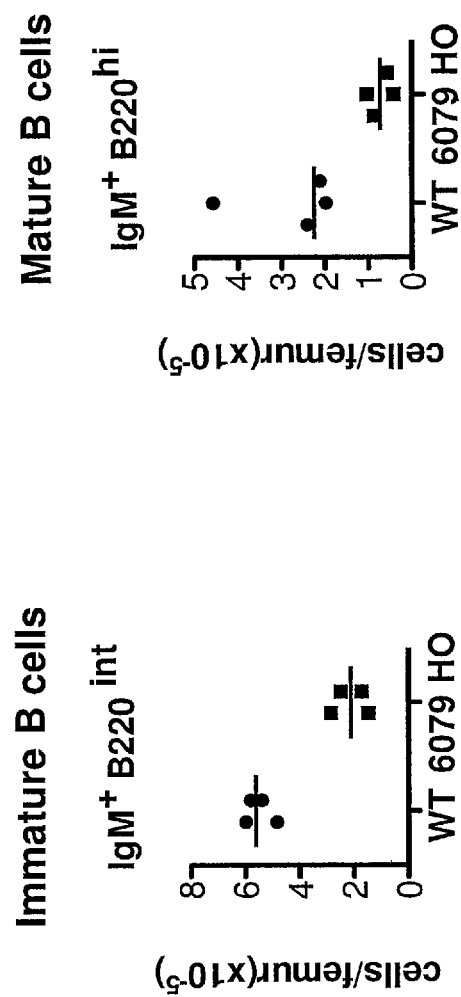
FIG. 51C shows the number of immature B (B220$^{int}$IgM$^+$) and mature B (B220$^{hi}$IgM$^+$) cells in bone marrow isolated from the femurs of wild type mice (WT) and mice homozygous for a rearranged heavy chain variable region nucleic acid sequence (hV$_H$3-23/D/J$_H$4) in the kappa light chain locus.
Figure 52:
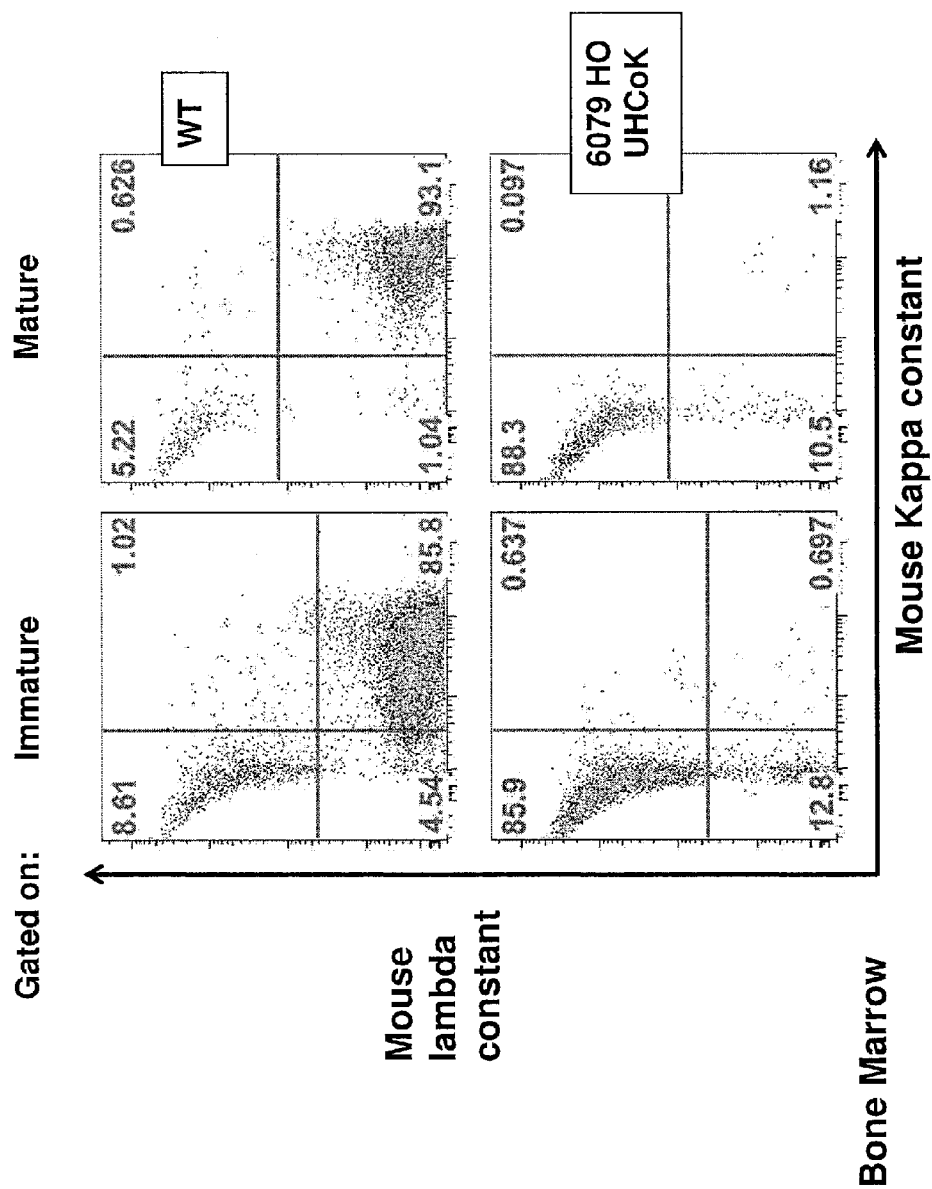
FIG. 52 shows representative contour plots of bone marrow gated on immature (B220$^{int}$IgM$^+$) and mature (B220$^{hi}$IgM$^+$) B cells stained for Igλ and Igκ expression isolated from the femurs of wild type mice (WT) and mice homozygous for a rearranged heavy chain variable region nucleic acid sequence (hV$_H$3-23/D/J$_H$4) in the kappa light chain locus.

The MAID 6079HO mice demonstrated numbers of pro- and pre-B cells in the bone marrow compartment that are substantially the same as observed in wild type littermates (FIGS. 50A-50B). In contrast, they demonstrated lower numbers of immature and mature B cells in the bone marrow compartment compared to wild type littermates (FIGS. 51A-51C). In fact, the mice had 2-fold less immature B cells, and almost 4-fold less mature B cells. The MAID 6079HO mice almost exclusively used lambda light chain sequences in immature and mature B cells in the bone marrow (FIG. 52).

Figure 53A:
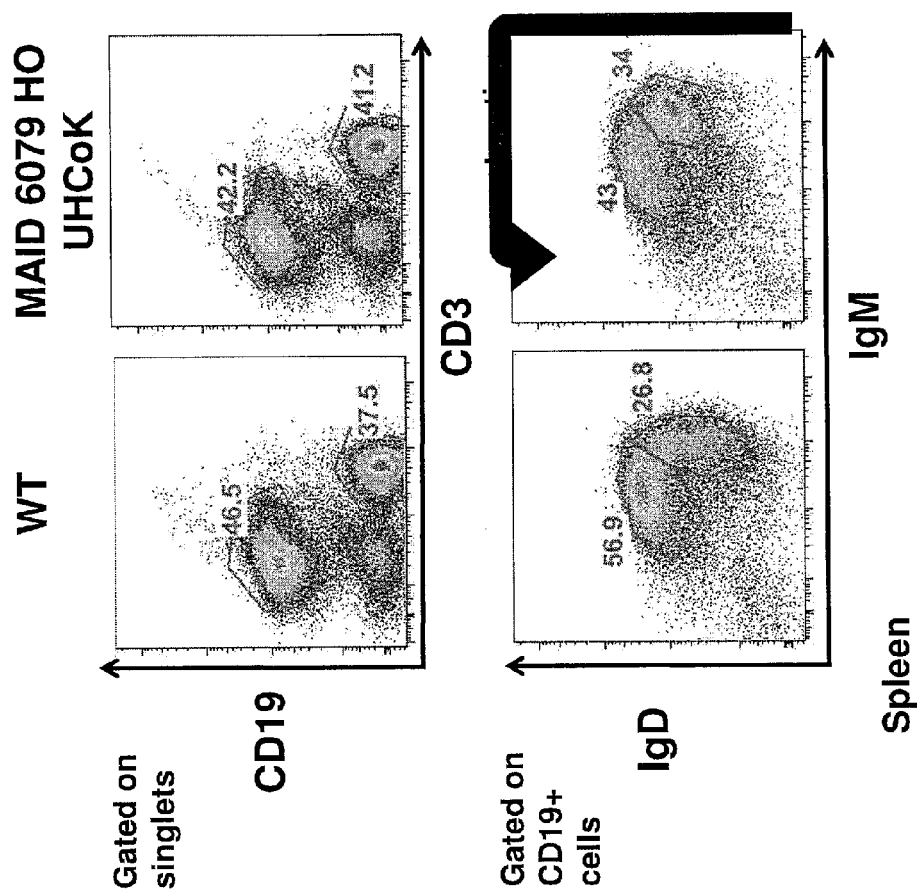
FIG. 53A, in the top panel, shows representative contour plots of splenocytes gated on singlets and stained for B and T cells (CD19$^+$ and CD3$^+$, respectively) from a wild type mouse (WT) and a mouse homozygous for a rearranged heavy chain variable region nucleic acid sequence (hV$_H$3-23/D/J$_H$4) in the kappa light chain locus. The bottom panel shows representative contour plots of splenocytes gated on CD19$^+$ and stained for immunoglobulin D (IgD) and immunoglobulin M (IgM) from a wild type mouse (WT) and a mouse homozygous for a rearranged heavy chain variable region nucleic acid sequence (hV$_H$3-23/D/J$_H$4) in the kappa light chain locus. Mature (56.9 for WT, 43 for hV$_H$3-23/D/J$_H$4 on kappa) and transitional (26.8 for WT, 34 for hV$_H$3-23/D/J$_H$4 on kappa) B cells are noted on each of the contour plots.
Figure 54A:
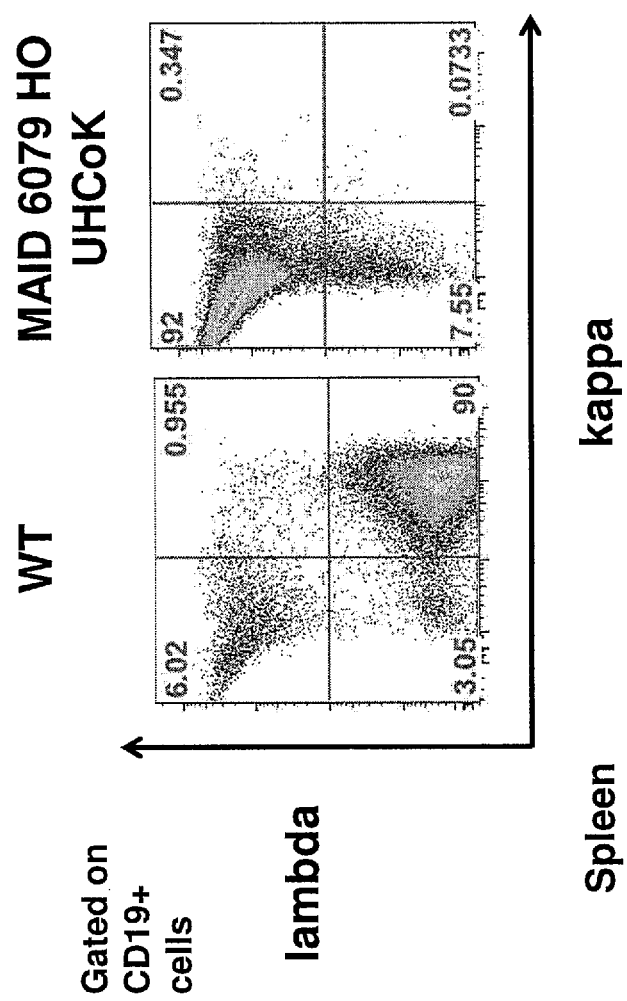
FIG. 54A shows representative contour plots of Igλ$^+$ and Igκ$^+$ splenocytes gated on CD19$^+$ from a wild type mouse (WT) and a rearranged heavy chain variable region nucleic acid sequence (hV$_H$3-23/D/J$_H$4) in the kappa light chain locus.
Figure 54B:
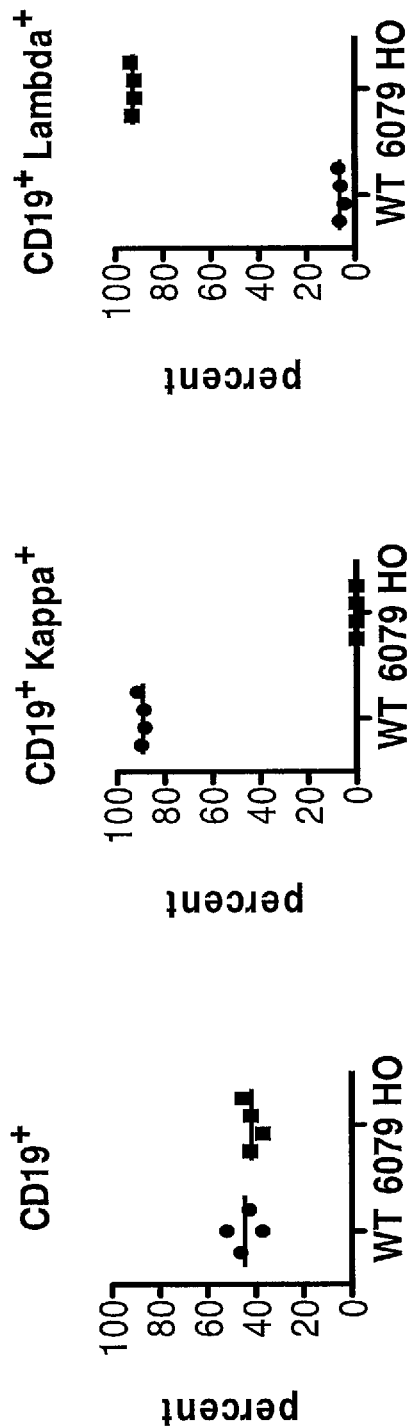
FIG. 54B shows the total number of B cells (CD19$^+$), Igκ$^+$ B cells (CD19$^+$Igκ$^+$) and Igλ$^+$ B cells (CD19$^+$Igλ$^+$) in harvested spleens from wild type (WT) and mice homozygous for a rearranged heavy chain variable region nucleic acid sequence (hV$_H$3-23/D/J$_H$4) in the kappa light chain locus.
Figure 55:
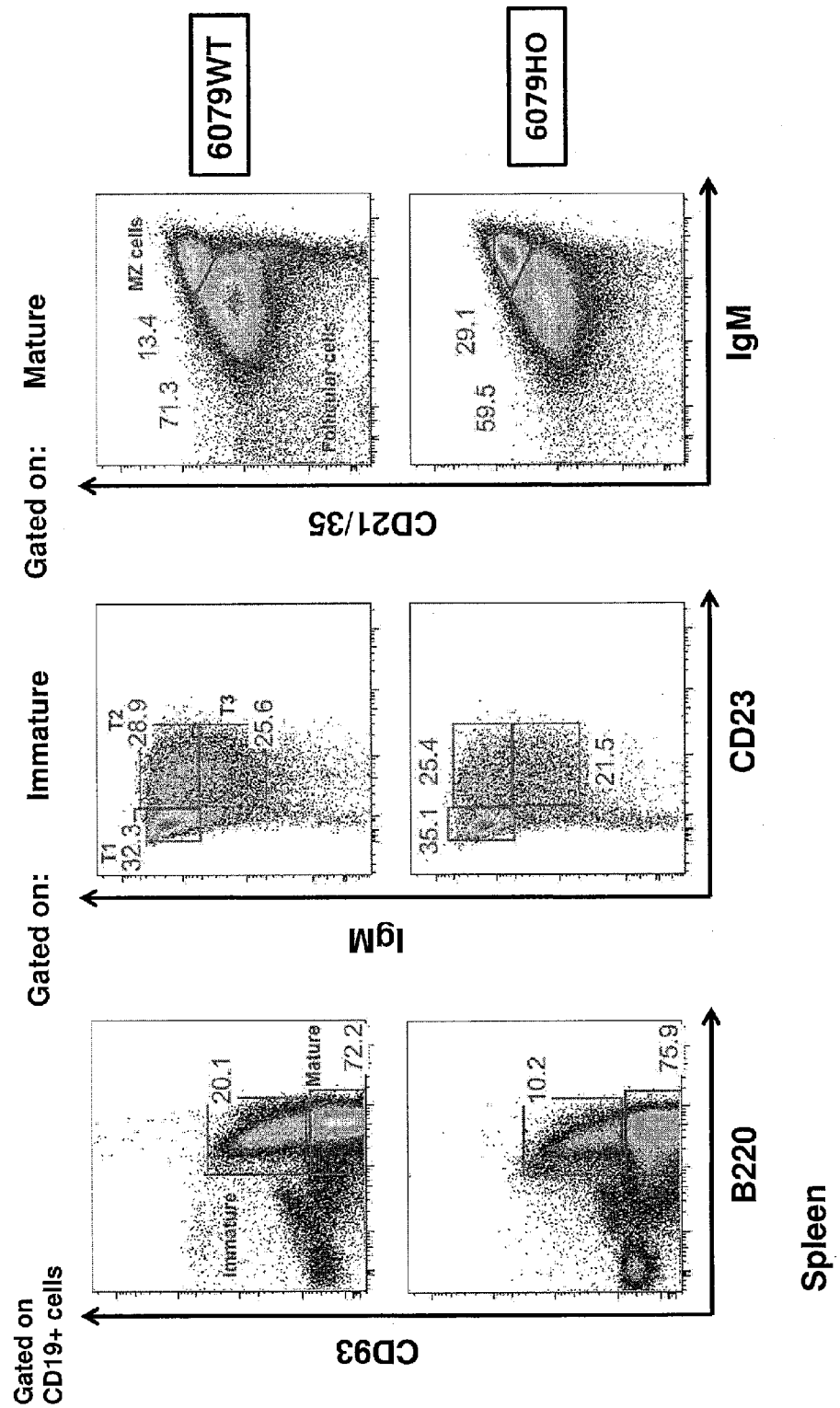
FIG. 55 shows the peripheral B cell development in the splenic compartment of mice homozygous for a rearranged heavy chain variable region nucleic acid sequence (hV$_H$3-23/D/J$_H$4) in the kappa light chain locus compared to wild type mice. The first (left) contour plot shows CD93$^+$ and B220$^+$ splenocytes gated on CD19$^+$ indicating immature and mature B cells. The second (middle) contour plot shows IgM$^+$ and CD23$^+$ expression in immature B cells indicating T1, T2 and T3 B cell populations. The third (right) contour plot shows CD21$^+$ (CD35$^+$) and IgM$^+$ expression of mature B cells indicating a first smaller population that give rise to marginal zone B cells and a second larger population that gives rise to follicular (FO) B cells. Percentage of cells within each gated region is shown.

In the splenic compartment, MAID 6079HO mice demonstrated fewer mature B cells compared to wild type littermates (FIGS. 53A-53B). Similar to what was observed in the bone marrow, MAID 6079HO mice almost exclusively used lambda light chain sequences in the splenic compartment (FIGS. 54A-54B). They also demonstrated fewer immature cells, an increase in marginal zone B cells and a decrease in follicular B cells compared to wild type littermates (FIG. 55).

Example 8

Generation and Analysis of Mice Comprising an Immunoglobulin Light Chain Locus Containing a Rearranged Heavy Chain VDJ Sequence and an Immunoglobulin Heavy Chain Locus Containing a Human Light Chain Variable Domain Sequence Mice homozygous for a rearranged heavy chain variable region nucleic acid sequence in the light chain locus (MAID 6079HO; homozygous "UHC on kappa mouse") were generated as described above. These mice were crossed to mice homozygous (MAID 1994HO) for a kappa light chain variable region nucleic acid sequence in a heavy chain locus (kappa on heavy ("KoH") mouse). The MAID 1994 homozygous KoH mice comprise 40 human Vκ genes and all human Jκ genes, with long IGCR and mouse ADAM6, inserted into a mouse Ig heavy chain constant chain locus (i.e., a deleted mouse Ig heavy chain locus)). KoH have been described previously; see, e.g., U.S. pre-grant publication 2012/0096572, incorporated herein by reference.

Figure 56:
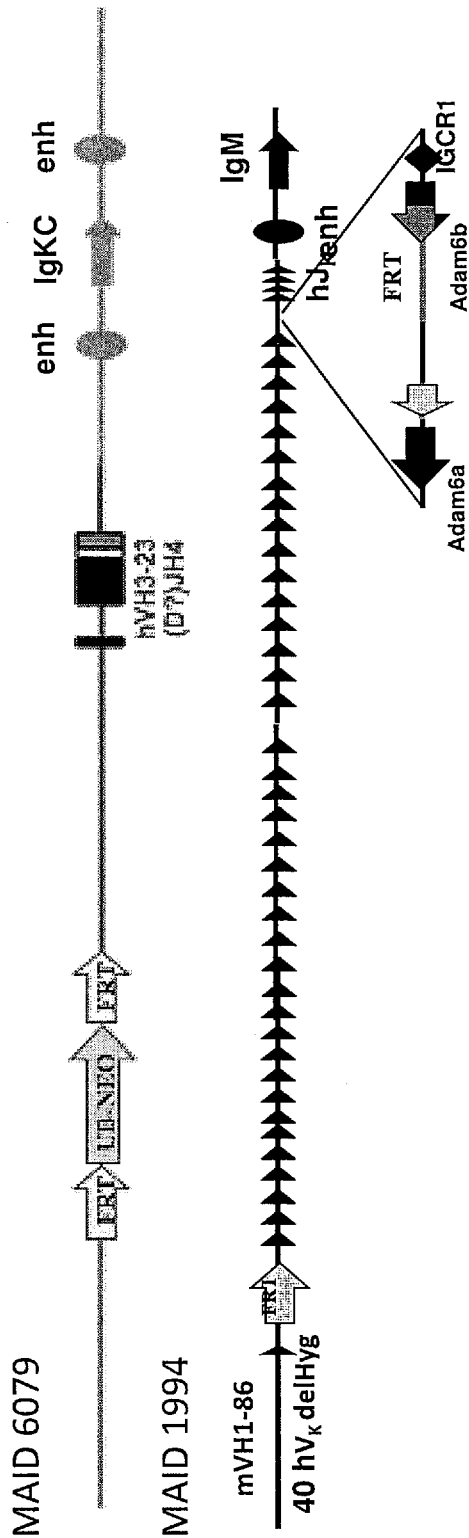
FIG. 56 illustrates the genomic structure of genetically modified F2 mice homozygous for a rearranged heavy chain variable region nucleic acid sequence in the kappa light chain locus (MAID 6079HO; homozygous "UHC on kappa mouse") and homozygous for a kappa light chain variable region nucleic acid sequence in a heavy chain locus (MAID 1994HO; kappa on heavy ("KoH") mouse).

All mice were housed and bred in specific pathogen-free conditions at Regeneron Pharmaceuticals. Two VELOCIMMUNE® (MAID 1242HO 1640HO ("VI3"); see U.S. Pat. No. 8,502,018, incorporated by reference herein) mice (15 weeks old, female n=2; Background: 28% C57/BL6, 13% 129 and 59% Balb/c), four MAID 1994HO 6079HO F2 mice (FIG. 56; 13-14 weeks old, male n=2; Background: 25% C57/BL6, 25% 129, and 50% Balb/c), and MAID 6079 wild type littermate control mice were sacrificed, and spleens and bone marrow were harvested from the animals. Bone marrow was collected from femurs by flushing with complete RPMI medium (RPMI medium supplemented with fetal calf serum, sodium pyruvate, Hepes, 2-mercaptoethanol, non-essential amino acids, and gentamycin). Red blood cells from spleen and bone marrow preparations were lysed with ACK lysis buffer and washed with complete RPMI medium.

Flow Cytometry

In order to examine the ability of the genetically modified homozygous "KoH×UHC on kappa" (MAID 1994HO 6079HO) mice described herein to produce antibodies derived from the genetically modified alleles (e.g., from the allele that contains a single copy of the rearranged V$_H$3-23/ D/J$_H$4 and the allele that contains a kappa light chain variable region nucleic acid sequence in a heavy chain locus), fluorescence-activated cell sorting (FACS) analysis was performed as in Example 3.

Figure 57A:
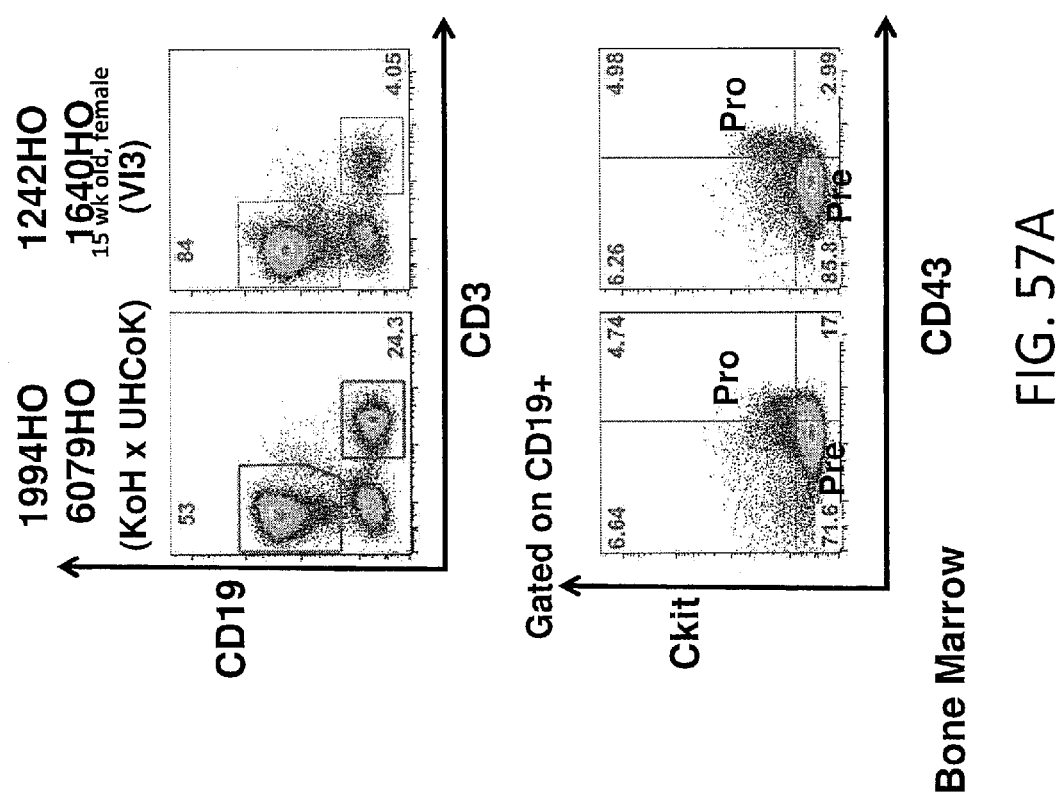
FIG. 57A in the top panel, shows representative contour plots of bone marrow stained for B and T cells (CD19$^+$ and CD3$^+$, respectively) from a VELOCIMMUNE® (VI3) and a mouse homozygous for a rearranged heavy chain variable region nucleic acid sequence in the kappa light chain locus and homozygous for a kappa light chain variable region nucleic acid sequence in a heavy chain locus. The bottom panel shows representative contour plots of bone marrow gated on CD19$^+$ and stained for ckit$^+$ and CD43$^+$ from a VELOCIMMUNE® (VI3) and a mouse homozygous for a rearranged heavy chain variable region nucleic acid sequence in the kappa light chain locus and homozygous for a kappa light chain variable region nucleic acid sequence in a heavy chain locus. Pro and Pre B cells are noted on the contour plots of the bottom panel.
Figure 57B:
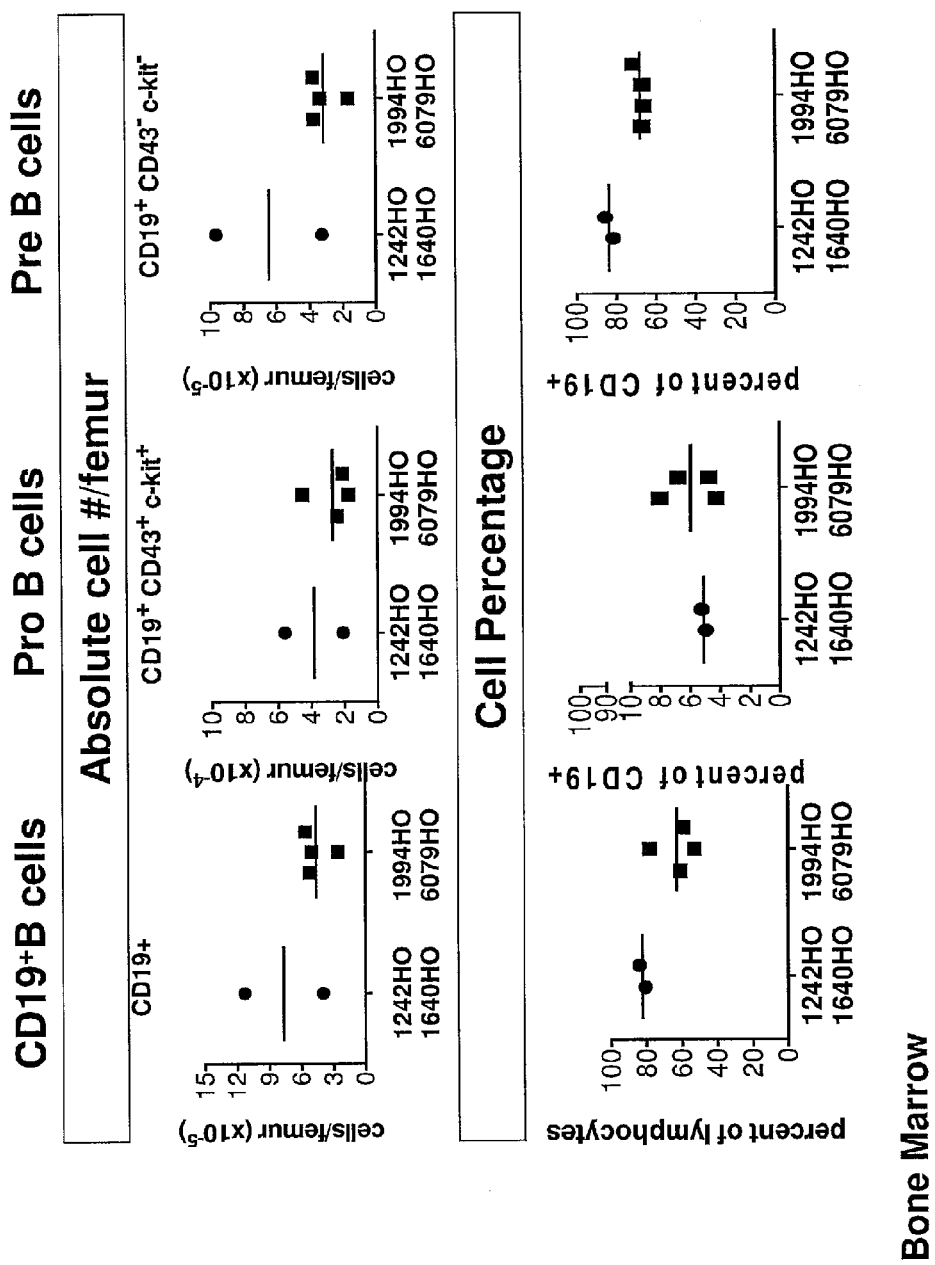
FIG. 57B shows the total number of B cells (CD19$^+$) and the numbers of Pro (CD19$^+$CD43$^+$ckit$^+$) and Pre (CD19$^+$CD43$^-$ckit$^-$) B cells in bone marrow harvested from the femurs of VELOCIMMUNE® mice (1242HO 1640HO) and mice homozygous for a rearranged heavy chain variable region nucleic acid sequence in the kappa light chain locus and homozygous for a kappa light chain variable region nucleic acid sequence in a heavy chain locus (1994HO 6079HO). Numbers are presented as both absolute number of cells per femur and cell percentage.
Figure 58A:
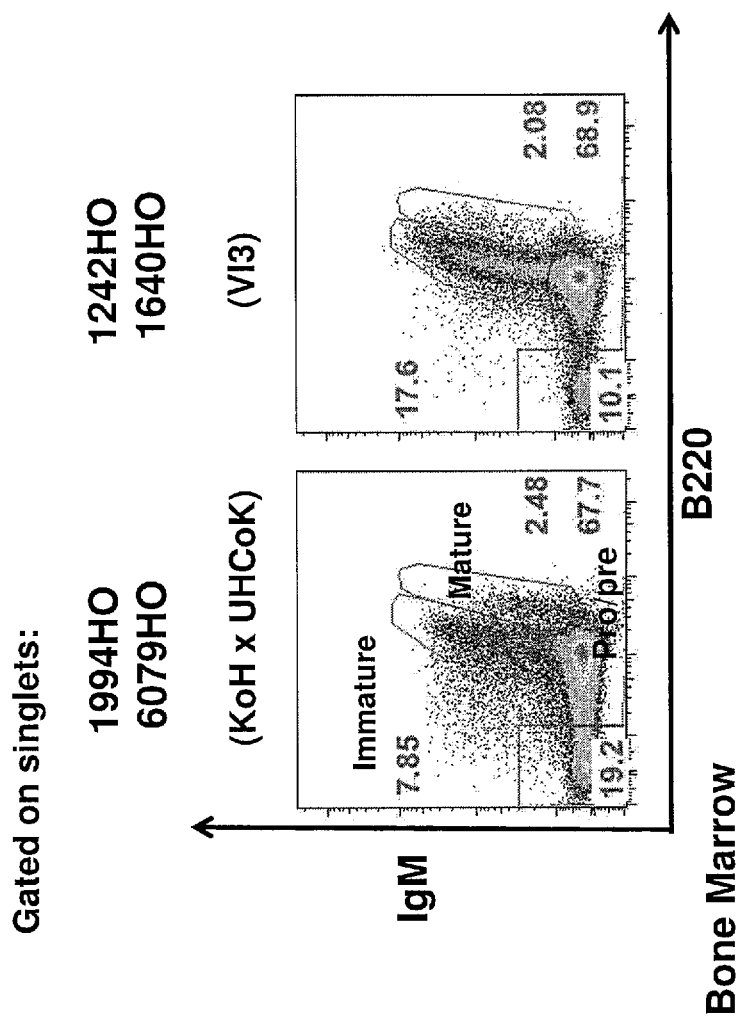
FIG. 58A shows representative contour plots of bone marrow gated on singlets stained for immunoglobulin M (IgM) and B220 from a VELOCIMMUNE® mouse (1242HO 1640HO) and a mouse homozygous for a rearranged heavy chain variable region nucleic acid sequence in the kappa light chain locus and homozygous for a kappa light chain variable region nucleic acid sequence in a heavy chain locus (1994HO 6079HO). Immature, mature and pro/pre B cells are noted on each of the contour plots.
Figure 58B:
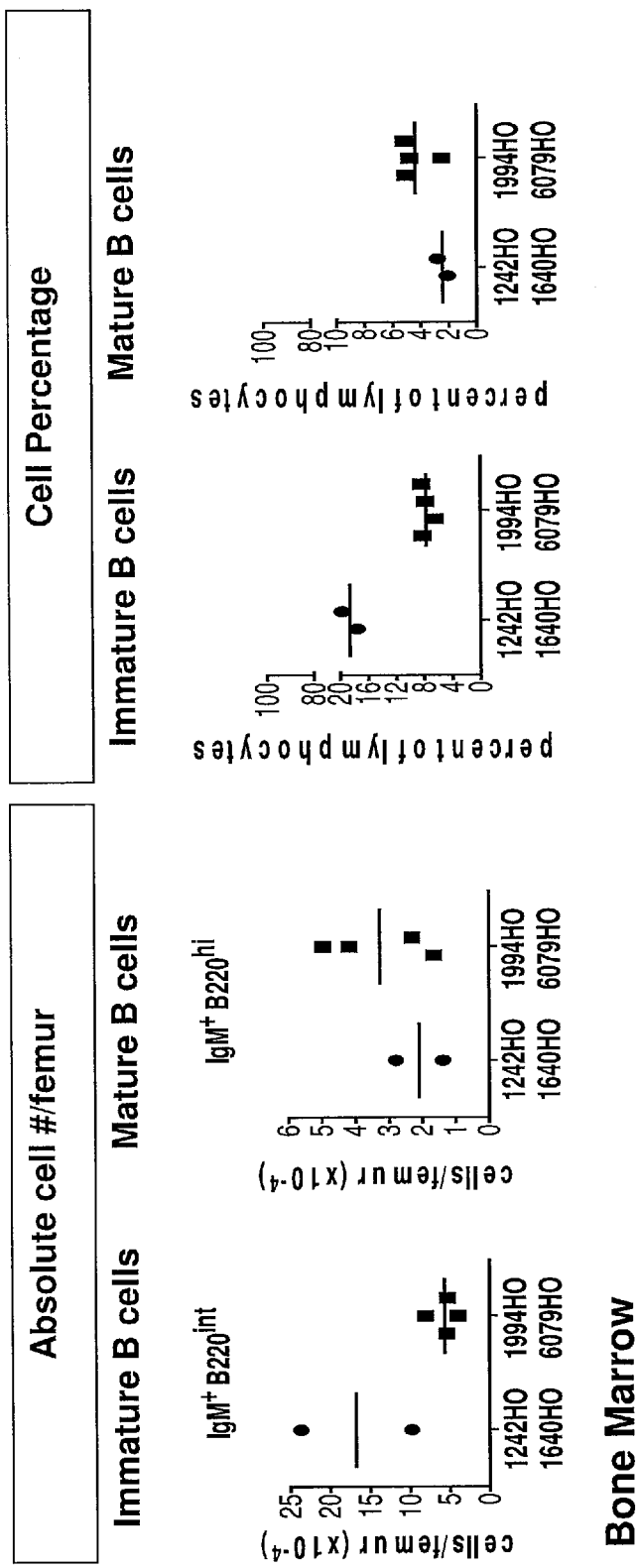
FIG. 58B shows the number of immature B (B220$^{int}$IgM$^+$) and mature B (B220$^{hi}$IgM$^+$) cells in bone marrow isolated from the femurs of VELOCIMMUNE® mice (1242HO 1640HO) and mice homozygous for a rearranged heavy chain variable region nucleic acid sequence in the kappa light chain locus and homozygous for a kappa light chain variable region nucleic acid sequence in a heavy chain locus (1994HO 6079HO). Numbers are presented as both absolute number of cells per femur and cell percentage.
Figure 59:
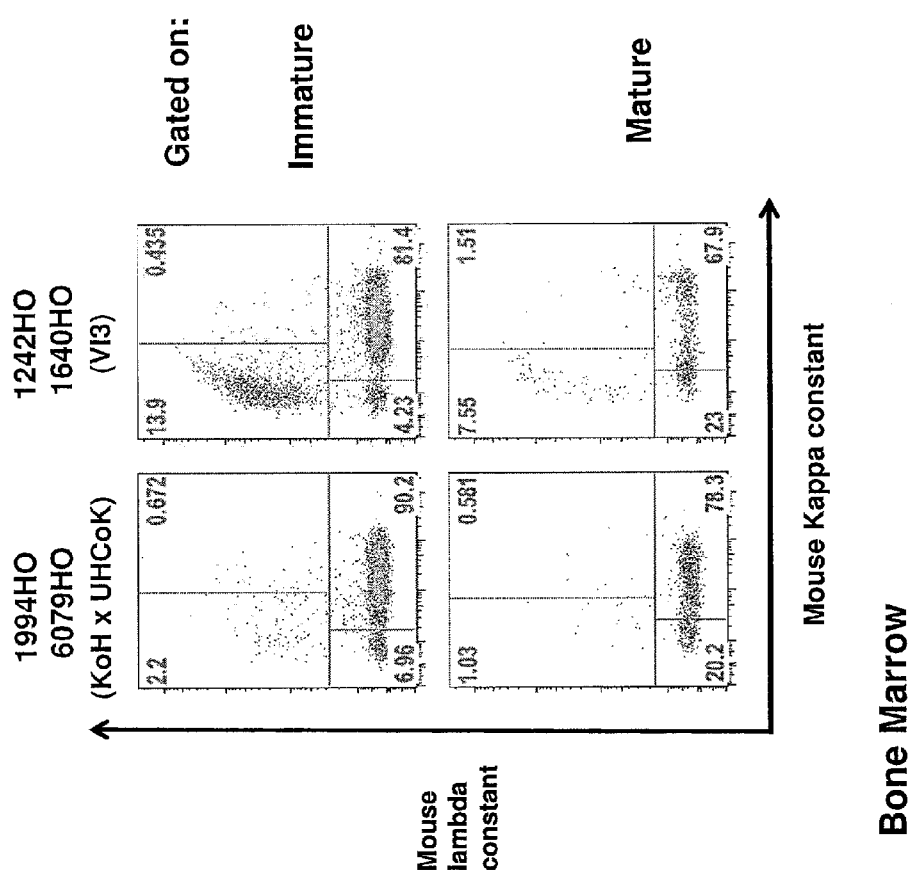
FIG. 59 shows representative contour plots of bone marrow gated on immature (B220$^{int}$IgM$^+$) and mature (B220$^{hi}$IgM$^+$) B cells stained for Igλ and Igκ expression isolated from the femurs of VELOCIMMUNE® mice (1242HO 1640HO) and mice homozygous for a rearranged heavy chain variable region nucleic acid sequence in the kappa light chain locus and homozygous for a kappa light chain variable region nucleic acid sequence in a heavy chain locus (1994HO 6079HO).

MAID 1994HO 6079HO mice demonstrated lower CD19+ and pre-B cell frequencies in the bone marrow compartment compared to VI3 mice (FIG. 57A). Specifically, the MAID 19940 6079HO mice demonstrated about a 2-fold lower CD19+ and pre-B cell numbers in the bone marrow compared to VI3 mice (FIG. 57B). Additionally, the MAID 1994HO 6079 HO mice demonstrated about 3-fold less immature B cells in the bone marrow compartment relative to VI3 mice (FIGS. 58A and 58B). It was also found that B cells from the MAID 1994HO 6079HO mice essentially lack expression of lambda light chain in the bone marrow (FIG. 59).

Figure 60A:
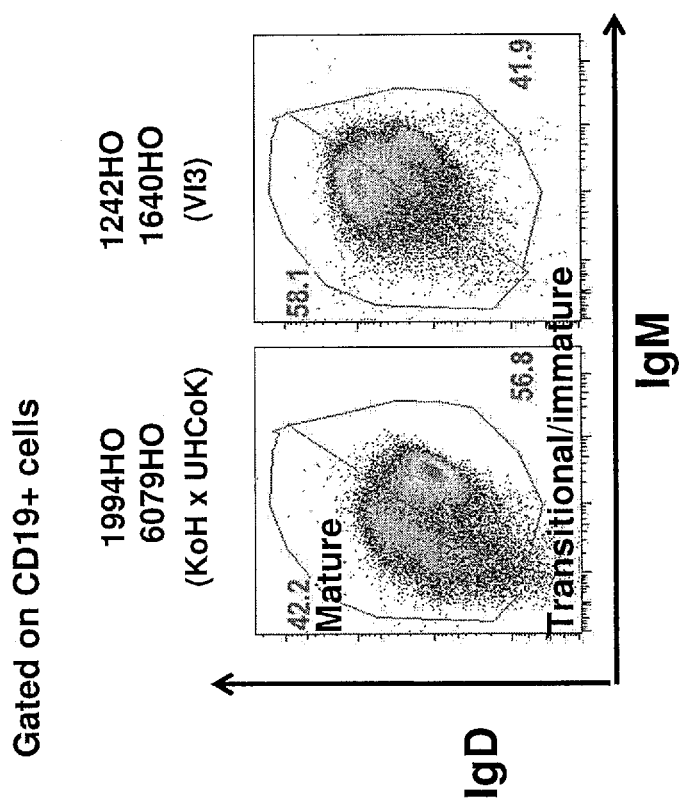
FIG. 60A shows representative contour plots of splenocytes gated on CD19$^+$ and stained for immunoglobulin D (IgD) and immunoglobulin M (IgM) from a VELOCIMMUNE® mouse (VI3; 1242HO 1640HO) and a mouse homozygous for a rearranged heavy chain variable region nucleic acid sequence in the kappa light chain locus and homozygous for a kappa light chain variable region nucleic acid sequence in a heavy chain locus (1994HO 6079HO). Mature and transitional/immature B cells are noted on each of the contour plots.
Figure 60B:
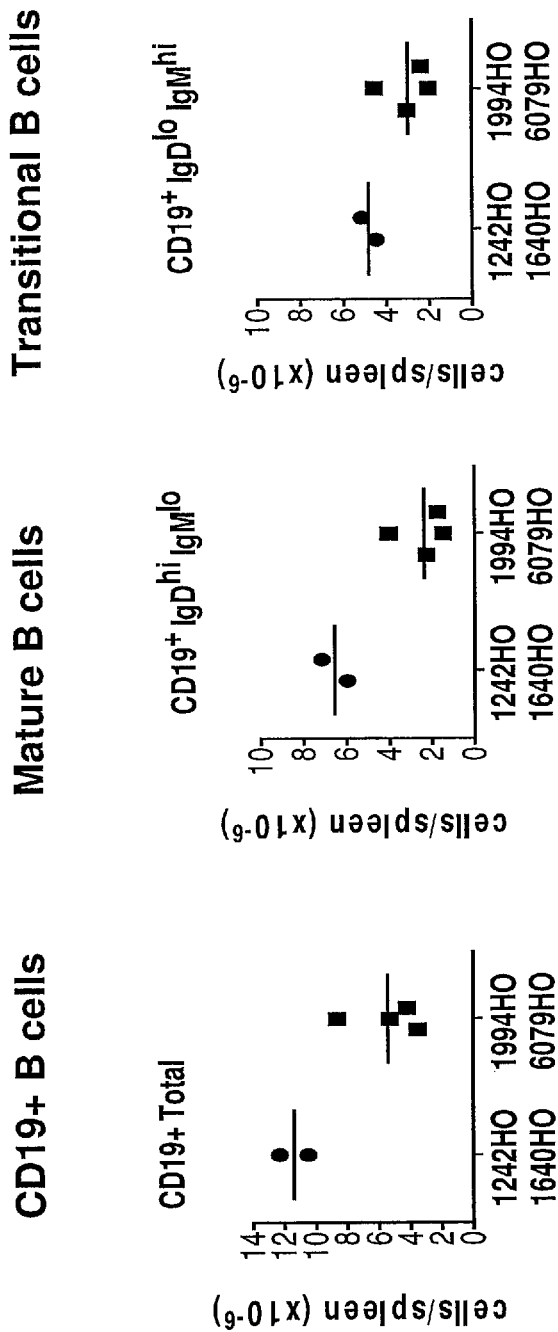
FIG. 60B shows the total number of CD19$^+$ B cells, mature B cells (CD19$^+$IgM$^{lo}$IgD$^{hi}$) and transitional B cells (CD19$^+$IgM$^{hi}$IgD$^{lo}$) in harvested spleens from VELOCIMMUNE® mice (1242HO 1640HO) and mice homozygous for a rearranged heavy chain variable region nucleic acid sequence in the kappa light chain locus and homozygous for a kappa light chain variable region nucleic acid sequence in a heavy chain locus (1994HO 6079HO).
Figure 61:
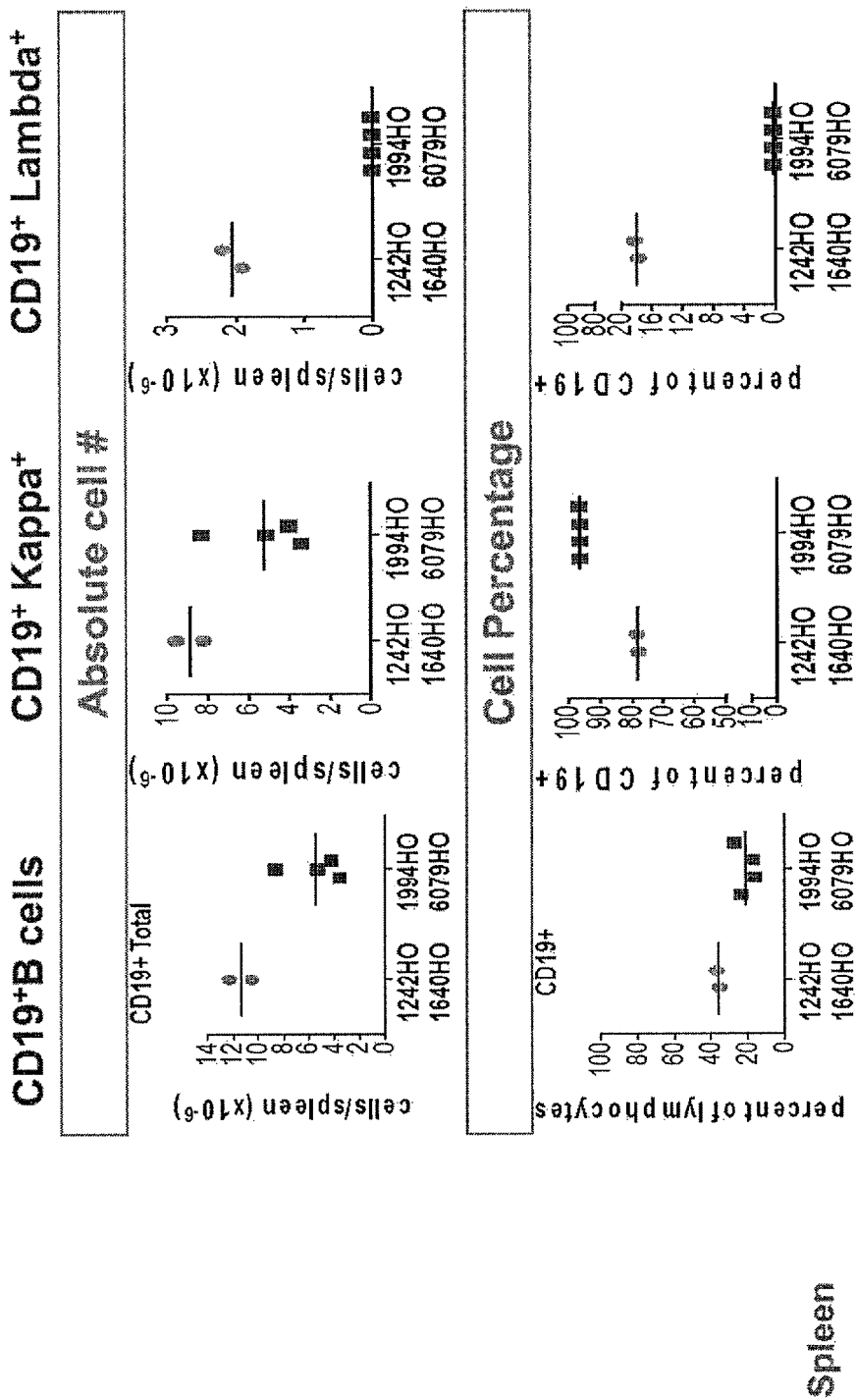
FIG. 61 shows the total number of B cells (CD19$^+$), Igκ$^+$ B cells (CD19$^+$Igκ$^+$) and Igλ$^+$ B cells (CD19$^+$Igλ$^+$) in harvested spleens from VELOCIMMUNE® mice (1242HO 1640HO) and mice homozygous for a rearranged heavy chain variable region nucleic acid sequence in the kappa light chain locus and homozygous for a kappa light chain variable region nucleic acid sequence in a heavy chain locus (1994HO 6079HO). Numbers are presented as both absolute cell number and cell percentage of lymphocytes.

MAID1994HO 6079HO mice demonstrated a lower frequency of B cells in the splenic compartment. Specifically, MAID 1994HO 6079HO mice had fewer splenic B cells (about 2-fold less) and mature B cells (about 3-fold less) numbers relative to VI3 mice (FIGS. 60A-60B. They again demonstrated a lack expression of lambda light chain as compared to VI3 mice (FIG. 61).

Figure 62:
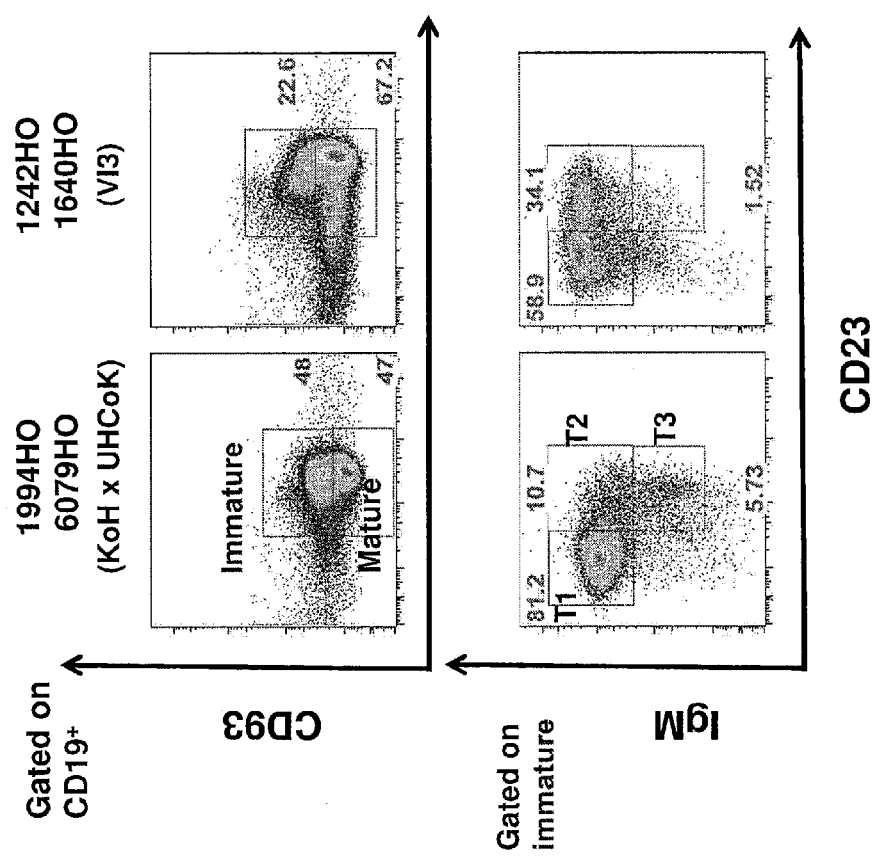
FIG. 62 shows the peripheral B cell development in the splenic compartment of VELOCIMMUNE® mice (1242HO 1640HO) and mice homozygous for a rearranged heavy chain variable region nucleic acid sequence in the kappa light chain locus and homozygous for a kappa light chain variable region nucleic acid sequence in a heavy chain locus (1994HO 6079HO). The top contour plot shows CD93$^+$ and B220$^+$ splenocytes gated on CD19$^+$ indicating immature and mature B cells. The bottom contour plot shows IgM$^+$ and CD23$^+$ expression in immature B cells indicating T1, T2 and T3 B cell populations. Percentage of cells within each gated region is shown.

Considering peripheral B cell development in the spleen, the FACS analysis indicated that MAID1994HO 6079HO mice have an increased frequency of cells in T1 phase in the spleen than VI3 mice (FIG. 62).

Those skilled in the art will recognize, or be able to ascertain using no more than routine experimentation, many equivalents of the specific embodiments of the invention described herein. Such equivalents are encompassed by the following claims.

Entire contents of all non-patent documents, patent applications and patents cited throughout this application are incorporated by reference herein in their entirety.

While the described invention has been described with reference to particular aspects and embodiments thereof, those skilled in the art understand that various changes may be made and equivalents may be substituted without departing from the true spirit and scope of the invention. In addition, many modifications may be made to adopt a particular situ-

What is claimed is:

1. A rodent comprising in its germline genome at an endogenous immunoglobulin heavy chain locus a rearranged human immunoglobulin heavy chain variable region nucleotide sequence operably linked to an endogenous heavy chain constant region gene sequence, wherein the rearranged heavy chain variable region nucleotide sequence encodes the sequence of $V_H3-23/X_1X_2/J_H$, wherein $X_1$ is any amino acid, and $X_2$ is any amino acid, and wherein the rodent is a rat or a mouse.

2. The rodent of claim 1, wherein $X_1$ is Gly and $X_2$ is Tyr.

3. The rodent of claim 1, wherein the human $J_H$ gene segment is selected from the group consisting of $J_H1$, $J_H2$, $J_H3$, $J_H4$, $J_H5$, $J_H6$, and a polymorphic variant thereof.

4. The rodent of claim 1, wherein the rearranged human immunoglobulin heavy chain variable region nucleotide sequence encodes the sequence of human $V_H3-23/GY/J_H4-4$ (SEQ ID NO:137).

5. The rodent of claim 4, wherein the rodent is a mouse.

6. The rodent of claim 1, wherein the heavy chain constant region gene sequence is selected from a $C_H1$, a hinge, a $C_H2$, a $C_H3$, and a combination thereof.

7. The rodent of claim 1, wherein substantially all endogenous functional $V_H$, D, and $J_H$ gene segments are deleted from the immunoglobulin heavy chain locus of the rodent or rendered non-functional.

8. The rodent of claim 1, wherein the rodent comprises a modification that deletes or renders non-functional endogenous functional $V_H$, D, and $J_H$ gene segments.

9. The rodent of claim 1, wherein an immunoglobulin heavy chain variable domain encoded by the rearranged heavy chain variable region nucleotide sequence is not immunogenic to the non-human animal.

10. The rodent of claim 1, wherein the rodent comprises an Adam6a gene, an Adam6b gene, or both.

11. The rodent of claim 1, wherein the rodent further comprises a nucleotide sequence encoding an unrearranged human immunoglobulin light chain V gene segment ($V_L$) and an unrearranged human immunoglobulin light chain J gene segment ($J_L$), wherein the nucleotide sequence is operably linked to an immunoglobulin light chain constant region gene sequence.

12. The rodent of claim 11, wherein the light chain constant region gene sequence is selected from a rodent and a human constant region gene sequence.

13. The rodent of claim 12, wherein the rodent is selected from a mouse, a rat, and a hamster.

14. The rodent of claim 11, wherein the unrearranged human immunoglobulin light chain ($V_L$) gene segment and the unrearranged human immunoglobulin ($J_L$) gene segment are operably linked, at an endogenous rodent locus, to a rodent immunoglobulin constant region gene sequence.

15. A method of making a rodent, the method comprising:
(a) modifying a genome of a rodent to delete or render non-functional substantially all endogenous functional immunoglobulin heavy chain $V_H$, D, and $J_H$ gene segments of an endogenous immunoglobulin heavy chain locus, wherein the rodent is a rat or a mouse; and
(b) placing in the genome at the endogenous immunoglobulin heavy chain locus a rearranged human immunoglobulin heavy chain variable region nucleotide sequence, wherein the rearranged heavy chain variable region nucleotide sequence encodes the sequence of $V_H 3-23/X_1 X_2/J_H$ operably linked to an endogenous heavy chain constant region gene sequence, wherein $X_1$ is any amino acid, and $X_2$ is any amino acid.

16. A modified rodent comprising in its genome:
(i) at an endogenous immunoglobulin heavy chain locus, a rearranged human heavy chain variable region nucleic acid sequence operably linked to an endogenous heavy chain constant region nucleic acid sequence, wherein the rearranged heavy chain variable region nucleic acid sequence encodes the sequence of $V_H 3-23/X_1 X_2/J_H$, wherein $X_1$ is any amino acid, and $X_2$ is any amino acid, wherein the rodent is a rat or a mouse; and
(ii) an immunoglobulin light chain locus comprising one or more but less than the wild type number of human immunoglobulin light chain $V_L$ and $J_L$ gene segments, operably linked to a light chain constant region nucleic acid sequence.

17. The modified rodent of claim 16, wherein $X_1$ is Gly and $X_2$ is Tyr.

18. The modified rodent of claim 16, wherein the human $J_H$ gene segment is selected from the group consisting of $J_H 1$, $J_H 2$, $J_H 3$, $J_H 4$, $J_H 5$, $J_H 6$, and a polymorphic variant thereof.

19. The modified rodent of claim 16, wherein the rearranged human immunoglobulin heavy chain variable region nucleotide sequence encodes the sequence of human $V_H 3-23$/GY/$J_H 4-4$ (SEQ ID NO:137).

20. The modified rodent of claim 16, wherein the one or more but less than the wild type number of human immunoglobulin light chain $V_L$ and $J_L$ gene segments are operably linked to the light chain constant region nucleic acid sequence at an endogenous locus.

21. The modified rodent of claim 16, wherein the immunoglobulin light chain locus comprises two human $V_L$ gene segments, Vκ1-39 and Vκ3-20.

22. The modified rodent of claim 16, wherein at least one of the human light chain $V_L$ or $J_L$ gene segments encode one or more histidine codons that are not encoded by a corresponding human germline light chain variable gene segment.

23. The modified rodent of claim 16, wherein at least one of the $V_L$ gene segments comprises an addition or substitution of at least one non-histidine codon encoded by the corresponding human germline $V_L$ segment sequence with a histidine codon.

24. The modified rodent of claim 23, wherein the added or substituted histidine codon is present in CDR3.

25. The mouse claim 5, wherein the mouse comprises an Adam6a gene, an Adam6b gene, or both.

26. The mouse of claim 5, wherein the non-human animal further comprises a nucleotide sequence encoding an unrearranged human immunoglobulin light chain V gene segment ($V_L$) and an unrearranged human immunoglobulin light chain J gene segment ($J_L$), wherein the nucleotide sequence is operably linked to an immunoglobulin light chain constant region gene sequence.

27. The rodent of claim 16, wherein the rodent is a mouse.

* * * * *

SEQUENCE LISTING

<160> NUMBER OF SEQ ID NOS: 183

<210> SEQ ID NO 1
<211> LENGTH: 95
<212> TYPE: PRT
<213> ORGANISM: Artificial
<220> FEATURE:
<223> OTHER INFORMATION: Synthetic

<400> SEQUENCE: 1

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 2
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 2 cag cag agc tac agc acc ccc                                        21
Gln Gln Ser Tyr Ser Thr Pro
1               5

<210> SEQ ID NO 3
<211> LENGTH: 7
<212> TYPE: PRT
<213> ORGANISM: Artificial
<220> FEATURE:
<223> OTHER INFORMATION: Synthetic Construct

<400> SEQUENCE: 3

Gln Gln Ser Tyr Ser Thr Pro
1               5

<210> SEQ ID NO 4
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 4 cac cat agc cac agc acc cac                                        21
His His Ser His Ser Thr His
1               5

```
<210> SEQ ID NO 5
<211> LENGTH: 7
<212> TYPE: PRT
<213> ORGANISM: Artificial
<220> FEATURE:
<223> OTHER INFORMATION: Synthetic Construct

<400> SEQUENCE: 5

His His Ser His Ser Thr His
1               5

<210> SEQ ID NO 6
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 6 cac cag agc tac agc acc ccc                                          21
His Gln Ser Tyr Ser Thr Pro
1               5

<210> SEQ ID NO 7
<211> LENGTH: 7
<212> TYPE: PRT
<213> ORGANISM: Artificial
<220> FEATURE:
<223> OTHER INFORMATION: Synthetic Construct

<400> SEQUENCE: 7

His Gln Ser Tyr Ser Thr Pro
1               5

<210> SEQ ID NO 8
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 8 cag cat agc tac agc acc ccc                                          21
Gln His Ser Tyr Ser Thr Pro
1               5

<210> SEQ ID NO 9
<211> LENGTH: 7
<212> TYPE: PRT
<213> ORGANISM: Artificial
<220> FEATURE:
<223> OTHER INFORMATION: Synthetic Construct

<400> SEQUENCE: 9

Gln His Ser Tyr Ser Thr Pro
1               5

<210> SEQ ID NO 10
<211> LENGTH: 21
<212> TYPE: DNA
<213> ORGANISM: Artificial
```

```
<220> FEATURE:
<223> OTHER INFORMATION: Synthetic
<220> FEATURE:
<221> NAME/KEY: CDS
<222> LOCATION: (1)..(21)

<400> SEQUENCE: 10 cag cag agc cac agc acc ccc                                          21
Gln Gln Ser His Ser Thr Pro
1               5

<210> SEQ ID NO 11
<211> LENGTH: 7
<212> TYPE: PRT
<213> ORGANISM: Artificial
<220> FEATURE:
<223> OTHER INFORMATION: Synthetic Construct

<400> SEQUENCE: 11

Gln Gln Ser His Ser Thr Pro
1               5

<210> SEQ ID NO 12
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 12 cag cag agc tac agc acc cac                                          21
Gln Gln Ser Tyr Ser Thr His
1               5

<210> SEQ ID NO 13
<211> LENGTH: 7
<212> TYPE: PRT
<213> ORGANISM: Artificial
<220> FEATURE:
<223> OTHER INFORMATION: Synthetic Construct

<400> SEQUENCE: 13

Gln Gln Ser Tyr Ser Thr His
1               5

<210> SEQ ID NO 14
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 14 cac cat agc tac agc acc ccc                                          21
His His Ser Tyr Ser Thr Pro
1               5

<210> SEQ ID NO 15
<211> LENGTH: 7
<212> TYPE: PRT
<213> ORGANISM: Artificial
<220> FEATURE:
<223> OTHER INFORMATION: Synthetic Construct
```

```
<400> SEQUENCE: 15

His His Ser Tyr Ser Thr Pro
1               5

<210> SEQ ID NO 16
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 16 cac cag agc cac agc acc ccc                                           21
His Gln Ser His Ser Thr Pro
1               5

<210> SEQ ID NO 17
<211> LENGTH: 7
<212> TYPE: PRT
<213> ORGANISM: Artificial
<220> FEATURE:
<223> OTHER INFORMATION: Synthetic Construct

<400> SEQUENCE: 17

His Gln Ser His Ser Thr Pro
1               5

<210> SEQ ID NO 18
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 18 cac cag agc tac agc acc cac                                           21
His Gln Ser Tyr Ser Thr His
1               5

<210> SEQ ID NO 19
<211> LENGTH: 7
<212> TYPE: PRT
<213> ORGANISM: Artificial
<220> FEATURE:
<223> OTHER INFORMATION: Synthetic Construct

<400> SEQUENCE: 19

His Gln Ser Tyr Ser Thr His
1               5

<210> SEQ ID NO 20
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 20
```

```
cag cat agc cac agc acc ccc                                          21
Gln His Ser His Ser Thr Pro
1               5

<210> SEQ ID NO 21
<211> LENGTH: 7
<212> TYPE: PRT
<213> ORGANISM: Artificial
<220> FEATURE:
<223> OTHER INFORMATION: Synthetic Construct

<400> SEQUENCE: 21

Gln His Ser His Ser Thr Pro
1               5

<210> SEQ ID NO 22
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 22 cag cat agc tac agc acc cac                                          21
Gln His Ser Tyr Ser Thr His
1               5

<210> SEQ ID NO 23
<211> LENGTH: 7
<212> TYPE: PRT
<213> ORGANISM: Artificial
<220> FEATURE:
<223> OTHER INFORMATION: Synthetic Construct

<400> SEQUENCE: 23

Gln His Ser Tyr Ser Thr His
1               5

<210> SEQ ID NO 24
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 24 cag cag agc cac agc acc cac                                          21
Gln Gln Ser His Ser Thr His
1               5

<210> SEQ ID NO 25
<211> LENGTH: 7
<212> TYPE: PRT
<213> ORGANISM: Artificial
<220> FEATURE:
<223> OTHER INFORMATION: Synthetic Construct

<400> SEQUENCE: 25

Gln Gln Ser His Ser Thr His
1               5

<210> SEQ ID NO 26
```

```
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 26 cac cat agc cac agc acc ccc                                          21
His His Ser His Ser Thr Pro
1               5

<210> SEQ ID NO 27
<211> LENGTH: 7
<212> TYPE: PRT
<213> ORGANISM: Artificial
<220> FEATURE:
<223> OTHER INFORMATION: Synthetic Construct

<400> SEQUENCE: 27

His His Ser His Ser Thr Pro
1               5

<210> SEQ ID NO 28
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 28 cac cat agc tac agc acc cac                                          21
His His Ser Tyr Ser Thr His
1               5

<210> SEQ ID NO 29
<211> LENGTH: 7
<212> TYPE: PRT
<213> ORGANISM: Artificial
<220> FEATURE:
<223> OTHER INFORMATION: Synthetic Construct

<400> SEQUENCE: 29

His His Ser Tyr Ser Thr His
1               5

<210> SEQ ID NO 30
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 30 cac cag agc cac agc acc cac                                          21
His Gln Ser His Ser Thr His
1               5

<210> SEQ ID NO 31
<211> LENGTH: 7
<212> TYPE: PRT
```

```
<213> ORGANISM: Artificial
<220> FEATURE:
<223> OTHER INFORMATION: Synthetic Construct

<400> SEQUENCE: 31

His Gln Ser His Ser Thr His
1               5

<210> SEQ ID NO 32
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 32 cag cat agc cac agc acc cac                               21
Gln His Ser His Ser Thr His
1               5

<210> SEQ ID NO 33
<211> LENGTH: 7
<212> TYPE: PRT
<213> ORGANISM: Artificial
<220> FEATURE:
<223> OTHER INFORMATION: Synthetic Construct

<400> SEQUENCE: 33

Gln His Ser His Ser Thr His
1               5

<210> SEQ ID NO 34
<211> LENGTH: 45
<212> TYPE: DNA
<213> ORGANISM: Artificial
<220> FEATURE:
<223> OTHER INFORMATION: Synthetic

<400> SEQUENCE: 34
cttactactg tcaacatagt cacagtaccc atccgatcac cttcg          45

<210> SEQ ID NO 35
<211> LENGTH: 50
<212> TYPE: DNA
<213> ORGANISM: Artificial
<220> FEATURE:
<223> OTHER INFORMATION: Synthetic

<400> SEQUENCE: 35
caacttacta ctgtcaccat agtcacagta cccatccgat caccttcggc     50

<210> SEQ ID NO 36
<211> LENGTH: 45
<212> TYPE: DNA
<213> ORGANISM: Artificial
<220> FEATURE:
<223> OTHER INFORMATION: Synthetic

<400> SEQUENCE: 36
cgaaggtgat cggatgggta ctgtgactat gttgacagta gtaag          45

<210> SEQ ID NO 37
<211> LENGTH: 50
<212> TYPE: DNA
```

```
<213> ORGANISM: Artificial
<220> FEATURE:
<223> OTHER INFORMATION: Synthetic

<400> SEQUENCE: 37
gccgaaggtg atcggatggg tactgtgact atggtgacag tagtaagttg          50

<210> SEQ ID NO 38
<211> LENGTH: 23
<212> TYPE: DNA
<213> ORGANISM: Artificial
<220> FEATURE:
<223> OTHER INFORMATION: Synthetic

<400> SEQUENCE: 38
tgggcacaac agacaatcgg ctg                                       23

<210> SEQ ID NO 39
<211> LENGTH: 19
<212> TYPE: DNA
<213> ORGANISM: Artificial
<220> FEATURE:
<223> OTHER INFORMATION: Synthetic

<400> SEQUENCE: 39
ggtggagagg ctattcggc                                            19

<210> SEQ ID NO 40
<211> LENGTH: 17
<212> TYPE: DNA
<213> ORGANISM: Artificial
<220> FEATURE:
<223> OTHER INFORMATION: Synthetic

<400> SEQUENCE: 40
gaacacggcg gcatcag                                              17

<210> SEQ ID NO 41
<211> LENGTH: 29
<212> TYPE: DNA
<213> ORGANISM: Artificial
<220> FEATURE:
<223> OTHER INFORMATION: Synthetic

<400> SEQUENCE: 41
ccattatgat gctccatgcc tctctgttc                                 29

<210> SEQ ID NO 42
<211> LENGTH: 28
<212> TYPE: DNA
<213> ORGANISM: Artificial
<220> FEATURE:
<223> OTHER INFORMATION: Synthetic

<400> SEQUENCE: 42
aggtgagggt acagataagt gttatgag                                  28

<210> SEQ ID NO 43
<211> LENGTH: 27
<212> TYPE: DNA
<213> ORGANISM: Artificial
<220> FEATURE:
<223> OTHER INFORMATION: Synthetic

<400> SEQUENCE: 43
tgacaaatgc cctaattata gtgatca                                   27
```

<210> SEQ ID NO 44
<211> LENGTH: 26
<212> TYPE: DNA
<213> ORGANISM: Artificial
<220> FEATURE:
<223> OTHER INFORMATION: Synthetic

<400> SEQUENCE: 44
atcagcagaa accagggaaa gcccct                                    26

<210> SEQ ID NO 45
<211> LENGTH: 21
<212> TYPE: DNA
<213> ORGANISM: Artificial
<220> FEATURE:
<223> OTHER INFORMATION: Synthetic

<400> SEQUENCE: 45
gggcaagtca gagcattagc a                                         21

<210> SEQ ID NO 46
<211> LENGTH: 21
<212> TYPE: DNA
<213> ORGANISM: Artificial
<220> FEATURE:
<223> OTHER INFORMATION: Synthetic

<400> SEQUENCE: 46
tgcaaactgg atgcagcata g                                         21

<210> SEQ ID NO 47
<211> LENGTH: 19
<212> TYPE: DNA
<213> ORGANISM: Artificial
<220> FEATURE:
<223> OTHER INFORMATION: Synthetic

<400> SEQUENCE: 47
ggccacattc catgggttc                                            19

<210> SEQ ID NO 48
<211> LENGTH: 20
<212> TYPE: DNA
<213> ORGANISM: Artificial
<220> FEATURE:
<223> OTHER INFORMATION: Synthetic

<400> SEQUENCE: 48
gcaaacaaaa accactggcc                                           20

<210> SEQ ID NO 49
<211> LENGTH: 37
<212> TYPE: DNA
<213> ORGANISM: Artificial
<220> FEATURE:
<223> OTHER INFORMATION: Synthetic

<400> SEQUENCE: 49
ctgttcctct aaaactggac tccacagtaa atggaaa                        37

<210> SEQ ID NO 50
<211> LENGTH: 22
<212> TYPE: DNA
<213> ORGANISM: Artificial
<220> FEATURE:

```
<223> OTHER INFORMATION: Synthetic

<400> SEQUENCE: 50
gggcactgga tacgatgtat gg                                              22

<210> SEQ ID NO 51
<211> LENGTH: 19
<212> TYPE: DNA
<213> ORGANISM: Artificial
<220> FEATURE:
<223> OTHER INFORMATION: Synthetic

<400> SEQUENCE: 51
cacagcttgt gcagcctcc                                                  19

<210> SEQ ID NO 52
<211> LENGTH: 37
<212> TYPE: DNA
<213> ORGANISM: Artificial
<220> FEATURE:
<223> OTHER INFORMATION: Synthetic

<400> SEQUENCE: 52
agaagaagcc tgtactacag catccgtttt acagtca                              37

<210> SEQ ID NO 53
<211> LENGTH: 19
<212> TYPE: DNA
<213> ORGANISM: Artificial
<220> FEATURE:
<223> OTHER INFORMATION: Synthetic

<400> SEQUENCE: 53
accatagtca cagtaccca                                                  19

<210> SEQ ID NO 54
<211> LENGTH: 23
<212> TYPE: DNA
<213> ORGANISM: Artificial
<220> FEATURE:
<223> OTHER INFORMATION: Synthetic

<400> SEQUENCE: 54
agcagtctgc aacctgaaga ttt                                             23

<210> SEQ ID NO 55
<211> LENGTH: 18
<212> TYPE: DNA
<213> ORGANISM: Artificial
<220> FEATURE:
<223> OTHER INFORMATION: Synthetic

<400> SEQUENCE: 55
cccttggccg aaggtgat                                                   18

<210> SEQ ID NO 56
<211> LENGTH: 19
<212> TYPE: DNA
<213> ORGANISM: Artificial
<220> FEATURE:
<223> OTHER INFORMATION: Synthetic

<400> SEQUENCE: 56
atagtcacag tacccatcc                                                  19
```

```
<210> SEQ ID NO 57
<211> LENGTH: 23
<212> TYPE: DNA
<213> ORGANISM: Artificial
<220> FEATURE:
<223> OTHER INFORMATION: Synthetic

<400> SEQUENCE: 57
agtctgcaac ctgaagattt tgc                                              23

<210> SEQ ID NO 58
<211> LENGTH: 18
<212> TYPE: DNA
<213> ORGANISM: Artificial
<220> FEATURE:
<223> OTHER INFORMATION: Synthetic

<400> SEQUENCE: 58
cccttggccg aaggtgat                                                    18

<210> SEQ ID NO 59
<211> LENGTH: 108
<212> TYPE: PRT
<213> ORGANISM: Artificial
<220> FEATURE:
<223> OTHER INFORMATION: Synthetic

<400> SEQUENCE: 59

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 60
<211> LENGTH: 54
<212> TYPE: DNA
<213> ORGANISM: Artificial
<220> FEATURE:
<223> OTHER INFORMATION: Synthetic

<400> SEQUENCE: 60
gattttgcag tgtattactg tcagcagtat ggtagctcac cttggacgtt cggc            54

<210> SEQ ID NO 61
<211> LENGTH: 54
<212> TYPE: DNA
<213> ORGANISM: Artificial
<220> FEATURE:
<223> OTHER INFORMATION: Synthetic

<400> SEQUENCE: 61
gattttgcag tgtattactg tcatcaccat ggtcactcac cttggacgtt cggc            54
```

```
<210> SEQ ID NO 62
<211> LENGTH: 54
<212> TYPE: DNA
<213> ORGANISM: Artificial
<220> FEATURE:
<223> OTHER INFORMATION: Synthetic

<400> SEQUENCE: 62
gccgaacgtc caaggtgagt gaccatggtg atgacagtaa tacactgcaa aatc        54

<210> SEQ ID NO 63
<211> LENGTH: 47
<212> TYPE: DNA
<213> ORGANISM: Artificial
<220> FEATURE:
<223> OTHER INFORMATION: Synthetic

<400> SEQUENCE: 63
gcagtgtatt actgtcatca ctatggtcac tcaccttgga cgttcgg                47

<210> SEQ ID NO 64
<211> LENGTH: 47
<212> TYPE: DNA
<213> ORGANISM: Artificial
<220> FEATURE:
<223> OTHER INFORMATION: Synthetic

<400> SEQUENCE: 64
ccgaacgtcc aaggtgagtg accatagtga tgacagtaat acactgc                47

<210> SEQ ID NO 65
<211> LENGTH: 24
<212> TYPE: DNA
<213> ORGANISM: Artificial
<220> FEATURE:
<223> OTHER INFORMATION: Synthetic

<400> SEQUENCE: 65
aaagagccac cctctcctgc aggg                                         24

<210> SEQ ID NO 66
<211> LENGTH: 19
<212> TYPE: DNA
<213> ORGANISM: Artificial
<220> FEATURE:
<223> OTHER INFORMATION: Synthetic

<400> SEQUENCE: 66
tccaggcacc ctgtctttg                                               19

<210> SEQ ID NO 67
<211> LENGTH: 26
<212> TYPE: DNA
<213> ORGANISM: Artificial
<220> FEATURE:
<223> OTHER INFORMATION: Synthetic

<400> SEQUENCE: 67
aagtagctgc tgctaacact ctgact                                       26

<210> SEQ ID NO 68
<211> LENGTH: 15
<212> TYPE: DNA
<213> ORGANISM: Artificial
<220> FEATURE:
<223> OTHER INFORMATION: Synthetic
```

```
<400> SEQUENCE: 68
ctgtcatcac catgg                                                    15

<210> SEQ ID NO 69
<211> LENGTH: 23
<212> TYPE: DNA
<213> ORGANISM: Artificial
<220> FEATURE:
<223> OTHER INFORMATION: Synthetic

<400> SEQUENCE: 69
gcagactgga gcctgaagat ttt                                           23

<210> SEQ ID NO 70
<211> LENGTH: 20
<212> TYPE: DNA
<213> ORGANISM: Artificial
<220> FEATURE:
<223> OTHER INFORMATION: Synthetic

<400> SEQUENCE: 70
ccgaacgtcc aaggtgagtg                                               20

<210> SEQ ID NO 71
<211> LENGTH: 17
<212> TYPE: DNA
<213> ORGANISM: Artificial
<220> FEATURE:
<223> OTHER INFORMATION: Synthetic

<400> SEQUENCE: 71
tactgtcatc actatgg                                                  17

<210> SEQ ID NO 72
<211> LENGTH: 22
<212> TYPE: DNA
<213> ORGANISM: Artificial
<220> FEATURE:
<223> OTHER INFORMATION: Synthetic

<400> SEQUENCE: 72
gcagactgga gcctgaagat tt                                            22

<210> SEQ ID NO 73
<211> LENGTH: 20
<212> TYPE: DNA
<213> ORGANISM: Artificial
<220> FEATURE:
<223> OTHER INFORMATION: Synthetic

<400> SEQUENCE: 73
ccgaacgtcc aaggtgagtg                                               20

<210> SEQ ID NO 74
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 74 cag cag tat ggt agc tca cct                                         21
Gln Gln Tyr Gly Ser Ser Pro
```

```
1               5

<210> SEQ ID NO 75
<211> LENGTH: 7
<212> TYPE: PRT
<213> ORGANISM: Artificial
<220> FEATURE:
<223> OTHER INFORMATION: Synthetic Construct

<400> SEQUENCE: 75

Gln Gln Tyr Gly Ser Ser Pro
1               5

<210> SEQ ID NO 76
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 76 cat cac cat ggt cac tca cct                                      21
His His His Gly His Ser Pro
1               5

<210> SEQ ID NO 77
<211> LENGTH: 7
<212> TYPE: PRT
<213> ORGANISM: Artificial
<220> FEATURE:
<223> OTHER INFORMATION: Synthetic Construct

<400> SEQUENCE: 77

His His His Gly His Ser Pro
1               5

<210> SEQ ID NO 78
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 78 cat cac tat ggt cac tca cct                                      21
His His Tyr Gly His Ser Pro
1               5

<210> SEQ ID NO 79
<211> LENGTH: 7
<212> TYPE: PRT
<213> ORGANISM: Artificial
<220> FEATURE:
<223> OTHER INFORMATION: Synthetic Construct

<400> SEQUENCE: 79

His His Tyr Gly His Ser Pro
1               5

<210> SEQ ID NO 80
<211> LENGTH: 108
<212> TYPE: PRT
```

<213> ORGANISM: Artificial
<220> FEATURE:
<223> OTHER INFORMATION: Synthetic

<400> SEQUENCE: 80

```
Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ser Tyr Ser Thr Pro Pro
            85                  90                  95

Ile Thr Phe Gly Gln Gly Thr Arg Leu Glu Ile Lys
        100                 105
```

<210> SEQ ID NO 81
<211> LENGTH: 50
<212> TYPE: DNA
<213> ORGANISM: Artificial
<220> FEATURE:
<223> OTHER INFORMATION: Synthetic

<400> SEQUENCE: 81

```
caacttacta ctgtcaacag agttacagta cccctccgat caccttcggc          50
```

<210> SEQ ID NO 82
<211> LENGTH: 9652
<212> TYPE: DNA
<213> ORGANISM: Artificial
<220> FEATURE:
<223> OTHER INFORMATION: synthetic

<400> SEQUENCE: 82

```
gcaccacttc gtcgcagcgc aggctttggt ctcccttgtc cgtgcggcgc acgcccaccg    60
agtttacgca ccagcacacc gaggtctggt tggtaccgaa gttcctattc cgaagttcct   120
attctctaga aagtatagga acttctcgcg cgtctggcct ccgaggcctc cgcgccgggt   180
tttggcgcct cccgcgggcg ccccctcct cacggcgagc gctgccacgt cagacgaagg    240
gcgcagcgag cgtcctgatc cttccgcccg gacgctcagg acagcggccc gctgctcata   300
agactcggcc ttagaacccc agtatcagca aaggacatt ttaggacggg acttgggtga    360
ctctagggca ctggttttct ttccagagag cggaacaggc gaggaaaagt agtcccttct   420
cggcgattct gcggagggat ctccgtgggg cggtgaacgc cgatgattat ataaggacgc   480
gccgggtgtg gcacagctag ttccgtcgca gccgggattt gggtcgcggt tcttgtttgt   540
ggatcgctgt gatcgtcact tggtgagtag cgggctgctg ggctggccgg ggctttcgtg   600
gccgccgggc cgctcggtgg gacggaagcg tgtggagaga ccgccaaggg ctgtagtctg   660
ggtccgcgag caaggttgcc ctgaactggg ggttgggggg agcgcagcaa aatggcggct   720
gttcccgagt cttgaatgga agacgcttgt gaggcgggct gtgaggtcgt tgaaacaagg   780
tgggggggcat ggtgggcggc aagaacccaa ggtcttgagg ccttcgctaa tgcgggaaag  840
ctcttattcg ggtgagatgg gctggggcac catctgggga ccctgacgtg aagttttgtca  900
```

```
ctgactggag aactcggttt gtcgtctgtt gcggggggcgg cagttatggc ggtgccgttg    960
ggcagtgcac ccgtaccttt gggagcgcgc gccctcgtcg tgtcgtgacg tcacccgttc   1020
tgttggctta taatgcaggg tggggccacc tgccggtagg tgtgcggtag cttttctcc    1080
gtcgcaggac gcaggggttcg ggcctagggt aggctctcct gaatcgacag cgcccggacc  1140
tctggtgagg ggagggataa gtgaggcgtc agtttctttg gtcggtttta tgtacctatc   1200
ttcttaagta gctgaagctc cggttttgaa ctatgcgctc ggggttggcg agtgtgtttt   1260
gtgaagtttt ttaggcacct tttgaaatgt aatcatttgg gtcaatatgt aattttcagt   1320
gttagactag taaattgtcc gctaaattct ggccgttttt ggcttttttg ttagacgtcg   1380
agctctagat tgggaacccg ggtctctcga attgttgaca attaatcatc ggcatagtat   1440
atcggcatag tataatacga caaggtgagg aactaaacca tccaccatga ttgaacaaga   1500
tggattgcac gcaggttctc cggccgcttg ggtggagagg ctattcggct atgactgggc   1560
acaacagaca atcggctgct ctgatgccgc cgtgttccgg ctgtcagcgc aggggcgccc   1620
ggttcttttt gtcaagaccg acctgtccgg tgccctgaat gaactgcagg acgaggcagc   1680
gcggctatcg tggctggcca cgacgggcgt tccttgcgca gctgtgctcg acgttgtcac   1740
tgaagcggga agggactggc tgctattggg cgaagtgccg gggcaggatc tcctgtcatc   1800
tcaccttgct cctgccgaga aagtatccat catggctgat gcaatgcggc ggctgcatac   1860
gcttgatccg gctacctgcc cattcgacca ccaagcgaaa catcgcatcg agcgagcacg   1920
tactcggatg gaagccggtc ttgtcgatca ggatgatctg gacgaagagc atcaggggct   1980
cgcgccagcc gaactgttcg ccaggctcaa ggcgcgcatg cccgacggcg aggatctcgt   2040
cgtgacccat ggcgatgcct gcttgccgaa tatcatggtg gaaaatggcc gcttttctgg   2100
attcatcgac tgtggccggc tgggtgtggc ggaccgctat caggacatag cgttggctac   2160
ccgtgatatt gctgaagagc ttggcggcga atgggctgac cgcttcctcg tgctttacgg   2220
tatcgccgct cccgattcgc agcgcatcgc cttctatcgc cttcttgacg agttcttctg   2280
aagatccgct gtaagtctgc agaaattgat gatctattaa acaataaaga tgtccactaa   2340
aatggaagtt tttcctgtca tactttgtta agaagggtga aacagagta cctacatttt   2400
gaatggaagg attggagcta cggggtggg ggtgggtgg gattagataa atgcctgctc   2460
tttactgaag gctctttact attgctttat gataatgttt catagttgga tatcataatt   2520
taaacaagca aaaccaaatt aagggccagc tcattcctcc cactcatgat ctatagatct   2580
atagatctct cgtgggatca ttgttttttct cttgattccc actttgtggt tctaagtact   2640
gtggtttcca aatgtgtcag tttcatagcc tgaagaacga gatcagcagc ctctgttcca   2700
catacacttc attctcagta ttgttttgcc aagttctaat tccatcagac ctcgacctgc   2760
agcccctaga gaagttccta ttccgaagtt cctattctct agaaagtata ggaacttcct   2820
agggtttcac cggtggcgcg ccgagagagg aaagagagca gcgataccga aaatgtcctc   2880
agcgagaagc taccacagag gatgaatgga gatcaagccc acgtgaaaac atgggaaaat   2940
gtctcagtat ttttccacct aagaagggag ggagatgggg tatgtataca cctccctgtc   3000
ctcactgatt gagggctttc cgagaggatg ctcattccag gtgctgtgat aggccatgtg   3060
tacaggcagg gctgccttct ccagcttcag atagagcagt gaggaaaaga tatggccatg   3120
gggggtcagc agaagtacag caaagggaaa agggaaaggg tagcaagagt gacaactata   3180
ttcaccccc ccacacacac acacacacac acgaaattgt gtattgcaat ccagaactgc   3240
ttctctctga acctaaatct tagcaagcag tttaccagta actgcccttg aaattcaggc   3300
```

-continued

```
ccctggaaag gagcaggggg ttgtgtacag gctataccac agcagtctgc ccacccttag    3360
tgatgcatga gtaatgctcc ctggactccc caggttctag tcttctcatg tcgatgtagt    3420
tgattccact tcccttgctg cacaaccagg ctgggatgcc tgggcagagg cagacatgtg    3480
aggtataggg gttcaaatct gtttccaagt tttatccagc ttcaaagcat ttctccgtgt    3540
acatgagcgg tggcttgaca ggagatggag actctctttc ctggatgtga ggcaaggagg    3600
caggcgtctg agtcaggatg atgtccctac tcactgctaa agagaaaagt ggctttgatg    3660
gtgcagggca gggaaatgca ctgagtggtc gccaccctca cagaagagaa agtgttcact    3720
gacctggcct ttccccaggg cctctccctc ccattgcttt ccagaaagcc atgattttg     3780 agagccacac ctgaacactc acaaacatta tggtgggaaa agcagatcag agcattaggc    3840
aagttgcatt accttggcct tcttcctttg gagacaattg atgtgggtt ctagattgac     3900 ccagagtttc aagtttatcc tgattcaggc ttcaacagct ggaggaagaa acagagatgt    3960
tttttgaagt aaacagatct agcattacta atcaaccctt catactgatg acctatggga    4020
aataataccc aagggcagaa aaatgggcag aataagggga gccccaaacc aagacgaagc    4080
tgctgcccat tgagaccctg ggtattacag agacctatag ctctggataa tggaagatct    4140
atgagtggca caggcgctga ggaatcacag catcattatc gtgcatctgc agggaattgc    4200
ttgtaaatat actggtaatt acaaatgttt aaggtcacta caaatacttt ggagtgtatt    4260
aaatatgctt ctgataaaga ctgttttct cacatgaaac aatgggaacc atgtgacaat      4320
cacagaggtg ttgttactat agcaaaaggg attgttactc tccacatccc tttaagtaac    4380
ttgaaggcct gatagaccca ccctctaaga cttcattaga cattccctac gaatggttat    4440
actctcctgt atactcccaa tacaactcta aaatatatta ttccatatag tccttaggtt    4500
tgtattaaag tttgactttt ttccttcaaa atatctcttg tcacaacagc ggctctagag    4560
agaaatacat tccctccagg caaatctatg ctgcgctggt ctgacctggg acctggggga   4620
cattgcccct gtgctgagtt actaagatga gccagccctg cagctgtgct cagcctgccc   4680
catgccctgc tgattgattt gcatgttcca gagcacagcc ccctgccctg aagactttt    4740 tatgggctgg tcgcaccctg tgcaggagtc agtctcagtc aggacacagc atggacatga   4800
gggtccccgc tcagctcctg gggctcctgc tactctggct ccgaggtaag gatggagaac   4860
actaggaatt tactcagcca gtgtgctcag tactgactgg aacttcaggg aagttctctg   4920
ataacatgat taatagtaag aatatttgtt tttatgtttc caatctcagg tgccagatgt    4980
gacatccaga tgacccagtc tccatcctcc ctgtctgcat ctgtaggaga cagagtcacc   5040
atcacttgcc gggcaagtca gagcattagc agctatttaa attggtatca gcagaaacca   5100
gggaaagccc ctaagctcct gatctatgct gcatccagtt tgcaaagtgg ggtcccatca   5160
aggttcagtg gcagtggatc tgggacagat ttcactctca ccatcagcag tctgcaacct   5220
gaagattttg caacttacta ctgtcaacag agttacagta cccctcccac agtgttacaa    5280
gtcataacat aaacctccaa ggaagcagat gtgtgaggac gagccacccc agatgctcct    5340
cctggtgcct ccatctgctg agagcatttc tcaaactcag tcaggttttg aaagtcattg    5400
ggagactttt gtagagggga ccaggaggc tcctctgaac tctaagcctc tttttgccccg    5460 gatccgatca ggaaaatagc aaccgagtga ctggactatt aaagcatccc ctctgtggag   5520
aaaaggacta tggcaacagc ttgccaccta taagagacaa atatgtcact cagctggatg   5580
ctgggtctac catgaccacc cttgagatga acttatgcca tgttttttgga tgcccactga   5640
```

```
gactttgctt tgaccaagga aagttcttta ctgcccaaat gacgtcaatg acacactct    5700 catgggacat gatggatttt ccatacacct tgttatccaa aggccaatgg atctatttaa    5760
tgctagaaca gctgactcac acggcaactg aagagtgtac atcagggcaa cctgctagta    5820
gagtggtacc ccatctgact acagcaattg acattaaac actgcactgc agagcaaggg     5880
aaagacggca cggaggtgca ggttgaaaaa cactgagttg agtgaggaag aagttgggca    5940
aggccagttt cctgatagag ctgccactgt gaaatcccaa actcagtgtt tccaatcatt    6000 ttttccttt tatagtgatg ttcttgggggg tgttgcagtt taggccacca tgataaccca    6060
gacaggcctc ctaactctaa ttggatggaa tgattcccct gggtgccttc tatgggttcc    6120
acaggatcaa gaaatatcag ggtgttaatt tccttctgct ggtaggaggg tcatctgatt    6180
cctccattag ggtggatgac gttatcagac atgtcaattt tctacagtac ttgacctgcc    6240
ttctagaact ggacaaccga gggtgaaagg actggatcaa gcaacaatgg caatgggtgc    6300
ccaaagaggt agtagtctca gaacagggag agacagactg agtccctcca ctaactcagc    6360
ccaacacctg tggatgagta ggggatgcct gagatcctgg ggtggatggg aggtggggca    6420
ctgatctgtc aatctgcttt ttcttcaagg atcaggcagc agagacccag aagcttcatg    6480
tctttgtaag gctcttccaa gccaacacag ataatttgac aaaacactgt atctgcatcc    6540
cagacctcac cctgtcacag actgaagtgg ttgtttcatc ctactaaggg taaactatac    6600
cagctataca gaataaaaag actggatagt ttagaggatc acccaagaaa tagttctttg    6660
cctgcatgga caaaaccatc ttctgtcttt agggaaatgg tatcactacc ctgaggattt    6720
ggagcccagg tctcacttat ctgtgcagtt gtgaaagtcc tcacacccac agtgctgagg    6780
ttaattgaat gttactcttt taatttctgc aaagaatgag acagcttctg gaccctcagg    6840
aaagatcact aacaagtaaa tacaagtata tccggaagat aaagttgtaa tagactcttc    6900
ctttcaacct gatccatcat gcatttaggg agctgactgg gcacaagttg gagcagaaag    6960
agaaaaatga aaccacagcc ttctattttg tttctaacag acttgtacca aacattctgt    7020
ggctcaatct aggtgatggt gagacaagag gacacagggg ttaaattctg tggccgcagg    7080
ggagaagttc taccctcaga ctgagccaac ggccttttct ggcctgatca cctgggcatg    7140
ggctgctgag agcagaaagg ggaggcagat tgtctctgca gctgcaagcc cagcacccgc    7200
cccagctgct ttgcatgtcc ctcccagccg ccctgcagtc cagagcccat atcaatgcct    7260
gggtcagagc tctggagaag agctgctcag ttaggaccca gagggaacca tggaaacccc    7320
agcgcagctt ctcttcctcc tgctactctg gctcccaggt gaggggaaca tgggatggtt    7380
ttgcatgtca gtgaaaaccc tctcaagtcc tgttacctgg caactctgct cagtcaatac    7440
aataattaaa gctcaatata aagcaataat tctggctctt ctgggaagac aatgggtttg    7500
atttagatta catgggtgac ttttctgttt tatttccaat ctcagatacc accggagaaa    7560
ttgtgttgac gcagtctcca ggcacccgt ctttgtctcc aggggaaaga gccaccctct     7620
cctgcagggc cagtcagagt gttagcagca gctacttagc ctggtaccag cagaaacctg    7680
gccaggctcc caggctcctc atctatggtg catccagcag ggccactggc atcccagaca    7740
ggttcagtgg cagtgggtct gggacagact tcactctcac catcagcaga ctggagcctg    7800
aagattttgc agtgtattac tgtcagcagt atggtagctc acctcccaca gtgattcagc    7860
ttgaaacaaa aacctctgca agaccttcat tgtttactag attataccag ctgcttcctt    7920
tacagatagc tgctgcaatg acaactcaat tttagcatct cttctctgct tgggcatttt    7980
ggggatctta aaaaagtaat cccttgatat attttttgact ctgattcctg cattttttcct   8040
```

```
cagaccaaga tggacagcca ggtttaagca cagtttcaca gtaatggcca ctggatcaga    8100
tttacatcag tggatgtcag taaaggtccc aaccagagcc ataaggcaac aacaatagca    8160
acaaataatc aaaattggaa agaagaatt aaagctgtca taattcactg atgaaggatt     8220
gtgtgcagat aaaattcaaa tttgtctaca gagaaactac taaaattgac atgagaaata    8280
gaaaatcatt agattcaaga tcaatttatt aattcataga ttcaaaaatc aatttcattt    8340
ctgcataata aaaatgcta aaaattaaca ttataaaaca aacacaccat ttacaaaaac     8400
atcaaagtat caattattta aaaaaatag actaaataca ctgacgtctc cagaatatta    8460
ttttgaaaaa taaagaaaa cctaagtaaa tagaaattca gttcaaagac tgaatgtctc    8520
agtactataa aaatgtcaat tcttcaaaga ttaaaatatt gattacatat aagaaaaatc    8580
aaaatcctaa agtatactcc aatttaaatt aagaagctaa tctaaatatt atatgggaat    8640
gtcaaggatg tagaatagcc acagtgaacc tgaagaaaca ccaaaatgag aacttccagt    8700
gcctgaatac ctggaatata gtgtgggtgg cagtatggtg atggtgagat cagaagttta    8760
aaaatttgca aacgtgctta ttttggaaa taatcactac gcagatgtag ccaaaccctc     8820
ttcaactgtg gcgtacgctc aggtcaattc caaagagtac cagattcttt caaaagtca    8880 gatgagtaag ggatagaaaa ttagttcatc ttaaggaaca gccaagcgct agccagttaa    8940
gtgaggcatc tcaattgcaa gattttctct gcatcggtca ggttagtgat attaacagcg    9000 aaagagatt tttgttaagg ggaaagtaat taagttaaca ctgtggatca ccttcggcca     9060
agggacacga ctggagatta aacgtaagta attttcact attgtcttct gaaatttggg     9120
tctgatggcc agtattgact tttagaggct taaataggag tttggtaaag attggtaaat    9180
gagggcattt aagatttgcc atgggttgca aaagttaaac tcagcttcaa aaatggattt    9240
ggagaaaaaa agattaaatt gctctaaact gaatgacaca agtaaaaaa aaaaagtgta     9300 actaaaaagg aacccttgta tttctaagga gcaaagtaa atttatttt gttcactctt      9360 gccaaatatt gtattggttg ttgctgatta tgcatgatac agaaaagtgg aaaaatacat    9420
tttttagtct ttctccctt tgtttgataa attattttgt cagacaacaa taaaaatcaa     9480
tagcacgccc taagatctag atgcatgctc gagtgccatt tcattacctc tttctccgca    9540
cccgacatag ataagcttat cgataccgtc gacctcgagg gggggcccgg taccccgtgg    9600
catacagtgt cagattttct gtttatcaag ctagtgagat tagggggcaaa aa           9652
```

<210> SEQ ID NO 83
<211> LENGTH: 10867
<212> TYPE: DNA
<213> ORGANISM: Artificial
<220> FEATURE:
<223> OTHER INFORMATION: Synthetic

<400> SEQUENCE: 83

```
gcaccacttc gtcgcagcgc aggctttggt ctcccttgtc cgtgcggcgc acgcccaccg     60
agtttacgca ccagcacacc gaggtctggt tggtaccgaa gttcctattc cgaagttcct    120
attctctaga aagtatagga acttctcgcg cgtctggcct ccgaggcctc cgcgccgggt    180
tttggcgcct cccgcgggcg cccccctcct cacggcgagc gctgccacgt cagacgaagg    240
gcgcagcgag cgtcctgatc cttccgcccg gacgctcagg acagcggccc gctgctcata    300
agactcggcc ttagaacccc agtatcagca gaaggcactt ttaggacggg acttgggtga    360
ctctagggca ctggttttct ttccagagag cggaacaggc gaggaaaagt agtcccttct    420
```

```
cggcgattct gcggagggat ctccgtgggg cggtgaacgc cgatgattat ataaggacgc    480
gccgggtgtg gcacagctag ttccgtcgca gccgggatt t gggtcgcggt tcttgtttgt   540
ggatcgctgt gatcgtcact tggtgagtag cgggctgctg ggctggccgg ggctttcgtg    600
gccgccgggc cgctcggtgg gacggaagcg tgtggagaga ccgccaaggg ctgtagtctg    660
ggtccgcgag caaggttgcc ctgaactggg ggttgggggg agcgcagcaa aatggcggct    720
gttcccgagt cttgaatgga agacgcttgt gaggcgggct gtgaggtcgt tgaaacaagg    780
tgggggcat  ggtgggcggc aagaacccaa ggtcttgagg ccttcgctaa tgcgggaaag    840
ctcttattcg ggtgagatgg gctggggcac catctgggga ccctgacgtg aagtttgtca    900
ctgactggag aactcggttt gtcgtctgtt gcggggcgg  cagttatggc ggtgccgttg    960
ggcagtgcac ccgtaccttt gggagcgcgc gccctcgtcg tgtcgtgacg tcacccgttc   1020
tgttggctta taatgcaggg tggggccacc tgccggtagg tgtgcggtag gcttttctcc   1080
gtcgcaggac gcagggttcg ggcctagggt aggctctcct gaatgacag  gcgccggacc   1140
tctggtgagg ggagggataa gtgaggcgtc agtttctttg gtcggtttta tgtacctatc   1200
ttcttaagta gctgaagctc cggttttgaa ctatgcgctc ggggttggcg agtgtgtttt   1260
gtgaagtttt ttaggcacct tttgaaatgt aatcatttgg gtcaatatgt aattttcagt   1320
gttagactag taaattgtcc gctaaattct ggccgttttt ggcttttttg ttagacgtcg   1380
agctctagat tgggaacccg ggtctctcga attgttgaca attaatcatc ggcatagtat   1440
atcggcatag tataatacga caaggtgagg aactaaacca tccaccatga ttgaacaaga   1500
tggattgcac gcaggttctc cggccgcttg ggtggagagg ctattcggct atgactgggc   1560
acaacagaca atcggctgct ctgatgccgc cgtgttccgg ctgtcagcgc aggggcgccc   1620
ggttcttttt gtcaagaccg acctgtccgg tgccctgaat gaactgcagg acgaggcagc   1680
gcggctatcg tggctggcca cgacgggcgt tccttgcgca gctgtgctcg acgttgtcac   1740
tgaagcggga agggactggc tgctattggg cgaagtgccg gggcaggatc tcctgtcatc   1800
tcaccttgct cctgccgaga aagtatccat catggctgat gcaatgcggc ggctgcatac   1860
gcttgatccg gctacctgcc cattcgacca ccaagcgaaa catcgcatcg agcgagcacg   1920
tactcggatg gaagccggtc ttgtcgatca ggatgatctg gacgaagagc atcaggggct   1980
cgcgccagcc gaactgttcg ccaggctcaa ggcgcgcatg cccgacggcg aggatctcgt   2040
cgtgacccat ggcgatgcct gcttgccgaa tatcatggtg gaaaatggcc gcttttctgg   2100
attcatcgac tgtggccggc tgggtgtggc ggaccgctat caggacatag cgttggctac   2160
ccgtgatatt gctgaagagc ttggcggcga atgggctgac cgcttcctcg tgctttacgg   2220
tatcgccgct cccgattcgc agcgcatcgc cttctatcgc cttcttgacg agttcttctg   2280
aagatccgct gtaagtctgc agaaattgat gatctattaa acaataaaga tgtccactaa   2340
aatgaaagtt tttcctgtca tactttgtta agaagggtga aacagagta  cctacatttt   2400
gaatggaagg attggagcta cggggg tggg ggtgggg tgg gattagataa atgcctgctc   2460
tttactgaag gctctttact attgctttat gataatgttt catagttgga tatcataatt   2520
taaacaagca aaaccaaatt aagggccagc tcattcctcc cactcatgat ctatagatct   2580
atagatctct cgtgggatca ttgttttttct cttgattccc actttgtggt tctaagtact   2640
gtggtttcca aatgtgtcag tttcatagcc tgaagaacga gatcagcagc ctctgttcca   2700
catacacttc attctcagta ttgttttgcc aagttctaat tccatcagac ctcgacctgc   2760
agcccctaga gaagttccta ttccgaagtt cctattctct agaaagtata ggaacttcct   2820
```

```
agggtttcac cggtggcgcg ccgagagagg aaagagagca gcgataccga aaatgtcctc    2880
agcgagaagc taccacagag gatgaatgga gatcaagccc acgtggaaac atgggaaaat    2940
gtctcagtat ttttccacct aagaagggag ggagatgggg tatgtataca cctccctgtc    3000
ctcactgatt gagggctttc cgagaggatg ctcattccag gtgctgtgat aggccatgtg    3060
tacaggcagg gctgccttct ccagcttcag atagagcagt gaggaaaaga tatggccatg    3120
gggggtcagc agaagtacag caaagggaaa agggaaaggg tagcaagagt gacaactata    3180
ttcacccccc ccacacacac acacacacac acgaaattgt gtattgcaat ccagaactgc    3240
ttctctctga acctaaatct tagcaagcag tttaccagta actgcccttg aaattcaggc    3300
ccctggaaag gagcagggg ttgtgtacag gctataccac agcagtctgc ccacccttag    3360
tgatgcatga gtaatgctcc ctggactccc caggttctag tcttctcatg tcgatgtagt    3420
tgattccact tcccttgctg cacaaccagg ctgggatgcc tgggcagagg cagacatgtg    3480
aggtataggg gttcaaatct gtttccaagt tttatccagc ttcaaagcat ttctccgtgt    3540
acatgagcgg tggcttgaca ggagatggag actctctttc ctggatgtga ggcaaggagg    3600
caggcgtctg agtcaggatg atgtccctac tcactgctaa agagaaaagt ggctttgatg    3660
gtgcagggca gggaaatgca ctgagtggtc gccaccctca cagaagagaa agtgttcact    3720
gacctggcct ttccccaggg cctctccctc ccattgcttt ccagaaagcc atgatttttg    3780
agagccacac ctgaacactc acaaacatta tggtgggaaa agcagatcag agcattaggc    3840
aagttgcatt accttggcct tcttcctttg gagacaattg atgtggggtt ctagattgac    3900
ccagagtttc aagtttatcc tgattcaggc ttcaacagct ggaggaagaa acagagatgt    3960
tttttgaagt aaacagatct agcattacta atcaacccct catactgatg acctatggga    4020
aataataccc aagggcagaa aaatgggcag aataagggga gccccaaacc aagacgaagc    4080
tgctgcccat tgagaccctg ggtattacag agacctatag ctctggataa tggaagatct    4140
atgagtggca caggcgctga ggaatcacag catcattatc gtgcatctgc agggaattgc    4200
ttgtaaatat actggtaatt acaaatgttt aaggtcacta caaatacttt ggagtgtatt    4260
aaatatgctt ctgataaaga ctgttttttct cacatgaaac aatgggaacc atgtgacaat    4320
cacagaggtg ttgttactat agcaaaaggg attgttactc tccacatccc tttaagtaac    4380
ttgaaggcct gatagaccca ccctctaaga cttcattaga cattccctac gaatggttat    4440
actctcctgt atactcccaa tacaactcta aaatatatta ttccatatag tccttaggtt    4500
tgtattaaag tttgacttt ttccttcaaa atatctcttg tcacaacagc ggctctagag    4560
agaaatacat tccctccagg caaatctatg ctgcgctggt ctgacctggg accctgggga    4620
cattgcccct gtgctgagtt actaagatga gccagccctg cagctgtgct cagcctgccc    4680
catgccctgc tgattgattt gcatgttcca gagcacagcc ccctgccctg aagactttt    4740 tatgggctgg tcgcaccctg tgcaggagtc agtctcagtc aggacacagc atggacatga    4800
gggtccccgc tcagctcctg gggctcctgc tactctggct ccgaggtaag gatggagaac    4860
actaggaatt tactcagcca gtgtgctcag tactgactgg aacttcaggg aagttctctg    4920
ataacatgat taatagtaag aatatttgtt tttatgtttc caatctcagg tgccagatgt    4980
gacatccaga tgacccagtc tccatcctcc ctgtctgcat ctgtaggaga cagagtcacc    5040
atcacttgcc gggcaagtca gagcattagc agctatttaa attggtatca gcagaaacca    5100
gggaaagccc ctaagctcct gatctatgct gcatccagtt tgcaaagtgg ggtcccatca    5160
```

```
aggttcagtg gcagtggatc tgggacagat ttcactctca ccatcagcag tctgcaacct    5220
gaagattttg caacttacta ctgtcaacag agttacagta cccctcccac agtgttacaa    5280
gtcataacat aaacctccaa ggaagcagat gtgtgaggac gagccacccc agatgctcct    5340
cctggtgcct ccatctgctg agagcatttc tcaaactcag tcaggttttg aaagtcattg    5400
ggagactttt gtagagggga ccagggaggc tcctctgaac tctaagcctc ttttgccccg    5460
gatccgatca ggaaaatagc aaccgagtga ctggactatt aaagcatccc ctctgtggag    5520
aaaaggacta tggcaacagc ttgccaccta taagagacaa atatgtcact cagctggatg    5580
ctgggtctac catgaccacc cttgagatga acttatgcca tgttttttgga tgcccactga    5640 gactttgctt tgaccaagga agttctttta ctgcccaaat gacgtcaatg acacactct    5700 catgggacat gatggatttt ccatacacct tgttatccaa aggccaatgg atctatttaa    5760
tgctagaaca gctgactcac acggcaactg aagagtgtac atcagggcaa cctgctagta    5820
gagtggtacc ccatctgact acagcaattg gacattaaac actgcactgc agagcaaggg    5880
aaagacggca cggaggtgca ggttgaaaaa cactgagttg agtgaggaag aagttgggca    5940
aggccagttt cctgatagag ctgccactgt gaaatcccaa actcagtgtt ccaatcatt    6000 ttttccttt tatagtgatg ttcttggggg tgttgcagtt taggccacca tgataaccca    6060
gacaggcctc ctaactctaa ttggatggaa tgattcccct gggtgccttc tatgggttcc    6120
acaggatcaa gaaatatcag ggtgttaatt tccttctgct ggtaggaggg tcatctgatt    6180
cctccattag ggtggatgac gttatcagac atgtcaattt tctacagtac ttgacctgcc    6240
ttctagaact ggacaaccga gggtgaaagg actggatcaa gcaacaatgg caatgggtgc    6300
ccaaagaggt agtagtctca gaacagggag agacagactg agtccctcca ctaactcagc    6360
ccaacacctg tggatgagta ggggatgcct gagatcctgg ggtggatggg aggtggggca    6420
ctgatctgtc aatctgcttt ttcttcaagg atcaggcagc agagacccag aagcttcatg    6480
tctttgtaag gctcttccaa gccaacacag ataatttgac aaaacactgt atctgcatcc    6540
cagacctcac cctgtcacag actgaagtgg ttgtttcatc ctactaaggg taaactatac    6600
cagctataca gaataaaaag actggatagt ttagaggatc acccaagaaa tagttctttg    6660
cctgcatgga caaaaccatc ttctgtcttt agggaaatgg tatcactacc ctgaggattt    6720
ggagcccagg tctcacttat ctgtgcagtt gtgaaagtcc tcacacccac agtgctgagg    6780
ttaattgaat gttactcttt taatttctgc aaagaatgag acagcttctg gaccctcagg    6840
aaagatcact aacaagtaaa tacaagtata tccggaagat aaagttgtaa tagactcttc    6900
ctttcaacct gatccatcat gcatttaggg agctgactgg gcacaagttg gagcagaaag    6960
agaaaaatga aaccacagcc ttctattttg tttctaacag acttgtacca aacattctgt    7020
ggctcaatct aggtgatggt gagacaagag gacacagggg ttaaattctg tggccgcagg    7080
ggagaagttc taccctcaga ctgagccaac ggccttttct ggcctgatca cctgggcatg    7140
ggctgctgag agcagaaagg ggaggcagat tgtctctgca gctgcaagcc cagcacccgc    7200
cccagctgct ttgcatgtcc ctcccagccg ccctgcagtc cagagcccat atcaatgcct    7260
gggtcagagc tctggagaag agctgctcag ttaggaccca gagggaacca tggaaacccc    7320
agcgcagctt ctcttcctcc tgctactctg gctcccaggt gaggggaaca tgggatggtt    7380
ttgcatgtca gtgaaaaccc tctcaagtcc tgttacctgg caactctgct cagtcaatac    7440
aataattaaa gctcaatata aagcaataat tctggctctt ctgggaagac aatgggtttg    7500
atttagatta catgggtgac ttttctgttt tatttccaat ctcagatacc accggagaaa    7560
```

-continued

```
ttgtgttgac gcagtctcca ggcaccctgt ctttgtctcc aggggaaaga gccaccctct    7620
cctgcagggc cagtcagagt gttagcagca gctacttagc ctggtaccag cagaaacctg    7680
gccaggctcc caggctcctc atctatggtg catccagcag ggccactggc atcccagaca    7740
ggttcagtgg cagtgggtct gggacagact tcactctcac catcagcaga ctggagcctg    7800
aagattttgc agtgtattac tgtcagcagt atggtagctc acctcccaca gtgattcagc    7860
ttgaaacaaa aacctctgca agaccttcat tgtttactag attataccag ctgcttcctt    7920
tacagatagc tgctgcaatg acaactcaat tttagcatct cttctctgct tgggcatttt    7980
ggggatctta aaaagtaat cccttgatat attttttgact ctgattcctg cattttttcct   8040
cagaccaaga tggacagcca ggtttaagca cagtttcaca gtaatggcca ctggatcaga    8100
tttacatcag tggatgtcag taaaggtccc aaccagagcc ataaggcaac aacaatagca    8160
acaaataatc aaaattggaa aagaagaatt aaagctgtca taattcactg atgaaggatt    8220
gtgtgcagat aaaattcaaa tttgtctaca gagaaactac taaaattgac atgagaaata    8280
gaaaatcatt agattcaaga tcaatttatt aattcataga ttcaaaaatc aatttcattt    8340
ctgcataata aaaatgcta aaaattaaca ttataaaaca aacacaccat ttacaaaaac    8400
atcaaagtat caattattta aaaaaaatag actaaataca ctgacgtctc cagaatatta    8460
ttttgaaaaa taaagaaaaa cctaagtaaa tagaaattca gttcaaagac tgaatgtctc    8520
agtactataa aaatgtcaat tcttcaaaga ttaaaatatt gattacatat aagaaaaatc    8580
aaaatcctaa agtatactcc aatttaaatt aagaagctaa tctaaatatt atatgggaat    8640
gtcaaggatg tagaatagcc acagtgaacc tgaagaaaca ccaaaatgag aacttccagt    8700
gcctgaatac ctggaatata gtgtgggtgg cagtatggtg atggtgagat cagaagttta    8760
aaaatttgca aacgtgctta ttttttggaaa taatcactac gcagatgtag ccaaaccctc    8820
ttcaactgtg gcgtacgcac ctgctcgaaa agggagttga gcttcagcag ctgacccagg    8880
actctgttcc cctttggtga aagggttttt tgttcagcaa gacaatggag agctctcact    8940
gtggtggacg ttcggccaag ggaccaaggt ggaaatcaaa cgtgagtaga atttaaactt    9000
tgcttcctca gttgtctgtg tcttctgttc cctgtgtcta tgaagtgatc tataagctga    9060
ctctgcaatc agcctctgat atccttcagg gaaaagataa agataagtct gtagtcaaac    9120
tcgagaattg attgcacatt ttctttgaag agcaagcaag attcagtcat tgggtgagaa    9180
taacttgtct aagtaatagc ttcagaaatg tcctggggaa cataacatgt tctggacaga    9240
gccttggtca attgtcagaa agggagtttt tgtataggag ggaagttaag aggaaccatt    9300
gtgtgtacac ttttggccag gggaccaagc tggagatcaa acgtaagtac ttttttccac    9360
tgattcttca ctgttgctaa ttagtttact ttgtgttcct ttgtgtggat tttcattagt    9420
cggatgccag ggatctaaca aacttcattc ccaggttagg tacagaggag gggaaattgt    9480
tccacaggaa gctagcttgt ggctaatttt taagatttct aaatcaaaat aacttcattg    9540
ggggaaagag gcttgctgag ctttcaggga ggttttttgta aagggaaaag ttaagacgaa    9600
tcactgtgat tcactttcgg ccctgggacc aaagtggata tcaaacgtaa gtacatctgt    9660
ctcaattatt cgtgagattt tagtgccatt gtatcatttg tgcaagtttt gtgatatttt    9720
ggttgaataa acctggtgac ccagaagtaa atagcaggac accagaaaat gaacttaaaa    9780
agctgagcaa atagacgaat cattgggttt gagaggagaa taggattcat gggggaaatg    9840
gggaagaaat agctagattt ttctctgaac aagcagccta tctcatatga ttggcttcaa    9900
```

-continued

```
gagaggtttt tgttgagggg aaagggtgag atccctcact gtggctcact ttcggcggag    9960
ggaccaaggt ggagatcaaa cgtaagtgca ctttcctaat gcttttcctt ataaggtttt   10020
aaatttggag cgtttttgtg tttgagatat tagctcaggt caattccaaa gagtaccaga   10080
ttctttcaaa aagtcagatg agtaagggat agaaaattag ttcatcttaa ggaacagcca   10140
agcgctagcc agttaagtga ggcatctcaa ttgcaagatt ttctctgcat cggtcaggtt   10200
agtgatatta acagcgaaaa gagattttttg ttaaggggaa agtaattaag ttaacactgt   10260
ggatcacctt cggccaaggg acacgactgg agattaaacg taagtaattt ttcactattg   10320
tcttctgaaa tttgggtctg atggccagta ttgacttttta gaggcttaaa taggagtttg   10380
gtaaagattg gtaaatgagg gcatttaaga tttgccatgg gttgcaaaag ttaaactcag   10440
cttcaaaaat ggatttggag aaaaaaagat taaattgctc taaactgaat gacacaaagt   10500
aaaaaaaaaa gtgtaactaa aaaggaaccc ttgtatttct aaggagcaaa agtaaattta   10560 ttttttgttca ctcttgccaa atattgtatt ggttgttgct gattatgcat gatacagaaa   10620
agtggaaaaa tacatttttt agtctttctc ccttttgttt gataaattat tttgtcagac   10680
aactataaaa atcaatagca cgccctaaga tctagatgca tgctcgagtg ccatttcatt   10740 acctcttttct ccgcacccga catagataaa gcttatcgat accgtcgacc tcagggggg   10800 gcccggtacc acgtggcata cagtgtcaga ttttctgttt atcaagctag tgagattagg   10860
ggcaaaa                                                              10867
```

<210> SEQ ID NO 84
<211> LENGTH: 23
<212> TYPE: DNA
<213> ORGANISM: Artificial
<220> FEATURE:
<223> OTHER INFORMATION: Synthetic

<400> SEQUENCE: 84
tcttttgccc cggatccgat cag                                              23

<210> SEQ ID NO 85
<211> LENGTH: 23
<212> TYPE: DNA
<213> ORGANISM: Artificial
<220> FEATURE:
<223> OTHER INFORMATION: Synthetic

<400> SEQUENCE: 85
gggaggctcc tctgaactct aag                                              23

<210> SEQ ID NO 86
<211> LENGTH: 21
<212> TYPE: DNA
<213> ORGANISM: Artificial
<220> FEATURE:
<223> OTHER INFORMATION: Synthetic

<400> SEQUENCE: 86
gtccagtcac tcggttgcta t                                                21

<210> SEQ ID NO 87
<211> LENGTH: 22
<212> TYPE: DNA
<213> ORGANISM: Artificial
<220> FEATURE:
<223> OTHER INFORMATION: Synthetic

<400> SEQUENCE: 87

-continued

```
<210> SEQ ID NO 88
<211> LENGTH: 21
<212> TYPE: DNA
<213> ORGANISM: Artificial
<220> FEATURE:
<223> OTHER INFORMATION: Synthetic

<400> SEQUENCE: 88
acgcagatgt agccaaaccc t                                              21

<210> SEQ ID NO 89
<211> LENGTH: 20
<212> TYPE: DNA
<213> ORGANISM: Artificial
<220> FEATURE:
<223> OTHER INFORMATION: Synthetic

<400> SEQUENCE: 89
cagctgctga agctcaactc                                                20

<210> SEQ ID NO 90
<211> LENGTH: 22
<212> TYPE: DNA
<213> ORGANISM: Artificial
<220> FEATURE:
<223> OTHER INFORMATION: Synthetic

<400> SEQUENCE: 90
aagaagcaca cgactgaggc ac                                             22

<210> SEQ ID NO 91
<211> LENGTH: 24
<212> TYPE: DNA
<213> ORGANISM: Artificial
<220> FEATURE:
<223> OTHER INFORMATION: Synthetic

<400> SEQUENCE: 91
ctcactggat ggtgggaaga tgga                                           24

<210> SEQ ID NO 92
<211> LENGTH: 16
<212> TYPE: DNA
<213> ORGANISM: Artificial
<220> FEATURE:
<223> OTHER INFORMATION: Synthetic

<400> SEQUENCE: 92
gtaaaacgac ggccag                                                    16

<210> SEQ ID NO 93
<211> LENGTH: 17
<212> TYPE: DNA
<213> ORGANISM: Artificial
<220> FEATURE:
<223> OTHER INFORMATION: Synthetic

<400> SEQUENCE: 93
caggaaacag ctatgac                                                   17

<210> SEQ ID NO 94
<211> LENGTH: 39
<212> TYPE: PRT
```
cttcaactgt ggcgtacgca cc                                             22

```
<213> ORGANISM: Artificial
<220> FEATURE:
<223> OTHER INFORMATION: Synthetic

<400> SEQUENCE: 94

Gln Pro Glu Asp Phe Ala Thr Tyr Tyr Cys Gln Gln Ser Tyr Ser Thr
1               5                   10                  15

Pro Tyr Thr Phe Gly Gln Gly Thr Lys Leu Glu Ile Lys Arg Ala Asp
            20                  25                  30

Ala Ala Pro Thr Val Ser Ile
            35

<210> SEQ ID NO 95
<211> LENGTH: 39
<212> TYPE: PRT
<213> ORGANISM: Artificial
<220> FEATURE:
<223> OTHER INFORMATION: Synthetic

<400> SEQUENCE: 95

Gln Pro Glu Asp Phe Ala Thr Tyr Tyr Cys Gln Gln Ser Tyr Ser Thr
1               5                   10                  15

Pro Phe Thr Phe Gly Pro Gly Thr Lys Val Asp Ile Lys Arg Ala Asp
            20                  25                  30

Ala Ala Pro Thr Val Ser Ile
            35

<210> SEQ ID NO 96
<211> LENGTH: 39
<212> TYPE: PRT
<213> ORGANISM: Artificial
<220> FEATURE:
<223> OTHER INFORMATION: Synthetic

<400> SEQUENCE: 96

Glu Pro Glu Asp Phe Ala Val Tyr Tyr Cys Gln Gln Tyr Gly Ser Ser
1               5                   10                  15

Pro Arg Thr Phe Gly Gln Gly Thr Lys Val Glu Ile Lys Arg Ala Asp
            20                  25                  30

Ala Ala Pro Thr Val Ser Ile
            35

<210> SEQ ID NO 97
<211> LENGTH: 38
<212> TYPE: PRT
<213> ORGANISM: Artificial
<220> FEATURE:
<223> OTHER INFORMATION: Synthetic

<400> SEQUENCE: 97

Glu Pro Glu Asp Phe Ala Val Tyr Tyr Cys Gln Gln Tyr Gly Ser Ser
1               5                   10                  15

Arg Thr Phe Gly Gln Gly Thr Lys Val Glu Ile Lys Arg Ala Asp Ala
            20                  25                  30

Ala Pro Thr Val Ser Ile
            35

<210> SEQ ID NO 98
<211> LENGTH: 39
<212> TYPE: PRT
<213> ORGANISM: Artificial
<220> FEATURE:
<223> OTHER INFORMATION: Synthetic
```

<400> SEQUENCE: 98

Glu Pro Glu Asp Phe Ala Val Tyr Tyr Cys Gln Gln Tyr Gly Ser Ser
1               5                   10                  15

Pro Trp Thr Phe Gly Gln Gly Thr Lys Val Glu Ile Lys Arg Ala Asp
            20                  25                  30

Ala Ala Pro Thr Val Ser Ile
        35

<210> SEQ ID NO 99
<211> LENGTH: 39
<212> TYPE: PRT
<213> ORGANISM: Artificial
<220> FEATURE:
<223> OTHER INFORMATION: Synthetic

<400> SEQUENCE: 99

Asp Pro Glu Asp Phe Ala Val Tyr Tyr Cys Gln Gln Tyr Gly Ser Ser
1               5                   10                  15

Pro Arg Thr Phe Gly Gln Gly Thr Lys Val Glu Ile Lys Arg Ala Asp
            20                  25                  30

Ala Ala Pro Thr Val Ser Ile
        35

<210> SEQ ID NO 100
<211> LENGTH: 39
<212> TYPE: PRT
<213> ORGANISM: Artificial
<220> FEATURE:
<223> OTHER INFORMATION: Synthetic

<400> SEQUENCE: 100

Glu Pro Glu Asp Phe Ala Val Tyr Tyr Cys Gln Gln Tyr Gly Ser Ser
1               5                   10                  15

Pro Arg Thr Phe Gly Gln Gly Thr Lys Val Glu Ile Lys Arg Ala Asp
            20                  25                  30

Ala Ala Pro Thr Val Ser Ile
        35

<210> SEQ ID NO 101
<211> LENGTH: 39
<212> TYPE: PRT
<213> ORGANISM: Artificial
<220> FEATURE:
<223> OTHER INFORMATION: Synthetic

<400> SEQUENCE: 101

Glu Pro Glu Asp Phe Ala Val Tyr Tyr Cys Gln Gln Tyr Gly Ser Ser
1               5                   10                  15

Pro Trp Thr Phe Gly Gln Gly Thr Lys Val Glu Ile Lys Arg Ala Asp
            20                  25                  30

Ala Ala Pro Thr Val Ser Ile
        35

<210> SEQ ID NO 102
<211> LENGTH: 39
<212> TYPE: PRT
<213> ORGANISM: Artificial
<220> FEATURE:
<223> OTHER INFORMATION: Synthetic

<400> SEQUENCE: 102

-continued

Glu Pro Glu Asp Phe Ala Val Tyr Tyr Cys Gln Gln Tyr Gly Ser Ser
1               5                   10                  15

Pro Pro Thr Phe Gly Gln Gly Thr Lys Val Glu Ile Lys Arg Ala Asp
            20                  25                  30

Ala Ala Pro Thr Val Ser Ile
        35

<210> SEQ ID NO 103
<211> LENGTH: 39
<212> TYPE: PRT
<213> ORGANISM: Artificial
<220> FEATURE:
<223> OTHER INFORMATION: Synthetic

<400> SEQUENCE: 103

Glu Pro Glu Asp Phe Ala Val Tyr Tyr Cys Gln Gln Tyr Gly Ser Ser
1               5                   10                  15

Pro Tyr Thr Phe Gly Gln Gly Thr Lys Leu Glu Ile Lys Arg Ala Asp
            20                  25                  30

Ala Ala Pro Thr Val Ser Ile
        35

<210> SEQ ID NO 104
<211> LENGTH: 39
<212> TYPE: PRT
<213> ORGANISM: Artificial
<220> FEATURE:
<223> OTHER INFORMATION: Synthetic

<400> SEQUENCE: 104

Glu Pro Glu Asp Phe Ala Val Tyr Tyr Cys Gln Gln Tyr Gly Ser Ser
1               5                   10                  15

Ile Phe Thr Phe Gly Pro Gly Thr Lys Val Asp Ile Lys Arg Ala Asp
            20                  25                  30

Ala Ala Pro Thr Val Ser Ile
        35

<210> SEQ ID NO 105
<211> LENGTH: 51
<212> TYPE: DNA
<213> ORGANISM: Artificial
<220> FEATURE:
<223> OTHER INFORMATION: Synthetic

<400> SEQUENCE: 105
caacttacta ctgtcaacag agttacagta cccctcccac agtgttacaa g         51

<210> SEQ ID NO 106
<211> LENGTH: 51
<212> TYPE: DNA
<213> ORGANISM: Artificial
<220> FEATURE:
<223> OTHER INFORMATION: Synthetic

<400> SEQUENCE: 106
caacttacta ctgtcaccat agtcacagta cccatcccac agtgttacaa g         51

<210> SEQ ID NO 107
<211> LENGTH: 51
<212> TYPE: DNA
<213> ORGANISM: Artificial
<220> FEATURE:
<223> OTHER INFORMATION: Synthetic

<400> SEQUENCE: 107
cttgtaacac tgtgggatgg gtactgtgac tatggtgaca gtagtaagtt g    51

<210> SEQ ID NO 108
<211> LENGTH: 41
<212> TYPE: DNA
<213> ORGANISM: Artificial
<220> FEATURE:
<223> OTHER INFORMATION: Synthetic

<400> SEQUENCE: 108
gcagtgtatt actgtcagca gtatggtagc tcacctccca c    41

<210> SEQ ID NO 109
<211> LENGTH: 60
<212> TYPE: DNA
<213> ORGANISM: Artificial
<220> FEATURE:
<223> OTHER INFORMATION: Synthetic

<400> SEQUENCE: 109
agattttgca gtgtattact gtcaccatca tggtcactca cctcccacag tgattcagct    60

<210> SEQ ID NO 110
<211> LENGTH: 60
<212> TYPE: DNA
<213> ORGANISM: Artificial
<220> FEATURE:
<223> OTHER INFORMATION: Synthetic

<400> SEQUENCE: 110
agattttgca gtgtattact gtcaccatca tggtcactca cctcccacag tgattcagct    60

<210> SEQ ID NO 111
<211> LENGTH: 18
<212> TYPE: DNA
<213> ORGANISM: Artificial
<220> FEATURE:
<223> OTHER INFORMATION: Synthetic

<400> SEQUENCE: 111
aacttactac tgtcacca    18

<210> SEQ ID NO 112
<211> LENGTH: 19
<212> TYPE: DNA
<213> ORGANISM: Artificial
<220> FEATURE:
<223> OTHER INFORMATION: Synthetic

<400> SEQUENCE: 112
cagcagtctg caacctgaa    19

<210> SEQ ID NO 113
<211> LENGTH: 18
<212> TYPE: DNA
<213> ORGANISM: Artificial
<220> FEATURE:
<223> OTHER INFORMATION: Synthetic

<400> SEQUENCE: 113
ggctcgtcct cacacatc    18

<210> SEQ ID NO 114
<211> LENGTH: 17

```
<212> TYPE: DNA
<213> ORGANISM: Artificial
<220> FEATURE:
<223> OTHER INFORMATION: Synthetic

<400> SEQUENCE: 114
ttactgtcac catcatg                                            17

<210> SEQ ID NO 115
<211> LENGTH: 19
<212> TYPE: DNA
<213> ORGANISM: Artificial
<220> FEATURE:
<223> OTHER INFORMATION: Synthetic

<400> SEQUENCE: 115
gcagactgga gcctgaaga                                          19

<210> SEQ ID NO 116
<211> LENGTH: 23
<212> TYPE: DNA
<213> ORGANISM: Artificial
<220> FEATURE:
<223> OTHER INFORMATION: Synthetic

<400> SEQUENCE: 116
aagctgaatc actgtgggag gtg                                     23

<210> SEQ ID NO 117
<211> LENGTH: 51
<212> TYPE: DNA
<213> ORGANISM: Artificial
<220> FEATURE:
<223> OTHER INFORMATION: Synthetic

<400> SEQUENCE: 117
caacttacta ctgtcaacag agttacagta cccctcccac agtgttacaa g      51

<210> SEQ ID NO 118
<211> LENGTH: 54
<212> TYPE: DNA
<213> ORGANISM: Artificial
<220> FEATURE:
<223> OTHER INFORMATION: Synthetic

<400> SEQUENCE: 118
attttgcaac ttactactgt caacatagtc acagtaccca tcccacagtg ttac   54

<210> SEQ ID NO 119
<211> LENGTH: 54
<212> TYPE: DNA
<213> ORGANISM: Artificial
<220> FEATURE:
<223> OTHER INFORMATION: Synthetic

<400> SEQUENCE: 119
gtaacactgt gggatgggta ctgtgactat gttgacagta gtaagttgca aaat   54

<210> SEQ ID NO 120
<211> LENGTH: 41
<212> TYPE: DNA
<213> ORGANISM: Artificial
<220> FEATURE:
<223> OTHER INFORMATION: Synthetic

<400> SEQUENCE: 120
```

```
gcagtgtatt actgtcagca gtatggtagc tcacctccca c                          41

<210> SEQ ID NO 121
<211> LENGTH: 56
<212> TYPE: DNA
<213> ORGANISM: Artificial
<220> FEATURE:
<223> OTHER INFORMATION: Synthetic

<400> SEQUENCE: 121
attttgcagt gtattactgt caccattatg gtcactcacc tcccacagtg attcag         56

<210> SEQ ID NO 122
<211> LENGTH: 56
<212> TYPE: DNA
<213> ORGANISM: Artificial
<220> FEATURE:
<223> OTHER INFORMATION: Synthetic

<400> SEQUENCE: 122
ctgaatcact gtgggaggtg agtgaccata atggtgacag taatacactg caaaat         56

<210> SEQ ID NO 123
<211> LENGTH: 19
<212> TYPE: DNA
<213> ORGANISM: Artificial
<220> FEATURE:
<223> OTHER INFORMATION: Synthetic

<400> SEQUENCE: 123
cttactactg tcaacatag                                                  19

<210> SEQ ID NO 124
<211> LENGTH: 19
<212> TYPE: DNA
<213> ORGANISM: Artificial
<220> FEATURE:
<223> OTHER INFORMATION: Synthetic

<400> SEQUENCE: 124
cagcagtctg caacctgaa                                                  19

<210> SEQ ID NO 125
<211> LENGTH: 18
<212> TYPE: DNA
<213> ORGANISM: Artificial
<220> FEATURE:
<223> OTHER INFORMATION: Synthetic

<400> SEQUENCE: 125
ggctcgtcct cacacatc                                                   18

<210> SEQ ID NO 126
<211> LENGTH: 17
<212> TYPE: DNA
<213> ORGANISM: Artificial
<220> FEATURE:
<223> OTHER INFORMATION: Synthetic

<400> SEQUENCE: 126
tactgtcacc attatgg                                                    17

<210> SEQ ID NO 127
<211> LENGTH: 19
<212> TYPE: DNA
<213> ORGANISM: Artificial
```

```
<220> FEATURE:
<223> OTHER INFORMATION: Synthetic

<400> SEQUENCE: 127
gcagactgga gcctgaaga                                                    19

<210> SEQ ID NO 128
<211> LENGTH: 23
<212> TYPE: DNA
<213> ORGANISM: Artificial
<220> FEATURE:
<223> OTHER INFORMATION: Synthetic

<400> SEQUENCE: 128
aagctgaatc actgtgggag gtg                                               23

<210> SEQ ID NO 129
<211> LENGTH: 22
<212> TYPE: DNA
<213> ORGANISM: Artificial
<220> FEATURE:
<223> OTHER INFORMATION: Synthetic

<400> SEQUENCE: 129
aagaagcaca cgactgaggc ac                                                22

<210> SEQ ID NO 130
<211> LENGTH: 22
<212> TYPE: DNA
<213> ORGANISM: Artificial
<220> FEATURE:
<223> OTHER INFORMATION: Synthetic

<400> SEQUENCE: 130
ggaagatgga tacagttggt gc                                                22

<210> SEQ ID NO 131
<211> LENGTH: 95
<212> TYPE: PRT
<213> ORGANISM: Artificial
<220> FEATURE:
<223> OTHER INFORMATION: Synthetic

<400> SEQUENCE: 131

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His His Tyr Gly His Ser
                85                  90                  95

<210> SEQ ID NO 132
<211> LENGTH: 96
<212> TYPE: PRT
<213> ORGANISM: Artificial
<220> FEATURE:
<223> OTHER INFORMATION: Synthetic
```

<400> SEQUENCE: 132

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 133
<211> LENGTH: 95
<212> TYPE: PRT
<213> ORGANISM: Artificial
<220> FEATURE:
<223> OTHER INFORMATION: Synthetic

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Ser His Ser Thr His
                85                  90                  95

<210> SEQ ID NO 134
<211> LENGTH: 95
<212> TYPE: PRT
<213> ORGANISM: Artificial
<220> FEATURE:
<223> OTHER INFORMATION: Synthetic

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 135
<211> LENGTH: 95

```
<212> TYPE: PRT
<213> ORGANISM: Artificial
<220> FEATURE:
<223> OTHER INFORMATION: Synthetic

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Ser His Ser Thr Lys
                85                  90                  95

<210> SEQ ID NO 136
<211> LENGTH: 506
<212> TYPE: DNA
<213> ORGANISM: Unknown
<220> FEATURE:
<223> OTHER INFORMATION: mammal

<400> SEQUENCE: 136
atggagtttg ggctgagctg gcttttctt gtggctattt taaaaggtaa ttcatggaga      60
aatagaaaaa ttgagtgtga atggataaga gtgagagaaa cagtggatac gtgtggcagt    120
ttctgaccag ggtttctttt tgtttgcagg tgtccagtgt gaggtgcagc tgttggagtc    180
tgggggaggc ttggtacagc ctggggggtc cctgagactc tcctgtgcag cctctggatt    240
cacctttagc aactctccaa tgagctgggt ccgccaggct ccagggaagg gctggagtg     300 ggtctcagct attagtggta gtggtagtaa cacattctac gcagactccg tgaagggccg    360
gttcaccatc tccagagaca attccaagaa cacgctgcat ctgcaagtga acagcctgag    420
agccgacgac acggccgtat attactgtgc gaaaggttac tactttgact actggggcca    480
gggaaccctg gtcaccgtct cctcag                                         506

<210> SEQ ID NO 137
<211> LENGTH: 134
<212> TYPE: PRT
<213> ORGANISM: Unknown
<220> FEATURE:
<223> OTHER INFORMATION: mammal

<400> SEQUENCE: 137

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Ser Pro Met Ser Trp Val Arg Gln Ala Pro Gly Lys Gly Leu
    50                  55                  60

Glu Trp Val Ser Ala Ile Ser Gly Ser Gly Ser Asn Thr Phe Tyr Ala
65                  70                  75                  80

Asp Ser Val Lys Gly Arg Phe Thr Ile Ser Arg Asp Asn Ser Lys Asn
```

```
                85                  90                  95
Thr Leu His Leu Gln Val Asn Ser Leu Arg Ala Asp Asp Thr Ala Val
            100                 105                 110
Tyr Tyr Cys Ala Lys Gly Tyr Tyr Phe Asp Tyr Trp Gly Gln Gly Thr
        115                 120                 125
Leu Val Thr Val Ser Ser
    130
```

<210> SEQ ID NO 138
<211> LENGTH: 263
<212> TYPE: DNA
<213> ORGANISM: Mus musculus

<400> SEQUENCE: 138

```
catctacagc atctgtctag gggttacaaa aagtctatgg gatacaattc ctcagaaagg    60
aataggattt ggacctgagc atactgctgc ctaacacatg aaatggcagt tcttctccag   120
ctggactagg tccttaacta agaaatgcac tgctcatgaa tatgcaaatt acccaagtct   180
atggcagtaa atacagagat gtccacaccc tgaagacaac ctatggccaa tgtcctctcc   240
acagtccctg aagacactga ttc                                           263
```

<210> SEQ ID NO 139
<211> LENGTH: 2239
<212> TYPE: DNA
<213> ORGANISM: Homo sapiens

<400> SEQUENCE: 139

```
ggtgtgtcct tccaagtatc cctgcccttc cttcaggtgt gatgctgatc catgcatctt    60
cctcccattc ctgggtagag ggtctccttg ttctttcccc aatcttctcc cagcagccac   120
tatgtcttcc cactgatgtc ttcagcttcc tcttttctgc ccttcccagc agatgagtct   180
gttattcctg agggaagaga gaggaggtgg gagatgaggc tttattcctg aaagaatgga   240
cagagctttg gagcttttct tcttctacc ccagtttcta cgagttcctc cagtgcctgt   300
aacacagagc tgtcagtggc tttgcccctg catgttaatt ctttggtcat gtagtggtgg   360
tgagggagct gggtctggat gcatttcagc cacagctgct gttccacttc cccacacaga   420
accgtctcag gaggaagagg ttggagattt ttctgatgtg tcctcaatcc tgggagaaaa   480
gttttcaata gcaataggaa tctctcagtt gtatgtccgc tgagaattta acaataact   540 tctttataat actaaatttt aaacaatcca atgaatatat ctaatttaat tttttattag   600
cttatgtgac atttgctggc ctctccccca gataaggtca tattctcttc ctgtttgttc   660
ctgcaagtca ctgaatttca caagatgtaa ggtctcttga ttatactata acatcaataa   720
tctggtgtac taaagaaaat gtgctaattt gcagcttact aaaattagtt gttttagtaa   780
aaataatata tttgttatag catgcctaca tctccaggct gagtagaagc tttgtttgta   840
atactcagaa actgcaaata acacacatat taaggagctt tctaaataaa tactatgggt   900
gaattcttta actggaatac tgttcctcat tagaatcaac acattcttta tacacaacca   960
aattactgac tcacaagtaa ttatactgag caagaagcca cacaaatgaa attgaaaata  1020
taagatttca ctttaacaaa atcttgaaaa atagatctga attaacaaag atgagaggtt  1080
gactcagtat ggtgagaggg aaataatggg gaggcaggaa tgagaggaac acagggaggc  1140
ttttaactgt aatcatcgtt atctcgattg ttatttggga tacacaggtg agcacacgtg  1200
aaattacgtt ttttttcctt cggagacatg gttttgcttt gtcgtccagg ctggagctcc  1260
```

```
gtggtgagat catagctctc tgcagcctca gaccctgggt ctccagcaat cctcctccct    1320
ctgccctatg tagctgggac tacaggtgtg caccaccatg ctcggcttca gtgcgtatta    1380
aaccgcacac ttcaattatg cagtatttat tatatagcaa taatgcctca ataagggtat    1440
tacaaataag tggatagata atttgttaaa gattgatgga aagatagata ccaacatgag    1500
aaatgtatga cactcaagaa aataaaactg taggaaactt gcttttcttt atatttgtta    1560
ggtaatcacc acagtgtgta cacatcacac catgttccca ttacagagaa aaggttctgc    1620
gaacctcacg agctgtgacc cctgtgtgct gggcttggtt cagggagaag tcaggtccag    1680
tggtgagaag cacaggccca gatgcccagg ctcactctga ccaaaagtga gcactgggga    1740
cattgtaaaa cccacctgtg cttttgctga taattttca tctttaacat ggaaataata    1800
ttgatactat ataccatggt ttctctgcgt atgtaaaaat aaaagatgat tggtgctaac    1860
tttaaaaata tgcagtttat gtagatctat ggtacctcaa taaaactgtt ttaaaataaa    1920
aattacaaaa ttataagatt tttaggtttt aaggtttaag tttatcacaa aacaaactga    1980
caataggaaa gcacaatttc ccaatgcttt caatatcaca gatctccccg aggacattct    2040
gacatgctct gagccccact atctccaaag gcctctcacc ccagagctta ctatatagta    2100
ggagatatgc aaatagagcc ctccgtctgc tgatgaaaac cagcccagcc ctgaccctgc    2160
agctctgaga gaggagccca gccctgggat tttcaggtgt tttcatttgg tgatcaggac    2220
tgaacagaga gaactcacc                                                 2239

<210> SEQ ID NO 140
<211> LENGTH: 200
<212> TYPE: DNA
<213> ORGANISM: Homo sapiens

<400> SEQUENCE: 140
gtgagtcctc acaacctctc tcctgcttta actctgaagg gttttgctgc atttttgggg     60
ggaaataagg gtgctgggtc tcctgccaag agagccccgg agcagcctgg ggggctcagg    120
aggatgccct gaggcaacag cggccacaca gacgaggggc aagggctcca gatgctcctt    180
cctcctgagc ccagcagcac                                                200

<210> SEQ ID NO 141
<211> LENGTH: 255
<212> TYPE: DNA
<213> ORGANISM: Mus musculus

<400> SEQUENCE: 141
ctgagcattg cagactaatc ttggatattt gtccctgagg gagccggctg agagaagttg     60
ggaaataaac tgtctaggga tctcagagcc tttaggacag attatctcca catctttgaa    120
aaactaagaa tctgtgtgat ggtgttggtg gagtccctgg atgatgggat agggactttg    180
gaggctcatt tgaagaagat gctaaaacaa tcctatggct ggagggatag ttggggctgt    240
agttggagat tttca                                                     255

<210> SEQ ID NO 142
<211> LENGTH: 4798
<212> TYPE: DNA
<213> ORGANISM: Unknown
<220> FEATURE:
<223> OTHER INFORMATION: mammal

<400> SEQUENCE: 142
ctcgagcatc tacagcatct gtctaggggt tacaaaaagt ctatgggata caattcctca     60
```

```
gaaaggaata ggatttggac ctgagcatac tgctgcctaa cacatgaaat ggcagttctt      120
ctccagctgg actaggtcct taactaagaa atgcactgct catgaatatg caaattaccc      180
aagtctatgg cagtaaatac agagatgtcc acaccctgaa gacaacctat ggccaatgtc      240
ctctccacag tccctgaaga cactgattct aactataacg gtcctaaggt agcgatcgag      300
tgccatttca ttacctcttt ctccgcaccc gacatagatg catctgcaga attcgccctt      360
ggggtaccga aaccttgcgc tcgttcgcca gccaggacag aaatgcctcg acttcgctgc      420
tgcccaaggt tgccgggtga cgcacaccgt ggaaacggat gaaggcacga acccagtgga      480
cataagcctg ttcggttcgt aagctgtaat gcaagtagcg tatgcgctca cgcaactggt      540
ccagaacctt gaccgaacgc agcggtggta acggcgcagt ggcggttttc atggcttgtt      600
atgactgttt ttttggggta cagtctatgc ctcgggcatc caagcagcaa gcgcgttacg      660
ccgtgggtcg atgtttgatg ttatggagca gcaacgatgt tacgcagcag ggcagtcgcc      720
ctaaaacaaa gttaaacatc atgagggaag cggtgatcgc cgaagtatcg actcaactat      780
cagaggtagt tggcgtcatc gagcgccatc tcgaaccgac gttgctggcc gtacatttgt      840
acggctccgc agtggatggc ggcctgaagc cacacagtga tattgatttg ctggttacgg      900
tgaccgtaag gcttgatgaa acaacgcggc gagctttgat caacgacctt ttggaaactt      960
cggcttcccc tggagagagc gagattctcc gcgctgtaga agtcaccatt gttgtgcacg     1020
acgacatcat tccgtggcgt tatccagcta agcgcgaact gcaatttgga gaatggcagc     1080
gcaatgacat tcttgcaggt atcttcgagc cagccacgat cgacattgat ctggctatct     1140
tgctgacaaa agcaagagaa catagcgttg ccttggtagg tccagcggcg gaggaactct     1200
ttgatccggt tcctgaacag gatctatttg aggcgctaaa tgaaaaccta acgctatgga     1260
actcgccgcc cgactgggct ggcgatgagc gaaatgtagt gcttacgttg tcccgcattt     1320
ggtacagcgc agtaaccggc aaaatcgcgc cgaaggatgt cgctgccgac tgggcaatgg     1380
agcgcctgcc ggcccagtat cagcccgtca tacttgaagc tagacaggct tatcttggac     1440
aagaagaaga tcgcttggcc tcgcgcgcag atcagttgga agaatttgtc cactacgtga     1500
aaggcgagat caccaaggta gtcggcaaat aatgtctcct aggcacgaag ggcgaattcc     1560
agcacactgg cggccgttac tagtggcgcg ccggtgtgtc cttccaagta tccctgccct     1620
tccttcaggt gtgatgctga tccatgcatc ttcctcccat tcctgggtag agggtctcct     1680
tgttctttcc ccaatcttct cccagcagcc actatgtctt cccactgatg tcttcagctt     1740
cctcttttct gcccttccca gcagatgagt ctgttattcc tgagggaaga gagaggaggt     1800
gggagatgag gctttattcc tgaaagaatg gacagagctt tggagctttt ctttcttcta     1860
ccccagtttc tacgagttcc tccagtgcct gtaacacaga gctgtcagtg gctttgcccc     1920
tgcatgttaa ttcttttggtc atgtagtggt ggtgagggag ctgggtctgg atgcatttca     1980
gccacagctg ctgttccact tccccacaca gaaccgtctc aggaggaaga ggttggagat     2040
ttttctgatg tgtcctcaat cctgggagaa aagttttcaa tagcaatagg aatctctcag     2100
ttgtatgtcc gctgagaatt taaacaataa cttctttata atactaaatt ttaaacaatc     2160
caatgaatat atctaattta attttttatt agcttatgtg acatttgctg gcctctcccc     2220
cagataaggt catattctct tcctgttttgt tcctgcaagt cactgaattt cacaagatgt     2280
aaggtctctt gattatacta taacatcaat aatctggtgt actaaagaaa atgtgctaat     2340
ttgcagctta ctaaaattag ttgttttagt aaaaataata tatttgttat agcatgccta     2400
```

-continued

```
catctccagg ctgagtagaa gctttgtttg taatactcag aaactgcaaa taacacacat  2460
attaaggagc tttctaaata aatactatgg gtgaattctt taactggaat actgttcctc  2520
attagaatca acacattctt tatacacaac caaattactg actcacaagt aattatactg  2580
agcaagaagc cacacaaatg aaattgaaaa tataagattt cactttaaca aaatcttgaa  2640
aaatagatct gaattaacaa agatgagagg ttgactcagt atggtgagag ggaaataatg  2700
gggaggcagg aatgagagga acacagggag gcttttaact gtaatcatcg ttatctcgat  2760
tgttattttg gatacacagg tgagcacacg tgaaattacg ttttttttcc ttcggagaca  2820
tggttttgct ttgtcgtcca ggctggagct ccgtggtgag atcatagctc tctgcagcct  2880
cagaccctgg gtctccagca atcctcctcc ctctgcccta tgtagctggg actacaggtg  2940
tgcaccacca tgctcggctt cagtgcgtat taaaccgcac acttcaatta tgcagtattt  3000
attatatagc aataatgcct caataagggt attacaaata agtggataga taatttgtta  3060
aagattgatg gaaagataga taccaacatg agaaatgtat gacactcaag aaaataaaac  3120
tgtaggaaac ttgcttttct ttatatttgt taggtaatca ccacagtgtg tacacatcac  3180
accatgttcc cattacagag aaaaggttct gcgaacctca cgagctgtga cccctgtgtg  3240
ctgggcttgg ttcagggaga agtcaggtcc agtggtgaga agcacaggcc cagatgccca  3300
ggctcactct gaccaaaagt gagcactggg gacattgtaa aacccacctg tgcttttgct  3360
gataattttt catctttaac atggaaataa tattgatact atataccatg gtttctctgc  3420
gtatgtaaaa ataaaagatg attggtgcta actttaaaaa tatgcagttt atgtagatct  3480
atggtacctc aataaaactg ttttaaaata aaaattacaa aattataaga ttttttaggtt  3540
ttaaggttta agtttatcac aaaacaaact gacaatagga aagcacaatt tcccaatgct  3600
ttcaatatca cagatctccc cgaggacatt ctgacatgct ctgagcccca ctatctccaa  3660
aggcctctca ccccagagct tactatatag taggagatat gcaaatagag ccctccgtct  3720
gctgatgaaa accagcccag ccctgaccct gcagctctga gagaggagcc cagccctggg  3780
attttcaggt gttttcattt ggtgatcagg actgaacaga gagaactcac catggagttt  3840
gggctgagct ggcttttcct tgtggctatt ttaaaaggta attcatggag aaatagaaaa  3900
attgagtgtg aatggataag agtgagagaa acagtggata cgtgtggcag tttctgacca  3960
gggtttcttt ttgtttgcag gtgtccagtg tgaggtgcag ctgttggagt ctgggggagg  4020
cttggtacag cctgggggt ccctgagact ctcctgtgca gcctctggat tcacctttag   4080
caactctcca atgagctggg tccgccaggc tccaggaaag gggctggagt gggtctcagc  4140
tattagtggt agtggtagta acacattcta cgcagactcc gtgaagggcc ggttcaccat  4200
ctccagagac aattccaaga acacgctgca tctgcaagtg aacagcctga gagccgacga  4260
cacggccgta tattactgtg cgaaaggtta ctactttgac tactggggcc agggaaccct  4320
ggtcaccgtc tcctcaggtg agtcctcaca acctctctcc tgctttaact ctgaagggtt  4380
ttgctgcatt tttgggggga ataagggtg ctgggtctcc tgccaagaga gccccggagc   4440
agcctggggg gctcaggagg atgccctgag gcaacagcgg ccacacagac gaggggcaag  4500
ggctccagat gctccttcct cctgagccca gcagcacctg agcattgcag actaatcttg  4560
gatatttgtc cctgagggag ccggctgaga gaagttggga aataaactgt ctagggatct  4620
cagagccttt aggacagatt atctccacat cttttgaaaaa ctaagaatct gtgtgatggt  4680
gttggtggag tccctggatg atgggatagg gactttggag gctcatttga agaagatgct  4740
aaaacaatcc tatggctgga gggatagttg gggctgtagt tggagatttt cactcgag    4798
```

<210> SEQ ID NO 143
<211> LENGTH: 8
<212> TYPE: PRT
<213> ORGANISM: Unknown
<220> FEATURE:
<223> OTHER INFORMATION: mammal

<400> SEQUENCE: 143

Ala Lys Gly Tyr Tyr Phe Asp Tyr
1               5

<210> SEQ ID NO 144
<211> LENGTH: 5
<212> TYPE: PRT
<213> ORGANISM: Unknown
<220> FEATURE:
<223> OTHER INFORMATION: mammal

<400> SEQUENCE: 144

Asp Tyr Ser Asn Tyr
1               5

<210> SEQ ID NO 145
<211> LENGTH: 445
<212> TYPE: DNA
<213> ORGANISM: Unknown
<220> FEATURE:
<223> OTHER INFORMATION: mammal

<400> SEQUENCE: 145

```
ctcgagccac catggagttc gggctgtcct ggcttttcct tgtggccatt ctgaagggtg     60
tgcaatgtga agtgcagttg ctggagtccg gggggggcct tgtgcagcct ggaggatcac    120
tccggctgag ctgcgcagcc agtggtttca cgttcagtag ttatgctatg tcttgggtgc    180
gccaggcccc tggtaagggg ctggaatggg tgtcagctat ttccggcagc ggcggatcta    240
cttattacgc tgatagcgtg aagggacgct tcacaatctc tcgggacaac tccaaaaaca    300
ccctctatct tcagatgaat agcctccgcg ctgaggacac cgctgtttat tactgcgcca    360
aaaccacagt gacatactac tactattatg gcatggacgt ctggggtcag ggaacaaccg    420
tcaccgtgtc cagcgcctga agagc                                         445
```

<210> SEQ ID NO 146
<211> LENGTH: 448
<212> TYPE: DNA
<213> ORGANISM: Unknown
<220> FEATURE:
<223> OTHER INFORMATION: mammal

<400> SEQUENCE: 146

```
ctcgagccac catggagttc gggctgtcct ggcttttcct tgtggccatt ctgaagggtg     60
tgcaatgtga agtgcagttg ctggagtccg gggggggcct tgtgcagcct ggaggatcac    120
tccggctgag ctgcgcagcc agtggtttca cgttcagtag ttatgctatg tcttgggtgc    180
gccaggcccc tggtaagggg ctggaatggg tgtcagctat ttccggcagc ggcggatcta    240
cttattacgc tgatagcgtg aagggacgct tcacaatctc tcgggacaac tccaaaaaca    300
ccctctatct tcagatgaat agcctccgcg ctgaggacac cgctgtttat tactgcgcca    360
aagattattc aaattactac tactactatt atggcatgga cgtctggggt cagggaacaa    420
ccgtcaccgt gtccagcgcc tgaagagc                                      448
```

<210> SEQ ID NO 147
<211> LENGTH: 430
<212> TYPE: DNA
<213> ORGANISM: Unknown
<220> FEATURE:
<223> OTHER INFORMATION: mammal

<400> SEQUENCE: 147

```
ctcgagccac catggagttc gggctgtcct ggcttttct tgtggccatt ctgaagggtg      60
tgcaatgtga agtgcagttg ctggagtccg ggggggcct tgtgcagcct ggaggatcac     120
tccggctgag ctgcgcagcc agtggtttca cgttcagtag ttatgctatg tcttgggtgc    180
gccaggcccc tggtaagggg ctggaatggg tgtcagctat ttccggcagc ggcggatcta    240
cttattacgc tgatagcgtg aagggacgct tcacaatctc tcgggacaac tccaaaaaca    300
ccctctatct tcagatgaat agcctccgcg ctgaggacac cgctgtttat tactgcgcca    360
aaaccacagt gacatacttt gattactggg gacagggac cctcgtcacc gtctcttctg    420
cctgaagagc                                                           430
```

<210> SEQ ID NO 148
<211> LENGTH: 433
<212> TYPE: DNA
<213> ORGANISM: Unknown
<220> FEATURE:
<223> OTHER INFORMATION: mammal

<400> SEQUENCE: 148

```
ctcgagccac catggagttc gggctgtcct ggcttttct tgtggccatt ctgaagggtg      60
tgcaatgtga agtgcagttg ctggagtccg ggggggcct tgtgcagcct ggaggatcac     120
tccggctgag ctgcgcagcc agtggtttca cgttcagtag ttatgctatg tcttgggtgc    180
gccaggcccc tggtaagggg ctggaatggg tgtcagctat ttccggcagc ggcggatcta    240
cttattacgc tgatagcgtg aagggacgct tcacaatctc tcgggacaac tccaaaaaca    300
ccctctatct tcagatgaat agcctccgcg ctgaggacac cgctgtttat tactgcgcca    360
aagattattc aaattactac tttgattact ggggacaggg gaccctcgtc accgtctctt    420
ctgcctgaag agc                                                       433
```

<210> SEQ ID NO 149
<211> LENGTH: 141
<212> TYPE: PRT
<213> ORGANISM: Unknown
<220> FEATURE:
<223> OTHER INFORMATION: mammal

<400> SEQUENCE: 149

```
Met Glu Phe Gly Leu Ser Trp Leu Phe Leu Val Ala Ile Leu Lys Gly
 1               5                  10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95
```

```
Thr Leu Tyr Leu Gln Met Asn Ser Leu Arg Ala Glu Asp Thr Ala Val
            100                 105                 110

Tyr Tyr Cys Ala Lys Thr Thr Val Thr Tyr Tyr Tyr Tyr Gly Met
            115                 120                 125

Asp Val Trp Gly Gln Gly Thr Thr Val Thr Val Ser Ser
            130                 135                 140

<210> SEQ ID NO 150
<211> LENGTH: 140
<212> TYPE: PRT
<213> ORGANISM: Unknown
<220> FEATURE:
<223> OTHER INFORMATION: mammal

<400> SEQUENCE: 150

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Asp Tyr Ser Asn Tyr Tyr Tyr Tyr Tyr Gly
            115                 120                 125

Met Asp Val Trp Gly Gln Gly Thr Thr Val Thr Val
        130                 135                 140

<210> SEQ ID NO 151
<211> LENGTH: 17
<212> TYPE: DNA
<213> ORGANISM: Unknown
<220> FEATURE:
<223> OTHER INFORMATION: mammal

<400> SEQUENCE: 151
tgcggccgat cttagcc                                                17

<210> SEQ ID NO 152
<211> LENGTH: 21
<212> TYPE: DNA
<213> ORGANISM: unknown
<220> FEATURE:
<223> OTHER INFORMATION: mammal

<400> SEQUENCE: 152
acgagcgggt tcggcccatt c                                           21

<210> SEQ ID NO 153
<211> LENGTH: 18
<212> TYPE: DNA
<213> ORGANISM: unknown
<220> FEATURE:
<223> OTHER INFORMATION: mammal
```

<400> SEQUENCE: 153
ttgaccgatt ccttgcgg					18

<210> SEQ ID NO 154
<211> LENGTH: 20
<212> TYPE: DNA
<213> ORGANISM: unknown
<220> FEATURE:
<223> OTHER INFORMATION: mammal

<400> SEQUENCE: 154
tcaggtgtga tgctgatcca					20

<210> SEQ ID NO 155
<211> LENGTH: 25
<212> TYPE: DNA
<213> ORGANISM: unknown
<220> FEATURE:
<223> OTHER INFORMATION: mammal

<400> SEQUENCE: 155
tgcatcttcc tcccattcct gggta					25

<210> SEQ ID NO 156
<211> LENGTH: 20
<212> TYPE: DNA
<213> ORGANISM: unknown
<220> FEATURE:
<223> OTHER INFORMATION: mammal

<400> SEQUENCE: 156
tggctgctgg gagaagattg					20

<210> SEQ ID NO 157
<211> LENGTH: 18
<212> TYPE: DNA
<213> ORGANISM: Unknown
<220> FEATURE:
<223> OTHER INFORMATION: mammal

<400> SEQUENCE: 157
cccagcagcc actatgtc					18

<210> SEQ ID NO 158
<211> LENGTH: 25
<212> TYPE: DNA
<213> ORGANISM: Unknown
<220> FEATURE:
<223> OTHER INFORMATION: mammal

<400> SEQUENCE: 158
tcccactgat gtcttcagct tcctc					25

<210> SEQ ID NO 159
<211> LENGTH: 23
<212> TYPE: DNA
<213> ORGANISM: Unknown
<220> FEATURE:
<223> OTHER INFORMATION: mammal

<400> SEQUENCE: 159
ccctcaggaa taacagactc atc					23

<210> SEQ ID NO 160
<211> LENGTH: 19

```
<212> TYPE: DNA
<213> ORGANISM: Unknown
<220> FEATURE:
<223> OTHER INFORMATION: mammal

<400> SEQUENCE: 160
aagggccggt tcaccatct                                                  19

<210> SEQ ID NO 161
<211> LENGTH: 26
<212> TYPE: DNA
<213> ORGANISM: Unknown
<220> FEATURE:
<223> OTHER INFORMATION: mammal

<400> SEQUENCE: 161
ccagagacaa ttccaagaac acgctg                                          26

<210> SEQ ID NO 162
<211> LENGTH: 18
<212> TYPE: DNA
<213> ORGANISM: Unknown
<220> FEATURE:
<223> OTHER INFORMATION: mammal

<400> SEQUENCE: 162
cggctctcag gctgttca                                                   18

<210> SEQ ID NO 163
<211> LENGTH: 20
<212> TYPE: DNA
<213> ORGANISM: Unknown
<220> FEATURE:
<223> OTHER INFORMATION: mammal

<400> SEQUENCE: 163
gcagcctctg gattcacctt                                                 20

<210> SEQ ID NO 164
<211> LENGTH: 24
<212> TYPE: DNA
<213> ORGANISM: Unknown
<220> FEATURE:
<223> OTHER INFORMATION: mammal

<400> SEQUENCE: 164
agcaactctc caatgagctg ggtc                                            24

<210> SEQ ID NO 165
<211> LENGTH: 21
<212> TYPE: DNA
<213> ORGANISM: Unknown
<220> FEATURE:
<223> OTHER INFORMATION: mammal

<400> SEQUENCE: 165
tcacggagtc tgcgtagaat g                                               21

<210> SEQ ID NO 166
<211> LENGTH: 20
<212> TYPE: DNA
<213> ORGANISM: Unknown
<220> FEATURE:
<223> OTHER INFORMATION: mammal

<400> SEQUENCE: 166
```
ctcagtgatt ctggccctgc                                           20

<210> SEQ ID NO 167
<211> LENGTH: 32
<212> TYPE: DNA
<213> ORGANISM: Unknown
<220> FEATURE:
<223> OTHER INFORMATION: mammal

<400> SEQUENCE: 167
tgctccacag ctacaaaccc cttcctataa tg                              32

<210> SEQ ID NO 168
<211> LENGTH: 21
<212> TYPE: DNA
<213> ORGANISM: Unknown
<220> FEATURE:
<223> OTHER INFORMATION: mammal

<400> SEQUENCE: 168
ggatgatggc tcagcacaga g                                         21

<210> SEQ ID NO 169
<211> LENGTH: 19
<212> TYPE: DNA
<213> ORGANISM: Unknown
<220> FEATURE:
<223> OTHER INFORMATION: mammal

<400> SEQUENCE: 169
ggtggagagg ctattcggc                                            19

<210> SEQ ID NO 170
<211> LENGTH: 23
<212> TYPE: DNA
<213> ORGANISM: Unknown
<220> FEATURE:
<223> OTHER INFORMATION: mammal

<400> SEQUENCE: 170
tgggcacaac agacaatcgg ctg                                       23

<210> SEQ ID NO 171
<211> LENGTH: 17
<212> TYPE: DNA
<213> ORGANISM: Unknown
<220> FEATURE:
<223> OTHER INFORMATION: mammal

<400> SEQUENCE: 171
gaacacggcg gcatcag                                              17

<210> SEQ ID NO 172
<211> LENGTH: 23
<212> TYPE: DNA
<213> ORGANISM: Unknown
<220> FEATURE:
<223> OTHER INFORMATION: mammal

<400> SEQUENCE: 172
ggtgtgcgat gtaccctctg aac                                       23

<210> SEQ ID NO 173
<211> LENGTH: 32
<212> TYPE: DNA
<213> ORGANISM: Unknown

```
<220> FEATURE:
<223> OTHER INFORMATION: mammal

<400> SEQUENCE: 173
ctaaaaatgc tacacctggg gcaaaacacc tg                                  32

<210> SEQ ID NO 174
<211> LENGTH: 25
<212> TYPE: DNA
<213> ORGANISM: Unknown
<220> FEATURE:
<223> OTHER INFORMATION: mammal

<400> SEQUENCE: 174
tgtggcagtt taatccagct ttatc                                          25

<210> SEQ ID NO 175
<211> LENGTH: 28
<212> TYPE: DNA
<213> ORGANISM: Unknown
<220> FEATURE:
<223> OTHER INFORMATION: mammal

<400> SEQUENCE: 175
gatgggaaga gactggtaac atttgtac                                       28

<210> SEQ ID NO 176
<211> LENGTH: 27
<212> TYPE: DNA
<213> ORGANISM: Unknown
<220> FEATURE:
<223> OTHER INFORMATION: mammal

<400> SEQUENCE: 176
cctccactgt gttaatggct gccacaa                                        27

<210> SEQ ID NO 177
<211> LENGTH: 26
<212> TYPE: DNA
<213> ORGANISM: Unknown
<220> FEATURE:
<223> OTHER INFORMATION: mammal

<400> SEQUENCE: 177
ttcctctatt tcactctttg aggctc                                         26

<210> SEQ ID NO 178
<211> LENGTH: 20
<212> TYPE: DNA
<213> ORGANISM: Unknown
<220> FEATURE:
<223> OTHER INFORMATION: mammal

<400> SEQUENCE: 178
tggtcacctc caggagcctc                                                20

<210> SEQ ID NO 179
<211> LENGTH: 30
<212> TYPE: DNA
<213> ORGANISM: Unknown
<220> FEATURE:
<223> OTHER INFORMATION: mammal

<400> SEQUENCE: 179
agtctctgct tcccccttgt ggctatgagc                                     30
```

```
<210> SEQ ID NO 180
<211> LENGTH: 21
<212> TYPE: DNA
<213> ORGANISM: Unknown
<220> FEATURE:
<223> OTHER INFORMATION: mammal

<400> SEQUENCE: 180
gctgcagggt gtatcaggtg c                                              21

<210> SEQ ID NO 181
<211> LENGTH: 17
<212> TYPE: DNA
<213> ORGANISM: Unknown
<220> FEATURE:
<223> OTHER INFORMATION: mammal

<400> SEQUENCE: 181
gccatgcaag gccaagc                                                   17

<210> SEQ ID NO 182
<211> LENGTH: 24
<212> TYPE: DNA
<213> ORGANISM: Unknown
<220> FEATURE:
<223> OTHER INFORMATION: mammal

<400> SEQUENCE: 182
ccaggaaaat gctgccagag cctg                                           24

<210> SEQ ID NO 183
<211> LENGTH: 24
<212> TYPE: DNA
<213> ORGANISM: Unknown
<220> FEATURE:
<223> OTHER INFORMATION: mammal

<400> SEQUENCE: 183
agttcttgag ccttagggtg ctag                                           24
```